US011702473B2

(12) United States Patent
Van Berkel et al.

(10) Patent No.: US 11,702,473 B2
(45) Date of Patent: Jul. 18, 2023

(54) SITE-SPECIFIC ANTIBODY-DRUG CONJUGATES

(71) Applicants: MEDIMMUNE LIMITED, Cambridge (GB); ADC THERAPEUTICS S.A., Epalinges (CH)

(72) Inventors: Patricius Hendrikus Cornelis Van Berkel, Epalinges (CH); Philip Wilson Howard, Cambridge (GB)

(73) Assignees: MEDIMMUNE LIMITED, Cambridge (GB); ADC THERAPEUTICS S.A., Epalinges (CH)

( * ) Notice: Subject to any disclaimer, the term of this patent is extended or adjusted under 35 U.S.C. 154(b) by 330 days.

(21) Appl. No.: 16/684,222

(22) Filed: Nov. 14, 2019

(65) Prior Publication Data

US 2020/0399365 A1 Dec. 24, 2020

Related U.S. Application Data

(63) Continuation of application No. 15/566,550, filed as application No. PCT/EP2016/058379 on Apr. 15, 2016, now abandoned.

(30) Foreign Application Priority Data

Apr. 15, 2015 (GB) ..................... 1506402

(51) Int. Cl.
*A61K 39/00* (2006.01)
*C07K 16/28* (2006.01)
*A61K 47/68* (2017.01)
*A61P 35/02* (2006.01)
*C07D 487/04* (2006.01)

(52) U.S. Cl.
CPC ...... *C07K 16/2803* (2013.01); *A61K 47/6803* (2017.08); *A61K 47/6867* (2017.08); *A61P 35/02* (2018.01); *C07D 487/04* (2013.01); *C07K 2317/24* (2013.01); *C07K 2317/53* (2013.01); *Y02P 20/55* (2015.11)

(58) Field of Classification Search
CPC ............ C07K 16/2803; C07K 2317/53; A61K 47/6803; A61K 47/6867; A61K 47/6851; A61P 35/02
See application file for complete search history.

(56) References Cited

U.S. PATENT DOCUMENTS

| | | |
|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 4,923,990 A | 5/1990 | Nakano et al. |
| 5,362,852 A | 11/1994 | Geoghegan |
| 5,418,241 A | 5/1995 | Jegham et al. |
| 5,440,021 A | 8/1995 | Chuntharapai et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,703,080 A | 12/1997 | Nakakura et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |

(Continued)

FOREIGN PATENT DOCUMENTS

| | | |
|---|---|---|
| EP | 0522868 | 1/1993 |
| EP | 0875569 | 11/1998 |

(Continued)

OTHER PUBLICATIONS

Hezareh et al J. Virol. (2001) 75(24): 12161 (Year: 2001).*
Adair, J.R. et al., "Antibody-drug conjugates—a perfect synergy," Exp. Opin. Biol. Ther. (2012), pp. 1-16.
Adams et al., "Molecular modelling of a sequence-specific DNA-binding agent based on the pyrrolo[2,1-c][1,4]benzodiazepines," Pharm. Pharmacol. Commun. (1999) 5:555-560.
Aird, R.E. et al., "ABCB1 genetic polymorphism influences the pharmacology of the new pyrrolobenzodiazepine derivative SJG-136," Pharmacogenomics Journal (2008) 8(4):289-296.

(Continued)

*Primary Examiner* — Sheela J. Huff
(74) *Attorney, Agent, or Firm* — Medler, Ferro, Woodhouse & Mills PLLC

(57) ABSTRACT

Site-specific antibody-drug conjugates are described, in particular conjugates comprising pyrrolobenzodiazepines (PBDs) having a labile protecting group in the form of a linker. The site of conjugation, along with modification of the antibody moiety, allows for improved safety and efficacy of the ADC.

10 Claims, 1 Drawing Sheet
Specification includes a Sequence Listing.

(56) References Cited

U.S. PATENT DOCUMENTS

| | | |
|---|---|---|
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,321,774 B2 | 4/2016 | Howard et al. |
| 9,376,440 B2 | 6/2016 | Howard et al. |
| 9,399,641 B2 | 7/2016 | Howard et al. |
| 9,624,227 B2 | 4/2017 | Howard et al. |
| 9,889,207 B2 * | 2/2018 | Howard ............ A61P 39/00 |
| 9,919,056 B2 * | 3/2018 | Van Berkel ........... A61K 45/06 |
| 10,646,584 B2 * | 5/2020 | Howard ............... C07D 519/00 |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | DeVaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0136049 A1 * | 6/2005 | Ledbetter ........... C07K 16/2878 530/387.3 |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2008/0305044 A1 * | 12/2008 | McDonagh ............ A61P 31/04 435/69.6 |
| 2009/0036431 A1 | 2/2009 | Gauzy et al. |
| 2009/0148942 A1 | 6/2009 | Mcdonagh et al. |
| 2009/0149449 A1 | 6/2009 | Liu et al. |
| 2009/0304710 A1 | 12/2009 | Park et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2011/0070227 A1 | 3/2011 | Novotney-Barry |
| 2011/0160192 A1 | 6/2011 | Howard et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0148580 A1 * | 6/2012 | Chennamsetty ........ A61P 35/00 435/69.6 |
| 2013/0011401 A1 * | 1/2013 | Huber ..................... A61P 19/02 435/69.6 |
| 2013/0028917 A1 | 1/2013 | Howard et al. |
| 2013/0028919 A1 | 1/2013 | Howard et al. |
| 2013/0266595 A1 | 10/2013 | Flygare et al. |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0275522 A1 | 9/2014 | Howard et al. |

(56) References Cited

U.S. PATENT DOCUMENTS

2014/0294868 A1 10/2014 Howard et al.
2016/0074527 A1 3/2016 Flygare et al.

FOREIGN PATENT DOCUMENTS

| | | |
|---|---|---|
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 53082792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 9216221 | 10/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 9733899 | 9/1997 |
| WO | WO 9734911 | 9/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 9923105 | 5/1999 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 2000053216 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |

(56) References Cited

FOREIGN PATENT DOCUMENTS

| | | |
|---|---|---|
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | 2005003170 A2 | 1/2005 |
| WO | 2005003171 A2 | 1/2005 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006111759 | 10/2006 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008047242 | 4/2008 |
| WO | WO 2008070593 | 6/2008 |
| WO | WO 2009016516 | 2/2009 |
| WO | WO 2009052249 | 4/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2011005481 | 1/2011 |
| WO | WO 2011023883 | 3/2011 |
| WO | WO 2011028811 | 3/2011 |
| WO | WO 2011038159 | 3/2011 |
| WO | WO 2011100227 | 8/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2012064733 A2 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013093809 | 6/2013 |
| WO | WO 2013177481 | 11/2013 |
| WO | WO 2014011518 | 1/2014 |
| WO | WO 2014022679 | 2/2014 |
| WO | WO 2014057072 | 4/2014 |
| WO | WO 2014057073 | 4/2014 |
| WO | WO 2014057074 | 4/2014 |
| WO | WO 2014057118 | 4/2014 |
| WO | WO 2014057122 | 4/2014 |
| WO | 2014/080251 * | 5/2014 |
| WO | WO 2015031693 A1 | 3/2015 |

OTHER PUBLICATIONS

Alley, M.C. et al., "''SJG-136 (NSC 694501), a novel rationally designed DNA minor groove interstrand cross-linking agent with potent and broad spectrum antitumor activity. Part 2: Efficacy evaluations,''" Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al., "The Lactonization of 2'-Hydroxyhydrocinnamic Acid Amides: A Potential Prodrug for Amines," (1990) J. Org. Chem. 55:5867-5877.

Antonow, D. et al., "'Synthesis of DNA-Interactive Pyrrolo [2,1-c][1,4] benzodiazepines (PBDs)'" Chemical Reviews, 2011, 111(4):2815-2864.

(56) References Cited

OTHER PUBLICATIONS

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., ""Molecular cloning of human endothelin receptors and their expressiOn in vascular endothelial cells and smooth muscle cells,"" Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., ""Impact on the cell cycle and involvement of ATM, ATR, chk1 and chk2 kinases in the cytotoxicity of SJG-136, a new pyrrolobenzodiazepine dimer,"" Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).

Attie T., et al., "Mutation of the endothelin-receptor B gene in Waardenburg-Hirschsprung disease," Hum. Mol. Genet. 4, 2407-2409, 1995.

Auricchio A., et al., "Endothelin-B receptor mutations in patients with isolated Hirschsprung disease from a non-inbred population," Hum. Mol. Genet. 5:351-354, 1996.

Axup et al., "Synthesis of site-specific antibody-drug conjugates using unnatural amino acids." Proc Natl Acad Sci U S A. Oct. 2, 2012; 109(40):16101-6.

Bahrenberg et al., ""Reduced Expression of PSCA, a Member of the LY-6 Family of Cell Surface Antigens, in Bladder, Esophagus, and Stomach Tumors,"" Biochem. Biophys. Res. Commun. (2000) 275(3):783-788.

Banker, G.S. et al., "Modern Pharmaceutics", Third edition, Marcel Dekker, New York (1996) 451 and 596.

Barel M., et al., "Evidence for a new transcript of the Epstein-Barr virus/C3d receptor (CR2, CD21) which is due to alternative exon usage," Mol. Immunol. 35, 1025-1031, 1998.

Barella et al., "Sequence variation of a novel heptahelical leucocyte receptor through alternative transcript formation," (1995) Biochem. J. 309:773-779.

Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.

Batisse, et al., "A new delivery system for Auristatin in STxB-drug conjugate therapy." European J. Medicinal Chemistry, 2015, 95: 483-491.

Beck et al., "DNA Sequence Analysis of 66 kb of the Human MHC Class II Region Encoding a Cluster of Genes for Antigen Processing," (1992) J. Mol. Biol. 228:433-441.

Beck et al., "Evolutionary Dynamics of Non-coding Sequences Within the Class II Region of the Human MHC," (1996) J. Mol. Biol. 25 255:1-13.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," Tetrahedron Letters (2000) 41:6171-6174.

Blanc et al., "SAR3419: an anti-CD19-Maytansinoid Immunoconjugate for the treatment of B-cell malignancies," Clin Cancer Res., 2011, 17(20):6448-58.

Bloom et al., "Intrachain disulfide bond in the core hinge region of human IgG4." Protein Sci. Feb. 1997; 6(2):407-15.

Blumberg H., et al., ""Interleukin 20: Discovery, Receptor Identification, and Role in Epidermal Function,"" Cell 104, 9-19, 2001.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).

Bourgeois C., et al., "Endothelin-1 and ETA Receptor Expression in Vascular Smooth Muscle Cells from Human Placenta: A New ETA Receptor Messenger Ribonucleic Acid is Generated by Alternative Splicing of Exon 3," J. Clin. Endocrinol. Metab. 82, 3116-3123, 1997.

Brand et al., Prospect for anti-HER2 receptor therapy in breast cancer. Anticancer Res. Jan.-Feb. 2006;26(1B):463-70.

Brinster et al., ""Introits increase transcriptional efficiency in transgenic mice,"" (1988) Proc. Natl. Acad. Sci. USA 85:836-840.

Buchman et al., "Comparison of Intron-Dependent and Intron-Independent Gene Expression," (1988) Mol. Cell. Biol. 8:4395-4405.

Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.

Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.

Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.

Burton, "Immunoglobulin G: functional sites." Mol Immunol. Mar. 1985; 22(3):161-206.

Calcutt, M.W., ""Determination of chemically reduced pyrrolobenzodiazepine SJG-136 in human plasma by HPLC-MS/MS: application to an anticancer phase I dose escalation study,"" J. Mass Spectrom. (2008) 43(1):42-52.

Capellas et al., "Enzymatic condensation of cholecystokinin CCK-8 (4-6) and CCK-8 (7-8) peptide fragments in organic media." Biotechnol Bioeng. Nov. 20, 1997; 56(4):456-63.

Carl et al., "A Novel Connector Linkage Applicable in Prodrug Design," (1981) J. Med. Chem. 24:479-480.

Carlsson et al., "Protein Thiolation and Reversible Protein-Protein Conjugation," (1978) Biochem. J. 173:723-737.

Carter, P., "Potent antibody therapeutics by design," (2006) Nature Reviews Immunology 6:343-357.

Casset et al., "A peptide mimetic of an anti-CD4 monoclonal antibody by rational design." Biochem Biophys Res Commun. Jul. 18, 2003; 307(1):198-205.

CellTiter-Glo Luminescent Cell Viability Assay, Promega Corp. Technical Bulletin TB288, dated Jan. 13, 2012 (14 pages).

Chakravarty et al., ""Plasmin-Activated Prodrugs for Cancer Chemotherapy. 2. Synthesis and Biological Activity of Peptidyl Derivatives of Doxorubicin,"" (1983) J. Med. Chem. 26:638-644.

Chan, J. and Watt, V.M., "eek and erk, new members of the eph subclass of receptor protein-tyrosine kinases," Oncogene 6 (6), 1057-1061 (1991).

Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).

Chen, Z. et al., ""A novel approach to the synthesis of cytotoxic C2-C3 unsaturated pyrrolo[2,1-c][1,4]benzodiazepines (PBDs) with conjugated acrylyl C2-substituents,"" Biorg. Med. Chem. Lett. (2004) 14:1547-1549.

Cheung, A., "Direct liquid chromatography determination of the reactive imine SJG-136 (NSC 694501)," J. Chromat. B: Anal. Techn. Biomed. Life Sci. (2005) 822(1-2):10-20.

Child et al., "Translational Control by an Upstream Open Reading Frame in the HER-2/neu Transcript," (1999) J. Biol. Chem. 274: 24335-24341.

(56) References Cited

OTHER PUBLICATIONS

Cho et al., ""Structure of the extracellular region of HER2 alone and in complex with the Herceptin Fab,"" Nature 421, 756-760, 2003.
Ciccodicola, A., et al., ""Molecular characterization of a gene of the 'EGF family' expressed in undifferentiated human NTERA2 teratocarcinoma cells,"" EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Clinical Trial, "Translational research: 4 ways to fix the clinical trial." 2011, http://www.nature.com/news/2011/110928/full/477526a.html.
Collins, "Generation and initial analysis of more than 15,000 full-length human and mouse eDNA sequences," Proc. Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey E. Quinn JE, Buhler KR, et al., "LuCap35: a new model of prostate cancer progression to androgen independence." The Prostate 2003;55:239-46.
Courtney, S. M. et al., "A new convenient procedure for the synthesis of pyrrolo[2,1-c][1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use- of ATP bioluminescence as a measure of cell proliferation and cytotoxicity," (1993) J. Immunol. Meth. 160:81-88.
Dall'acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Davis et al., "Identification of a family of Fe receptor homo logs with preferential B cell expression," (2001) Proc. Natl. Acad. Sci. USA 98(17):9772-9777.
De Groot et al., ""Cascade-Release Dendrimers"" Liberate All End Groups upon a Single Triggering Event in the Dendritic Core, (2003) Angew. Chern. Int. Ed. 42:4490-4494.
De Groot et al., "Elongated Multiple Electronic Cascade and Cyclization Spacer Systems in Activatible Anticancer Prodrug for Enhanced Drug Release," (2001) J. Org. Chern. 66:8815-8830.

De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Dennis et al., (2002) "Albumin Binding as a General Strategy For Improving The Pharmacokinetics of Proteins" J Biol Chem. 277:35035-35043.
Dijke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove crosslinking pyrrolobenzodiazepine dimer," J. Antimicrob. Chemo., Aug. 2009, 64(5):949-959.
Dubowchik et al., "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al, "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation By IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8):4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs," Chemical Abstracts, Abstract No. 239940r, vol. 114, No. 25, 25 899-903 (1991).

(56) References Cited

OTHER PUBLICATIONS

Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Fisch et al., "Site-specific modification of a fragment of a chimeric monoclonal antibody using reverse proteolysis." Bioconjug Chem. Mar.-Apr. 1992; 3(2):147-53.
Flanagan et al., "The ephrins and Eph receptors in neural development," Annu. Rev. Neurosci. 21:309-345 (1998).
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients with Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k,"Benzodiazepine derivatives", Chemical Abstracts, vol. 99, No. 17, 603 (1983).
Fujisawa Pharmaceutical Co., Ltd., Abstract No. 72145x,"Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al. "Automation of solid-phase peptide synthesis" in Macromolecular Sequencing and Synthesis, Alan R. Liss, Inc., 1988, pp. 199-218.
Genbank accession No. 11038674 (2013).
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank Accession No. BAB15489.1 (2006).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. NM_000626 (2013).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_006424 (2013).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "Tenb2, A Proteogl Ycan Identified In Prostate Cancer That is Associated with Disease Progression and Androgen Independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, 2003, vol. 100, No. 7, 4126-4131.
Greene & Wuts, Protective Groups in Organic Synthesis, John Wiley & Sons, 2nd ed Ch 7, 315-345 (1991).
Greene, et al., Protective Groups in Organic Synthesis, John Wiley & Sons (1999) 3rd Edition, 23-200.
Greene, et al., Protective Groups in Organic Synthesis, John Wiley & Sons (1999) 3rd Edition, 503-549.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

(56) References Cited

OTHER PUBLICATIONS

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41 (12):1811-1818.
Guiotto, A. et al., "Synthesis of novel C7-aryl substituted pyrrolo[2,1-c][1,4]benzodiazepines (PBDs) via Pro-N10-troc protection and Suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "Molecular Cloning and Expression Pattern of a Human Gene Homologous To The Murine mb-1 Gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant Staphylococcus aureus," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Hamaguchi, A., "DNA cross-linking and in vivo antitumour activity of the extended pyrrolo[2,1- c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by Streptomyces sp.", J. Antibiotics, 41, 702-704 (1988).
Hartley, "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (lg-alpha/mb-1) gene," (1994) Immunogenetics 40(4):287-295.
Hay et al., "A 2-Nitroimidazole Carbamate Prodrug Of 5-Amin0-1-(Chloromethyl)-3-[(5,6,7-Trimethoxyindol-2-Yl)Carbonyl]-1,2-Dihydr0-3h-Benz[E]Indole (Amino-Seco-Cbi-Tmi) For Use with Adept and Gdept," (1999) Bioorg. Med. Chern. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hermanson, G.T., Bioconjugate Techniques, Academic Press: San Diego, Calif. (1996)—(Table of Contents Only).
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mutation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Survival Factor for Hippocampal and Mesencephalic Neurons," (2000) Genomics 67: 146-152.
Howard, et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1- c][1,4]benzodiazepine monomers," Proceedings of the American Association for Cancer Research Annual Meeting (Apr. 2006) 47:132.
Hubert, R.S., et al., "Steap: A prostate-specific cell-surface antigen highly expressed in human prostate tumors," (1999) Proc. Natl. Acad. Sci. U.S.A. 96 (25):14523-14528.
Humphreys et al., "Formation of dimeric Fabs in Escherichia coli: effect of hinge size and isotype, presence of interchain disulphide bond, Fab' expression levels, tail piece sequences and growth conditions." J Immunol Methods. Dec. 1, 1997; 209(2):193-202.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.

(56) References Cited

OTHER PUBLICATIONS

International Search Report and Written Opinion for Application No. PCT/EP2012/070233 dated Jan. 28, 2013 (8 pages).
International Search Report and Written Opinion for Application No. PCT/EP2013/071352 dated Feb. 5, 2014 (14 pages).
International Search Report and Written Opinion for Application No. PCT/GB2015/052629 dated Nov. 2, 2015 (12 pages).
International Search Report and Written Opinion for Application No. PCT/US2011/032668 dated May 26, 2011 (12 pages).
Itoh et al., "Application of Inverse Substrates to Trypsin-Catalyzed Peptide Synthesis" Bioorg. Chem., 24(1): 59-68 (1996).
Itoh et al., "Sibanomicin, a new pyrrolo(1,4)benzodiazepine antitumor antibiotic produced by a *Micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "'Tamoxifen: a most unlikely pioneering medicine,'" Nature Reviews: Drug Discovery (2003) 2:205-213.
Junutula et al., "Rapid identification of reactive cysteine residues for site-specific labeling of antibody—Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22): 3955-3958.
Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anti-cancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1- c][1,4]benzodiazepines and their anticancer potential," Bioorg. Med. Chem., Jan. 2009, 17(4): 1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kasahara et al., "Nucleotide sequence of a chimpanzee DOB cDNA clone," (1989) Immunogenetics 30(1):66-68.
King et al., "Facile synthesis of maleimide bifunctional Jinkers," (2002) Tetrahedron Letters 43:1987-1990.
Kingsbury et al., "'A Novel Peptide Delivery System Involving Peptidase Activated Prodrugs as Antimicrobial Agents. Synthesis and Biological Activity of Peptidyl Derivatives of 5 Fluorouracil,'" (1984) J. Med. Chem. 27:1447-1451.
Kohn, K., "Anthramycin," Antibiotics III, Springer-Verlag, NY, 3-11 (1975).
Kojima et al., "Molecular Cloning and Expression of Megakaryocyte Potentiating Factor cDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman & Pastan "Immunotoxins for targeted cancer therapy." Adv Drug Deliv Rev. Apr. 6, 1998; 31(1-2):53-88.
Kuhns J.J., et al., "Poor Binding of a HER-2/neu Epitope (GP2) to HLA-A2.1 is due to a Lack of Interactions with the Center of the Peptide," J. Biol. Chem. 274, 36422-36427, 1999.
Kumaran et al., "Conformationally driven protease-catalyzed splicing of peptide segments: V8 protease-mediated synthesis of fragments derived from thermolysin and ribonuclease A." Protein Sci. Oct. 1997; 6(10):2233-41.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin-6," (1999) Brit. Jour. Cancer 79(5-6):707-717.
Lambert J., "Drug-conjugated monoclonal antibodies for the treatment of cancer," (2005) Current Opin. in Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and cDNA Encoding Murine Major Histocompatibility Complex Class II Gene AP2*," (1985) J. Biol. Chem. 260(26):14111-14119.
Launay et al., "TRPM4 is a Ca2+ -Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma is a Potential Therapeutic Target for Anti-CD70 Antibody-Drug Conjugates," (2006) Cancer Res. 66(4):2328-2337.

(56) References Cited

OTHER PUBLICATIONS

Lazar et al., "A molecular immunology approach to antibody humanization and functional optimization" Molecular Immunology, 2007, 44(8), 1986-1998.

Le et al., "Primary structure and expression of a naturally truncated human P2X ATP receptor subunit from brain and immune system," (1997) FEBS Lett. 418(1-2):195-199.

Leabman; et al., "Effects of altered FcγR binding on antibody pharmacokinetics in cynomolgus monkeys." MAbs. Nov.-Dec. 2013; 5(6):896-903.

Leber, J.D. et al., "A revised structure for sibiromycin," J. Am. Chem. Soc., 110, 2992-2993 (1988).

Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).

Leimgruber, W. et al., "Total synthesis of anthramycin," J. Am. Chem. Soc., 90, 5641-5643 (1968).

Leonard et al., "Phase I/II trial of epratuzumab (humanized anti-CD22 antibody) in indolent non-Hodgkin's lymphoma," J. Clin. Oncology (2003) 21(16):3051-3059.

Leonard et al., "Preclinical and clinical evaluation of epratuzumab (anti-CD22 IgG) in B-cell malignancies," Oncogene (2007) 26:3704-3713.

Leung et al., "Construction and characterization of a humanized, internalizing, B-cell (CD22)-specific, leukemia/lymphoma antibody, LL2," Mol. Immunol. (1995) 32(17-18):1413-1427.

Levenson et al., "MCF-7: The First Hormone-responsive Breast Cancer Cell Line," (1997) Cancer Res. 57(15):3071-3078.

Lewis Phillips et al., "Targeting HER2-Positive Breast Cancer with Trastuzumab-DM1, an Antibody-Cytotoxic Drug Conjugate," Cancer Res, 2008, 68: (22).

Liang et al., "The Gene fora Novel Transmembrane Protein Containing Epidermal Growth Factor and Follistatin Domains is Frequently Hypermethylated in Human Tumor Cells," (2000) Cancer Res. 60:4907-4912.

Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.

Lonberg, "Fully Human antibodies from transgenic mouse and phage display platforms" Curr. Opinion, 20(4), 450-459 (2008).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.

Marin, D., "Voltammetric studies of the interaction of pyrrolo[2,1-c][1,4]benzodiazepine (PBD) monomers and dimers with DNA," J. Electroanal. Chem. (2006) 593(1-2):241-246.

Marks et al., "By-passing Immunization, Human Antibodies from V-gene Libraries Displayed on Phage," (1991) J. Mol. Biol., 222:581-597.

Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mastroberardino et al., "Amino-acid transport by heterodimers of 4F2hc/CD98 and members of a permease family," Nature 395 (6699):288-291 (1998).

McDonagh, "Engineered antibody-drug conjugates with defined sites and stoichiometries of drug attachment," (2006) Protein Eng. Design & Sel. 19(7): 299-307.

Mendoza et al., "Inhibition of Ligand-mediated HER2 Activation in Androgenindependent Prostate Cancer," (2002) Cancer Res. 62:5485-5488.

Miller et al., "Design, Construction, and In Vitro Analyses of Multivalent Antibodies," (2003) Jour. of Immunology 170:4854-4861.

Miller et al., "IRTAs: a new family of immunoglobulinlike receptors differentially expressed in B cells," Blood 99 (8):2662-2669 (2002).

Miura et al., "Molecular cloning of a human RP105 homologue and chromosomal localization of the mouse and human RP105 genes (Ly64 and LY64)." Genomics. Dec. 15, 1996;38(3):299-304.

Miura et al., "RP105 is Associated With MD-1 and Transmits an Activation Signal in Human B Cells," (1998) Blood 92:2815-2822.

Moore M., et al., "Molecular cloning of the cDNA encoding the Epstein-Barr virus/C3d receptor (complement receptor type 2) of human B lymphocytes," Proc. Natl. Acad. Sci. U.S.A. 84, 9194-9198, 1987.

Mori, M. et al., "Total syntheses of prothracarcin and tomaymycin by use of palladium catalyzed carbonylation," Tetrahedron (1986) 42(14):3793-3806.

Morrison et al., "Chimeric human antibody molecules: Mouse antigen-binding domains with human constant region domains," (1984) Proc. Natl. Acad. Sci. USA, 81:6851-6855.

Mountzouris, J.A. et al., "Comparison of a DSB-120 DNA interstrand cross-linked adduct with the corresponding bis-Tomamycin adduct," J. Med. Chem. (1994) 37:3132-3140.

Muller et al., "Cloning and sequencing of the cDNA encoding the human homologue of the murine immunoglobulin-associated protein B29," (1992) Eur. J. Immunol. 22 (6): 1621-1625.

Mungall A.J., et al., "The DNA sequence and analysis of human chromosome 6," Nature 425, 805-811, 2003.

Nagasaka, T. et al., "Stereoselective Synthesis of Tilivalline," Tetrahedron Letters, 30:14, 1871-1872 (1989).

Nagase T., et al., "Prediction of the Coding Sequences of Unidentified Human Genes. XVII. The Complete Sequences of 100 New cDNA Clones from Brain Which Code for Large Proteins in vitro," (2000) DNA Res. 7 (2):143-150.

Nakamuta M., et al., "Cloning and Sequence Analysis of a cDNA Encoding Human Non-Selective Type of Endothelin Receptor," Biochem. Biophys. Res. Commun. 177, 34-39, 1991.

Nakayama et al., "Altered Gene Expression upon BCR Cross-Linking in Burkitt's Lymphoma B Cell Line," (2000) Biochem. Biophys. Res. Commun. 277(1):124-127.

Narayanaswamy, M., "A novel HPLC/MS assay to measure DNA interstrand cross-linking efficacy in oligonucleotides of varying sequence," EJC Supplements (Nov. 2006) 4(12):92-93.

Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.

Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.

Narukawa, Y., "General and efficient synthesis of 2-alkylcarbapenems synthesis of dethia carba analogs of clinically useful carbapenems via palladium-catalyzed crosscoupling reaction," Tetrahedron (1997) 53:539-556.

Naruse et al., "The HLA-DOB gene displays limited polymorphism with only one amino acid substitution," (2002) Tissue Antigens 59:512-519.

Neuberger and Williams, "The intron requirement for immunoglobulin gene expression is dependent upon the promoter," (1988) Nucleic Acids Res. 16:6713-6724.

Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.

Nilius et al., "Voltage Dependence of the Ca2+-activated Cation Channel TRPM4," The Journal of Biological Chemistry, vol. 278, No. 33, Issue of Aug. 15, pp. 30813-30820, 2003.

(56) References Cited

OTHER PUBLICATIONS

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular cloning of a non-isopeptide-selective human endothelin receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
Pepper, C., "Fludarabine-mediated suppression of the excision repair enzyme ERCC1 contributes to the cytotoxic synergy with the DNA minor groove crosslinking agent SJG-136 (Nsc 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.

Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131 (38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Ross et al., "Prostate Stem Cell Antigen as Therapy Target: Tissue Expression and in Vivo Efficacy of an Immunoconjugate," (2002) Cancer Res. 62:2546-2553.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA For the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, p. 11531-11536, Sep. 1999.
Schroder and Lubke, The Peptides, vol. 1. pp 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, p. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, THE DOBeta Gene is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).

(56) References Cited

OTHER PUBLICATIONS

Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Stimmel et al., "Site-specific conjugation on serine right-arrow cysteine variant monoclonal antibodies." J Biol Chem. Sep. 29, 2000; 275(39):30445-50.
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse Edna sequences," (2002) Proc. Natl. Acad. Sci USA 99:16899-16903.
Strop et al., "Location matters: site of conjugation modulates stability and pharmacokinetics of antibody drug conjugates." Chem Biol. Feb. 21, 2013; 20(2):161-7.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues forthe Preparation of Antibody- Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takahashi et al., "Human Fas ligand: gene structure, chromosomal location and species specificity." Int Immunol. Oct. 1994; 6(10):1567-74.
Takeuchi, T. et al., "Neothramycins A and B, New Antitumor Antibiotics," J. Antibiotics, 29, 93-96 (1976).
Tawaragi Y., et al., "Primary Structure of Nonspecific Crossreacting Antigen (NCA), a Member of Carcinoembryonic Antigen (CEA) Gene Family, Deduced From cDNA Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001 ).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies forthe 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Verheij J.B., et al., "ABCD Syndrome is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identification of a Human Protein Homologous to the Mouse Lyb-2 B Cell Differentiation Antigen and Sequence of the Corresponding cDNA," (1990) J. Immunol. 144(12):4870-4877.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone forthe C3d/Epstein-Barr virus receptor of human B lymphocytes: Homol-

(56) References Cited

OTHER PUBLICATIONS ogy with the receptor for fragments C3b and C4b of the third and fourth components of complement," Proc. Natl. Acad. Sci. U.S.A. 83, 5639-5643, 1986.

Weis J.J., et al., "Structure of the human b lymphocyte receptor for c3d and the epstein-barr virus and relatedness to other members of the family of c3/c4 binding proteins," J. Exp. Med. 167, 1047-1066, 1988.

Wells, G. et al., "Design, synthesis and biophysical and biological evaluation of a series of pyrrolobenzodiazepine-poly(N-methylpyrrole) conjugates," J. Med. Chem. (2006) 49:5442-5461.

Werlen et al., "Site-specific conjugation of an enzyme and an antibody fragment." Bioconjug Chem. Sep.-Oct. 1994; 5(5):411-7.

Wikipedia, "How many types of cancer are there?", 2012, 3 pages; http://wiki.answers.com/Q/How-many-different-types_of_cancer_are_there.

Wikipedia, "Management of Cancer," 2012, 1 page; http://en.wikipedia.org/wiki/Management of cancer.

Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.

Wilkinson, G.P., "Pharmacokinetics, metabolism and glutathione reactivity of SJG-136," Br. J. Cancer (2003) 88(Supp. 1):S29.

Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.

Wilson et al., "cDNA Cloning of the B Cell Membrane Protein CD22: A Mediator of B-B Cell Interactions," (1991) J. Exp. Med. 173:137-146.

Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).

Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A." J Immunol. May 15, 2000; 164(10):5313-8.

Wolff, M.E., Burger's Medicinal Chemistry, 4th Edition, Part I, Wiley: New York (1979) 336-337.

Wolff, M.E., Burger's Medicinal Chemistry, 5th Edition, Part I, John Wiley & Sons (1995) 975-977.

Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.

Wu et al., "Arming antibodies: prospects and challenges for immunoconjugates," (2005) Nature Biotech. 23(9):1137-1145.

Xie et al., "In vivo behaviour of antibody-drug conjugates for the targeted treatment of cancer," (2006) Expert. Opin Biol. Ther. 6(3):281-291.

Xie, G. et al., "Bisindolylmaleimides linked to DNA minor groove binding lexitropsins: synthesis, inhibitory activity against topoisomeraseI, and biological evaluation," J. Med. Chem. (1996) 39:1049-1055.

Xu et al., "Molecular Cloning, Functional Characterization, Tissue Distribution, and Chromosomal Localization of a Human, Small Intestinal Sodium-Phosphate (Na+-Pi) Transporter (SLC34A2)," Genomics 62 (2):281-284 (1999).

Xu, M.J., et al., "Molecular Cloning and Characterization of SPAP1, an Inhibitory Receptor," (2001) Biochem. Biophys. Res. Commun. 280 (3):768-775.

Xu, X.Z., et al., "Regulation of melastatin, a TRP-related protein, through interaction with a cytoplasmic isoform," Proc. Natl. Acad. Sci. U.S.A. 98 (19):10692-10697 (2001).

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Yu et al., "Human mb-1 Gene: Complete cDNA Sequence and Its Expression in B Cells Bearing Membrane Ig of Various Isotypes," (1992) J. Immunol. 148(2) 633-637.

Zalevsky et al., "Enhanced antibody half-life improves in vivo activity." Nat Biotechnol. Feb. 2010; 28(2):157-9.

\* cited by examiner

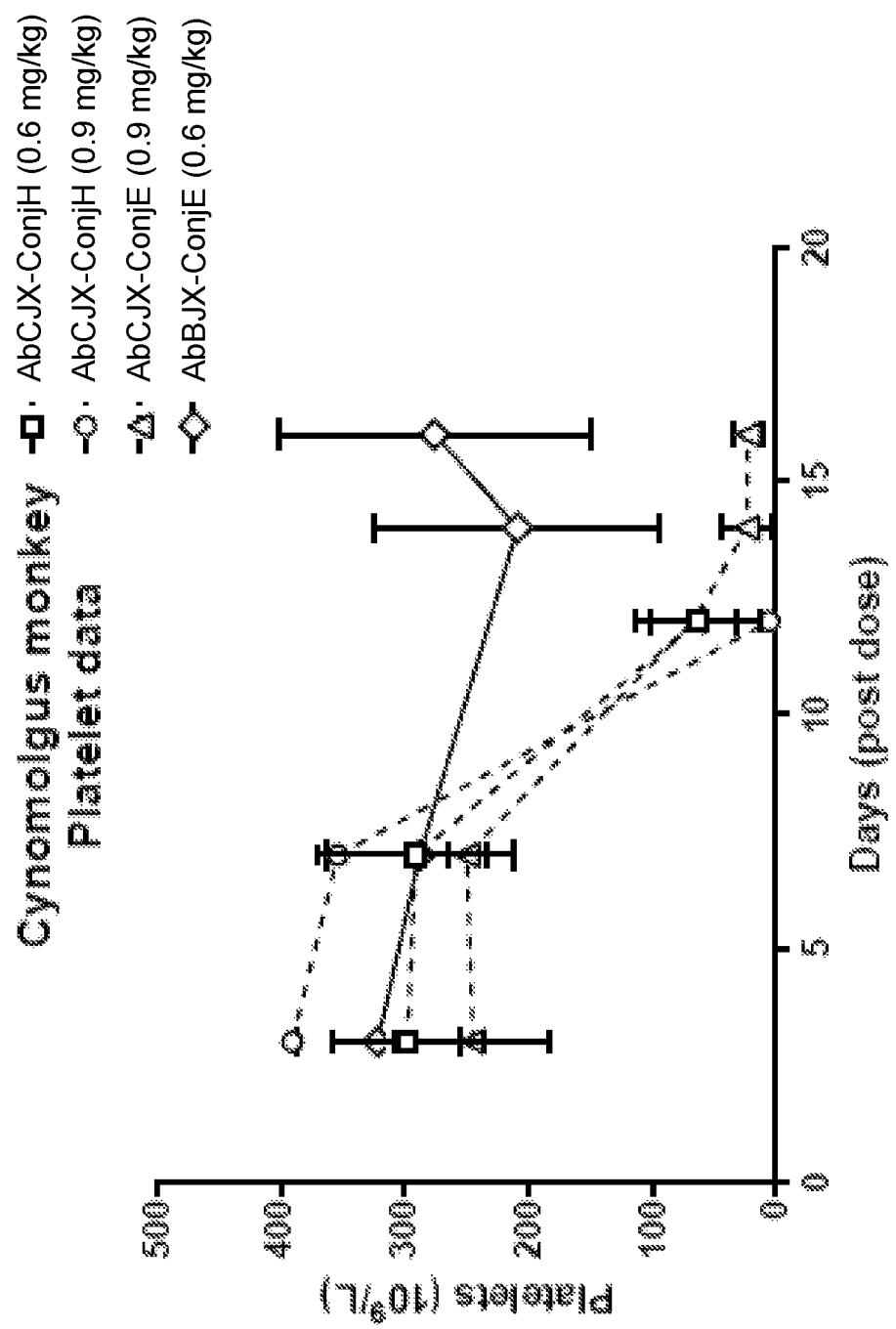

SEQUENCE LISTING

<160> NUMBER OF SEQ ID NOS: 1166

<210> SEQ ID NO 1
<211> LENGTH: 109
<212> TYPE: PRT
<213> ORGANISM: Artificial sequence
<220> FEATURE:
<223> OTHER INFORMATION: Synthetic Epratuzumab VH

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly
            100                 105
```

<210> SEQ ID NO 2
<211> LENGTH: 106
<212> TYPE: PRT
<213> ORGANISM: Artificial sequence
<220> FEATURE:
<223> OTHER INFORMATION: Synthetic Epratuzumab VL

<400> SEQUENCE: 2

```
Asp Ile Gln Leu Thr Gln Ser Pro Ser Ser Leu Ser Ala Ser Val Gly
1               5                   10                  15

Asp Arg Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gln Gly
            100                 105
```

```
<210> SEQ ID NO 3
<400> SEQUENCE: 3
000

<210> SEQ ID NO 4
<400> SEQUENCE: 4
000

<210> SEQ ID NO 5
<400> SEQUENCE: 5
000

<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
```

```
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
```

000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

```
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
```

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<211> LENGTH: 330
<212> TYPE: PRT
<213> ORGANISM: Artificial sequence
<220> FEATURE:
<223> OTHER INFORMATION: Synthetic IgG1 HC constant region

<400> SEQUENCE: 110

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 111
<211> LENGTH: 330
<212> TYPE: PRT
<213> ORGANISM: Artificial sequence
<220> FEATURE:
<223> OTHER INFORMATION: Synthetic IgG1 HC constant region, HJ C->S

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 112
<211> LENGTH: 330
<212> TYPE: PRT
<213> ORGANISM: Artificial sequence
<220> FEATURE:
<223> OTHER INFORMATION: Synthetic IgG1 HC constant region, HJ C->V

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 113
<211> LENGTH: 330
<212> TYPE: PRT
<213> ORGANISM: Artificial sequence
<220> FEATURE:
<223> OTHER INFORMATION: Synthetic IgG1 HC constant region, BJ C->S

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 114
<211> LENGTH: 330
<212> TYPE: PRT
<213> ORGANISM: Artificial sequence
<220> FEATURE:
<223> OTHER INFORMATION: Synthetic IgG1 HC constant region, BJ C->V

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 115
<211> LENGTH: 330
<212> TYPE: PRT
<213> ORGANISM: Artificial sequence
<220> FEATURE:
<223> OTHER INFORMATION: Synthetic IgG1 HC constant region, DJ C->S

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Ser Pro Pro Ser
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 116
<211> LENGTH: 330
<212> TYPE: PRT
<213> ORGANISM: Artificial sequence
<220> FEATURE:
<223> OTHER INFORMATION: Synthetic IgG1 HC constant region, DJ C->V

<400> SEQUENCE: 116

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 117

<400> SEQUENCE: 117

<210> SEQ ID NO 118

<400> SEQUENCE: 118

000

<210> SEQ ID NO 119

<400> SEQUENCE: 119

000

<210> SEQ ID NO 120
<211> LENGTH: 326
<212> TYPE: PRT
<213> ORGANISM: Artificial sequence
<220> FEATURE:
<223> OTHER INFORMATION: Synthetic IgG2 HC constant region

<400> SEQUENCE: 120

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130
<211> LENGTH: 377
<212> TYPE: PRT
<213> ORGANISM: Artificial sequence
<220> FEATURE:
```

<223> OTHER INFORMATION: Synthetic IgG3 HC constant region

<400> SEQUENCE: 130

```
Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Cys Pro Arg
        115                 120                 125
Cys Pro Glu Pro Lys Ser Cys Asp Thr Pro Pro Cys Pro Arg Cys
130                 135                 140
Pro Glu Pro Lys Ser Cys Asp Thr Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Asn Trp Tyr
        195                 200                 205
Val Asp Gly Val Glu Val His Asn Ala Lys Thr Lys Pro Arg Glu Glu
    210                 215                 220
Gln Tyr Asn Ser Thr Tyr Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
Tyr Lys Thr Thr Pro Pro Val Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn His Phe Thr Gln
        355                 360                 365
Lys Ser Leu Ser Leu Ser Pro Gly Lys
    370                 375
```

<210> SEQ ID NO 131
<211> LENGTH: 377

```
<212> TYPE: PRT
<213> ORGANISM: Artificial sequence
<220> FEATURE:
<223> OTHER INFORMATION: Synthetic IgG3 HC constant region, L164A

<400> SEQUENCE: 131

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Ala Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn His Phe Thr Gln
        355                 360                 365

Lys Ser Leu Ser Leu Ser Pro Gly Lys
    370                 375
```

<210> SEQ ID NO 132
<211> LENGTH: 377
<212> TYPE: PRT
<213> ORGANISM: Artificial sequence
<220> FEATURE:
<223> OTHER INFORMATION: Synthetic IgG3 HC constant region, L165A

<400> SEQUENCE: 132

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Ala Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn His Phe Thr Gln
        355                 360                 365
```

```
Lys Ser Leu Ser Leu Ser Pro Gly Lys
    370                 375

<210> SEQ ID NO 133
<211> LENGTH: 377
<212> TYPE: PRT
<213> ORGANISM: Artificial sequence
<220> FEATURE:
<223> OTHER INFORMATION: Synthetic IgG3 HC constant region, L164A &
      L165A

<400> SEQUENCE: 133

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Ala Ala Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

Phe Ser Cys Ser Val Met His Glu Ala Leu His Asn His Phe Thr Gln
        355                 360                 365

Lys Ser Leu Ser Leu Ser Pro Gly Lys
    370                 375

<210> SEQ ID NO 134
<211> LENGTH: 377
<212> TYPE: PRT
<213> ORGANISM: Artificial sequence
<220> FEATURE:
<223> OTHER INFORMATION: Synthetic IgG3 HC constant region, L164G &
      L165G

<400> SEQUENCE: 134

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Gly Gly Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu

```
              325                 330                 335
Tyr Ser Lys Leu Thr Val Asp Lys Ser Arg Trp Gln Gln Gly Asn Ile
        340                 345                 350

Phe Ser Cys Ser Val Met His Glu Ala Leu His Asn His Phe Thr Gln
        355                 360                 365

Lys Ser Leu Ser Leu Ser Pro Gly Lys
        370                 375

<210> SEQ ID NO 135
<211> LENGTH: 377
<212> TYPE: PRT
<213> ORGANISM: Artificial sequence
<220> FEATURE:
<223> OTHER INFORMATION: Synthetic IgG3 HC constant region, L164V &
      L165V

<400> SEQUENCE: 135

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Val Val Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn His Phe Thr Gln
        355                 360                 365

Lys Ser Leu Ser Leu Ser Pro Gly Lys
    370                 375

<210> SEQ ID NO 136
<211> LENGTH: 377
<212> TYPE: PRT
<213> ORGANISM: Artificial sequence
<220> FEATURE:
<223> OTHER INFORMATION: Synthetic IgG3 HC constant region, L164I &
      L165I

<400> SEQUENCE: 136

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Ile Ile Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

```
Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn His Phe Thr Gln
        355                 360                 365

Lys Ser Leu Ser Leu Ser Pro Gly Lys
370                 375

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140
<211> LENGTH: 327
<212> TYPE: PRT
<213> ORGANISM: Artificial sequence
<220> FEATURE:
<223> OTHER INFORMATION: Synthetic IgG4 HC constant region

<400> SEQUENCE: 140

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 141
<211> LENGTH: 327
<212> TYPE: PRT
<213> ORGANISM: Artificial sequence
<220> FEATURE:
<223> OTHER INFORMATION: Synthetic IgG4 HC constant region, L115A

<400> SEQUENCE: 141

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 142
<211> LENGTH: 327
<212> TYPE: PRT
<213> ORGANISM: Artificial sequence
<220> FEATURE:
<223> OTHER INFORMATION: Synthetic IgG4 HC constant region, L115G

<400> SEQUENCE: 142

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
        100                 105                 110

Glu Phe Gly Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 143
<211> LENGTH: 327
<212> TYPE: PRT
<213> ORGANISM: Artificial sequence
<220> FEATURE:
<223> OTHER INFORMATION: Synthetic IgG4 HC constant region, L115V

<400> SEQUENCE: 143

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Val Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 144
<211> LENGTH: 327
<212> TYPE: PRT
<213> ORGANISM: Artificial sequence
<220> FEATURE:
<223> OTHER INFORMATION: Synthetic IgG4 HC constant region, L115I

<400> SEQUENCE: 144

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Ile Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 105
<212> TYPE: PRT
<213> ORGANISM: Artificial sequence
<220> FEATURE:
<223> OTHER INFORMATION: kappa LC constant region

<400> SEQUENCE: 150

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 151
<211> LENGTH: 105

```
<212> TYPE: PRT
<213> ORGANISM: Artificial sequence
<220> FEATURE:
<223> OTHER INFORMATION: kappa LC constant region, C105S

<400> SEQUENCE: 151

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Ser
            100                 105

<210> SEQ ID NO 152
<211> LENGTH: 105
<212> TYPE: PRT
<213> ORGANISM: Artificial sequence
<220> FEATURE:
<223> OTHER INFORMATION: kappa LC constant region, C105V

<400> SEQUENCE: 152

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Val
            100                 105

<210> SEQ ID NO 153
<211> LENGTH: 104
<212> TYPE: PRT
<213> ORGANISM: Artificial sequence
<220> FEATURE:
<223> OTHER INFORMATION: kappa LC constant region, C105del

<400> SEQUENCE: 153

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60
```

```
            50                  55                  60
Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu
            100
```

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160
<211> LENGTH: 103
<212> TYPE: PRT
<213> ORGANISM: Artificial sequence
<220> FEATURE:
<223> OTHER INFORMATION: lambda LC constant region

<400> SEQUENCE: 160

```
Lys Ala Ala Pro Ser Val Thr Leu Phe Pro Pro Ser Ser Glu Glu Leu
 1               5                  10                  15

Gln Ala Asn Lys Ala Thr Leu Val Cys Leu Ile Ser Asp Phe Tyr Pro
             20                  25                  30

Gly Ala Val Thr Val Ala Trp Lys Ala Asp Ser Ser Pro Val Lys Ala
         35                  40                  45

Gly Val Glu Thr Thr Thr Pro Ser Lys Gln Ser Asn Asn Lys Tyr Ala
     50                  55                  60

Ala Ser Ser Tyr Leu Ser Leu Thr Pro Glu Gln Trp Lys Ser His Arg
 65                  70                  75                  80

Ser Tyr Ser Cys Gln Val Thr His Glu Gly Ser Thr Val Glu Lys Thr
```

Val Ala Pro Thr Glu Cys Ser
            100

<210> SEQ ID NO 161
<211> LENGTH: 103
<212> TYPE: PRT
<213> ORGANISM: Artificial sequence
<220> FEATURE:
<223> OTHER INFORMATION: lambda LC constant region, C102S

<400> SEQUENCE: 161

Lys Ala Ala Pro Ser Val Thr Leu Phe Pro Pro Ser Ser Glu Glu Leu
1               5                   10                  15

Gln Ala Asn Lys Ala Thr Leu Val Cys Leu Ile Ser Asp Phe Tyr Pro
            20                  25                  30

Gly Ala Val Thr Val Ala Trp Lys Ala Asp Ser Ser Pro Val Lys Ala
        35                  40                  45

Gly Val Glu Thr Thr Thr Pro Ser Lys Gln Ser Asn Asn Lys Tyr Ala
    50                  55                  60

Ala Ser Ser Tyr Leu Ser Leu Thr Pro Glu Gln Trp Lys Ser His Arg
65                  70                  75                  80

Ser Tyr Ser Cys Gln Val Thr His Glu Gly Ser Thr Val Glu Lys Thr
                85                  90                  95

Val Ala Pro Thr Glu Ser Ser
            100

<210> SEQ ID NO 162
<211> LENGTH: 103
<212> TYPE: PRT
<213> ORGANISM: Artificial sequence
<220> FEATURE:
<223> OTHER INFORMATION: lambda LC constant region, C102V

<400> SEQUENCE: 162

Lys Ala Ala Pro Ser Val Thr Leu Phe Pro Pro Ser Ser Glu Glu Leu
1               5                   10                  15

Gln Ala Asn Lys Ala Thr Leu Val Cys Leu Ile Ser Asp Phe Tyr Pro
            20                  25                  30

Gly Ala Val Thr Val Ala Trp Lys Ala Asp Ser Ser Pro Val Lys Ala
        35                  40                  45

Gly Val Glu Thr Thr Thr Pro Ser Lys Gln Ser Asn Asn Lys Tyr Ala
    50                  55                  60

Ala Ser Ser Tyr Leu Ser Leu Thr Pro Glu Gln Trp Lys Ser His Arg
65                  70                  75                  80

Ser Tyr Ser Cys Gln Val Thr His Glu Gly Ser Thr Val Glu Lys Thr
                85                  90                  95

Val Ala Pro Thr Glu Val Ser
            100

<210> SEQ ID NO 163
<211> LENGTH: 101
<212> TYPE: PRT
<213> ORGANISM: Artificial sequence
<220> FEATURE:
<223> OTHER INFORMATION: lambda LC constant region, C102&S103del

<400> SEQUENCE: 163

Lys Ala Ala Pro Ser Val Thr Leu Phe Pro Pro Ser Ser Glu Glu Leu
1               5                   10                  15

```
Gln Ala Asn Lys Ala Thr Leu Val Cys Leu Ile Ser Asp Phe Tyr Pro
                 20                  25                  30

Gly Ala Val Thr Val Ala Trp Lys Ala Asp Ser Ser Pro Val Lys Ala
             35                  40                  45

Gly Val Glu Thr Thr Thr Pro Ser Lys Gln Ser Asn Asn Lys Tyr Ala
         50                  55                  60

Ala Ser Ser Tyr Leu Ser Leu Thr Pro Glu Gln Trp Lys Ser His Arg
 65                  70                  75                  80

Ser Tyr Ser Cys Gln Val Thr His Glu Gly Ser Thr Val Glu Lys Thr
                 85                  90                  95

Val Ala Pro Thr Glu
            100

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172
```

000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000

<210> SEQ ID NO 179
<400> SEQUENCE: 179
000

<210> SEQ ID NO 180
<400> SEQUENCE: 180
000

<210> SEQ ID NO 181
<400> SEQUENCE: 181
000

<210> SEQ ID NO 182
<400> SEQUENCE: 182
000

<210> SEQ ID NO 183
<400> SEQUENCE: 183
000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229
<400> SEQUENCE: 229
000

<210> SEQ ID NO 230
<400> SEQUENCE: 230
000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000

<210> SEQ ID NO 234
<400> SEQUENCE: 234
000

<210> SEQ ID NO 235
<400> SEQUENCE: 235
000

<210> SEQ ID NO 236
<400> SEQUENCE: 236
000

<210> SEQ ID NO 237
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

```
<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
```

-continued

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

```
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
<400> SEQUENCE: 326
000

<210> SEQ ID NO 327
<400> SEQUENCE: 327
000

<210> SEQ ID NO 328
<400> SEQUENCE: 328
000

<210> SEQ ID NO 329
<400> SEQUENCE: 329
000

<210> SEQ ID NO 330
<400> SEQUENCE: 330
```

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

-continued

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000

<210> SEQ ID NO 396
<400> SEQUENCE: 396
000

<210> SEQ ID NO 397
<400> SEQUENCE: 397
000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410
<400> SEQUENCE: 410
000

<210> SEQ ID NO 411
<400> SEQUENCE: 411
000

<210> SEQ ID NO 412
<400> SEQUENCE: 412
000

<210> SEQ ID NO 413
<400> SEQUENCE: 413
000

<210> SEQ ID NO 414
<400> SEQUENCE: 414
000

<210> SEQ ID NO 415
<400> SEQUENCE: 415
000

<210> SEQ ID NO 416
<400> SEQUENCE: 416
000

<210> SEQ ID NO 417
<400> SEQUENCE: 417
000

<210> SEQ ID NO 418
<400> SEQUENCE: 418
000

<210> SEQ ID NO 419
<400> SEQUENCE: 419
000

<210> SEQ ID NO 420
<400> SEQUENCE: 420
000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

-continued

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

```
<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488
```

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534
<400> SEQUENCE: 534
000

<210> SEQ ID NO 535
<400> SEQUENCE: 535
000

<210> SEQ ID NO 536
<400> SEQUENCE: 536
000

<210> SEQ ID NO 537
<400> SEQUENCE: 537
000

<210> SEQ ID NO 538
<400> SEQUENCE: 538
000

<210> SEQ ID NO 539
<400> SEQUENCE: 539
000

<210> SEQ ID NO 540
<400> SEQUENCE: 540
000

<210> SEQ ID NO 541
<400> SEQUENCE: 541
000

<210> SEQ ID NO 542
<400> SEQUENCE: 542
000

<210> SEQ ID NO 543
<400> SEQUENCE: 543
000

<210> SEQ ID NO 544
<400> SEQUENCE: 544
000

-continued

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

```
<400> SEQUENCE: 556
000

<210> SEQ ID NO 557
<400> SEQUENCE: 557
000

<210> SEQ ID NO 558
<400> SEQUENCE: 558
000

<210> SEQ ID NO 559
<400> SEQUENCE: 559
000

<210> SEQ ID NO 560
<400> SEQUENCE: 560
000

<210> SEQ ID NO 561
<400> SEQUENCE: 561
000

<210> SEQ ID NO 562
<400> SEQUENCE: 562
000

<210> SEQ ID NO 563
<400> SEQUENCE: 563
000

<210> SEQ ID NO 564
<400> SEQUENCE: 564
000

<210> SEQ ID NO 565
<400> SEQUENCE: 565
000

<210> SEQ ID NO 566
<400> SEQUENCE: 566
000

<210> SEQ ID NO 567
<400> SEQUENCE: 567
```

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

```
<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612
```

000

<210> SEQ ID NO 613
<400> SEQUENCE: 613
000

<210> SEQ ID NO 614
<400> SEQUENCE: 614
000

<210> SEQ ID NO 615
<400> SEQUENCE: 615
000

<210> SEQ ID NO 616
<400> SEQUENCE: 616
000

<210> SEQ ID NO 617
<400> SEQUENCE: 617
000

<210> SEQ ID NO 618
<400> SEQUENCE: 618
000

<210> SEQ ID NO 619
<400> SEQUENCE: 619
000

<210> SEQ ID NO 620
<400> SEQUENCE: 620
000

<210> SEQ ID NO 621
<400> SEQUENCE: 621
000

<210> SEQ ID NO 622
<400> SEQUENCE: 622
000

<210> SEQ ID NO 623
<400> SEQUENCE: 623
000

-continued

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

-continued

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

-continued

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

```
<210> SEQ ID NO 669
<400> SEQUENCE: 669
000

<210> SEQ ID NO 670
<400> SEQUENCE: 670
000

<210> SEQ ID NO 671
<400> SEQUENCE: 671
000

<210> SEQ ID NO 672
<400> SEQUENCE: 672
000

<210> SEQ ID NO 673
<400> SEQUENCE: 673
000

<210> SEQ ID NO 674
<400> SEQUENCE: 674
000

<210> SEQ ID NO 675
<400> SEQUENCE: 675
000

<210> SEQ ID NO 676
<400> SEQUENCE: 676
000

<210> SEQ ID NO 677
<400> SEQUENCE: 677
000

<210> SEQ ID NO 678
<400> SEQUENCE: 678
000

<210> SEQ ID NO 679
<400> SEQUENCE: 679
000

<210> SEQ ID NO 680
```

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

-continued

<210> SEQ ID NO 703
<400> SEQUENCE: 703
000

<210> SEQ ID NO 704
<400> SEQUENCE: 704
000

<210> SEQ ID NO 705
<400> SEQUENCE: 705
000

<210> SEQ ID NO 706
<400> SEQUENCE: 706
000

<210> SEQ ID NO 707
<400> SEQUENCE: 707
000

<210> SEQ ID NO 708
<400> SEQUENCE: 708
000

<210> SEQ ID NO 709
<400> SEQUENCE: 709
000

<210> SEQ ID NO 710
<400> SEQUENCE: 710
000

<210> SEQ ID NO 711
<400> SEQUENCE: 711
000

<210> SEQ ID NO 712
<400> SEQUENCE: 712
000

<210> SEQ ID NO 713
<400> SEQUENCE: 713
000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

```
<210> SEQ ID NO 748
<400> SEQUENCE: 748
000

<210> SEQ ID NO 749
<400> SEQUENCE: 749
000

<210> SEQ ID NO 750
<400> SEQUENCE: 750
000

<210> SEQ ID NO 751
<400> SEQUENCE: 751
000

<210> SEQ ID NO 752
<400> SEQUENCE: 752
000

<210> SEQ ID NO 753
<400> SEQUENCE: 753
000

<210> SEQ ID NO 754
<400> SEQUENCE: 754
000

<210> SEQ ID NO 755
<400> SEQUENCE: 755
000

<210> SEQ ID NO 756
<400> SEQUENCE: 756
000

<210> SEQ ID NO 757
<400> SEQUENCE: 757
000

<210> SEQ ID NO 758
<400> SEQUENCE: 758
000

<210> SEQ ID NO 759
```

```
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769
<400> SEQUENCE: 769
000

<210> SEQ ID NO 770
<400> SEQUENCE: 770
```

000

<210> SEQ ID NO 771
<400> SEQUENCE: 771
000

<210> SEQ ID NO 772
<400> SEQUENCE: 772
000

<210> SEQ ID NO 773
<400> SEQUENCE: 773
000

<210> SEQ ID NO 774
<400> SEQUENCE: 774
000

<210> SEQ ID NO 775
<400> SEQUENCE: 775
000

<210> SEQ ID NO 776
<400> SEQUENCE: 776
000

<210> SEQ ID NO 777
<400> SEQUENCE: 777
000

<210> SEQ ID NO 778
<400> SEQUENCE: 778
000

<210> SEQ ID NO 779
<400> SEQUENCE: 779
000

<210> SEQ ID NO 780
<400> SEQUENCE: 780
000

<210> SEQ ID NO 781
<400> SEQUENCE: 781
000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

-continued

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801

<400> SEQUENCE: 801

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

-continued

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

```
<400> SEQUENCE: 872
000

<210> SEQ ID NO 873
<400> SEQUENCE: 873
000

<210> SEQ ID NO 874
<400> SEQUENCE: 874
000

<210> SEQ ID NO 875
<400> SEQUENCE: 875
000

<210> SEQ ID NO 876
<400> SEQUENCE: 876
000

<210> SEQ ID NO 877
<400> SEQUENCE: 877
000

<210> SEQ ID NO 878
<400> SEQUENCE: 878
000

<210> SEQ ID NO 879
<400> SEQUENCE: 879
000

<210> SEQ ID NO 880
<400> SEQUENCE: 880
000

<210> SEQ ID NO 881
<400> SEQUENCE: 881
000

<210> SEQ ID NO 882
<400> SEQUENCE: 882
000

<210> SEQ ID NO 883
<400> SEQUENCE: 883
```

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

```
<210> SEQ ID NO 906
<400> SEQUENCE: 906
000

<210> SEQ ID NO 907
<400> SEQUENCE: 907
000

<210> SEQ ID NO 908
<400> SEQUENCE: 908
000

<210> SEQ ID NO 909
<400> SEQUENCE: 909
000

<210> SEQ ID NO 910
<400> SEQUENCE: 910
000

<210> SEQ ID NO 911
<400> SEQUENCE: 911
000

<210> SEQ ID NO 912
<400> SEQUENCE: 912
000

<210> SEQ ID NO 913
<400> SEQUENCE: 913
000

<210> SEQ ID NO 914
<400> SEQUENCE: 914
000

<210> SEQ ID NO 915
<400> SEQUENCE: 915
000

<210> SEQ ID NO 916
<400> SEQUENCE: 916
000

<210> SEQ ID NO 917
```

<400> SEQUENCE: 917

000

<210> SEQ ID NO 918

<400> SEQUENCE: 918

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929
<400> SEQUENCE: 929
000

<210> SEQ ID NO 930
<400> SEQUENCE: 930
000

<210> SEQ ID NO 931
<400> SEQUENCE: 931
000

<210> SEQ ID NO 932
<400> SEQUENCE: 932
000

<210> SEQ ID NO 933
<400> SEQUENCE: 933
000

<210> SEQ ID NO 934
<400> SEQUENCE: 934
000

<210> SEQ ID NO 935
<400> SEQUENCE: 935
000

<210> SEQ ID NO 936
<400> SEQUENCE: 936
000

<210> SEQ ID NO 937
<400> SEQUENCE: 937
000

<210> SEQ ID NO 938
<400> SEQUENCE: 938
000

<210> SEQ ID NO 939
<400> SEQUENCE: 939
000

<210> SEQ ID NO 940
<400> SEQUENCE: 940
000

<210> SEQ ID NO 941
<400> SEQUENCE: 941
000

<210> SEQ ID NO 942
<400> SEQUENCE: 942
000

<210> SEQ ID NO 943
<400> SEQUENCE: 943
000

<210> SEQ ID NO 944
<400> SEQUENCE: 944
000

<210> SEQ ID NO 945
<400> SEQUENCE: 945
000

<210> SEQ ID NO 946
<400> SEQUENCE: 946
000

<210> SEQ ID NO 947
<400> SEQUENCE: 947
000

<210> SEQ ID NO 948
<400> SEQUENCE: 948
000

<210> SEQ ID NO 949
<400> SEQUENCE: 949
000

<210> SEQ ID NO 950
<400> SEQUENCE: 950
000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

```
<400> SEQUENCE: 996
000

<210> SEQ ID NO 997
<400> SEQUENCE: 997
000

<210> SEQ ID NO 998
<400> SEQUENCE: 998
000

<210> SEQ ID NO 999
<400> SEQUENCE: 999
000

<210> SEQ ID NO 1000
<400> SEQUENCE: 1000
000

<210> SEQ ID NO 1001
<400> SEQUENCE: 1001
000

<210> SEQ ID NO 1002
<400> SEQUENCE: 1002
000

<210> SEQ ID NO 1003
<400> SEQUENCE: 1003
000

<210> SEQ ID NO 1004
<400> SEQUENCE: 1004
000

<210> SEQ ID NO 1005
<400> SEQUENCE: 1005
000

<210> SEQ ID NO 1006
<400> SEQUENCE: 1006
000

<210> SEQ ID NO 1007
<400> SEQUENCE: 1007
```

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064
<400> SEQUENCE: 1064
000

<210> SEQ ID NO 1065
<400> SEQUENCE: 1065
000

<210> SEQ ID NO 1066
<400> SEQUENCE: 1066
000

<210> SEQ ID NO 1067
<400> SEQUENCE: 1067
000

<210> SEQ ID NO 1068
<400> SEQUENCE: 1068
000

<210> SEQ ID NO 1069
<400> SEQUENCE: 1069
000

<210> SEQ ID NO 1070
<400> SEQUENCE: 1070
000

<210> SEQ ID NO 1071
<400> SEQUENCE: 1071
000

<210> SEQ ID NO 1072
<400> SEQUENCE: 1072
000

<210> SEQ ID NO 1073
<400> SEQUENCE: 1073
000

<210> SEQ ID NO 1074
<400> SEQUENCE: 1074
000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101
<211> LENGTH: 330
<212> TYPE: PRT
<213> ORGANISM: Artificial sequence
<220> FEATURE:
<223> OTHER INFORMATION: Synthetic IgG1 HC constant region, L117A

<400> SEQUENCE: 1101

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1102
<211> LENGTH: 330
<212> TYPE: PRT
<213> ORGANISM: Artificial sequence
<220> FEATURE:
<223> OTHER INFORMATION: Synthetic IgG1 HC constant region, L118A

<400> SEQUENCE: 1102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1103
<211> LENGTH: 330
<212> TYPE: PRT
<213> ORGANISM: Artificial sequence
<220> FEATURE:
<223> OTHER INFORMATION: Synthetic IgG1 HC constant region, L117A &
      L118A

<400> SEQUENCE: 1103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330

<210> SEQ ID NO 1104
<211> LENGTH: 330
<212> TYPE: PRT
<213> ORGANISM: Artificial sequence
<220> FEATURE:
<223> OTHER INFORMATION: Synthetic IgG1 HC constant region, L117G &
      L118G

<400> SEQUENCE: 1104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Gly Gly Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 1105
<211> LENGTH: 330
<212> TYPE: PRT
<213> ORGANISM: Artificial sequence
<220> FEATURE:
<223> OTHER INFORMATION: Synthetic IgG1 HC constant region, L117V & L118V

<400> SEQUENCE: 1105

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Val Val Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1106
<211> LENGTH: 330
<212> TYPE: PRT
<213> ORGANISM: Artificial sequence
<220> FEATURE:

<223> OTHER INFORMATION: Synthetic IgG1 HC constant region, L117I & L118I

<400> SEQUENCE: 1106

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ile Ile Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111
<211> LENGTH: 330
<212> TYPE: PRT
<213> ORGANISM: Artificial sequence
<220> FEATURE:
<223> OTHER INFORMATION: Synthetic IgG1 HC constant region, HJ C->S, L117A

<400> SEQUENCE: 1111

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Cys Pro Pro Cys
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1112
<211> LENGTH: 330
<212> TYPE: PRT
<213> ORGANISM: Artificial sequence
<220> FEATURE:
<223> OTHER INFORMATION: Synthetic IgG1 HC constant region, HJ C->S,
      L118A

<400> SEQUENCE: 1112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Cys Pro Pro Cys
            100                 105                 110

Pro Ala Pro Glu Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1113
<211> LENGTH: 330
<212> TYPE: PRT
<213> ORGANISM: Artificial sequence
<220> FEATURE:
<223> OTHER INFORMATION: Synthetic IgG1 HC constant region, HJ C->S,
      L117A & L118A

<400> SEQUENCE: 1113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 1114
<211> LENGTH: 330
<212> TYPE: PRT
<213> ORGANISM: Artificial sequence
<220> FEATURE:
<223> OTHER INFORMATION: Synthetic IgG1 HC constant region, HJ C->S, L117G & L118G

<400> SEQUENCE: 1114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Cys Pro Pro Cys
            100                 105                 110

Pro Ala Pro Glu Gly Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1115
<211> LENGTH: 330

```
<212> TYPE: PRT
<213> ORGANISM: Artificial sequence
<220> FEATURE:
<223> OTHER INFORMATION: Synthetic IgG1 HC constant region, HJ C->S,
      L117V & L118V

<400> SEQUENCE: 1115
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | | 50 | | | | | 55 | | | | | 60 | | | |
| Leu | Ser | Ser | Val | Val | Thr | Val | Pro | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Pro | Lys | Ser | Ser | Asp | Lys | Thr | His | Thr | Cys | Pro | Pro | Cys |
| | | | 100 | | | | | 105 | | | | | 110 | | |
| Pro | Ala | Pro | Glu | Val | Val | Gly | Gly | Pro | Ser | Val | Phe | Leu | Phe | Pro | Pro |
| | | | 115 | | | | | 120 | | | | | 125 | | |
| Lys | Pro | Lys | Asp | Thr | Leu | Met | Ile | Ser | Arg | Thr | Pro | Glu | Val | Thr | Cys |
| | | | 130 | | | | 135 | | | | | 140 | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | | | 210 | | | | 215 | | | | | 220 | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | | 275 | | | | | 280 | | | | | 285 | | |
| Leu | Tyr | Ser | Lys | Leu | Thr | Val | Asp | Lys | Ser | Arg | Trp | Gln | Gln | Gly | Asn |
| | | | 290 | | | | 295 | | | | | 300 | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys |
| | | | | 325 | | | | | 330 |

```
<210> SEQ ID NO 1116
<211> LENGTH: 330
<212> TYPE: PRT
<213> ORGANISM: Artificial sequence
<220> FEATURE:
<223> OTHER INFORMATION: Synthetic IgG1 HC constant region, HJ C->S,
      L117I & L118I
```

```
<400> SEQUENCE: 1116

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Ser Asp Lys Thr His Thr Cys Pro Pro Cys
            100                 105                 110

Pro Ala Pro Glu Ile Ile Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1117

<400> SEQUENCE: 1117

000

<210> SEQ ID NO 1118

<400> SEQUENCE: 1118

000
```

<210> SEQ ID NO 1119

<400> SEQUENCE: 1119

000

<210> SEQ ID NO 1120

<400> SEQUENCE: 1120

000

<210> SEQ ID NO 1121
<211> LENGTH: 330
<212> TYPE: PRT
<213> ORGANISM: Artificial sequence
<220> FEATURE:
<223> OTHER INFORMATION: Synthetic IgG1 HC constant region, HJ C->V, L117A

<400> SEQUENCE: 1121

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Cys Pro Pro Cys
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1122
<211> LENGTH: 330
<212> TYPE: PRT
<213> ORGANISM: Artificial sequence
<220> FEATURE:
<223> OTHER INFORMATION: Synthetic IgG1 HC constant region, HJ C->V,
      L118A

<400> SEQUENCE: 1122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Cys Pro Pro Cys
            100                 105                 110

Pro Ala Pro Glu Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
305                 310                 315                 320
Gln Lys Ser Leu Ser Leu Ser Pro Gly Lys
                325                 330

<210> SEQ ID NO 1123
<211> LENGTH: 330
<212> TYPE: PRT
<213> ORGANISM: Artificial sequence
<220> FEATURE:
<223> OTHER INFORMATION: Synthetic IgG1 HC constant region, HJ C->V,
      L117A & L118A

<400> SEQUENCE: 1123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1124
<211> LENGTH: 330
<212> TYPE: PRT
<213> ORGANISM: Artificial sequence
<220> FEATURE:
<223> OTHER INFORMATION: Synthetic IgG1 HC constant region, HJ C->V, L117G & L118G

<400> SEQUENCE: 1124

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Val Asp Lys Thr His Thr Cys Pro Pro Cys
            100                 105                 110

Pro Ala Pro Glu Gly Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1125
<211> LENGTH: 330
<212> TYPE: PRT
<213> ORGANISM: Artificial sequence

```
<220> FEATURE:
<223> OTHER INFORMATION: Synthetic IgG1 HC constant region, HJ C->V,
      L117V & L118V

<400> SEQUENCE: 1125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Cys Pro Pro Cys
            100                 105                 110

Pro Ala Pro Glu Val Val Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1126
<211> LENGTH: 330
<212> TYPE: PRT
<213> ORGANISM: Artificial sequence
<220> FEATURE:
<223> OTHER INFORMATION: Synthetic IgG1 HC constant region, HJ C->V,
      L117I & L118I

<400> SEQUENCE: 1126
```

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Cys Pro Pro Cys
            100                 105                 110

Pro Ala Pro Glu Ile Ile Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1127

<400> SEQUENCE: 1127

000

<210> SEQ ID NO 1128

<400> SEQUENCE: 1128

000

<210> SEQ ID NO 1129

<400> SEQUENCE: 1129

000

<210> SEQ ID NO 1130

<400> SEQUENCE: 1130

000

<210> SEQ ID NO 1131
<211> LENGTH: 330
<212> TYPE: PRT
<213> ORGANISM: Artificial sequence
<220> FEATURE:
<223> OTHER INFORMATION: Synthetic IgG1 HC constant region, BJ C->S, L117A

<400> SEQUENCE: 1131

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1132
<211> LENGTH: 330
<212> TYPE: PRT
<213> ORGANISM: Artificial sequence
<220> FEATURE:
<223> OTHER INFORMATION: Synthetic IgG1 HC constant region, BJ C->S,
      L118A

<400> SEQUENCE: 1132

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
                100                 105                 110

Pro Ala Pro Glu Leu Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 1133
<211> LENGTH: 330
<212> TYPE: PRT
<213> ORGANISM: Artificial sequence
<220> FEATURE:
<223> OTHER INFORMATION: Synthetic IgG1 HC constant region, BJ C->S,
      L117A & L118A

<400> SEQUENCE: 1133

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1134

```
<211> LENGTH: 330
<212> TYPE: PRT
<213> ORGANISM: Artificial sequence
<220> FEATURE:
<223> OTHER INFORMATION: Synthetic IgG1 HC constant region, BJ C->S,
      L117G & L118G

<400> SEQUENCE: 1134
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Pro | Lys | Ser | Cys | Asp | Lys | Thr | His | Thr | Ser | Pro | Pro | Ser |
| | | | 100 | | | | | 105 | | | | | 110 | | |
| Pro | Ala | Pro | Glu | Gly | Gly | Gly | Pro | Ser | Val | Phe | Leu | Phe | Pro | Pro | |
| | | | 115 | | | | | 120 | | | | | 125 | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | | 275 | | | | | 280 | | | | | 285 | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

```
<210> SEQ ID NO 1135
<211> LENGTH: 330
<212> TYPE: PRT
<213> ORGANISM: Artificial sequence
<220> FEATURE:
<223> OTHER INFORMATION: Synthetic IgG1 HC constant region, BJ C->S,
```

L117V & L118V

<400> SEQUENCE: 1135

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Val Val Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1136
<211> LENGTH: 330
<212> TYPE: PRT
<213> ORGANISM: Artificial sequence
<220> FEATURE:
<223> OTHER INFORMATION: Synthetic IgG1 HC constant region, BJ C->S, L117I & L118I

<400> SEQUENCE: 1136

Ala Ser Thr Lys Gly Pro Ser Val Phe Pro Leu Ala Pro Ser Ser Lys

```
              1               5                  10                 15
            Ser Thr Ser Gly Gly Thr Ala Ala Leu Gly Cys Leu Val Lys Asp Tyr
                            20                  25                 30

Phe Pro Glu Pro Val Thr Val Ser Trp Asn Ser Gly Ala Leu Thr Ser
                            35                  40                 45

Gly Val His Thr Phe Pro Ala Val Leu Gln Ser Ser Gly Leu Tyr Ser
                            50                  55                 60

Leu Ser Ser Val Val Thr Val Pro Ser Ser Leu Gly Thr Gln Thr
             65                 70                  75                 80

Tyr Ile Cys Asn Val Asn His Lys Pro Ser Asn Thr Lys Val Asp Lys
                            85                  90                 95

Arg Val Glu Pro Lys Ser Cys Asp Lys Thr His Thr Ser Pro Pro Ser
                            100                 105                110

Pro Ala Pro Glu Ile Ile Gly Gly Pro Ser Val Phe Leu Phe Pro Pro
                            115                 120                125

Lys Pro Lys Asp Thr Leu Met Ile Ser Arg Thr Pro Glu Val Thr Cys
             130                135                 140

Val Val Val Asp Val Ser His Glu Asp Pro Glu Val Lys Phe Asn Trp
             145                150                 155                160

Tyr Val Asp Gly Val Glu Val His Asn Ala Lys Thr Lys Pro Arg Glu
                            165                 170                175

Glu Gln Tyr Asn Ser Thr Tyr Arg Val Val Ser Val Leu Thr Val Leu
                            180                 185                190

His Gln Asp Trp Leu Asn Gly Lys Glu Tyr Lys Cys Lys Val Ser Asn
                            195                 200                205

Lys Ala Leu Pro Ala Pro Ile Glu Lys Thr Ile Ser Lys Ala Lys Gly
                            210                 215                220

Gln Pro Arg Glu Pro Gln Val Tyr Thr Leu Pro Pro Ser Arg Glu Glu
             225                230                 235                240

Met Thr Lys Asn Gln Val Ser Leu Thr Cys Leu Val Lys Gly Phe Tyr
                            245                 250                255

Pro Ser Asp Ile Ala Val Glu Trp Glu Ser Asn Gly Gln Pro Glu Asn
                            260                 265                270

Asn Tyr Lys Thr Thr Pro Pro Val Leu Asp Ser Asp Gly Ser Phe Phe
                            275                 280                285

Leu Tyr Ser Lys Leu Thr Val Asp Lys Ser Arg Trp Gln Gln Gly Asn
                            290                 295                300

Val Phe Ser Cys Ser Val Met His Glu Ala Leu His Asn His Tyr Thr
             305                310                 315                320

Gln Lys Ser Leu Ser Leu Ser Pro Gly Lys
                            325                 330

<210> SEQ ID NO 1137

<400> SEQUENCE: 1137

000

<210> SEQ ID NO 1138

<400> SEQUENCE: 1138

000

<210> SEQ ID NO 1139
```

<400> SEQUENCE: 1139

000

<210> SEQ ID NO 1140

<400> SEQUENCE: 1140

000

<210> SEQ ID NO 1141
<211> LENGTH: 330
<212> TYPE: PRT
<213> ORGANISM: Artificial sequence
<220> FEATURE:
<223> OTHER INFORMATION: Synthetic IgG1 HC constant region, BJ C->V, L117A

<400> SEQUENCE: 1141

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1142
<211> LENGTH: 330
<212> TYPE: PRT
<213> ORGANISM: Artificial sequence
<220> FEATURE:
<223> OTHER INFORMATION: Synthetic IgG1 HC constant region, BJ C->V,
      L118A

<400> SEQUENCE: 1142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1143
<211> LENGTH: 330
<212> TYPE: PRT
<213> ORGANISM: Artificial sequence
<220> FEATURE:
<223> OTHER INFORMATION: Synthetic IgG1 HC constant region, BJ C->V, L117A & L118A

<400> SEQUENCE: 1143

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1144
<211> LENGTH: 330
<212> TYPE: PRT

<213> ORGANISM: Artificial sequence
<220> FEATURE:
<223> OTHER INFORMATION: Synthetic IgG1 HC constant region, BJ C->V, L117G & L118G

<400> SEQUENCE: 1144

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Gly Gly Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1145
<211> LENGTH: 330
<212> TYPE: PRT
<213> ORGANISM: Artificial sequence
<220> FEATURE:
<223> OTHER INFORMATION: Synthetic IgG1 HC constant region, BJ C->V, L117V & L118V

<400> SEQUENCE: 1145

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Val Val Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1146
<211> LENGTH: 330
<212> TYPE: PRT
<213> ORGANISM: Artificial sequence
<220> FEATURE:
<223> OTHER INFORMATION: Synthetic IgG1 HC constant region, BJ C->V, L117I & L118I

<400> SEQUENCE: 1146

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Val Pro Pro Val
            100                 105                 110

Pro Ala Pro Glu Ile Ile Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149
```

000

<210> SEQ ID NO 1150

<400> SEQUENCE: 1150

000

<210> SEQ ID NO 1151
<211> LENGTH: 330
<212> TYPE: PRT
<213> ORGANISM: Artificial sequence
<220> FEATURE:
<223> OTHER INFORMATION: Synthetic IgG1 HC constant region, DJ C->S, L117A

<400> SEQUENCE: 1151

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Ser Pro Pro Ser
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
                325                 330

<210> SEQ ID NO 1152
<211> LENGTH: 330
<212> TYPE: PRT
<213> ORGANISM: Artificial sequence
<220> FEATURE:
<223> OTHER INFORMATION: Synthetic IgG1 HC constant region, DJ C->S,
      L118A

<400> SEQUENCE: 1152

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Ser Pro Pro Ser
            100                 105                 110

Pro Ala Pro Glu Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 1153
<211> LENGTH: 330
<212> TYPE: PRT
<213> ORGANISM: Artificial sequence
<220> FEATURE:
<223> OTHER INFORMATION: Synthetic IgG1 HC constant region, DJ C->S,
      L117A & L118A

<400> SEQUENCE: 1153
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Lys |
| 1 | | | | 5 | | | | | 10 | | | | | 15 |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Pro | Lys | Ser | Ser | Asp | Lys | Thr | His | Thr | Ser | Pro | Pro | Ser |
| | | | 100 | | | | | 105 | | | | | 110 | | |
| Pro | Ala | Pro | Glu | Ala | Ala | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys |
| | | | | 325 | | | | | 330 |

```
<210> SEQ ID NO 1154
<211> LENGTH: 330
<212> TYPE: PRT
<213> ORGANISM: Artificial sequence
<220> FEATURE:
```

<223> OTHER INFORMATION: Synthetic IgG1 HC constant region, DJ C->S, L117G & L118G

<400> SEQUENCE: 1154

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Ser Asp Lys Thr His Thr Ser Pro Pro Ser
            100                 105                 110
Pro Ala Pro Glu Gly Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 1155
<211> LENGTH: 330
<212> TYPE: PRT
<213> ORGANISM: Artificial sequence
<220> FEATURE:
<223> OTHER INFORMATION: Synthetic IgG1 HC constant region, DJ C->S, L117V & L118V

<400> SEQUENCE: 1155

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Ser Pro Pro Ser
            100                 105                 110

Pro Ala Pro Glu Val Val Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1156
<211> LENGTH: 330
<212> TYPE: PRT
<213> ORGANISM: Artificial sequence
<220> FEATURE:
<223> OTHER INFORMATION: Synthetic IgG1 HC constant region, DJ C->S,
      L117I & L118I

<400> SEQUENCE: 1156

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Ser Asp Lys Thr His Thr Ser Pro Pro Ser
             100                 105                 110

Pro Ala Pro Glu Ile Ile Gly Gly Pro Ser Val Phe Leu Phe Pro Pro
             115                 120                 125

Lys Pro Lys Asp Thr Leu Met Ile Ser Arg Thr Pro Glu Val Thr Cys
 130                 135                 140

Val Val Val Asp Val Ser His Glu Asp Pro Glu Val Lys Phe Asn Trp
 145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
             195                 200                 205

Lys Ala Leu Pro Ala Pro Ile Glu Lys Thr Ile Ser Lys Ala Lys Gly
 210                 215                 220

Gln Pro Arg Glu Pro Gln Val Tyr Thr Leu Pro Pro Ser Arg Glu Glu
 225                 230                 235                 240

Met Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
 290                 295                 300

Val Phe Ser Cys Ser Val Met His Glu Ala Leu His Asn His Tyr Thr
 305                 310                 315                 320

Gln Lys Ser Leu Ser Leu Ser Pro Gly Lys
                 325                 330

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000
```

<210> SEQ ID NO 1160

<400> SEQUENCE: 1160

000

<210> SEQ ID NO 1161
<211> LENGTH: 330
<212> TYPE: PRT
<213> ORGANISM: Artificial sequence
<220> FEATURE:
<223> OTHER INFORMATION: Synthetic IgG1 HC constant region, DJ C->V, L117A

<400> SEQUENCE: 1161

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1162
<211> LENGTH: 330
<212> TYPE: PRT
<213> ORGANISM: Artificial sequence
<220> FEATURE:
<223> OTHER INFORMATION: Synthetic IgG1 HC constant region, DJ C->V, L118A

<400> SEQUENCE: 1162

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1163
<211> LENGTH: 330

<212> TYPE: PRT
<213> ORGANISM: Artificial sequence
<220> FEATURE:
<223> OTHER INFORMATION: Synthetic IgG1 HC constant region, DJ C->V,
      L117A & L118A

<400> SEQUENCE: 1163

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1164
<211> LENGTH: 330
<212> TYPE: PRT
<213> ORGANISM: Artificial sequence
<220> FEATURE:
<223> OTHER INFORMATION: Synthetic IgG1 HC constant region, DJ C->V,
      L117G & L118G

<400> SEQUENCE: 1164

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Gly Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 1165
<211> LENGTH: 330
<212> TYPE: PRT
<213> ORGANISM: Artificial sequence
<220> FEATURE:
<223> OTHER INFORMATION: Synthetic IgG1 HC constant region, DJ C->V, L117V & L118V

<400> SEQUENCE: 1165

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Val Val Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 1166
<211> LENGTH: 330
<212> TYPE: PRT
<213> ORGANISM: Artificial sequence
<220> FEATURE:
<223> OTHER INFORMATION: Synthetic IgG1 HC constant region, DJ C->V,
      L117I & L118I
```

<400> SEQUENCE: 1166

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Val Asp Lys Thr His Thr Val Pro Pro Val
            100                 105                 110

Pro Ala Pro Glu Ile Ile Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

SITE-SPECIFIC ANTIBODY-DRUG CONJUGATES

CROSS-REFERENCE TO RELATED APPLICATIONS

This application is a continuation of U.S. patent application Ser. No. 15/556,550, filed Oct. 13, 2017, now abandoned, which is a 35 U.S.C. § 371 National Stage Entry of International Application No. PCT/EP2016/058379 having an international filing date of Apr. 15, 2016, which claims the benefit of Great Britain Patent Application No. 1506402.5, filed Apr. 15, 2015, the contents of which are incorporated by reference herein in their entireties.

The present disclosure relates to site-specific antibody-drug conjugates. Conjugates comprising pyrrolobenzodiazepines (PBDs) having a labile protecting group in the form of a linker to the antibody which binds CD22 are described.

Incorporation-by-Reference of Material Submitted Electronically

Incorporated by reference in its entirety herein is a computer-readable nucleotide/amino acid sequence listing submitted concurrently herewith and identified as follows: One 232,578 Byte ASCII (Text) file named "2020-05-22_35707-302_SQL_ST25.TXT," created on May 22, 2020.

BACKGROUND

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein (Junutula, et al., 2008b Nature Biotech., 26(8):925-932; Dornan et al (2009) Blood 114(13):2721-2729; U.S. Pat. Nos. 7,521,541; 7,723,485; WO2009/052249; McDonagh (2006) Protein Eng. Design & Sel. 19(7): 299-307; Doronina et al (2006) Bioconj. Chem. 17:114-124; Erickson et al (2006) Cancer Res. 66(8):1-8; Sanderson et al (2005) Clin. Cancer Res. 11:843-852; Jeffrey et al (2005) J. Med. Chem. 48:1344-1358; Hamblett et al (2004) Clin. Cancer Res. 10:7063-7070).

The present inventors have developed particular antibody-drug conjugates in which the antibody moiety is modified so as to increase the safety and efficacy of the ADC.

Site-Specific Conjugation

In ADCs cytotoxic drugs have typically been conjugated to the antibodies in a non-site-specific manner via lysine side chains or by reducing interchain disulfide bonds present in the antibodies to provide activated native cysteine sulfhydryl groups.

Site-specific conjugation of drug to antibody has also been considered with a view to provide ADC populations with high homogeneity and batch-to-batch consistency with respect to drug-to-antibody ratio (DAR) and attachment site. Site-specific attachment has typically been achieved by substituting a native amino acid in the antibody with an amino acid such as cysteine, to which a drug moiety can be conjugated (see Stimmel et al., JBC, Vol. 275, No. 39, Issue of September 29, pp. 30445-30450—conjugation of an IgG S442C variant with bromoacetyl-TMT); also Junutula et al., Nature Biotechnology, vol. 26, no.8, pp. 925-932). Jujuntula et al. report that site-specific ADCs in which drug moieties were attached to specific cysteine residues engineered into the antibody sequence exhibited comparable efficacy and reduced systemic toxicity compared to non-specifically conjugated ADCs.

Other studies have investigated the biological characteristics of ADCs comprising cytotoxic drug moieties conjugated to antibodies at specific sites. For example, WO2013/093809 discusses a number of engineered antibody constant regions, a sub-set of which are exemplified as part of conjugates to cytotoxic drugs such as monomethyl auristatin D (MMAD). WO2011/005481 describes engineered antibody Fc regions for site-specific conjugation, including exemplification of biotin-PEG2-maleimide to a number of the engineered antibodies. WO2006-065533 describes antibody Fc regions in which one or more of the 'native' interchain-disulphide-forming cysteines present in the heavy and/or light chain is substituted with another amino acid, so as to leave the complementary cysteine sulphydryl available for conjugation to a drug moiety.

Strop et al., Chemistry & Biology 20, 161-167, Feb. 21, 2013 assessed the stability and pharmacokinetics of a number of site-specific ADCs which differed from each other only in the location of the site used to conjugate the drug to the antibody. The authors report that for the tested ADCs the conjugation site influences the ADC stability and pharmacokinetics in a species-dependent manner.

The present inventors have developed particular antibody-drug conjugates in which the drug moiety is conjugated in a site-specific manner.

BRIEF DESCRIPTION OF FIGURES

FIG. 1

Comparative systemic toxicity of site-specific ADCs, as described in Example 7.

SUMMARY

The present inventors have found that antibody-drug conjugates where the Drug unit ($D^L$) is conjugated to particular interchain cysteine residues have unexpected and advantageous properties. In particular, these newly developed ADCs have advantageous manufacturing and pharmacological properties which are described herein.

Accordingly, in a first aspect—in order to increase the efficacy and efficiency of conjugation of Drug unit ($D^L$) to the desired interchain cysteine residue(s)—the antibody of the conjugates described herein comprises one or more substitution of an interchain cysteine residue by an amino acid that is not cysteine.

The antibody of the conjugates described herein retains at least one unsubstituted interchain cysteine residue for conjugation of the drug moiety to the antibody. The number of retained interchain cysteine residues in the antibody is greater than zero but less than the total number of interchain cysteine residues in the parent (native) antibody. Thus, in some embodiments, the antibody has at least one, at least two, at least three, at least four, at least five, at least six or at least seven interchain cysteine residues. In typical embodiments, the antibody has an even integral number of interchain cysteine residues (e.g., at least two, four, six or eight). In some embodiments, the antibody has less than eight interchain cysteine residues.

AbLJ

In some embodiments the antibody of the conjugates described herein: (i) retain the unsubstituted hinge region interchain cysteines, (ii) comprise light chains each having an amino acid substitution of the interchain cysteine residue located in the $C_L$ domain, and (iii) comprise heavy chains each retaining the unsubstituted interchain cysteine located in the $CH_1$ domain. For example, In some embodiments the antibody of the conjugates described herein: (i) retains unsubstituted HC226 and HC229 according to the EU index as set forth in Kabat, (ii) comprise light chains each having an amino acid substitution of the interchain cysteine residue κLC214 or λLC213 according to the EU index as set forth in Kabat, and (iii) comprise heavy chains each retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 103 of SEQ ID NO.110.

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 14 of SEQ ID NO.120.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 14 of SEQ ID NO.130.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 14 of SEQ ID NO.140.

AbHJ

In some embodiments the antibody of the conjugates described herein: (i) retain the unsubstituted hinge region interchain cysteines, (ii) comprise light chains each retaining the unsubstituted interchain cysteine located in the $C_L$ domain, and (iii) comprise heavy chains each having an amino acid substitution of the interchain cysteine residue located in the $CH_1$ domain. For example, In some embodiments the antibody of the conjugates described herein: (i) retains unsubstituted HC226 and HC229 according to the EU index as set forth in Kabat, (ii) comprise light chains each retaining the unsubstituted interchain cysteine κLC214 or λLC213 according to the EU index as set forth in Kabat, and (iii) comprise heavy chains each having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein the cysteine at position 103 in SEQ ID NO: 110 is substituted by an amino acid that is not cysteine. Preferably the drug moiety is conjugated to the cysteine at position 105 of SEQ ID NO.150, the cysteine at position 102 of SEQ ID NO.160.

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;
  wherein each of the cysteines at positions 14 and 103 in SEQ ID NO: 120 is substituted by an amino acid that is not cysteine. Preferably the drug moiety is conjugated to the cysteine at position 105 of SEQ ID NO.150, the cysteine at position 102 of SEQ ID NO.160.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
  wherein the cysteine at position 14 in SEQ ID NO: 130 is substituted by an amino acid that is not cysteine. Preferably the drug moiety is conjugated to the cysteine at position 105 of SEQ ID NO.150, the cysteine at position 102 of SEQ ID NO.160.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
  wherein the cysteine at position 14 in SEQ ID NO: 140 is substituted by an amino acid that is not cysteine. Preferably the drug moiety is conjugated to the cysteine at position 105 of SEQ ID NO.150, the cysteine at position 102 of SEQ ID NO.160.

AbBJ

In some embodiments the antibody of the conjugates described herein: (i) has an amino acid substitution of each of the hinge region interchain cysteines, (ii) comprise light chains each having an amino acid substitution of the interchain cysteine residue located in the $C_L$ domain, and (iii) comprise heavy chains each retaining the unsubstituted interchain cysteine located in the $CH_1$ domain. For example, in some embodiments the antibody of the conjugates described herein: (i) has an amino acid substitution of each of HC226 and HC229 according to the EU index as set forth in Kabat, (ii) comprise light chains each having an amino acid substitution of the interchain cysteine residue κLC214 or λLC213 according to the EU index as set forth in Kabat, and (iii) comprise heavy chains each retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
wherein each of the cysteines at positions 109 and 112 in SEQ ID NO: 110 is substituted by an amino acid that is not cysteine;
and wherein the cysteine at position 105 in SEQ ID NO: 150 or the cysteine at position 102 in SEQ ID NO: 160, is substituted by an amino acid that is not cysteine.
Preferably the drug moiety is conjugated to the cysteine at position 103 of SEQ ID NO.110.

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;
wherein each of the cysteines at positions 103, 106, and 109 in SEQ ID NO: 120 is substituted by an amino acid that is not cysteine;
and wherein the cysteine at position 105 in SEQ ID NO: 150 or the cysteine at position 102 in SEQ ID NO: 160, is substituted by an amino acid that is not cysteine. In some embodiments, the cysteine at position 102 in SEQ ID NO: 120 is also substituted by an amino acid that is not cysteine. Preferably the drug moiety is conjugated to the cysteine at position 14 of SEQ ID NO.120.

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;
wherein each of the cysteines at positions 14, 106, and 109 in SEQ ID NO: 120 is substituted by an amino acid that is not cysteine;
and wherein the cysteine at position 105 in SEQ ID NO: 150 or the cysteine at position 102 in SEQ ID NO: 160, is substituted by an amino acid that is not cysteine. In some embodiments, the cysteine at position 102 in SEQ ID NO: 120 is also substituted by an amino acid that is not cysteine. Preferably the drug moiety is conjugated to the cysteine at position 103 of SEQ ID NO.120.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
wherein each of the cysteines at positions 111, 114, 120, 126, 129, 135, 141, 144, 150, 156, and 159 in SEQ ID NO: 130 is substituted by an amino acid that is not cysteine;
and wherein the cysteine at position 105 in SEQ ID NO: 150 or the cysteine at position 102 in SEQ ID NO: 160, is substituted by an amino acid that is not cysteine.
Preferably the drug moiety is conjugated to the cysteine at position 14 of SEQ ID NO.130.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
wherein each of the cysteines at positions 106 and 109 in SEQ ID NO: 140 is substituted by an amino acid that is not cysteine;
and wherein the cysteine at position 105 in SEQ ID NO: 150 or the cysteine at position 102 in SEQ ID NO: 160, is substituted by an amino acid that is not cysteine.
Preferably the drug moiety is conjugated to the cysteine at position 14 of SEQ ID NO.140.

AbDJ

In some embodiments the antibody of the conjugates described herein: (i) has an amino acid substitution of each of the hinge region interchain cysteines, (ii) comprises light chains each retaining the unsubstituted interchain cysteine located in the $C_L$ domain, and (iii) comprises heavy chains each having an amino acid substitution of the interchain cysteine residue located in the $CH_1$ domain. For example, in some embodiments the antibody of the conjugates described herein: (i) has an amino acid substitution of each of HC226 and HC229 according to the EU index as set forth in Kabat, (ii) comprises light chains each retaining the unsubstituted interchain cysteine κLC214 or λLC213 according to the EU index as set forth in Kabat, and (iii) comprises heavy chains each having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

In some embodiments, some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
wherein each of the cysteines at positions 103, 109 and 112 in SEQ ID NO: 110 is substituted by an amino acid that is not cysteine. Preferably the drug moiety is conjugated to the cysteine at position 105 of SEQ ID NO.150, the cysteine at position 102 of SEQ ID NO.160.

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;
wherein each of the cysteines at positions 14, 103, 106 and 109 in SEQ ID NO: 120 is substituted by an amino acid that is not cysteine. Preferably the drug moiety is conjugated to the cysteine at position 105 of SEQ ID NO.150, the cysteine at position 102 of SEQ ID NO.160.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
wherein each of the cysteines at positions 14, 111, 114, 120, 126, 129, 135, 141, 144, 150, 156, and 159 in SEQ ID NO: 130 is substituted by an amino acid that is not cysteine. Preferably the drug moiety is conjugated to the cysteine at position 105 of SEQ ID NO.150, the cysteine at position 102 of SEQ ID NO.160.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein each of the cysteines at positions 14, 106, and 109 in SEQ ID NO: 140 is substituted by an amino acid that is not cysteine. Preferably the drug moiety is conjugated to the cysteine at position 105 of SEQ ID NO.150, the cysteine at position 102 of SEQ ID NO.160.

The present inventors have further found that antibody-drug conjugates wherein the antibody comprises specific mutations, or combinations of mutations, in the heavy chain have unexpected and advantageous properties. In particular, the present inventors have identified antibody mutations in the heavy chain which reduce the toxicity and increase the serum half-lives of the ADCs they are incorporated into, as compared to otherwise identical ADCs comprising antibodies which lack the specific mutations.

For example, in the IgG1 isotype the present inventors have identified the Leucine residues at positions 234 and 235 in the EU index set forth in Kabat (residues L117 and L118 in SEQ ID NO.110) as residues which, when substituted by an amino acid that is not leucine, allow for ADCs with advantageous properties.

Accordingly, in a second aspect the antibody of the conjugates described herein comprises a heavy chain having a substitution of the residue at position 234 in the EU index set forth in Kabat and/or a substitution of the residue at position 235 in the EU index set forth in Kabat by any other amino acid (that is, an amino acid that is not identical to that found in the 'wild-type' sequence). Preferably both the residues at position 234 and 235 in the EU index set forth in Kabat are substituted by any other amino acid.

In some embodiments the antibody is an IgG1 isotype and the leucine at position 234 in the EU index set forth in Kabat and/or the leucine at position 235 in the EU index set forth in Kabat is substituted by an amino acid that is not leucine. Preferably both the leucines at position 234 and 235 in the EU index set forth in Kabat are substituted by an amino acid that is not leucine, such as alanine. One or both Leucines may be also substituted by other amino acids which are not Leucine, such as Glycine, Valine, or Isoleucine.

For example, in some embodiments the antibody of the conjugates described herein comprises a heavy chain comprising the amino acid sequence of SEQ ID NO.110, wherein the leucine at position 117 and/or the leucine at position 118 is substituted by an amino acid that is not leucine, such as alanine. Preferably both the leucines at position 117 and 118 are substituted by an amino acid that is not leucine, such as alanine. One or both Leucines may be also substituted by other amino acids which are not Leucine, such as Glycine, Valine, or Isoleucine.

In some embodiments the antibody is an IgG3 isotype and the leucine at position 234 in the EU index set forth in Kabat and/or the leucine at position 235 in the EU index set forth in Kabat is substituted by an amino acid that is not leucine. Preferably both the leucines at position 234 and 235 in the EU index set forth in Kabat are substituted by an amino acid that is not leucine, such as alanine. One or both Leucines may be also substituted by other amino acids which are not Leucine, such as Glycine, Valine, or Isoleucine.

For example, in some embodiments the antibody of the conjugates described herein comprises a heavy chain comprising the amino acid sequence of SEQ ID NO.130, wherein the leucine at position 164 and/or the leucine at position 165 is substituted by an amino acid that is not leucine, such as alanine. Preferably both the leucines at position 164 and 165 are substituted by an amino acid that is not leucine, such as alanine. One or both Leucines may be also substituted by other amino acids which are not Leucine, such as Glycine, Valine, or Isoleucine.

In some embodiments the antibody is an IgG4 isotype and the leucine at position 235 in the EU index set forth in Kabat is substituted by an amino acid that is not leucine, such as alanine. The Leucine may be also substituted by other amino acids which are not Leucine, such as Glycine, Valine, or Isoleucine.

For example, in some embodiments the antibody of the conjugates described herein comprises a heavy chain comprising the amino acid sequence of SEQ ID NO.140, wherein the leucine at position 115 is substituted by an amino acid that is not leucine, such as alanine. The Leucine may be also substituted by other amino acids which are not Leucine, such as Glycine, Valine, or Isoleucine.

The modifications described in the first aspect can be advantageously combined in the same antibody with the modifications described in the second aspect.

Accordingly, in a third aspect the antibody of the conjugates described herein:
(1) comprises one or more substitution of an interchain cysteine residue by an amino acid that is not cysteine and retains at least one unsubstituted interchain cysteine residue for conjugation of the drug moiety to the antibody; and
(2) comprises a heavy chain having a substitution of the residue at position 234 in the EU index set forth in Kabat and/or a substitution of the residue at position 235 in the EU index set forth in Kabat by any other amino acid (that is, an amino acid that is not identical to that found in the 'wild-type' sequence).

AbLJ(LALA)

In some embodiments the antibody of the conjugates described herein: (i) retain the unsubstituted hinge region interchain cysteines, (ii) comprise light chains each having an amino acid substitution of the interchain cysteine residue located in the $C_L$ domain, (iii) comprise heavy chains each retaining the unsubstituted interchain cysteine located in the $CH_1$ domain, and (iv) comprise heavy chains each having an amino acid substitution of the the residue at position 234 in the EU index set forth in Kabat and/or a substitution of the residue at position 235 in the EU index set forth in Kabat.

For example, In some embodiments the antibody of the conjugates described herein: (i) retains unsubstituted HC226 and HC229 according to the EU index as set forth in Kabat, (ii) comprise light chains each having an amino acid substitution of the interchain cysteine residue κLC214 or λLC213 according to the EU index as set forth in Kabat, (iii) comprise heavy chains each retaining the unsubstituted interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $CH_1$ domain, for example to HC220 according to the EU index as set forth in Kabat.

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;

wherein the cysteine at position 105 in SEQ ID NO: 150 or the cysteine at position 102 in SEQ ID NO: 160, is substituted by an amino acid that is not cysteine;
and wherein the leucine at position 117 in SEQ ID NO: 110 and/or the leucine at position 118 in SEQ ID NO: 110 is substituted by an amino acid that is not leucine, such as alanine. Preferably the drug moiety is conjugated to the cysteine at position 103 of SEQ ID NO.110. Preferably both the leucines at position 117 and 118 in SEQ ID NO: 110 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
wherein the cysteine at position 105 in SEQ ID NO: 150 or the cysteine at position 102 in SEQ ID NO: 160, is substituted by an amino acid that is not cysteine;
and wherein the leucine at position 164 in SEQ ID NO: 130 and/or the leucine at position 165 in SEQ ID NO: 130 is substituted by an amino acid that is not leucine, such as alanine. Preferably the drug moiety is conjugated to the cysteine at position 14 of SEQ ID NO.130. Preferably both the leucines at position 164 and 165 in SEQ ID NO: 130 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
wherein the cysteine at position 105 in SEQ ID NO: 150 or the cysteine at position 102 in SEQ ID NO: 160, is substituted by an amino acid that is not cysteine;
and wherein the leucine at position 115 in SEQ ID NO: 140 is substituted by an amino acid that is not leucine, such as alanine. Preferably the drug moiety is conjugated to the cysteine at position 14 of SEQ ID NO.140. The Leucine may be also substituted by other amino acids which are not Leucine, such as Glycine, Valine, or Isoleucine.

AbHJ(LALA)

In some embodiments the antibody of the conjugates described herein: (i) retain the unsubstituted hinge region interchain cysteines, (ii) comprise light chains each retaining the unsubstituted interchain cysteine located in the $C_L$ domain, (iii) comprise heavy chains each having an amino acid substitution of the interchain cysteine residue located in the $CH_1$ domain, and (iv) comprise heavy chains each having an amino acid substitution of the residue at position 234 in the EU index set forth in Kabat and/or a substitution of the residue at position 235 in the EU index set forth in Kabat.

For example, In some embodiments the antibody of the conjugates described herein: (i) retains unsubstituted HC226 and HC229 according to the EU index as set forth in Kabat, (ii) comprise light chains each retaining the unsubstituted interchain cysteine κLC214 or λLC213 according to the EU index as set forth in Kabat, (iii) comprise heavy chains each having an amino acid substitution of interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $C_L$ domain, for example to κLC214 or λLC213 according to the EU index as set forth in Kabat.

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
wherein the cysteine at position 103 in SEQ ID NO: 110 is substituted by an amino acid that is not cysteine;
and wherein the leucine at position 117 in SEQ ID NO: 110 and/or the leucine at position 118 in SEQ ID NO: 110 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 117 and 118 in SEQ ID NO: 110 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
wherein the cysteine at position 14 in SEQ ID NO: 130 is substituted by an amino acid that is not cysteine;
and wherein the leucine at position 164 in SEQ ID NO: 130 and/or the leucine at position 165 in SEQ ID NO: 130 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 164 and 165 in SEQ ID NO: 130 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
wherein the cysteine at position 14 in SEQ ID NO: 140 is substituted by an amino acid that is not cysteine;
and wherein the leucine at position 115 in SEQ ID NO: 140 is substituted by an amino acid that is not leucine, such as alanine. Preferably the drug moiety is conjugated to the cysteine at position 105 of SEQ ID NO.150, the cysteine at position 102 of SEQ ID NO.160. The Leucine may be also substituted by other amino acids which are not Leucine, such as Glycine, Valine, or Isoleucine.

AbBJ(LALA)

In some embodiments the antibody of the conjugates described herein: (i) has an amino acid substitution of each of the hinge region interchain cysteines, (ii) comprise light chains each having an amino acid substitution of the interchain cysteine residue located in the $C_L$ domain, (iii) comprise heavy chains each retaining the unsubstituted interchain cysteine located in the $CH_1$ domain, and (iv) comprise heavy chains each having an amino acid substitution of the residue at position 234 in the EU index set forth in Kabat and/or a substitution of the residue at position 235 in the EU index set forth in Kabat.

For example, in some embodiments the antibody of the conjugates described herein: (i) has an amino acid substitution of each of HC226 and HC229 according to the EU index as set forth in Kabat, (ii) comprise light chains each having an amino acid substitution of the interchain cysteine residue κLC214 or λLC213 according to the EU index as set forth in Kabat, (iii) comprise heavy chains each retaining the unsubstituted interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $CH_1$ domain, for example to HC220 according to the EU index as set forth in Kabat.

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein each of the cysteines at positions 109 and 112 in SEQ ID NO: 110 is substituted by an amino acid that is not cysteine;
  and wherein the cysteine at position 105 in SEQ ID NO: 150 or the cysteine at position 102 in SEQ ID NO: 160, is substituted by an amino acid that is not cysteine;
  and wherein the leucine at position 117 in SEQ ID NO: 110 and/or the leucine at position 118 in SEQ ID NO: 110 is substituted by an amino acid that is not leucine, such as alanine. Preferably the drug moiety is conjugated to the cysteine at position 103 of SEQ ID NO.110. Preferably both the leucines at position 117 and 118 in SEQ ID NO: 110 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
  wherein each of the cysteines at positions 111, 114, 120, 126, 129, 135, 141, 144, 150, 156, and 159 in SEQ ID NO: 130 is substituted by an amino acid that is not cysteine;
  and wherein the cysteine at position 105 in SEQ ID NO: 150 or the cysteine at position 102 in SEQ ID NO: 160, is substituted by an amino acid that is not cysteine;
  and wherein the leucine at position 164 in SEQ ID NO: 130 and/or the leucine at position 165 in SEQ ID NO: 130 is substituted by an amino acid that is not leucine, such as alanine. Preferably the drug moiety is conjugated to the cysteine at position 14 of SEQ ID NO.130. Preferably both the leucines at position 164 and 165 in SEQ ID NO: 130 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
  wherein each of the cysteines at positions 106 and 109 in SEQ ID NO: 140 is substituted by an amino acid that is not cysteine;
  and wherein the cysteine at position 105 in SEQ ID NO: 150 or the cysteine at position 102 in SEQ ID NO: 160, is substituted by an amino acid that is not cysteine;
  and wherein the leucine at position 115 in SEQ ID NO: 140 is substituted by an amino acid that is not leucine, such as alanine. Preferably the drug moiety is conjugated to the cysteine at position 14 of SEQ ID NO.140. The Leucine may be also substituted by other amino acids which are not Leucine, such as Glycine, Valine, or Isoleucine.

AbDJ(LALA)

In some embodiments the antibody of the conjugates described herein: (i) has an amino acid substitution of each of the hinge region interchain cysteines, (ii) comprises light chains each retaining the unsubstituted interchain cysteine located in the $C_L$ domain, (iii) comprises heavy chains each having an amino acid substitution of the interchain cysteine residue located in the $CH_1$ domain, and (iv) comprise heavy chains each having an amino acid substitution of the residue at position 234 in the EU index set forth in Kabat and/or a substitution of the residue at position 235 in the EU index set forth in Kabat.

For example, in some embodiments the antibody of the conjugates described herein: (i) has an amino acid substitution of each of HC226 and HC229 according to the EU index as set forth in Kabat, (ii) comprises light chains each retaining the unsubstituted interchain cysteine κLC214 or λLC213 according to the EU index as set forth in Kabat, (iii) comprises heavy chains each having an amino acid substitution of interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $C_L$ domain, for example to κLC214 or λLC213 according to the EU index as set forth in Kabat.

In some embodiments, some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein each of the cysteines at positions 103, 109 and 112 in SEQ ID NO: 110 is substituted by an amino acid that is not cysteine;
  and wherein the leucine at position 117 in SEQ ID NO: 110 and/or the leucine at position 118 in SEQ ID NO: 110 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 117 and 118 in SEQ ID NO: 110 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;

wherein each of the cysteines at positions 14, 111, 114, 120, 126, 129, 135, 141, 144, 150, 156, and 159 in SEQ ID NO: 130 is substituted by an amino acid that is not cysteine;

and wherein the leucine at position 164 in SEQ ID NO: 130 and/or the leucine at position 165 in SEQ ID NO: 130 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 164 and 165 in SEQ ID NO: 130 are substituted by an amino acid that is not leucine, such as alanine. One or both Leucines may be also substituted by other amino acids which are not Leucine, such as Glycine, Valine, or Isoleucine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein each of the cysteines at positions 14, 106, and 109 in SEQ ID NO: 140 is substituted by an amino acid that is not cysteine;

and wherein the leucine at position 115 in SEQ ID NO: 140 is substituted by an amino acid that is not leucine, such as alanine. Preferably the drug moiety is conjugated to the cysteine at position 105 of SEQ ID NO.150, the cysteine at position 102 of SEQ ID NO.160. The Leucine may be also substituted by other amino acids which are not Leucine, such as Glycine, Valine, or Isoleucine.

DETAILED DESCRIPTION

Described herein are conjugates comprising a pyrrolobenzodiazepine (PBD) drug moiety with a labile C2 or N10 protecting group and an antibody which binds CD22, wherein the antibody comprises an amino acid substitution of an interchain cysteine residue by an amino acid that is not cysteine, and wherein the drug moiety is conjugated to an interchain cysteine residue.

Also described herein are conjugates comprising the antibodies described herein conjugated to other (i.e. non-PBD) functional moieties. Examples of a functional moiety include a drug (PBD or non-PBD), a reporter, an organic moiety, and/or a binding moiety.

Also contemplated are conjugates comprising an antibody fragment as described herein, along with pharmaceutical compositions comprising the conjugates. Example antibodies or antibody fragment include scFv-Fc fusions and minibodies. Methods of preparing the conjugates and using the conjugates are disclosed, along with methods of using the conjugates to treat a number of diseases.

Pyrrolobenzodiazepines

In some embodiments, the conjugates described herein comprise a PBD drug moiety. Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., J. Am. Chem. Soc., 87, 5793-5795 (1965); Leimgruber, et al., J. Am. Chem. Soc., 87, 5791-5793 (1965)). Since then, a number of naturally occurring PBDs have been reported, and over 10 synthetic routes have been developed to a variety of analogues (Thurston, et al., Chem. Rev. 1994, 433-465 (1994); Antonow, D. and Thurston, D. E., Chem. Rev. 2011 111 (4), 2815-2864). Family members include abbeymycin (Hochlowski, et al., J. Antibiotics, 40, 145-148 (1987)), chicamycin (Konishi, et al., J. Antibiotics, 37, 200-206 (1984)), DC-81 (Japanese Patent 58-180 487; Thurston, et al., Chem. Brit., 26, 767-772 (1990); Bose, et al., Tetrahedron, 48, 751-758 (1992)), mazethramycin (Kuminoto, et al., J. Antibiotics, 33, 665-667 (1980)), neothramycins A and B (Takeuchi, et al., J. Antibiotics, 29, 93-96 (1976)), porothramycin (Tsunakawa, et al., J. Antibiotics, 41, 1366-1373 (1988)), prothracarcin (Shimizu, et a, J. Antibiotics, 29, 2492-2503 (1982); Langley and Thurston, J. Org. Chem., 52, 91-97 (1987)), sibanomicin (DC-102)(Hara, et al., J. Antibiotics, 41, 702-704 (1988); Itoh, et al., J. Antibiotics, 41, 1281-1284 (1988)), sibiromycin (Leber, et al., J. Am. Chem. Soc., 110, 2992-2993 (1988)) and tomamycin (Arima, et al., J. Antibiotics, 25, 437-444 (1972)). PBDs are of the general structure:

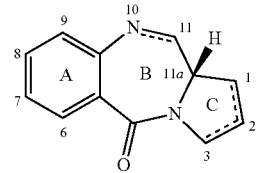

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, Acc. Chem. Res., 19, 230-237 (1986)). Their ability to form an adduct in the minor groove, enables them to interfere with DNA processing, hence their use as antitumour agents.

One pyrrolobenzodiazepine compound is described by Gregson et al. (Chem. Commun. 1999, 797-798) as compound 1, and by Gregson et al. (J. Med. Chem. 2001, 44, 1161-1174) as compound 4a. This compound, also known as SG2000, is shown below:

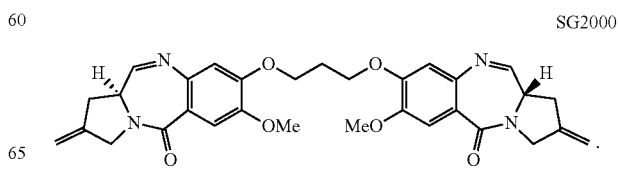

SG2000

WO 2007/085930 describes the preparation of dimer PBD compounds having linker groups for connection to a cell binding agent, such as an antibody. The linker is present in the bridge linking the monomer PBD units of the dimer.

WO 2011/130613 and WO 2011/130616 describe dimer PBD compounds having linker groups for connection to a cell binding agent, such as an antibody. The linker in these compounds is attached to the PBD core via the C2 position, and are generally cleaved by action of an enzyme on the linker group. In WO 2011/130598, the linker in these compounds is attached to one of the available N10 positions on the PBD core, and are generally cleaved by action of an enzyme on the linker group.

Conjugates Comprising PBD Drug Moieties

The present inventors have found that conjugates where the Drug unit ($D^L$) is conjugated to particular interchain cysteine residues have unexpected and advantageous properties including increased efficacy and stability, improved ease of manufacture, and reduced systemic toxicity.

Accordingly, in one aspect the disclosure provides a conjugate of formula L-(DL)p, where DL is of formula I or II:

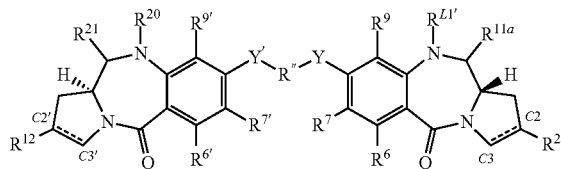

I

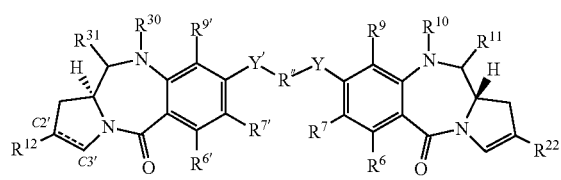

II wherein:

L is an antibody (Ab) which binds CD22;

when there is a double bond present between C2' and C3', $R^{12}$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

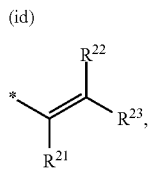

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

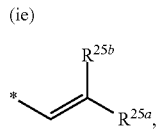

wherein one of $R^{25a}$ and $R^{25b}$ is H and the other is selected from: phenyl, which phenyl is optionally substituted by a group selected from halo, methyl, methoxy; pyridyl; and thiophenyl; and (if)

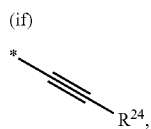

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

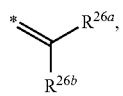

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

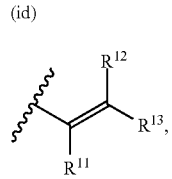

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

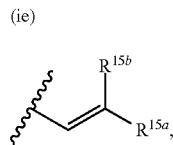

wherein one of $R^{15a}$ and $R^{15b}$ is H and the other is selected from: phenyl, which phenyl is optionally substituted by a group selected from halo, methyl, methoxy; pyridyl; and thiophenyl; and (if)

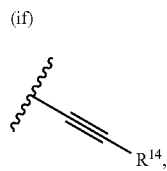

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, R2 is

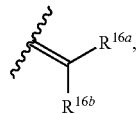

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]
$R^{22}$ is of formula IIIa, formula IIIb or formula IIIc:

(a)

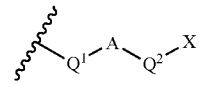

IIIa where A is a $C_{5-7}$ aryl group, and either
(i) $Q^1$ is a single bond, and $Q^2$ is selected from a single bond and —Z—$(CH_2)_n$—, where Z is selected from a single bond, O, S and NH and n is from 1 to 3; or
(ii) $Q^1$ is —CH=CH—, and $Q^2$ is a single bond;

(b)

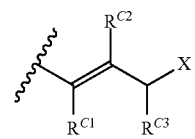

IIIb where;
$R^{C1}$, $R^{C2}$ and $R^{C3}$ are independently selected from H and unsubstituted $C_{1-2}$ alkyl;

(c)

IIIc where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

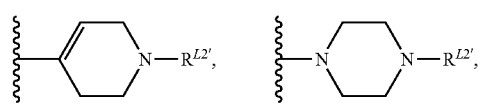

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

[Formula I and II]
wherein:
(1) the antibody comprises an amino acid substitution of an interchain cysteine residue by an amino acid that is not cysteine and the conjugation of the drug moiety to the antibody is at an interchain cysteine residue; and/or
(2) the antibody comprises a heavy chain having a substitution of the amino acid at position 234 in the EU index set forth in Kabat and/or a substitution of the residue at position 235 in the EU index set forth in Kabat.
In some embodiments, it may be preferred that the conjugate is selected from a conjugate of formula ConjA, ConjB, ConjC, ConjD, ConjE, ConjF, ConjG and ConjH:
ConjA
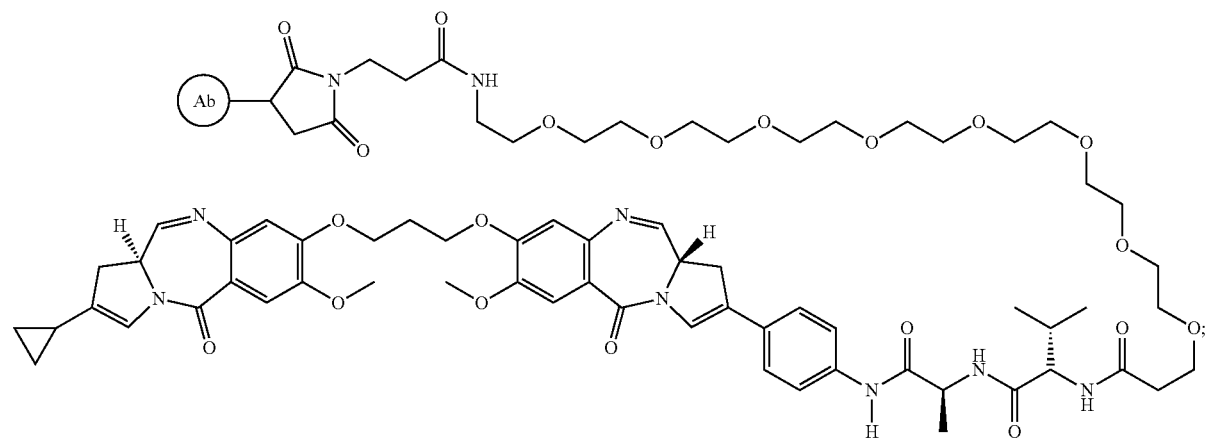
ConjA
ConjB
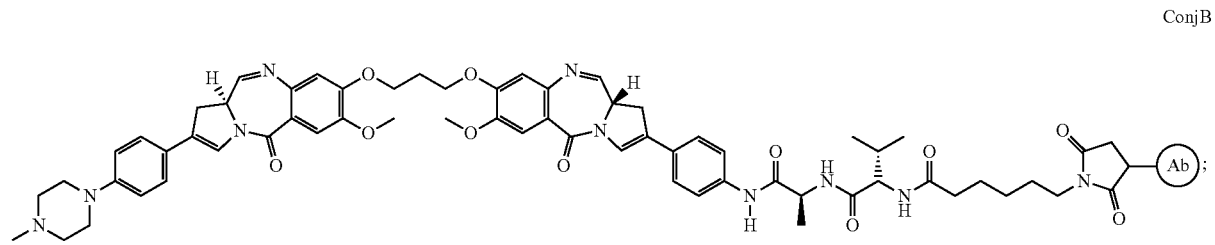
ConjB
ConjC
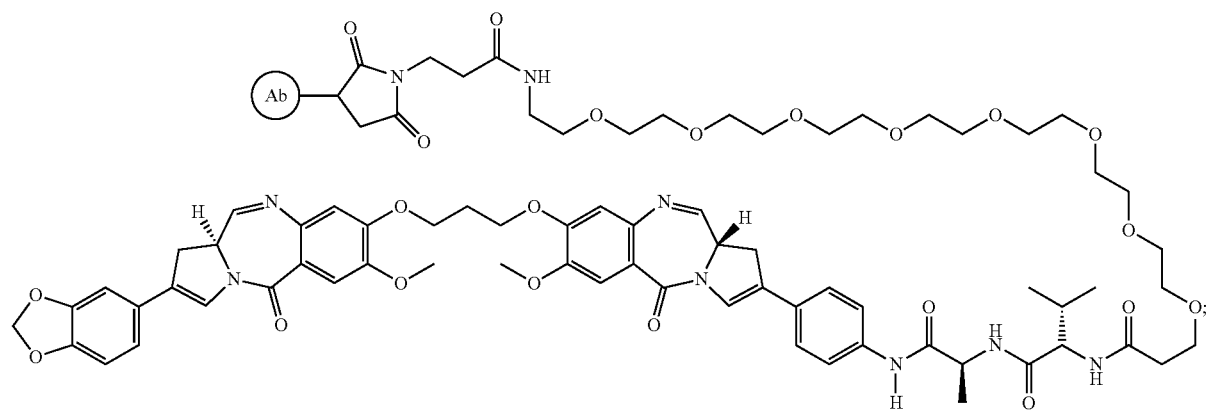
ConjC ConjD
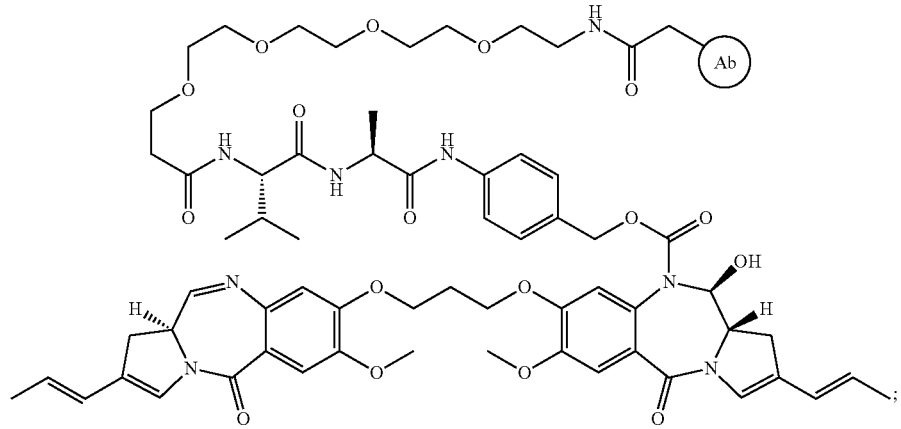
ConjE
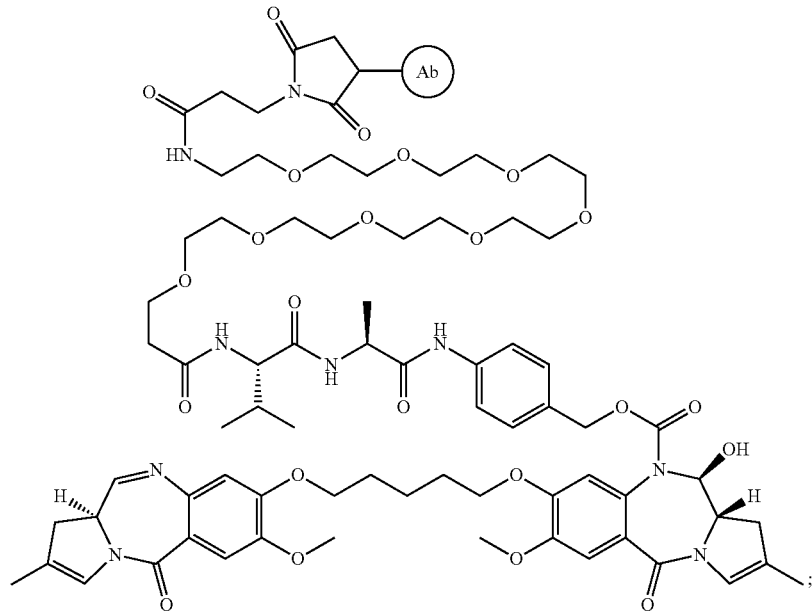
ConjF
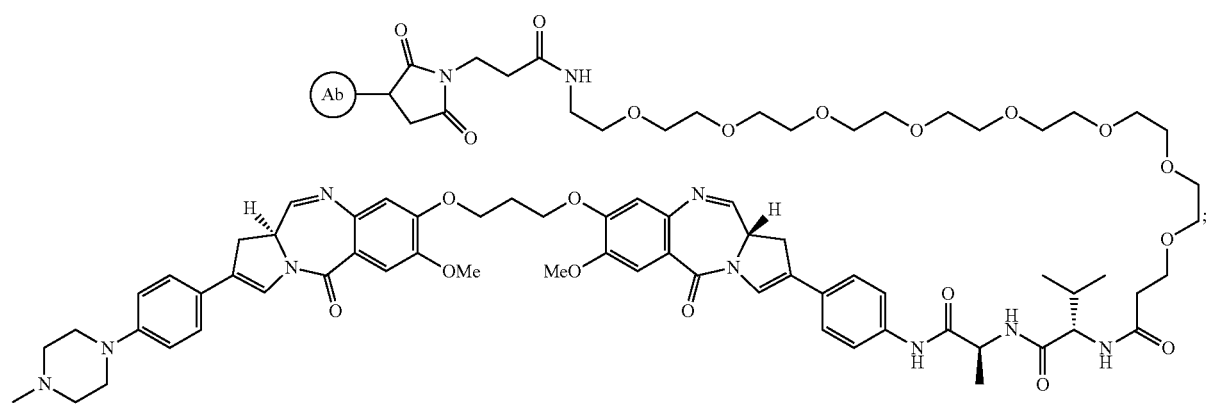

-continued

ConjG

ConjG

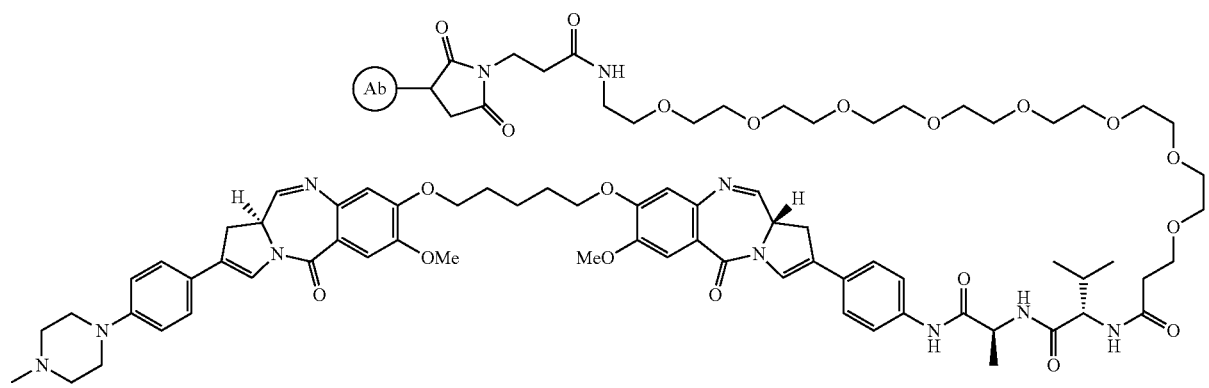

ConjH

ConjH

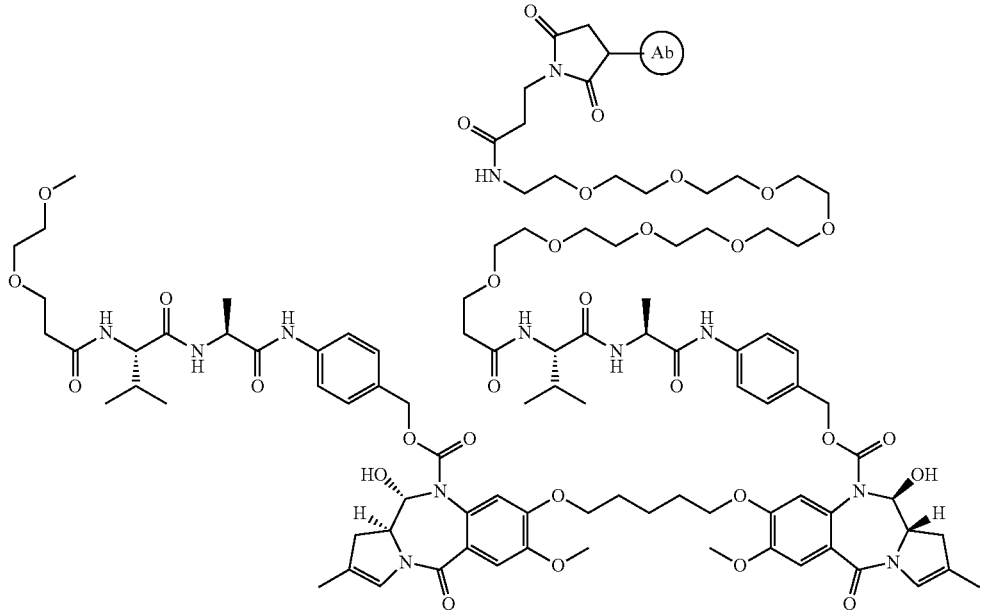

The link to the moiety shown is via a free S (active thiol) of an interchain cysteine residue on the cell binding agent.

The subscript p in the formula I is an integer of from 1 to 20. Accordingly, the Conjugates comprise an antibody (Ab) as defined herein covalently linked to at least one Drug unit by a Linker unit. The Ligand unit, described more fully below, is a targeting agent that binds to a target moiety. Accordingly, also described herein are methods for the treatment of, for example, various cancers and autoimmune disease. The drug loading is represented by p, the number of drug molecules per antibody. Drug loading may range from 1 to 20 Drug units ($D^L$) per antibody. For compositions, p represents the average drug loading of the Conjugates in the composition, and p ranges from 1 to 20.

A second aspect of the disclosure provides a method of making a conjugate according to the first aspect of the disclosure comprising conjugating a compound of formula $I^L$ or $II^L$:

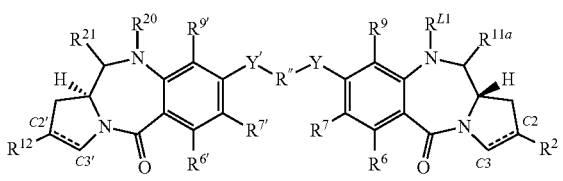

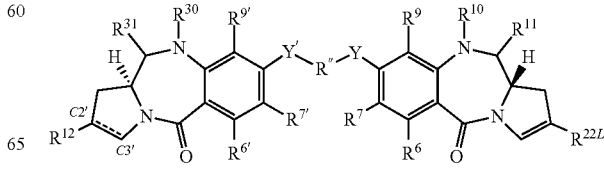

to the antibody (Ab) as defined below, wherein:

$R^{L1}$ is a linker suitable for conjugation to the antibody (Ab);

$R^{22L}$ is of formula $IIIa^L$, formula $IIIb^L$ or formula $IIIc^L$:

(a)

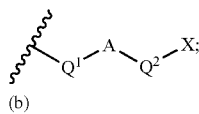

(b)

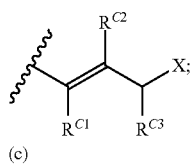

(c)

where $Q^L$ is selected from $O-R^{L2}$, $S-R^{L2}$ and $NR^N-R^{L2}$, and $R^N$ is selected from H, methyl and ethyl $X^L$ is selected from the group comprising: $O-R^{L2}$, $S-R^{L2}$, $CO_2-R^{L2}$, $CO-R^{L2}$, $N=C=O-R^{L2}$, $NHNH-R^{L2}$, $CONHNH-R^{L2}$, IIIa

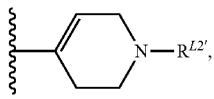

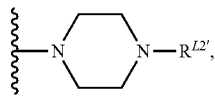

IIIb $NR^NR^L$, wherein $R^N$ is selected from the group comprising H and $C_{1-4}$ alkyl;

$R^{L2}$ is a linker suitable for conjugation to the antibody (Ab);

IIIc and all the remaining groups are as defined in the first aspect.

Thus it may be preferred in the second aspect, that the disclosure provides a method of making a conjugate selected from the group consisting of ConjA, ConjB, ConjC, ConjD, ConjE, ConjF, ConjG and ConjH comprising conjugating a compound which is selected respectively from

A

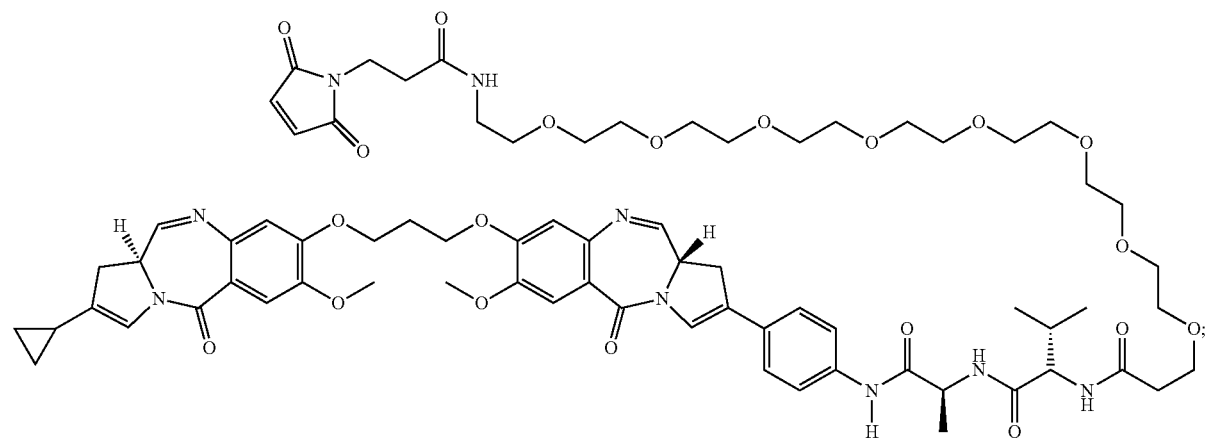

B

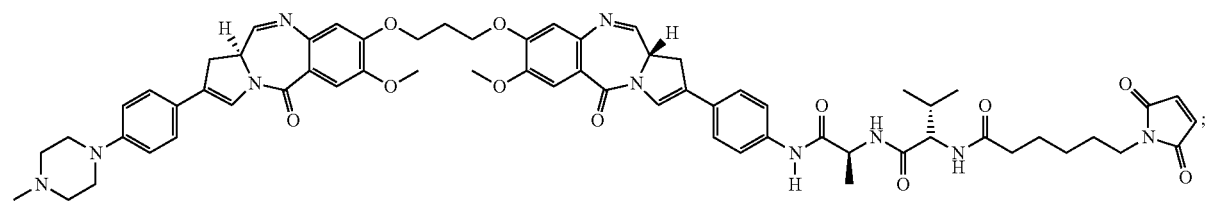

-continued
C
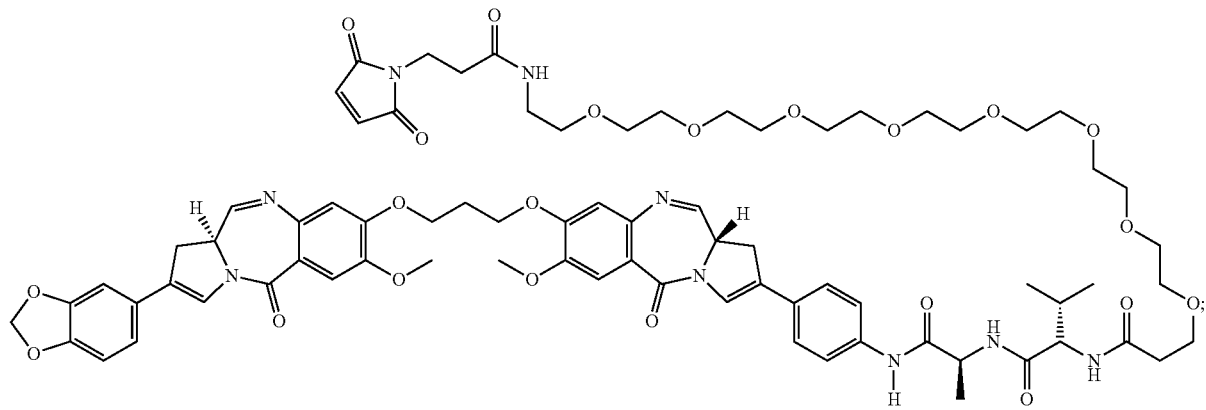
D
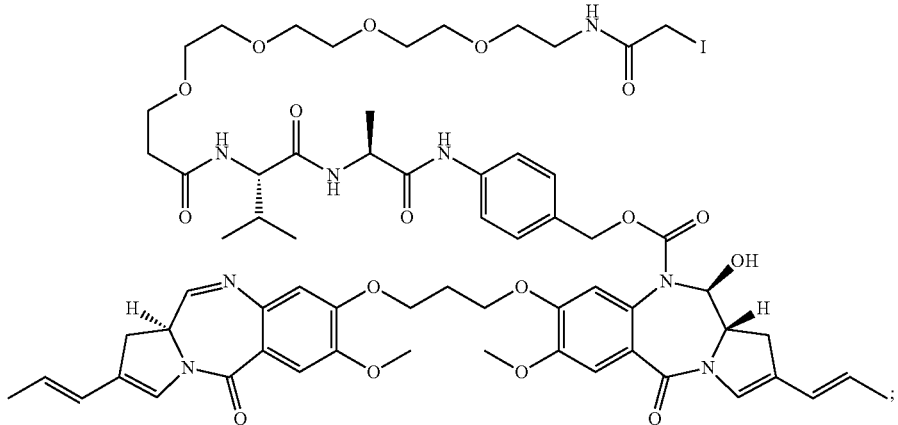
E
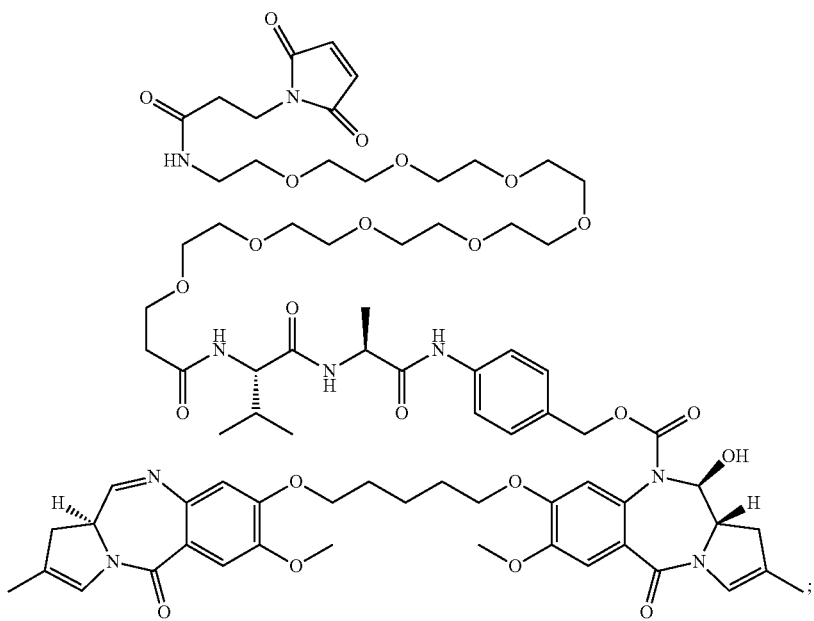

F
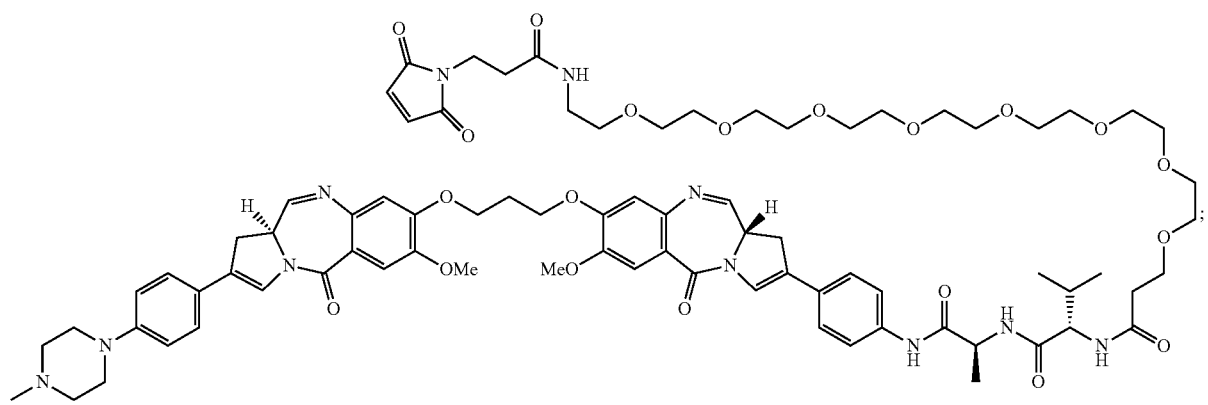
G
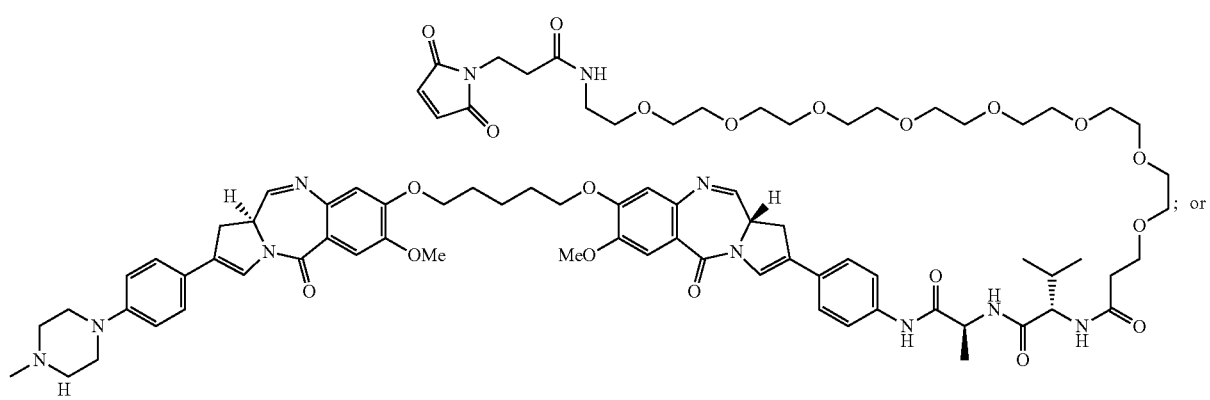
H
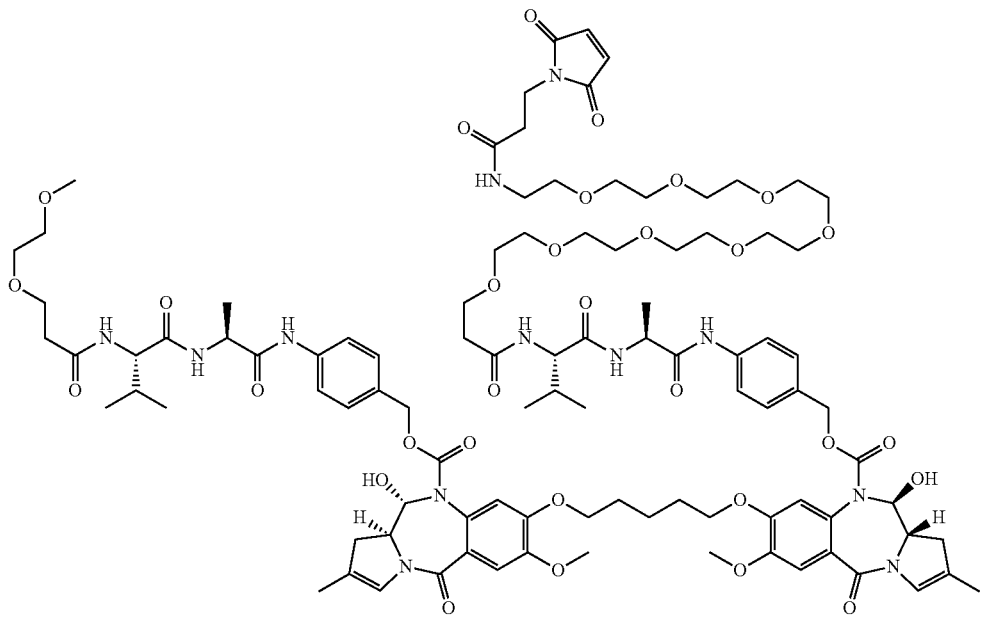
with an antibody as defined below.
Compounds A to E are disclosed in WO 2014/057073 and WO 2014/057074.

WO 2011/130613 discloses compound 51:

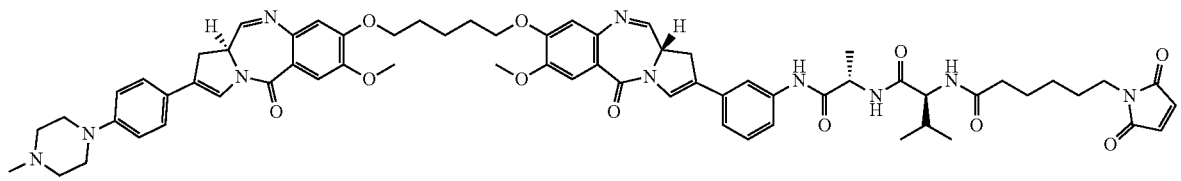

WO 2013/041606 discloses Compound F (see compound 13e in WO 2013/041606). Compound F differs from compound 30 by only having a (CH$_2$)$_3$ tether between the PBD moieties, instead of a (CH$_2$)$_5$ tether, which reduces the lipophilicity of the released PBD dimer. The linking group in compounds F and G is attached to the C2-phenyl group in the para rather than meta position.

Compound H has a cleavable protecting group on the second imine group which avoids cross-reactions during its synthesis and in the final product avoids the formation of carbinolamine and carbinolamine methyl ethers. This protection also avoids the presence of an reactive imine group in the molecule.

Compounds A, B, C, D, E, F, G and H have two sp$^2$ centres in each C-ring, which may allow for stronger binding in the minor groove of DNA, than for compounds with only one sp$^2$ centre in each C-ring.

The drug linkers disclosed in WO 2010/043880, WO 2011/130613, WO 2011/130598, WO 2013/041606 and WO 2011/130616 may be used in the present disclosure, and are incorporated herein by reference. The drug linkers described herein may be synthesised as described in these disclosures.

Delivery of PBD Compounds

The present disclosure is suitable for use in providing a PBD compound to a preferred site in a subject. The conjugate may allow the release of an active PBD compound that does not retain any part of the linker. In such as case there is no stub present that could affect the reactivity of the PBD compound.

ConjA would release the compound ReIA

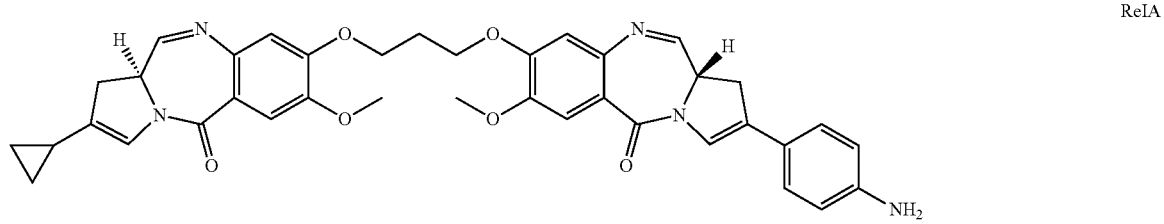

ConjB and ConjF would release the compound ReIB

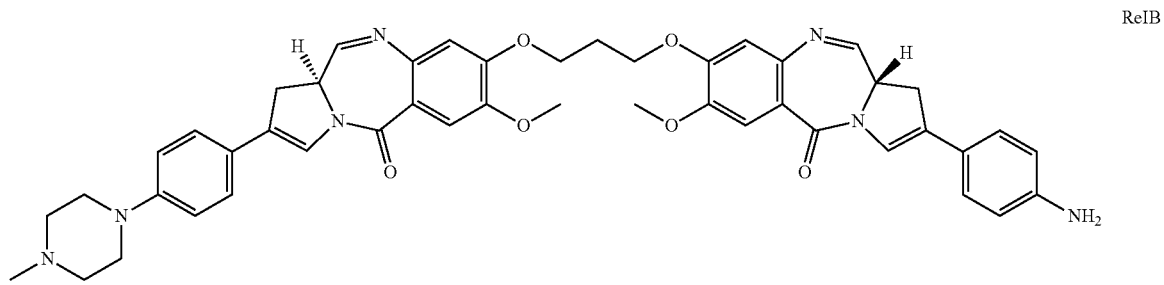

ConjC would release the compound ReIC

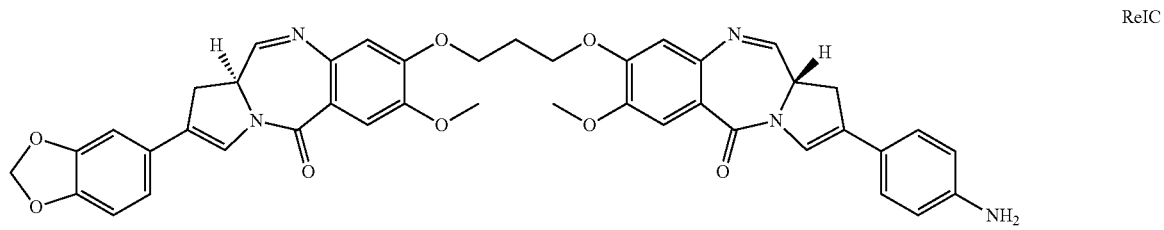

ConjD would release the compound ReID

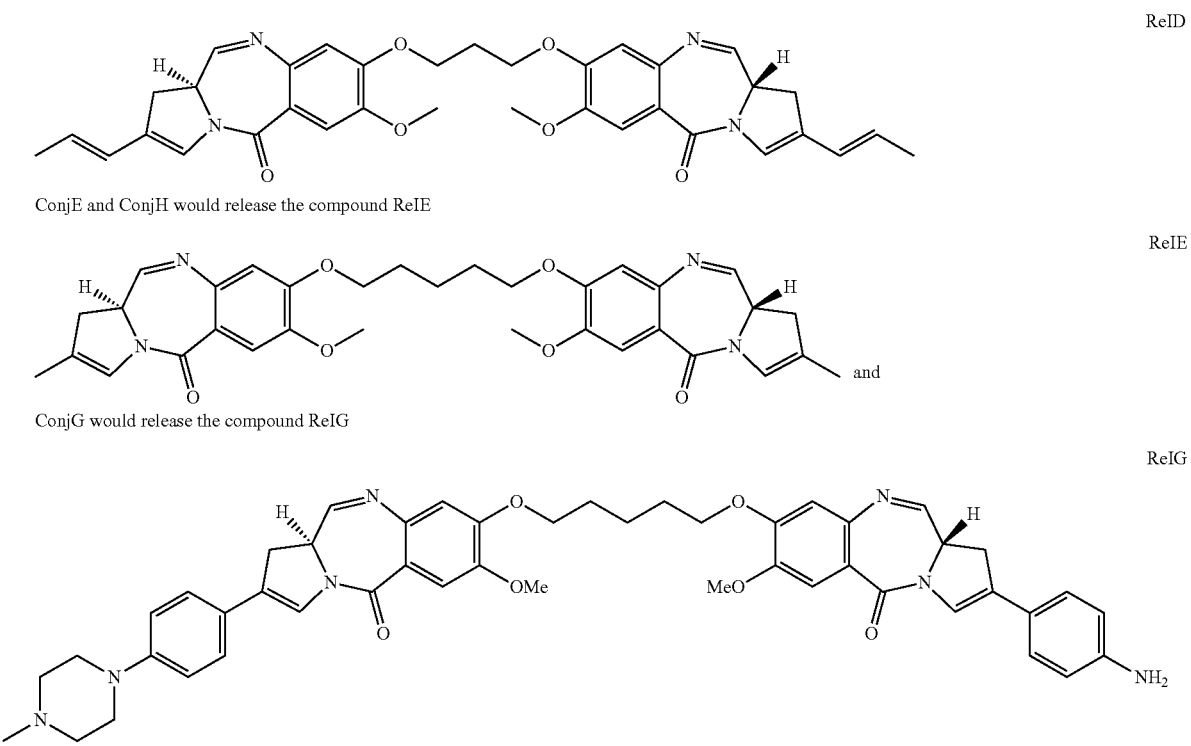

ConjE and ConjH would release the compound ReIE

ConjG would release the compound ReIG

The specified link between the PBD dimer and the antibody, in the present disclosure is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow specific intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as in vitro cytotoxicity, mass spectroscopy, HPLC, and the separation/analysis technique LC/MS.

Delivery of the compounds of formulae ReIA, ReIB, ReIC, ReID, ReIE or ReIG is achieved at the desired activation site of the conjugates of formulae ConjA, ConjB, ConjC, ConjD, ConjE, ConhF, ConjG or ConjH by the action of an enzyme, such as cathepsin, on the linking group, and in particular on the valine-alanine dipeptide moiety.

The Antibody: Substitution of Interchain Cysteine Residues

In a first aspect, the antibody of the conjugates described herein comprise an amino acid substitution of an interchain cysteine residue by an amino acid that is not cysteine.

Interchain Cysteine Residues

Naturally occurring antibodies generally include two larger heavy chains and two smaller light chains. In the case of native full-length antibodies, these chains join together to form a "Y-shaped" protein. Heavy chains and light chains include cysteine amino acids that can be joined to one another via disulphide linkages. Heavy chains are joined to one another in an antibody by disulphide linkages between cysteine amino acids in each chain. Light chains are joined to heavy chains also by disulphide linkages between cysteine amino acids in the chains. Such disulphide linkages generally are formed between thiol side chain moieties of the free cysteine amino acids. The cysteine amino acids which typically take part in these interchain disulphide linkages in naturally occurring antibodies are described herein as "interchain cysteine residues" or "interchain cysteines". For example, three particular cysteine amino acids in each IgG1 isotype heavy chain ('HC'-220, 226, and 229 in the EU index set forth in Kabat) and one particular cysteine in each light chain ('LC'-κ(kappa)214 or λ(lambda) 213) are "interchain cysteines" as they generally participate in disulphide linkages between the antibody chains.

The interchain cysteine residues are located in the CL domain of the light chain, the $CH_1$ domain of the heavy chain, and in the hinge region. The number of interchain cysteine residues in an antibody depends on the antibody isotype.

Nature of Substitutions

As noted above, the antibody of the conjugates described herein comprise an amino acid substitution of an interchain cysteine residue by an amino acid that is not cysteine. The amino acid substituted for an interchain cysteine typically does not include a thiol moiety, and often is a valine, serine, threonine, alanine, glycine, leucine, isoleucine, other naturally occurring amino acid, or non-naturally occurring amino acid. In some preferred embodiments, the amino acid substitution is a valine for the interchain cysteine residue.

In some embodiments, one or more or all interchain cysteines are 'substituted' for no amino acid; that is, the one or more or all interchain cysteines is deleted and not replaced by another amino acid. Accordingly, in some embodiments the phrase " . . . a light chain comprising the amino acid sequence of SEQ ID NO. XXX wherein the cysteine at position YYY in SEQ ID NO: XXX, is substituted by an amino acid that is not cysteine." Has the same meaning as " . . . a light chain comprising the amino acid sequence of SEQ ID NO. XXX wherein the cysteine at position YYY in SEQ ID NO: XXX, is deleted."

For example, SEQ ID NO.153 as disclosed herein is an example of "a light chain comprising the amino acid sequence of SEQ ID NO. 150 wherein the cysteine at position 105 in SEQ ID NO: 150, is substituted by an amino acid that is not cysteine" wherein the cysteine is substituted for no amino acid i.e. deleted.

In embodiments comprising "a light chain comprising the amino acid sequence of SEQ ID NO. 160 wherein the cysteine at position 102 in SEQ ID NO: 160, is deleted" the serine at positon 103 is also preferably deleted. See, for example, SEQ ID NO: 163.

Even when not explicitly stated, the terms "substituted" and "a substitution" as used herein in reference to amino acids is used to mean the replacement of an amino acid residue with a different—that is, non-identical—amino acid residue (or with no amino acid residue—that is, a deletion—as explained above). Thus, an amino acid residue nominally 'replacement' by an identical residue—for example replacing a cysteine residue with a cysteine residue—is not considered "substituted" or "a substitution".

As used herein, "substitution of a leucine by an amino acid which is not leucine" means the replacement of the specified with any non-leucine amino acid. This can be—for example—Asp, Glu, Lys, Arg, His, Asn, Gin, Ser, Thr, Tyr, Cys, Gly, Ala, Val, lie, Phe, Trp, Pro, or Met, but is preferably Gly, Ala, Val, or lie, and most preferably Ala, The statement in this "Nature of substitutions" section are applicable to all three aspects of the disclosure described herein.

Retention of Unsubstituted Interchain Cysteines

The antibody of the conjugates described herein retains at least one unsubstituted interchain cysteine residue for conjugation of the drug moiety to the antibody. The number of retained interchain cysteine residues in the antibody is greater than zero but less than the total number of interchain cysteine residues in the parent (native) antibody. Thus, in some embodiments, the antibody has at least one, at least two, at least three, at least four, at least five, at least six or at least seven interchain cysteine residues. In typical embodiments, the antibody has an even integral number of interchain cysteine residues (e.g., at least two, four, six or eight). In some embodiments, the antibody has less than eight interchain cysteine residues.

In some embodiments, the antibody of the conjugates described herein retains the unsubstituted hinge region interchain cysteines. For example, in some embodiments the antibody retains unsubstituted HC226 and HC229 according to the EU index as set forth in Kabat.

In some embodiments, the antibody of the conjugates described herein has an amino acid substitution of each of the hinge region interchain cysteines. For example, in some embodiments the antibody has an amino acid substitution of each of HC226 and HC229 according to the EU index as set forth in Kabat.

In some embodiments, the antibody of the conjugates described herein retains at least one unsubstituted hinge region interchain cysteine. For example, in some embodiments the antibody retains an unsubstituted HC226 according to the EU index as set forth in Kabat. In some embodiments the antibody retains an unsubstituted HC229 according to the EU index as set forth in Kabat. In some embodiments each heavy chain retains exactly one (i.e. not more than one) unsubstituted hinge region interchain cysteine.

In some embodiments, the antibody of the conjugates described herein has the amino acid substitution of valine for each of the hinge region interchain cysteines. For example, in some embodiments the antibody has the amino acid substitution of valine each of HC226 and HC229 according to the EU index as set forth in Kabat Embodiments Defined Using the EU Index of Kabat In some embodiments, the antibody of the conjugates described herein comprise: (i) a light chain having an amino acid substitution of the interchain cysteine residue located in the $C_L$ domain, and (ii) a heavy chain retaining the unsubstituted interchain cysteine located in the $CH_1$ domain. For example, in some embodiments, the antibody of the conjugates described herein comprise: (i) a light chain having an amino acid substitution of the interchain cysteine residue κLC214 or λLC213 according to the EU index as set forth in Kabat, and (ii) a heavy chain retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments, the antibody of the conjugates described herein comprise: (i) light chains each having an amino acid substitution of the interchain cysteine residue located in the $C_L$ domain, and (ii) heavy chains each retaining the unsubstituted interchain cysteine located in the $CH_1$ domain. For example, in some embodiments, the antibody of the conjugates described herein comprise: (i) light chains each having an amino acid substitution of the interchain cysteine residue κLC214 or λLC213 according to the EU index as set forth in Kabat, and (ii) heavy chains each retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments, the antibody of the conjugates described herein comprise: (i) a light chain retaining the unsubstituted interchain cysteine located in the $C_L$ domain, and (ii) a heavy chain having an amino acid substitution of the interchain cysteine residue located in the $CH_1$ domain. For example, in some embodiments, the antibody of the conjugates described herein comprise: (i) a light chain retaining the unsubstituted interchain cysteine κLC214 or λLC213 according to the EU index as set forth in Kabat, and (ii) a heavy chain having an amino acid substitution of the interchain cysteine residue HC220 according to the EU index as set forth in Kabat. In some embodiments the drug moiety is conjugated to the unsubstituted interchain cysteine located in the $C_L$ domain, for example to κLC214 or λLC213 according to the EU index as set forth in Kabat.

In some embodiments, the antibody of the conjugates described herein comprise: (i) light chains each retaining the unsubstituted interchain cysteine located in the $C_L$ domain, and (ii) heavy chains each having an amino acid substitution of the interchain cysteine residue located in the $CH_1$ domain. For example, in some embodiments, the antibody of the conjugates described herein comprise: (i) light chains each retaining the unsubstituted interchain cysteine κLC214 or λLC213 according to the EU index as set forth in Kabat, and (ii) heavy chains each having an amino acid substitution of the interchain cysteine residue HC220 according to the EU index as set forth in Kabat. In some embodiments the drug moiety is conjugated to the unsubstituted interchain cysteine located in the $C_L$ domain, for example to κLC214 or λLC213 according to the EU index as set forth in Kabat.

AbLJ

In some embodiments the antibody of the conjugates described herein: (i) retain the unsubstituted hinge region interchain cysteines, (ii) comprise a light chain having an amino acid substitution of the interchain cysteine residue located in the $C_L$ domain, and (iii) comprise a heavy chain retaining the unsubstituted interchain cysteine located in the $CH_1$ domain. For example, In some embodiments the antibody of the conjugates described herein: (i) retains unsubstituted HC226 and HC229 according to the EU index as set forth in Kabat, (ii) comprise a light chain having an amino acid substitution of the interchain cysteine residue κLC214 or λLC213 according to the EU index as set forth in Kabat, and (iii) comprise a heavy chain retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments the antibody of the conjugates described herein: (i) retain the unsubstituted hinge region interchain cysteines, (ii) comprise light chains each having an amino acid substitution of the interchain cysteine residue located in the $C_L$ domain, and (iii) comprise heavy chains each retaining the unsubstituted interchain cysteine located in the $CH_1$ domain. For example, In some embodiments the antibody of the conjugates described herein: (i) retains unsubstituted HC226 and HC229 according to the EU index as set forth in Kabat, (ii) comprise light chains each having an amino acid substitution of the interchain cysteine residue κLC214 or λLC213 according to the EU index as set forth in Kabat, and (iii) comprise heavy chains each retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

AbHJ

In some embodiments the antibody of the conjugates described herein: (i) retain the unsubstituted hinge region interchain cysteines, (ii) comprise a light chain retaining the unsubstituted interchain cysteine located in the $C_L$ domain, and (iii) comprise a heavy chain having an amino acid substitution of the interchain cysteine residue located in the $CH_1$ domain. For example, In some embodiments the antibody of the conjugates described herein: (i) retains unsubstituted HC226 and HC229 according to the EU index as set forth in Kabat, (ii) comprise a light chain retaining the unsubstituted interchain cysteine κLC214 or λLC213 according to the EU index as set forth in Kabat, and (iii) comprise a heavy chain having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

In some embodiments the antibody of the conjugates described herein: (i) retain the unsubstituted hinge region interchain cysteines, (ii) comprise light chains each retaining the unsubstituted interchain cysteine located in the $C_L$ domain, and (iii) comprise heavy chains each having an amino acid substitution of the interchain cysteine residue located in the $CH_1$ domain. For example, In some embodiments the antibody of the conjugates described herein: (i) retains unsubstituted HC226 and HC229 according to the EU index as set forth in Kabat, (ii) comprise light chains each retaining the unsubstituted interchain cysteine κLC214 or λLC213 according to the EU index as set forth in Kabat, and (iii) comprise heavy chains each having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

AbBJ

In some embodiments the antibody of the conjugates described herein: (i) has an amino acid substitution of each of the hinge region interchain cysteines, (ii) comprise a light chain having an amino acid substitution of the interchain cysteine residue located in the $C_L$ domain, and (iii) comprise a heavy chain retaining the unsubstituted interchain cysteine located in the $CH_1$ domain. For example, in some embodiments the antibody of the conjugates described herein: (i) has an amino acid substitution of each of HC226 and HC229 according to the EU index as set forth in Kabat, (ii) comprise a light chain having an amino acid substitution of the interchain cysteine residue κLC214 or λLC213 according to the EU index as set forth in Kabat, and (iii) comprise a heavy chain retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments the antibody of the conjugates described herein: (i) has an amino acid substitution of each of the hinge region interchain cysteines, (ii) comprise light chains each having an amino acid substitution of the interchain cysteine residue located in the $C_L$ domain, and (iii) comprise heavy chains each retaining the unsubstituted interchain cysteine located in the $CH_1$ domain. For example, in some embodiments the antibody of the conjugates described herein: (i) has an amino acid substitution of each of HC226 and HC229 according to the EU index as set forth in Kabat, (ii) comprise light chains each having an amino acid substitution of the interchain cysteine residue κLC214 or λLC213 according to the EU index as set forth in Kabat, and (iii) comprise heavy chains each retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments the antibody of the conjugates described herein: (i) has the amino acid substitution of valine for each of the hinge region interchain cysteines, (ii) comprises a light chain having an amino acid substitution of the interchain cysteine residue located in the $C_L$ domain, and (iii) comprises a heavy chain retaining the unsubstituted interchain cysteine located in the $CH_1$ domain. For example, in some embodiments the antibody of the conjugates described herein: (i) has the amino acid substitution of valine for each of HC226 and HC229 according to the EU index as set forth in Kabat, (ii) comprises a light chain having an amino acid substitution of the interchain cysteine residue κLC214 or λLC213 according to the EU index as set forth in Kabat, and (iii) comprises a heavy chain retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

In some embodiments the antibody of the conjugates described herein: (i) has the amino acid substitution of valine for each of the hinge region interchain cysteines, (ii) comprises light chains each having an amino acid substitution of the interchain cysteine residue located in the $C_L$ domain, and (iii) comprises heavy chains each retaining the unsubstituted interchain cysteine located in the $CH_1$ domain. For example, in some embodiments the antibody of the conjugates described herein: (i) has the amino acid substitution of valine for each of HC226 and HC229 according to the EU index as set forth in Kabat, (ii) comprises light chains each having an amino acid substitution of the interchain cysteine residue κLC214 or λLC213 according to the EU index as set forth in Kabat, and (iii) comprises heavy chains each retaining the unsubstituted interchain cysteine HC220 according to the EU index as set forth in Kabat. Preferably the drug moiety is conjugated to the unsubstituted interchain cysteine located in the $CH_1$ domain, for example to HC220 according to the EU index as set forth in Kabat.

AbDJ

In some embodiments the antibody of the conjugates described herein: (i) has the amino acid substitution of valine for each of the hinge region interchain cysteines, (ii) comprises a light chain retaining the unsubstituted interchain cysteine located in the $C_L$ domain, and (iii) comprises a heavy chain having an amino acid substitution of the interchain cysteine residue located in the $CH_1$ domain. For example, in some embodiments the antibody of the conjugates described herein: (i) has an amino acid substitution of each of HC226 and HC229 according to the EU index as set forth in Kabat, (ii) comprises a light chain retaining the unsubstituted interchain cysteine κLC214 or λLC213 according to the EU index as set forth in Kabat, and (iii) comprises a heavy chain having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

In some embodiments the antibody of the conjugates described herein: (i) has an amino acid substitution of each of the hinge region interchain cysteines, (ii) comprises light chains each retaining the unsubstituted interchain cysteine located in the $C_L$ domain, and (iii) comprises heavy chains each having an amino acid substitution of the interchain cysteine residue located in the $CH_1$ domain. For example, in some embodiments the antibody of the conjugates described herein: (i) has an amino acid substitution of each of HC226 and HC229 according to the EU index as set forth in Kabat, (ii) comprises light chains each retaining the unsubstituted interchain cysteine κLC214 or λLC213 according to the EU index as set forth in Kabat, and (iii) comprises heavy chains each having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

In some embodiments the antibody of the conjugates described herein: (i) has an amino acid substitution of each of the hinge region interchain cysteines, (ii) comprises a light chain retaining the unsubstituted interchain cysteine located in the $C_L$ domain, and (iii) comprises a heavy chain having an amino acid substitution of the interchain cysteine residue located in the $CH_1$ domain. For example, in some embodiments the antibody of the conjugates described herein: (i) has the amino acid substitution of valine for each of HC226 and HC229 according to the EU index as set forth in Kabat, (ii) comprises a light chain retaining the unsubstituted interchain cysteine κLC214 or λLC213 according to the EU index as set forth in Kabat, and (iii) comprises a heavy chain having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

In some embodiments the antibody of the conjugates described herein: (i) has the amino acid substitution of valine for each of the hinge region interchain cysteines, (ii) comprises light chains each retaining the unsubstituted interchain cysteine located in the $C_L$ domain, and (iii) comprises heavy chains each having an amino acid substitution of the interchain cysteine residue located in the $CH_1$ domain. For example, in some embodiments the antibody of the conjugates described herein: (i) has the amino acid substitution of valine for each of HC226 and HC229 according to the EU index as set forth in Kabat, (ii) comprises light chains each retaining the unsubstituted interchain cysteine κLC214 or λLC213 according to the EU index as set forth in Kabat, and (iii) comprises heavy chains each having an amino acid substitution of interchain cysteine HC220 according to the EU index as set forth in Kabat. Preferably the drug moiety is conjugated to the unsubstituted interchain cysteine located in the $C_L$ domain, for example to κLC214 or λLC213 according to the EU index as set forth in Kabat.

Correspondence Between the Kabat System and the Disclosed Sequences

The following Table 1 illustrates positions of interchain cysteines in the heavy chain constant region and light chain constant region of particular antibody isotypes according to the EU index as set forth in Kabat and with reference to the sequences disclosed herein. Each of the interchain cysteine positions present in an antibody or antibody fragment may be substituted with an amino acid that is not a cysteine.

TABLE 1

| Antibody Isotype | Kabat EU/SEQ ID NO | Position of Cysteine | | | | | |
|---|---|---|---|---|---|---|---|
| HC | Kabat EU position | 131 | 220 | n/a | n/a | 226 | 229 |
| IgG1 | Corresponding position in SEQ ID NO: 110 | n/a | 103 | n/a | n/a | 109 | 112 |
| IgG2 | Corresponding position in SEQ ID NO: 120 | 14 | 103 | n/a | n/a | 106 | 109 |
| IgG3 | Corresponding position in SEQ ID NO: 130 | 14 | n/a | n/a | n/a | 111 | 114 |
| IgG4 | Corresponding position in SEQ ID NO: 140 | 14 | n/a | n/a | n/a | 106 | 109 |
| LC | | | | | | | |
| κ | Kabat EU position | | | | 214 | | |
| | Corresponding position in SEQ ID NO: 150 | | | | 105 | | |
| λ | Kabat EU position | | | | 213 | | |
| | Corresponding position in SEQ ID NO: 160 | | | | 102 | | |

Heavy Chain and Light Chain Embodiments Defined Using Disclosed Sequences

AbLJ Heavy Chain

In some embodiments, the antibody of the conjugates described herein comprises a heavy chain comprising the amino acid sequence of SEQ ID NO.110 or fragment thereof, SEQ ID NO.120 or fragment thereof, SEQ ID NO.130 or fragment thereof, or SEQ ID NO.140 or fragment thereof. Preferably the drug moiety is conjugated to the cysteine at position 103 of SEQ ID NO.110, the cysteine at position 14 of SEQ ID NO.120, the cysteine at position 14 of SEQ ID NO.130, or the cysteine at position 14 of SEQ ID NO.140.

AbHJ Heavy Chain

In some embodiments, the antibody of the conjugates described herein comprises a heavy chain comprising the amino acid sequence of SEQ ID NO.110, or fragment thereof, wherein the cysteine at position 103 of SEQ ID NO.110, if present, is substituted by an amino acid that is not cysteine. For example, SEQ ID NO. 111 discloses a heavy chain comprising the amino acid sequence of SEQ ID NO.110 wherein the cysteine at position 103 of SEQ ID NO.110 is substituted by a serine residue. SEQ ID NO. 112 discloses a heavy chain comprising the amino acid sequence of SEQ ID NO.110 wherein the cysteine at position 103 of SEQ ID NO.110 is substituted by a valine residue.

In some embodiments, the antibody of the conjugates described herein comprises a heavy chain comprising the amino acid sequence of SEQ ID NO.120, or fragment thereof, wherein the cysteine at positions 14 of SEQ ID NO.120, if present, is substituted by an amino acid that is not cysteine.

In some embodiments, the antibody of the conjugates described herein comprises a heavy chain comprising the amino acid sequence of SEQ ID NO.130, or fragment thereof, wherein the cysteine at position 14 in SEQ ID NO: 130, if present, is substituted by an amino acid that is not cysteine.

In some embodiments, the antibody of the conjugates described herein comprises a heavy chain comprising the amino acid sequence of SEQ ID NO.140, or fragment thereof, wherein the cysteine at position 14 in SEQ ID NO: 140, if present, is substituted by an amino acid that is not cysteine.

AbBJ Heavy Chain

In some embodiments, the antibody of the conjugates described herein comprises a heavy chain comprising the amino acid sequence of SEQ ID NO.110, or fragment thereof, wherein each of the cysteines at positions 109 and 112 in SEQ ID NO: 110, if present, is substituted by an amino acid that is not cysteine. For example, SEQ ID NO: 113 discloses a heavy chain comprising the amino acid sequence of SEQ ID NO.110 wherein each of the cysteines at positions 109 and 112 in SEQ ID NO: 110 is substituted by a serine residue. SEQ ID NO: 114 discloses a heavy chain comprising the amino acid sequence of SEQ ID NO.110 wherein each of the cysteines at positions 109 and 112 in SEQ ID NO: 110 is substituted by a valine residue. Preferably the drug moiety is conjugated to the cysteine at position 103 of SEQ ID NO.110. In some embodiments, the cysteine at position 109 in SEQ ID NO: 110, if present, is substituted by an amino acid that is not cysteine, and the cysteine at position 112 in SEQ ID NO: 110, if present, is unsubstituted. In some embodiments, the cysteine at position 112 in SEQ ID NO: 110, if present, is substituted by an amino acid that is not cysteine, and the cysteine at position 109 in SEQ ID NO: 110, if present, is unsubstituted.

In some embodiments, the antibody of the conjugates described herein comprises a heavy chain comprising the amino acid sequence of SEQ ID NO.120, or fragment thereof, wherein each of the cysteines at positions 103, 106, and 109 in SEQ ID NO: 120, if present, is substituted by an amino acid that is not cysteine. In some embodiments, the cysteine at position 102 in SEQ ID NO: 120, if present, is also substituted by an amino acid that is not cysteine. In some embodiments, all but one of the cysteines at positions 103, 106, 109, and 102 in SEQ ID NO: 120, if present, are substituted by an amino acid that is not cysteine. For example, in some embodiments, the cysteine at position 103, 106, 109, or 102 in SEQ ID NO: 120, if present, is unsubstituted. Preferably the drug moiety is conjugated to the cysteine at position 14 of SEQ ID NO.120.

In some embodiments, the antibody of the conjugates described herein comprises a heavy chain comprising the amino acid sequence of SEQ ID NO.130, or fragment thereof, wherein each of the cysteines at positions 111, 114, 120, 126, 129, 135, 141, 144, 150, 156, and 159 in SEQ ID NO: 130, if present, is substituted by an amino acid that is not cysteine. In some embodiments, all but one of the cysteines at positions 111, 114, 120, 126, 129, 135, 141, 144, 150, 156, and 159 in SEQ ID NO: 130, if present, are substituted by an amino acid that is not cysteine. For example, in some embodiments, the cysteine at position 111, 114, 120, 126, 129, 135, 141, 144, 150, 156, or 159 in SEQ ID NO: 130, if present, is unsubstituted. Preferably the drug moiety is conjugated to the cysteine at position 14 of SEQ ID NO.130.

In some embodiments, the antibody of the conjugates described herein comprises a heavy chain comprising the amino acid sequence of SEQ ID NO.140, or fragment thereof, wherein each of the cysteines at positions 106 and 109 in SEQ ID NO: 140, if present, is substituted by an amino acid that is not cysteine. In some embodiments, the cysteine at position 106 in SEQ ID NO: 140, if present, is substituted by an amino acid that is not cysteine, and the cysteine at position 109 in SEQ ID NO: 140, if present, is unsubstituted. In some embodiments, the cysteine at position 109 in SEQ ID NO: 140, if present, is substituted by an amino acid that is not cysteine, and the cysteine at position 106 in SEQ ID NO: 140, if present, is unsubstituted. Preferably the drug moiety is conjugated to the cysteine at position 14 of SEQ ID NO.140.

AbDJ Heavy Chain

In some embodiments, the antibody of the conjugates described herein comprises a heavy chain comprising the amino acid sequence of SEQ ID NO.110, or fragment thereof, wherein each of the cysteines at positions 103, 109 and 112 in SEQ ID NO: 110, if present, is substituted by an amino acid that is not cysteine. For example, SEQ ID NO: 115 discloses a heavy chain comprising the amino acid sequence of SEQ ID NO.110 wherein each of the cysteines at positions 103, 109 and 112 in SEQ ID NO: 110 is substituted by a serine residue. SEQ ID NO: 116 discloses a heavy chain comprising the amino acid sequence of SEQ ID NO.110 wherein each of the cysteines at positions 103, 109 and 112 in SEQ ID NO: 110 is substituted by a valine residue. In some embodiments, the cysteine at position 109 in SEQ ID NO: 110, if present, is substituted by an amino acid that is not cysteine, and the cysteine at position 112 in SEQ ID NO: 110, if present, is unsubstituted. In some embodiments, the cysteine at position 112 in SEQ ID NO: 110, if present, is substituted by an amino acid that is not cysteine, and the cysteine at position 109 in SEQ ID NO: 110, if present, is unsubstituted.

In some embodiments, the antibody of the conjugates described herein comprises a heavy chain comprising the amino acid sequence of SEQ ID NO.120, or fragment thereof, wherein each of the cysteines at positions 14, 103, 106 and 109 in SEQ ID NO: 120, if present, is substituted by an amino acid that is not cysteine. In some embodiments, all but one of the cysteines at positions 103, 106, 109, and 102 in SEQ ID NO: 120, if present, are substituted by an amino acid that is not cysteine. For example, in some embodiments, the cysteine at position 103, 106, 109, or 102 in SEQ ID NO: 120, if present, is unsubstituted.

In some embodiments, the antibody of the conjugates described herein comprises a heavy chain comprising the amino acid sequence of SEQ ID NO.130, or fragment thereof, wherein each of the cysteines at positions 14, 111, 114, 120, 126, 129, 135, 141, 144, 150, 156, and 159 in SEQ ID NO: 130, if present, is substituted by an amino acid that is not cysteine. In some embodiments, all but one of the cysteines at positions 111, 114, 120, 126, 129, 135, 141, 144, 150, 156, and 159 in SEQ ID NO: 130, if present, are substituted by an amino acid that is not cysteine. For example, in some embodiments, the cysteine at position 111, 114, 120, 126, 129, 135, 141, 144, 150, 156, or 159 in SEQ ID NO: 130, if present, is unsubstituted.

In some embodiments, the antibody of the conjugates described herein comprises a heavy chain comprising the amino acid sequence of SEQ ID NO.140, or fragment thereof, wherein each of the cysteines at positions 14, 106, and 109 in SEQ ID NO: 140, if present, is substituted by an amino acid that is not cysteine. In some embodiments, the cysteine at position 106 in SEQ ID NO: 140, if present, is substituted by an amino acid that is not cysteine, and the cysteine at position 109 in SEQ ID NO: 140, if present, is unsubstituted. In some embodiments, the cysteine at position 109 in SEQ ID NO: 140, if present, is substituted by an amino acid that is not cysteine, and the cysteine at position 106 in SEQ ID NO: 140, if present, is unsubstituted.

Light Chains

In some embodiments, the antibody of the conjugates described herein comprises a light chain comprising the amino acid sequence of SEQ ID NO. 150, or fragment thereof, or SEQ ID NO. 160 or fragment thereof. Preferably the drug moiety is conjugated to the cysteine at position 105 of SEQ ID NO.150, the cysteine at position 102 of SEQ ID NO.160.

In some embodiments, the antibody of the conjugates described herein comprises a light chain comprising the amino acid sequence of SEQ ID NO. 150, or fragment thereof, wherein the cysteine at position 105, if present, is substituted by an amino acid that is not cysteine. For example, SEQ ID NO. 151 discloses a light chain comprising the amino acid sequence of SEQ ID NO. 150 wherein the cysteine at position 105 is substituted by a serine residue. SEQ ID NO. 152 discloses a light chain comprising the amino acid sequence of SEQ ID NO. 150 wherein the cysteine at position 105 is substituted by a valine residue. SEQ ID NO. 153 discloses a light chain having the amino acid sequence of SEQ ID NO. 150, wherein the cysteine at position 105 has been deleted.

In some embodiments, the antibody of the conjugates described herein comprises a light chain comprising the amino acid sequence of SEQ ID NO. 160, or fragment thereof, wherein the cysteine at position 102, if present, is substituted by an amino acid that is not cysteine. For example, SEQ ID NO. 161 discloses a light chain comprising the amino acid sequence of SEQ ID NO. 160 wherein the cysteine at position 102 is substituted by a serine residue. SEQ ID NO. 162 discloses a light chain comprising the amino acid sequence of SEQ ID NO. 160 wherein the cysteine at position 102 is substituted by a valine residue.

SEQ ID NO. 163 discloses a light chain having the amino acid sequence of SEQ ID NO. 160, wherein the cysteine at position 102 and the serine at position 103 have been deleted.

Immunoglobulin Embodiments Defined Using Disclosed Sequences AbLJ IgG1

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 103 of SEQ ID NO.110.

AbLJ IgG2

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 14 of SEQ ID NO.120.

AbLJ IgG3

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 14 of SEQ ID NO.130.

AbLJ IgG4

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 14 of SEQ ID NO.140.

AbHJ IgG1

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein the cysteine at position 103 in SEQ ID NO: 110 is substituted by an amino acid that is not cysteine. Preferably the drug moiety is conjugated to the cysteine at position 105 of SEQ ID NO.150, the cysteine at position 102 of SEQ ID NO.160.

AbHJ IgG2

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;

wherein each of the cysteines at positions 14 and 103 in SEQ ID NO: 120 is substituted by an amino acid that is not cysteine. Preferably the drug moiety is conjugated to the cysteine at position 105 of SEQ ID NO.150, the cysteine at position 102 of SEQ ID NO.160.

AbHJ IgG3

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;

wherein the cysteine at position 14 in SEQ ID NO: 130 is substituted by an amino acid that is not cysteine. Preferably the drug moiety is conjugated to the cysteine at position 105 of SEQ ID NO.150, the cysteine at position 102 of SEQ ID NO.160.

AbHJ IgG4

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein the cysteine at position 14 in SEQ ID NO: 140 is substituted by an amino acid that is not cysteine. Preferably the drug moiety is conjugated to the cysteine at position 105 of SEQ ID NO.150, the cysteine at position 102 of SEQ ID NO.160.

AbBJ IgG1

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;

wherein each of the cysteines at positions 109 and 112 in SEQ ID NO: 110 is substituted by an amino acid that is not cysteine;

and wherein the cysteine at position 105 in SEQ ID NO: 150 or the cysteine at position 102 in SEQ ID NO: 160, is substituted by an amino acid that is not cysteine.

Preferably the drug moiety is conjugated to the cysteine at position 103 of SEQ ID NO.110.

In some embodiments the cysteines at positions 109 and 112 in SEQ ID NO: 110 are substituted for valine. In some embodiments the cysteine at position 105 in SEQ ID NO: 150 or the cysteine at position 102 in SEQ ID NO: 160 is substituted by serine.

AbBJ IgG2A

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;

wherein each of the cysteines at positions 103, 106, and 109 in SEQ ID NO: 120 is substituted by an amino acid that is not cysteine;

and wherein the cysteine at position 105 in SEQ ID NO: 150 or the cysteine at position 102 in SEQ ID NO: 160, is substituted by an amino acid that is not cysteine.

In some embodiments, the cysteine at position 102 in SEQ ID NO: 120 is also substituted by an amino acid that is not cysteine.

Preferably the drug moiety is conjugated to the cysteine at position 14 of SEQ ID NO.120.

In some embodiments the cysteines at positions 103, 106, and 109 in SEQ ID NO: 120 are substituted for valine. In some embodiments the cysteine at position 105 in SEQ ID NO: 150 or the cysteine at position 102 in SEQ ID NO: 160, is substituted by serine.

AbBJ IgG2B

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;

wherein each of the cysteines at positions 14, 106, and 109 in SEQ ID NO: 120 is substituted by an amino acid that is not cysteine;

and wherein the cysteine at position 105 in SEQ ID NO: 150 or the cysteine at position 102 in SEQ ID NO: 160, is substituted by an amino acid that is not cysteine.

In some embodiments, the cysteine at position 102 in SEQ ID NO: 120 is also substituted by an amino acid that is not cysteine.

Preferably the drug moiety is conjugated to the cysteine at position 103 of SEQ ID NO.120.

In some embodiments the cysteines at positions 14, 106, and 109 in SEQ ID NO: 120 are substituted for valine. In some embodiments the cysteine at position 105 in SEQ ID NO: 150 or the cysteine at position 102 in SEQ ID NO: 160, is substituted by serine.

AbBJ IgG3

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;

wherein each of the cysteines at positions 111, 114, 120, 126, 129, 135, 141, 144, 150, 156, and 159 in SEQ ID NO: 130 is substituted by an amino acid that is not cysteine;

and wherein the cysteine at position 105 in SEQ ID NO: 150 or the cysteine at position 102 in SEQ ID NO: 160, is substituted by an amino acid that is not cysteine.

Preferably the drug moiety is conjugated to the cysteine at position 14 of SEQ ID NO.130.

In some embodiments each of the cysteines at positions 111, 114, 120, 126, 129, 135, 141, 144, 150, 156, and 159 in SEQ ID NO: 130 for valine. In some embodiments the cysteine at position 105 in SEQ ID NO: 150 or the cysteine at position 102 in SEQ ID NO: 160, is substituted by serine.

AbBJ IgG4

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein each of the cysteines at positions 106 and 109 in SEQ ID NO: 140 is substituted by an amino acid that is not cysteine;

and wherein the cysteine at position 105 in SEQ ID NO: 150 or the cysteine at position 102 in SEQ ID NO: 160, is substituted by an amino acid that is not cysteine.

Preferably the drug moiety is conjugated to the cysteine at position 14 of SEQ ID NO.140.

Preferably the drug moiety is conjugated to the cysteine at position 14 of SEQ ID NO.140.

In some embodiments each of the cysteines at positions 106 and 109 in SEQ ID NO: 140 are substituted for valine. In some embodiments the cysteine at position 105 in SEQ ID NO: 150 or the cysteine at position 102 in SEQ ID NO: 160, is substituted by serine.

AbDJ IgG1

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;

wherein each of the cysteines at positions 103, 109 and 112 in SEQ ID NO: 110 is substituted by an amino acid that is not cysteine.

Preferably the drug moiety is conjugated to the cysteine at position 105 of SEQ ID NO.150, the cysteine at position 102 of SEQ ID NO.160.

AbDJ IgG2

In some embodiments, the antibody of the conjugates described herein comprises a heavy chain comprising the amino acid sequence of SEQ ID NO.120, and a light chain comprising the amino acid sequence of SEQ ID NO. 150 or SEQ ID NO. 160;

wherein each of the cysteines at positions 14, 103, 106 and 109 in SEQ ID NO: 120 is substituted by an amino acid that is not cysteine.

Preferably the drug moiety is conjugated to the cysteine at position 105 of SEQ ID NO.150, the cysteine at position 102 of SEQ ID NO.160.

AbDJ IgG3

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;

wherein each of the cysteines at positions 14, 111, 114, 120, 126, 129, 135, 141, 144, 150, 156, and 159 in SEQ ID NO: 130 is substituted by an amino acid that is not cysteine.

Preferably the drug moiety is conjugated to the cysteine at position 105 of SEQ ID NO.150, the cysteine at position 102 of SEQ ID NO.160.

AbDJ IgG4

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein each of the cysteines at positions 14, 106, and 109 in SEQ ID NO: 140 is substituted by an amino acid that is not cysteine.

Preferably the drug moiety is conjugated to the cysteine at position 105 of SEQ ID NO.150, the cysteine at position 102 of SEQ ID NO.160.

The Antibody: Substitution of Kabat EU Residues 234 and/or 235

In a second aspect, the antibody of the conjugates described herein comprises a heavy chain having a substitution of the residue at position 234 in the EU index set forth in Kabat and/or a substitution of the residue at position 235 in the EU index set forth in Kabat. It has been unexpectedly found that ADCs in which the antibody bears one, or preferably both, of these substitutions have improved tolerability and increased serum half-lives as compared to otherwise identical ADCs comprising antibodies which lack the specific mutations.

Substitution at Kabat EU 234/235

Hezareh, M. et al., Journal of Virology, Vol. 75, No. 24, pp. 12161-12168 (2001) discloses an IgG1 antibody mutant comprising a heavy chain in which the leucine residue at Kabat EU 234 and the leucine residue at Kabat EU 235 are both substituted for alanine; the antibody is described in that reference as "IgG1 b12 (L234A, L235A)". Hazareh et al. does not disclose the IgG1 b12 (L234A, L235A) as part of an ADC.

Hazareh et al. report that introduction of the L234A/L235A double mutation resulted in complete loss of antibody binding by the Fc(gamma)R and C1q proteins, with consequent abolition of both antibody-dependent cellular cytotoxicity (ADCC) and complement-dependent cytotoxicity (CDC).

Wines, B. D., et al., Journal of Immunology, Vol. 164, pp. 5313-5318 (2000) shares authors with Hazareh et al. and also describes an L234A/L235A double mutant. There the authors report that the L234A/L235A double mutant slightly reduces (<25%) antibody binding to the FcRn receptor. The FcRn receptor is known to have an important role in antibody recycling, with increased antibody/FcRn affinity reported to extend antibody half-life in vivo and improve anti-tumour activity (see Zalevsky, J., Nature Biotechnology 28, 157-159 (2010) [doi:10.1038/nbt.1601]). However, in view of the size of the decrease in FcRn affinity, the authors of Hazareh et al. conclude that the L234A/L235A double mutation is not expected to significantly reduce the antibody's serum half-life.

Contrary to the expectation following from the above disclosures, it has been found that the ADCs disclosed herein which comprise a heavy chain having substitutions of the residues at positions 234 and 235 in the EU index set forth in Kabat actually have increased serum half-lives as compared to otherwise identical ADCs comprising antibodies which lack the mutations. Furthermore, the ADCs comprising a heavy chain having substitutions of the residues at positions 234 and 235 in the EU index set forth also exhibit improved tolerability/reduced toxicity as compared to otherwise identical ADCs comprising antibodies which lack the mutations.

Embodiments Defined Using the EU Index of Kabat

Accordingly, in a second aspect the antibody of the conjugates described herein comprises a heavy chain having a substitution of the residue at position 234 in the EU index set forth in Kabat and/or a substitution of the residue at position 235 in the EU index set forth in Kabat. Preferably both the residues at position 234 and 235 in the EU index set forth in Kabat are substituted by any other amino acid.

In some embodiments the antibody is an IgG1 isotype and the leucine at position 234 in the EU index set forth in Kabat and/or the leucine at position 235 in the EU index set forth in Kabat is substituted by an amino acid that is not leucine.

In some embodiments the antibody is an IgG3 isotype and the leucine at position 234 in the EU index set forth in Kabat and/or the leucine at position 235 in the EU index set forth in Kabat is substituted by an amino acid that is not leucine.

In some embodiments the antibody is an IgG4 isotype and the leucine at position 235 in the EU index set forth in Kabat is substituted by an amino acid that is not leucine, such as alanine.

Correspondence Between the Kabat System and the Disclosed Sequences.

The following Table 2 illustrates positions of corresponding residues in the heavy chain constant region of particular antibody isotypes according to the EU index as set forth in Kabat and with reference to the sequences disclosed herein.

TABLE 2

| Antibody Isotype | Kabat EU/SEQ ID NO | Position of Residue | |
|---|---|---|---|
| HC | Kabat EU position | 234 | 235 |
| IgG1 | Corresponding position in SEQ ID NO: 110 | 117 | 118 |
| IgG2 | Corresponding position in SEQ ID NO: 120 | — | — |
| IgG3 | Corresponding position in SEQ ID NO: 130 | 164 | 165 |
| IgG4 | Corresponding position in SEQ ID NO: 140 | — | 115 |

Immunoglobulin Embodiments Defined Using Disclosed Sequences

In some embodiments the antibody of the conjugates described herein comprises a heavy chain comprising the amino acid sequence of SEQ ID NO.110, wherein the leucine at position 117 and/or the leucine at position 118 is substituted by an amino acid that is not leucine, such as alanine. Preferably both the leucines at position 117 and 118 are substituted by an amino acid that is not leucine, such as alanine.

In some embodiments the antibody of the conjugates described herein comprises a heavy chain comprising the amino acid sequence of SEQ ID NO.130, wherein the leucine at position 164 and/or the leucine at position 165 is substituted by an amino acid that is not leucine, such as alanine. Preferably both the leucines at position 164 and 165 are substituted by an amino acid that is not leucine, such as alanine.

In some embodiments the antibody of the conjugates described herein comprises a heavy chain comprising the amino acid sequence of SEQ ID NO.140, wherein the leucine at position 115 is substituted by an amino acid that is not leucine, such as alanine.

The Antibody: Substitution of Interchain Cysteine Residues Combined with Substitution of Kabat EU Residues 234 and/or 235

The modifications described in the first aspect can be advantageously combined in the same antibody with the modifications described in the second aspect. Accordingly, in a third aspect the antibody of the conjugates described herein:

(1) comprises one or more substitution of an interchain cysteine residue by an amino acid that is not cysteine and retains at least one unsubstituted interchain cysteine residue for conjugation of the drug moiety to the antibody; and (2) comprises a heavy chain having a substitution of the residue at position 234 in the EU index set forth in Kabat and/or a substitution of the residue at position 235 in the EU index set forth in Kabat by any other amino acid (that is, an amino acid that is not identical to that found in the 'wild-type' sequence).

Embodiments Defined Using the Kabat EU Numbering
AbLJ(LALA)

In some embodiments the antibody of the conjugates described herein: (i) retain the unsubstituted hinge region interchain cysteines, (ii) comprise light chains each having an amino acid substitution of the interchain cysteine residue located in the $C_L$ domain, (iii) comprise heavy chains each retaining the unsubstituted interchain cysteine located in the $CH_1$ domain, and (iv) comprise heavy chains each having an amino acid substitution of the the residue at position 234 in the EU index set forth in Kabat and/or a substitution of the residue at position 235 in the EU index set forth in Kabat.

For example, In some embodiments the antibody of the conjugates described herein: (i) retains unsubstituted HC226 and HC229 according to the EU index as set forth in Kabat, (ii) comprise light chains each having an amino acid substitution of the interchain cysteine residue κLC214 or λLC213 according to the EU index as set forth in Kabat, (iii) comprise heavy chains each retaining the unsubstituted interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $CH_1$ domain, for example to HC220 according to the EU index as set forth in Kabat.

AbHJ(LALA)

In some embodiments the antibody of the conjugates described herein: (i) retain the unsubstituted hinge region interchain cysteines, (ii) comprise light chains each retaining the unsubstituted interchain cysteine located in the $C_L$ domain, (iii) comprise heavy chains each having an amino acid substitution of the interchain cysteine residue located in the $CH_1$ domain, and (iv) comprise heavy chains each having an amino acid substitution of the residue at position 234 in the EU index set forth in Kabat and/or a substitution of the residue at position 235 in the EU index set forth in Kabat.

For example, In some embodiments the antibody of the conjugates described herein: (i) retains unsubstituted HC226 and HC229 according to the EU index as set forth in Kabat, (ii) comprise light chains each retaining the unsubstituted interchain cysteine κLC214 or λLC213 according to the EU index as set forth in Kabat, (iii) comprise heavy chains each having an amino acid substitution of interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $C_L$ domain, for example to κLC214 or λLC213 according to the EU index as set forth in Kabat.

AbBJ(LALA)

In some embodiments the antibody of the conjugates described herein: (i) has an amino acid substitution of each of the hinge region interchain cysteines, (ii) comprise light chains each having an amino acid substitution of the interchain cysteine residue located in the $C_L$ domain, (iii) comprise heavy chains each retaining the unsubstituted interchain cysteine located in the $CH_1$ domain, and (iv) comprise heavy chains each having an amino acid substitution of the residue at position 234 in the EU index set forth in Kabat and/or a substitution of the residue at position 235 in the EU index set forth in Kabat.

For example, in some embodiments the antibody of the conjugates described herein: (i) has an amino acid substitution of each of HC226 and HC229 according to the EU index as set forth in Kabat, (ii) comprise light chains each having an amino acid substitution of the interchain cysteine residue κLC214 or λLC213 according to the EU index as set forth in Kabat, (iii) comprise heavy chains each retaining the unsubstituted interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $CH_1$ domain, for example to HC220 according to the EU index as set forth in Kabat.

AbDJ(LALA)

In some embodiments the antibody of the conjugates described herein: (i) has an amino acid substitution of each of the hinge region interchain cysteines, (ii) comprises light chains each retaining the unsubstituted interchain cysteine located in the $C_L$ domain, (iii) comprises heavy chains each having an amino acid substitution of the interchain cysteine residue located in the $CH_1$ domain, and (iv) comprise heavy chains each having an amino acid substitution of the residue at position 234 in the EU index set forth in Kabat and/or a substitution of the residue at position 235 in the EU index set forth in Kabat.

For example, in some embodiments the antibody of the conjugates described herein: (i) has an amino acid substitution of each of HC226 and HC229 according to the EU index as set forth in Kabat, (ii) comprises light chains each retaining the unsubstituted interchain cysteine κLC214 or λLC213 according to the EU index as set forth in Kabat, (iii) comprises heavy chains each having an amino acid substitution of interchain cysteine HC220 according to the EU index as set forth in Kabat, and (iv) comprise heavy chains each having an amino acid substitution of the residue at position 234 in the EU index set forth in Kabat and/or a substitution of the residue at position 235 in the EU index set forth in Kabat by any other amino acid. Preferably both the residues at position 234 and 235 in the EU index set forth in Kabat are substituted. Preferably the drug moiety is conjugated to the unsubstituted interchain cysteine located in the $C_L$ domain, for example to κLC214 or λLC213 according to the EU index as set forth in Kabat.

Embodiments Defined Using Disclosed Sequences

AbLJ(LALA)

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine;
  and wherein the leucine at position 117 and/or the leucine at position 118 is substituted by an amino acid that is not leucine, such as alanine. Preferably the drug moiety is conjugated to the cysteine at position 103 of SEQ ID NO.110. Preferably both the leucines at position 117 and 118 are substituted by an amino acid that is not leucine, such as alanine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine;
  and wherein the leucine at position 164 and/or the leucine at position 165 is substituted by an amino acid that is not leucine, such as alanine. Preferably the drug moiety is conjugated to the cysteine at position 14 of SEQ ID NO.130. Preferably both the leucines at position 164 and 165 are substituted by an amino acid that is not leucine, such as alanine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
  wherein the cysteine at position 105 in SEQ ID NO: 150 or the cysteine at position 102 in SEQ ID NO: 160, is substituted by an amino acid that is not cysteine;
  and wherein the leucine at position 115 is substituted by an amino acid that is not leucine, such as alanine. Preferably the drug moiety is conjugated to the cysteine at position 14 of SEQ ID NO.140.

AbHJ(LALA)

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;
  wherein the cysteine at position 103 in SEQ ID NO: 110 is substituted by an amino acid that is not cysteine;
  and wherein the leucine at position 117 and/or the leucine at position 118 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 117 and 118 are substituted by an amino acid that is not leucine, such as alanine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;
  wherein the cysteine at position 14 in SEQ ID NO: 130 is substituted by an amino acid that is not cysteine;
  and wherein the leucine at position 164 and/or the leucine at position 165 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 164 and 165 are substituted by an amino acid that is not leucine, such as alanine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;
  wherein the cysteine at position 14 in SEQ ID NO: 140 is substituted by an amino acid that is not cysteine;
  and wherein the leucine at position 115 is substituted by an amino acid that is not leucine, such as alanine. Preferably the drug moiety is conjugated to the cysteine at position 105 of SEQ ID NO.150, the cysteine at position 102 of SEQ ID NO.160.

AbBJ(LALA)

In some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;

wherein each of the cysteines at positions 109 and 112 in SEQ ID NO: 110 is substituted by an amino acid that is not cysteine;

and wherein the cysteine at position 105 in SEQ ID NO: 150 or the cysteine at position 102 in SEQ ID NO: 160, is substituted by an amino acid that is not cysteine;

and wherein the leucine at position 117 and/or the leucine at position 118 is substituted by an amino acid that is not leucine, such as alanine. Preferably the drug moiety is conjugated to the cysteine at position 103 of SEQ ID NO.110. Preferably both the leucines at position 117 and 118 are substituted by an amino acid that is not leucine, such as alanine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;

wherein each of the cysteines at positions 111, 114, 120, 126, 129, 135, 141, 144, 150, 156, and 159 in SEQ ID NO: 130 is substituted by an amino acid that is not cysteine;

and wherein the cysteine at position 105 in SEQ ID NO: 150 or the cysteine at position 102 in SEQ ID NO: 160, is substituted by an amino acid that is not cysteine;

and wherein the leucine at position 164 and/or the leucine at position 165 is substituted by an amino acid that is not leucine, such as alanine. Preferably the drug moiety is conjugated to the cysteine at position 14 of SEQ ID NO.130. Preferably both the leucines at position 164 and 165 are substituted by an amino acid that is not leucine, such as alanine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein each of the cysteines at positions 106 and 109 in SEQ ID NO: 140 is substituted by an amino acid that is not cysteine;

and wherein the cysteine at position 105 in SEQ ID NO: 150 or the cysteine at position 102 in SEQ ID NO: 160, is substituted by an amino acid that is not cysteine;

and wherein the leucine at position 115 is substituted by an amino acid that is not leucine, such as alanine. Preferably the drug moiety is conjugated to the cysteine at position 14 of SEQ ID NO.140.

AbDJ(LALA)

In some embodiments, some embodiments, the antibody of the conjugates described herein comprises a heavy chain comprising the amino acid sequence of SEQ ID NO.110, and a light chain comprising the amino acid sequence of SEQ ID NO. 150 or SEQ ID NO. 160;

wherein each of the cysteines at positions 103, 109 and 112 in SEQ ID NO: 110 is substituted by an amino acid that is not cysteine;

and wherein the leucine at position 117 and/or the leucine at position 118 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 117 and 118 are substituted by an amino acid that is not leucine, such as alanine.

In some embodiments, the antibody of the conjugates described herein comprises a heavy chain comprising the amino acid sequence of SEQ ID NO.130, and a light chain comprising the amino acid sequence of SEQ ID NO. 150 or SEQ ID NO. 160;

wherein each of the cysteines at positions 14, 111, 114, 120, 126, 129, 135, 141, 144, 150, 156, and 159 in SEQ ID NO: 130 is substituted by an amino acid that is not cysteine;

and wherein the leucine at position 164 and/or the leucine at position 165 is substituted by an amino acid that is not leucine, such as alanine. Preferably the drug moiety is conjugated to the cysteine at position 105 of SEQ ID NO.150, the cysteine at position 102 of SEQ ID NO.160. Preferably both the leucines at position 164 and 165 are substituted by an amino acid that is not leucine, such as alanine.

In some embodiments, the antibody of the conjugates described herein comprises a heavy chain comprising the amino acid sequence of SEQ ID NO.140, and a light chain comprising the amino acid sequence of SEQ ID NO. 150 or SEQ ID NO. 160;

wherein each of the cysteines at positions 14, 106, and 109 in SEQ ID NO: 140 is substituted by an amino acid that is not cysteine;

and wherein the leucine at position 115 is substituted by an amino acid that is not leucine, such as alanine. Preferably the drug moiety is conjugated to the cysteine at position 105 of SEQ ID NO.150, the cysteine at position 102 of SEQ ID NO.160.

Conjugate/Antibody Properties

Maximum Tolerated Dose (MTD) The conjugates described herein have been found to be well-tolerated in in vivo disease models, allowing for reduced side-effects in subjects receiving the conjugates. Accordingly, in some embodiments the conjugates described herein have a higher MTD than an otherwise identical conjugate where the drug moieties are to the antibody at non-site specifically. MTD is typically tested in animals such as mouse (for example, *Mus musculus*), rat (for example, *Rattus norvegicus*), or monkey (for example, *Macaca fascicularis*). In some embodiments, the conjugates described herein have an MTD in rat of at least 1 mg/kg delivered as a single-dose, for example at least 1.2 mg/kg, at least 1.4 mg/kg, at least 1.6 mg/kg, at least 1.8 mg/kg, at least 2.0 mg/kg, at least 2.2 mg/kg, at least 2.4 mg/kg, at least 2.6 mg/kg, at least 2.8 mg/kg, at least 3.0 mg/kg, at least 4.0 mg/kg, or at least 5.0 mg/kg delivered as a single-dose.

Therapeutic Index

In some embodiments the site-specific conjugates described herein have an improved therapeutic index as compared to an otherwise identical non site-specific conjugate. In some embodiments the therapeutic index for a site specific conjugate descried herein is at least 2% higher than an otherwise identical non site-specific conjugate. That is, if the non site-specific conjugate has a therapeutic index of 100:1, the site specific conjugate has a therapeutic index of at least 102:1. In some embodiments the therapeutic index for a site specific conjugate descried herein is at least 5% higher than an otherwise identical non site-specific conjugate, for example at least 5% higher, at least 7% higher, at least 10% higher, at least 12% higher, at least 15% higher, at least 20% higher, at least 25% higher, at least 30% higher, at least 40% higher, at least 50% higher, at least 70% higher, at least 100% higher, at least 150% higher, or at least 200% higher than an otherwise identical non site-specific conjugate.

Systemic Toxicity

Strop et al., Chemistry & Biology 20, 161-167, Feb. 21, 2013 reported that the conjugation site of the drug moiety on the antibody can influence the stability and pharmacokinetics of an ADC.

The relative systemic toxicity of a site-specific ADC newly described herein was compared to that of a known type of site-specific ADC—see Example 7 and FIG. 1. The site-specific ADC newly described herein was not observed to induce significant systemic toxicity, in contrast to the known site-specific ADC.

Antibody Affinity

In some embodiments, the site-specific conjugate has the same affinity for the cognate antigen as compared to an otherwise identical non site-specific conjugate. In some embodiments, the site-specific conjugate has a greater affinity for the cognate antigen as compared to an otherwise identical non site-specific conjugate. In some embodiments the site-specific conjugate binds the cognate antigen with a dissociation constant (Kd) of at least $10^{-6}$ M, such as at least $5 \times 10^{-7}$ M, at least $10^{-7}$ M, at least $5 \times 10^{-8}$ M, at least $10^{-9}$ M, such as at least $5 \times 10^{-10}$ M, at least $10^{-10}$ M, at least $5 \times 10^{-11}$ M, at least $10^{-11}$ M, at least $5 \times 10^{-12}$ M, at least $10^{-12}$ M, at least $5 \times 10^{-13}$ M, at least $10^{-13}$ M, at least $5 \times 10^{-14}$ M, at least $10^{-14}$ M, at least $5 \times 10^{-15}$ M, or at least $10^{-15}$ M. In one embodiment the site-specific conjugate competitively inhibits the in vivo and/or in vitro binding to the cognate antigen of an otherwise identical non site-specific conjugate.

As used herein, "binds [antigen X]" is used to mean the antibody binds [antigen X] with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds [antigen X] with an association constant (Ka) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the disclosure can typically bind [antigen X] with a high affinity. For example, in some embodiments the antibody can bind [antigen X] with a KD equal to or less than about $10^{-6}$ M, such as $1 \times 10^{-6}$, $10^{-7}$, $10^{-8}$, $10^{-9}$, $10^{-10}$, $10^{-11}$, $10^{-12}$, $10^{-13}$ or $10^{-14}$ M.

Effective Dose

In some embodiments the site-specific conjugate has an $EC_{50}$ of less than 35 ng/ml, such as less than 30 ng/ml, less than 25 ng/ml, less than 20 ng/ml, or less than 15 ng/ml. In some embodiments the $EC_{50}$ of the site-specific conjugate is no higher than an otherwise identical non site-specific conjugate. In some embodiments the $EC_{50}$ of the site-specific conjugate is at least 2 ng/ml lower than an otherwise identical non site-specific conjugate, for example at least 5 ng/ml lower, at least 10 ng/ml lower, at least 15 ng/ml lower, at least 20 ng/ml lower, at least 25 ng/ml lower, or at least 30 ng/ml lower.

Ease of Manufacture

Embodiments of the site-specific ADCs newly described herein allow for simplification of the ADC manufacture procedure.

For example, in a cysteine engineered IgG version such as those described in Junutula et al., Nature Biotechnology, vol. 26, no.8, pp. 925-932, additional cysteines are engineered into the IgG1 to allow for site-specific conjugation on the engineered cysteines. When such cysteine engineered IgG are recombinantly expressed in mammalian cells, the engineered cysteines are typically capped with other sulphydryl containing molecules such as GSH, cysteine etc. In order to release the engineered cysteines for conjugation, the molecule must be reduced. This typically will also reduce the interchain disulphide bond between the heavy and light chains, as well as those in the hinge region. This reduction of native interchain cysteines is undesirable, since drug conjugation can also occur on these native cysteines. Thus, the antibody molecule must be re-oxidized to re-establish these native interchain disulphide bonds before the cysteines engineered into the antibody can be conjugated to the drug.

In contrast, the present disclosure specifically contemplates embodiments where the antibody comprises only two interchain cysteines suitable for conjugation (for example, one on each heavy chain) with the other interchain cysteine residues present in a native antibody having been substituted for an amino acid which is not cysteine. This format allows the complex-reduction-reoxidation procedure described above to be dispensed with. Instead a straight forward reduction-conjugation procedure can be followed. This is possible because the site-specific antibody formats described herein typically do not contain interchain cysteines that are not ultimately intended to be conjugated to drug moieties. For example, in preferred embodiments the site-specific antibody contains only two interchain cysteines suitable for conjugation (for example, one on each heavy chain). It is therefore not necessary to reoxidize the antibody molecule after the initial reduction step. Instead the molecule is reduced with a reducatant such as TCEP which reduces the (two) remaining interchain cysteines (with the other interchain cysteines having been substituted for amino acids which are not cysteine). The reduced cysteine sulphydryl moities can then be conjugated to the drug-linker.

In the preferred embodiments where there are only two intercahin cysteines, it is not possible to generate IgG species with DAR 3 or higher. This can be advantageous, since higher DAR species can contribute to ADC toxicity—see Junutula et al., (Nature Biotech 26_925-932 (2008)).

The newly described site-specific ADCs also avoid other potential manufacturing problems. For example, during the analysis of cysteine engineered IgGs secreted by stably transfected Chinese Hamster Ovary (CHO) cells, the existence of Triple Light Chain antibodies (3LC) has been observed; the 3LC species appears to be the product of a disulfide bond formed between an extra light chain and an additional cysteine engineered into an IgG (Gomez et al., Biotechnol. Bioeng. 105(4)_748-60 (2010); Gomez et al., Biotechnol. Prog. 26(5)_1438-1445 (2010)). The newly described site-specific ADCs do not have inserted cysteines in the light chain, so have no potential to form contamination 3LC species.

Terminal Half-Life

In some embodiments, conjugates in which the antibody comprises a heavy chain having a substitution of the residue at position 234 in the EU index set forth in Kabat and/or a substitution of the residue at position 235 in the EU index set forth in Kabat have improved terminal half-life as compared to another otherwise identical conjugate lacking the 234/235 substitution(s). The terminal-half life may be measured as described herein in Example 6. Accordingly, in some embodiments conjugates in which the antibody comprises a heavy chain having a substitution of the residue at position 234 in the EU index set forth in Kabat and/or a substitution of the residue at position 235 in the EU index set forth in Kabat have a half-life which is at least 110% of the half-life of an otherwise identical conjugate lacking the 234/235 substitution(s); for example at least 115% of the half-life, at least 120% of the half-life, at least 125% of the half-life, at least 130% of the half-life, at least 135% of the half-life, at least 140% of the half-life, at least 145% of the half-life, at least 150% of the half-life, at least 160% of the half-life, at least 170% of the half-life, at least 180% of the half-life, at least 190% of the half-life, or at least 200% of the half-life of an otherwise identical conjugate lacking the 234/235 substitution(s).

Antigen Binding

The antibody of the conjugates described herein is an antibody (Ab) which binds CD22. That is, the conjugates described herein are conjugates comprising antibodies which specifically bind to CD22.

In some embodiments, CD22 polypeptide corresponds to Genbank accession no. BAB15489, version no. BAB15489.1 GI:10439338, record update date: Sep. 11, 2006 11:24 PM. In one embodiment, the nucleic acid encoding CD22 polypeptide corresponds to Genbank accession no AK026467, version no. AK026467.1 GI:10439337, record update date: Sep. 11, 2006 11:24 PM.

In one aspect the antibody is an antibody that binds to CD22, the antibody comprising a VH domain having the sequence according to SEQ ID NO. 1.

The antibody may further comprise a VL domain. In some embodiments the antibody further comprises a VL domain having the sequence according to SEQ ID NO. 2.

In some embodiments the antibody comprises a VH domain paired with a VL domain, the VH and VL domains having the sequences of SEQ ID NO. 1 paired with SEQ ID NO. 2.

The VH and VL domain(s) may pair so as to form an antibody antigen binding site that binds CD22.

In some embodiments the antibody is an intact antibody comprising a VH domain paired with a VL domain, the VH and VL domains having sequences of SEQ ID NO. 1 paired with SEQ ID NO. 2.

In aspect the antibody is an antibody as described herein which has been modified (or further modified) as described below. In some embodiments the antibody is a humanised, deimmunized or resurfaced version of an antibody disclosed herein.

Some Embodiments

Listed below are some specifically contemplated embodiments.

Substitution of Interchain Cysteine Residues
AbLJ-CD22 IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
  wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 103 of SEQ ID NO.110.

An antibody of the conjugates described herein comprising:
  a heavy chain comprising the amino acid sequence of SEQ ID NO.110;
  a light chain comprising the amino acid sequence of SEQ ID NO.151, SEQ ID NO.152, SEQ ID NO.153, SEQ ID NO.161, SEQ ID NO.162, or SEQ ID NO.163; a VH domain having the sequence SEQ ID NO. 1; and
  a VL domain having the sequence SEQ ID NO. 2.

An antibody of the conjugates described herein comprising:
  a heavy chain comprising the amino acid sequence of SEQ ID NO.110;
  a light chain comprising the amino acid sequence of SEQ ID NO.151;
  a VH domain having the sequence SEQ ID NO. 1; and
  a VL domain having the sequence SEQ ID NO. 2.

An antibody of the conjugates described herein comprising:
  a heavy chain comprising the amino acid sequence of SEQ ID NO.110;
  a light chain comprising the amino acid sequence of SEQ ID NO.152;
  a VH domain having the sequence SEQ ID NO. 1; and
  a VL domain having the sequence SEQ ID NO. 2.

An antibody of the conjugates described herein comprising:
  a heavy chain comprising the amino acid sequence of SEQ ID NO.110;
  a light chain comprising the amino acid sequence of SEQ ID NO.153;
  a VH domain having the sequence SEQ ID NO. 1; and
  a VL domain having the sequence SEQ ID NO. 2.

An antibody of the conjugates described herein comprising:
  a heavy chain comprising the amino acid sequence of SEQ ID NO.110;
  a light chain comprising the amino acid sequence of SEQ ID NO.161;
  a VH domain having the sequence SEQ ID NO. 1; and
  a VL domain having the sequence SEQ ID NO. 2.

An antibody of the conjugates described herein comprising:
  a heavy chain comprising the amino acid sequence of SEQ ID NO.110;
  a light chain comprising the amino acid sequence of SEQ ID NO.162;
  a VH domain having the sequence SEQ ID NO. 1; and
  a VL domain having the sequence SEQ ID NO. 2.

An antibody of the conjugates described herein comprising:
  a heavy chain comprising the amino acid sequence of SEQ ID NO.110;
  a light chain comprising the amino acid sequence of SEQ ID NO.163;
  a VH domain having the sequence SEQ ID NO. 1; and
  a VL domain having the sequence SEQ ID NO. 2.

AbHJ-CD22 IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
  wherein the cysteine at position 103 in SEQ ID NO: 110 is substituted by an amino acid that is not cysteine. Preferably the drug moiety is conjugated to the cysteine at position 105 of SEQ ID NO.150, the cysteine at position 102 of SEQ ID NO.160.

An antibody of the conjugates described herein comprising:
  a heavy chain comprising the amino acid sequence of SEQ ID NO.111;
  a light chain comprising the amino acid sequence of SEQ ID NO.150 or SEQ ID NO.160;
  a VH domain having the sequence SEQ ID NO. 1; and
  a VL domain having the sequence SEQ ID NO. 2.

An antibody of the conjugates described herein comprising:
- a heavy chain comprising the amino acid sequence of SEQ ID NO.112;
- a light chain comprising the amino acid sequence of SEQ ID NO.150 or SEQ ID NO.160;
- a VH domain having the sequence SEQ ID NO. 1; and
- a VL domain having the sequence SEQ ID NO. 2.

AbBJ-CD22 IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
- wherein each of the cysteines at positions 109 and 112 in SEQ ID NO: 110 is substituted by an amino acid that is not cysteine;
- and wherein the cysteine at position 105 in SEQ ID NO: 150 or the cysteine at position 102 in SEQ ID NO: 160, is substituted by an amino acid that is not cysteine. Preferably the drug moiety is conjugated to the cysteine at position 103 of SEQ ID NO.110. Preferably the cysteines at positions 109 and 112 in SEQ ID NO: 110 are substituted by valine.

An antibody of the conjugates described herein comprising:
- a heavy chain comprising the amino acid sequence of SEQ ID NO.113;
- a light chain comprising the amino acid sequence of SEQ ID NO.151, SEQ ID NO.152, SEQ ID NO.153, SEQ ID NO.161, SEQ ID NO.162, or SEQ ID NO.163;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.113;
- a light chain comprising the amino acid sequence of SEQ ID NO.151;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.113;
- a light chain comprising the amino acid sequence of SEQ ID NO.152;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.113;
- a light chain comprising the amino acid sequence of SEQ ID NO.153;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.113;
- a light chain comprising the amino acid sequence of SEQ ID NO.161;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.113;
- a light chain comprising the amino acid sequence of SEQ ID NO.162;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.113;
- a light chain comprising the amino acid sequence of SEQ ID NO.163;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.114;
- a light chain comprising the amino acid sequence of SEQ ID NO.151, SEQ ID NO.152, SEQ ID NO.153, SEQ ID NO.161, SEQ ID NO.162, or SEQ ID NO.163;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.114;
- a light chain comprising the amino acid sequence of SEQ ID NO.151;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.114;
- a light chain comprising the amino acid sequence of SEQ ID NO.152;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.114;
- a light chain comprising the amino acid sequence of SEQ ID NO.153;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.114;
- a light chain comprising the amino acid sequence of SEQ ID NO.161;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.114;
- a light chain comprising the amino acid sequence of SEQ ID NO.162;
- a VH domain having the sequence SEQ ID NO. 1; and
- a VL domain having the sequence SEQ ID NO. 2.

An antibody of the conjugates described herein comprising:
a heavy chain comprising the amino acid sequence of SEQ ID NO.114;
a light chain comprising the amino acid sequence of SEQ ID NO.163;
a VH domain having the sequence SEQ ID NO. 1; and
a VL domain having the sequence SEQ ID NO. 2.

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein the cysteine at positions 109 in SEQ ID NO: 110 is substituted by an amino acid that is not cysteine and the cysteine at positions 112 in SEQ ID NO: 110 is unsubstituted;
and wherein the cysteine at position 105 in SEQ ID NO: 150 or the cysteine at position 102 in SEQ ID NO: 160, is substituted by an amino acid that is not cysteine. Preferably the drug moieties are conjugated to the cysteines at positions 103 and 112 of SEQ ID NO.110. Preferably the cysteine at position 109 in SEQ ID NO: 110 is substituted by valine.

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein the cysteine at positions 112 in SEQ ID NO: 110 is substituted by an amino acid that is not cysteine and the cysteine at positions 109 in SEQ ID NO: 110 is unsubstituted;
and wherein the cysteine at position 105 in SEQ ID NO: 150 or the cysteine at position 102 in SEQ ID NO: 160, is substituted by an amino acid that is not cysteine. Preferably the drug moieties are conjugated to the cysteines at positions 103 and 109 of SEQ ID NO.110. Preferably the cysteine at position 112 in SEQ ID NO: 110 is substituted by valine.

AbDJ-CD22 IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein each of the cysteines at positions 103, 109 and 112 in SEQ ID NO: 110 is substituted by an amino acid that is not cysteine. Preferably the drug moiety is conjugated to the cysteine at position 105 of SEQ ID NO.150, or the cysteine at position 102 of SEQ ID NO.160. Preferably the cysteines at positions 109 and 112 in SEQ ID NO: 110 are substituted by valine.

An antibody of the conjugates described herein comprising:
a heavy chain comprising the amino acid sequence of SEQ ID NO.115;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.116;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein each of the cysteines at positions 109 and 112 in SEQ ID NO: 110 are substituted by an amino acid that is not cysteine and the cysteine at positions 103 in SEQ ID NO: 110 is unsubstituted. Preferably the drug moieties are conjugated to: (i) the cysteine at position 105 of SEQ ID NO.150, or the cysteine at position 102 of SEQ ID NO.160; and (ii) the cysteine at position 103 of SEQ ID NO.110. Preferably the cysteines at positions 109 and 112 in SEQ ID NO: 110 are substituted by valine.

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein each of the cysteines at positions 103 and 112 in SEQ ID NO: 110 are substituted by an amino acid that is not cysteine and the cysteine at position 109 in SEQ ID NO: 110 is unsubstituted. Preferably the drug moieties are conjugated to: (i) the cysteine at position 105 of SEQ ID NO.150, or the cysteine at position 102 of SEQ ID NO.160; and (ii) the cysteine at position 109 of SEQ ID NO.110. Preferably the cysteine at position 112 in SEQ ID NO: 110 is substituted by valine.

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein each of the cysteines at positions 103 and 109 in SEQ ID NO: 110 are substituted by an amino acid that is not cysteine and the cysteine at position 112 in SEQ ID NO: 110 is unsubstituted. Preferably the drug moieties are conjugated to: (i) the cysteine at position 105 of SEQ ID NO.150, or the cysteine at position 102 of SEQ ID NO.160; and (ii) the cysteine at position 112 of SEQ ID NO.110. Preferably the cysteine at position 109 in SEQ ID NO: 110 is substituted by valine.

Substitution of Kabat EU Residues 234 and/or 235

An antibody of the conjugates described herein comprising a heavy chain comprising the amino acid sequence of SEQ ID NO.110, a light chain, a VH domain having the sequence SEQ ID NO. 1, and a VL domain having the sequence SEQ ID NO. 2;
wherein the leucine at position 117 of SEQ ID NO.110 and/or the leucine at position 118 of SEQ ID NO.110 is substituted by an amino acid that is not leucine.

An antibody of the conjugates described herein comprising:
a heavy chain comprising the amino acid sequence of SEQ ID NO.1101;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1102;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1104;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1105;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1106;
a light chain;
a VH domain having the sequence SEQ ID NO. 1; and
a VL domain having the sequence SEQ ID NO. 2.

An antibody of the conjugates described herein comprising a heavy chain comprising the amino acid sequence of SEQ ID NO.130, a light chain, a VH domain having the sequence SEQ ID NO. 1, and a VL domain having the sequence SEQ ID NO. 2;
wherein the leucine at position 164 of SEQ ID NO.130 and/or the leucine at position 165 of SEQ ID NO.130 is substituted by an amino acid that is not leucine.

An antibody of the conjugates described herein comprising:
a heavy chain comprising the amino acid sequence of SEQ ID NO.131;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.132;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.133;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.134;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.135;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.136;
a light chain;
a VH domain having the sequence SEQ ID NO. 1; and
a VL domain having the sequence SEQ ID NO. 2.

An antibody of the conjugates described herein comprising a heavy chain comprising the amino acid sequence of SEQ ID NO.140, a light chain, a VH domain having the sequence SEQ ID NO. 1, and a VL domain having the sequence SEQ ID NO. 2;
wherein the leucine at position 115 of SEQ ID NO.140 is substituted by an amino acid that is not leucine.

An antibody of the conjugates described herein comprising:
a heavy chain comprising the amino acid sequence of SEQ ID NO.141;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.142;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.143;
a light chain;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.144;
a light chain;
a VH domain having the sequence SEQ ID NO. 1; and
a VL domain having the sequence SEQ ID NO. 2.

Substitution of Interchain Cysteine Residues Combined with Substitution of Kabat EU Residues 234 and/or 235 AbLJ(LALA) IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein the cysteine at position 105 in SEQ ID NO: 150 or the cysteine at position 102 in SEQ ID NO: 160, is substituted by an amino acid that is not cysteine;

and wherein the leucine at position 117 of SEQ ID NO.110 and/or the leucine at position 118 of SEQ ID NO.110 is substituted by an amino acid that is not leucine. Preferably the drug moiety is conjugated to the cysteine at position 103 of SEQ ID NO.110.

An antibody of the conjugates described herein comprising:
a heavy chain comprising the amino acid sequence of SEQ ID NO.1101, SEQ ID NO.1102, SEQ ID NO.1103, SEQ ID NO.1104, SEQ ID NO.1105, SEQ ID NO.1106;
a light chain comprising the amino acid sequence of SEQ ID NO.151, SEQ ID NO.152, SEQ ID NO.153, SEQ ID NO.161, SEQ ID NO.162, or SEQ ID NO.163;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain comprising the amino acid sequence of SEQ ID NO.151;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain comprising the amino acid sequence of SEQ ID NO.152;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain comprising the amino acid sequence of SEQ ID NO.153;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain comprising the amino acid sequence of SEQ ID NO.161;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain comprising the amino acid sequence of SEQ ID NO.162;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1103;
a light chain comprising the amino acid sequence of SEQ ID NO.163;
a VH domain having the sequence SEQ ID NO. 1; and
a VL domain having the sequence SEQ ID NO. 2.

AbHJ(LALA) IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein the cysteine at position 103 in SEQ ID NO: 110 is substituted by an amino acid that is not cysteine;
and wherein the leucine at position 117 of SEQ ID NO.110 and/or the leucine at position 118 of SEQ ID NO.110 is substituted by an amino acid that is not leucine. Preferably the drug moiety is conjugated to the cysteine at position 105 of SEQ ID NO.150, the cysteine at position 102 of SEQ ID NO.160.

An antibody of the conjugates described herein comprising:
a heavy chain comprising the amino acid sequence of SEQ ID NO.1111;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1112;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1113;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1114;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1115;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1116;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1121;
a light chain comprising the amino acid sequence of SEQ ID NO.150 or SEQ ID NO.160;
a VH domain having the sequence SEQ ID NO. 1; and a VL domain having the sequence SEQ ID NO. 2.

An antibody of the conjugates described herein comprising:
- a heavy chain comprising the amino acid sequence of SEQ ID NO.1122;
- a light chain comprising the amino acid sequence of SEQ ID NO.150 or SEQ ID NO.160;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1123;
- a light chain comprising the amino acid sequence of SEQ ID NO.150 or SEQ ID NO.160;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1124;
- a light chain comprising the amino acid sequence of SEQ ID NO.150 or SEQ ID NO.160;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1125;
- a light chain comprising the amino acid sequence of SEQ ID NO.150 or SEQ ID NO.160;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1126;
- a light chain comprising the amino acid sequence of SEQ ID NO.150 or SEQ ID NO.160;
- a VH domain having the sequence SEQ ID NO. 1; and
- a VL domain having the sequence SEQ ID NO. 2.

AbBJ(LALA) IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
- wherein each of the cysteines at positions 109 and 112 in SEQ ID NO: 110 is substituted by an amino acid that is not cysteine;
- and wherein the cysteine at position 105 in SEQ ID NO: 150 or the cysteine at position 102 in SEQ ID NO: 160, is substituted by an amino acid that is not cysteine; and wherein the leucine at position 117 of SEQ ID NO.110 and/or the leucine at position 118 of SEQ ID NO.110 is substituted by an amino acid that is not leucine. Preferably the drug moiety is conjugated to the cysteine at position 103 of SEQ ID NO.110. Preferably the cysteines at positions 109 and 112 in SEQ ID NO: 110 are substituted by valine.

An antibody of the conjugates described herein comprising:
- a heavy chain comprising the amino acid sequence of SEQ ID NO.1131, SEQ ID NO.1132, SEQ ID NO.1133, SEQ ID NO.1134, SEQ ID NO.1135, SEQ ID NO.1136;
- a light chain comprising the amino acid sequence of SEQ ID NO.151, SEQ ID NO.152, SEQ ID NO.153, SEQ ID NO.161, SEQ ID NO.162, or SEQ ID NO.163;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1133;
- a light chain comprising the amino acid sequence of SEQ ID NO.151;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1133;
- a light chain comprising the amino acid sequence of SEQ ID NO.152;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1133;
- a light chain comprising the amino acid sequence of SEQ ID NO.153;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1133;
- a light chain comprising the amino acid sequence of SEQ ID NO.161;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1133;
- a light chain comprising the amino acid sequence of SEQ ID NO.162;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1133;
- a light chain comprising the amino acid sequence of SEQ ID NO.163;
- a VH domain having the sequence SEQ ID NO. 1; and
- a VL domain having the sequence SEQ ID NO. 2.

An antibody of the conjugates described herein comprising:
- a heavy chain comprising the amino acid sequence of SEQ ID NO.1141, SEQ ID NO.1142, SEQ ID NO.1143, SEQ ID NO.1144, SEQ ID NO.1145, SEQ ID NO.1146;
- a light chain comprising the amino acid sequence of SEQ ID NO.151, SEQ ID NO.152, SEQ ID NO.153, SEQ ID NO.161, SEQ ID NO.162, or SEQ ID NO.163;
- a VH domain having the sequence SEQ ID NO. 1; and
- a VL domain having the sequence SEQ ID NO. 2.

An antibody of the conjugates described herein comprising:
a heavy chain comprising the amino acid sequence of SEQ ID NO.1143;
a light chain comprising the amino acid sequence of SEQ ID NO.151;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1143;
a light chain comprising the amino acid sequence of SEQ ID NO.152;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1143;
a light chain comprising the amino acid sequence of SEQ ID NO.153;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1143;
a light chain comprising the amino acid sequence of SEQ ID NO.161;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1143;
a light chain comprising the amino acid sequence of SEQ ID NO.162;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1143;
a light chain comprising the amino acid sequence of SEQ ID NO.163;
a VH domain having the sequence SEQ ID NO. 1; and
a VL domain having the sequence SEQ ID NO. 2.

AbDJ591 IgG1

An antibody of the conjugates described herein comprising a heavy chain comprising the amino acid sequence of SEQ ID NO.110, a light chain comprising the amino acid sequence of SEQ ID NO. 150 or SEQ ID NO. 160, a VH domain having the sequence SEQ ID NO. 1, and a VL domain having the sequence SEQ ID NO. 2;
wherein each of the cysteines at positions 103, 109 and 112 in SEQ ID NO: 110 is substituted by an amino acid that is not cysteine;
and wherein the leucine at position 117 of SEQ ID NO.110 and/or the leucine at position 118 of SEQ ID NO.110 is substituted by an amino acid that is not leucine. Preferably the drug moiety is conjugated to the cysteine at position 105 of SEQ ID NO.150, or the cysteine at position 102 of SEQ ID NO.160. Preferably the cysteines at positions 109 and 112 in SEQ ID NO: 110 are substituted by valine.

An antibody of the conjugates described herein comprising:
a heavy chain comprising the amino acid sequence of SEQ ID NO.1151;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1152;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1153;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1154;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1155;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1156;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO. 116;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1161;
a light chain comprising the amino acid sequence of SEQ ID NO.150 or SEQ ID NO.160;
a VH domain having the sequence SEQ ID NO. 1; and
a VL domain having the sequence SEQ ID NO. 2.

An antibody of the conjugates described herein comprising:
a heavy chain comprising the amino acid sequence of SEQ ID NO.1162;

a light chain comprising the amino acid sequence of SEQ ID NO.150 or SEQ ID NO.160;
a VH domain having the sequence SEQ ID NO. 1; and
a VL domain having the sequence SEQ ID NO. 2.
An antibody of the conjugates described herein comprising:
a heavy chain comprising the amino acid sequence of SEQ ID NO.1163;
a light chain comprising the amino acid sequence of SEQ ID NO.150 or SEQ ID NO.160;
a VH domain having the sequence SEQ ID NO. 1; and
a VL domain having the sequence SEQ ID NO. 2.
An antibody of the conjugates described herein comprising:
a heavy chain comprising the amino acid sequence of SEQ ID NO.1164;
a light chain comprising the amino acid sequence of SEQ ID NO.150 or SEQ ID NO.160;
a VH domain having the sequence SEQ ID NO. 1; and
a VL domain having the sequence SEQ ID NO. 2.
An antibody of the conjugates described herein comprising:
a heavy chain comprising the amino acid sequence of SEQ ID NO.1165;
a light chain comprising the amino acid sequence of SEQ ID NO.150 or SEQ ID NO.160;
a VH domain having the sequence SEQ ID NO. 1; and
a VL domain having the sequence SEQ ID NO. 2.
An antibody of the conjugates described herein comprising:
a heavy chain comprising the amino acid sequence of SEQ ID NO.1166;
a light chain comprising the amino acid sequence of SEQ ID NO.150 or SEQ ID NO.160;
a VH domain having the sequence SEQ ID NO. 1; and
a VL domain having the sequence SEQ ID NO. 2.

Definitions

Numbering of Amino Acid Positions in Immunoglobulin (Ig) Molecules

The numbering of the amino acids used herein is according to the numbering system of the EU index as set forth in Kabat et al. (1991, NIH Publication 91-3242, National Technical Information Service, Springfield, Va., hereinafter "Kabat"). The "EU index as set forth in Kabat" refers to the residue numbering of the human IgG 1 EU antibody as described in Kabat et al. supra.

In the case of substitutions in, for example, IgG2, IgG3, and IgG4 (or of IgA1, IgA2, IgD, IgE, IgM etc.) the skilled person can readily use sequence alignment programs such as NCBI BLAST® (blast.ncbi.nlm.nih.gov/Blast.cgi) to align the sequences with IgG1 to determine which residues of the desired isoform correspond to the Kabat positions described herein.

Antibody

The term "antibody" as used encompasses any molecule comprising an antibody antigen-binding site (as, for example, formed by a paired VH domain and a VL domain). Thus, for example, the term "antibody" encompasses monoclonal antibodies (including intact monoclonal antibodies), polyclonal antibodies, multispecific antibodies formed from at least two different epitope binding fragments (e.g., bispecific antibodies), human antibodies, humanized antibodies, camelised antibodies, chimeric antibodies, single-chain antibodies (such as scFv fusions with CH3), antibody fragments that exhibit the desired biological activity (e.g. the antigen binding portion; for example minibodies), and anti-idiotypic (anti-Id) antibodies, intrabodies, and epitope-binding fragments of any of the above, so long as they exhibit the desired biological activity, for example, the ability to bind the cognate antigen. Antibodies may be murine, human, humanized, chimeric, or derived from other species. In one embodiment the antibody is a single-chain Fv antibody fused to a CH3 domain (scFv-CH3). In one embodiment the antibody is a single-chain Fv antibody fused to a Fc region (scFv-Fc). In one embodiment the antibody is a minibody.

An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes an intact immunoglobulin molecule or an immunologically active portion of a intact immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease.

In particular, antibodies include immunoglobulin molecules and immunologically active fragments of immunoglobulin molecules, i.e., molecules that contain at least one antigen binding site. The antibody can be of any isotype (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2m1, A2m2, Km1, Km2 and Km3) of antibody molecule. The immunoglobulins can be derived from any species, including human, murine, or rabbit origin.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Antibody Heavy Chain Constant Region, or a Portion Thereof

The terms "antibody heavy chain constant region", "Fc region", "Fc domain" and "Fc", as used herein refer to the portion of an antibody molecule that correlates to a crystallizable fragment obtained by papain digestion of an IgG molecule.

As used herein, the terms "Fc region", "Fc domain" and "Fc" relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain.

For IgG, Fc comprises immunoglobulin domains Cy2 and Cy3 (C gamma 2 and C gamma 3) and the hinge between Cy1 (C gamma 1) and Cy2 (C gamma 2). Although the boundaries of the Fc region may vary, the human IgG heavy chain Fc region is usually defined to comprise residues C226 or P230 to its carboxyl-terminus, as numbered according to the numbering system of the EU index as set forth in Kabat et al. supra. Typically, the Fc domain comprises from about amino acid residue 236 to about 447 of the human IgG1 constant domain.

Fc polypeptide may refer to this region in isolation, or this region in the context of an antibody, or an antigen-binding portion thereof, or Fc fusion protein.

The "intact heavy chain constant region" comprises the Fc region and further comprises the CH1 domain and hinge as well as the CH2 and CH3 (and, optionally, CH4 of IgA and IgE) domains of the IgG heavy chain.

"Hinge region" as used herein, is generally defined as stretching from Glu216 to Pro230 of human IgG1 (Burton, 1985, Malec. Immunol. 22: 161-206), and refers to the portion of an IgG molecule comprising the C-terminal portion of the CH1 domain and the N-terminal portion of the CH2 domain. Exemplary hinge regions for human IgG1, IgG2, IgG2 and IgG4 and mouse IgG1 and IgG2A are provided in U.S. Pat. No. 6,165,476, at the Table shown at column 4, line 54 to column 5, line 15, and also illustrated, for example, in Janeway et al., 1999, Immunology: The Immune System in Health and Disease, 4th ed. (Elsevier Science Ltd.); Bloom et al., 1997, Protein Science 6:407-415; Humphreys et al., 1997, J. Immunol. Methods 209: 193-202. Hinge regions of other IgG isotypes may be aligned with the IgG 1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region The term "IgG hinge-Fc region" or "hinge-Fc fragment" as used herein refers to a hinge region (approximately residues 216-230) and an Fc region (residues 231-44 7) C-terminal thereto.

The term "fragment" is used herein to describe a portion of sequence that is shorter than the full-length sequence disclosed herein. Preferably antibodies comprising "fragments" as disclosed herein retain the ability to bind the target antigen, most preferably with a specific binding activity of about 70% or more compared to of an otherwise identical antibody comprising the full-length sequence disclosed herein (for example, about 10% or more, 50% or more, 75% or more, 80% or more, 85% or more, 90% or more, 95% or more of the binding activity). In certain embodiments, the specific binding activity is in vitro. The specific binding activity sometimes is quantified by an in vitro homogeneous assay or an in vitro heterogeneous assay. In some embodiments the specific binding activity is in vivo, and sometimes, the specific binding activity is determined in situ. In some embodiments a "fragment" is at least 50 amino acids long, such as at least 75, at least 100, at least 150, at least 200, at least 250, or at least 300 amino acids long.

Sequence Modifications

The sequences of the antibody heavy chain variable regions and/or the light chain variable regions disclosed herein may be modified by substitution, insertion or deletion. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Preferred conservative substitutions are those wherein one amino acid is substituted for another within the groups of amino acids indicated herein below:

Amino acids having polar side chains (Asp, Glu, Lys, Arg, His, Asn, Gin, Ser, Thr, Tyr, and Cys)
Amino acids having non-polar side chains (Gly, Ala, Val, Leu, lie, Phe, Trp, Pro, and Met)
Amino acids having aliphatic side chains (Gly, Ala Val, Leu, lie)
Amino acids having cyclic side chains (Phe, Tyr, Trp, His, Pro)
Amino acids having aromatic side chains (Phe, Tyr, Trp)
Amino acids having acidic side chains (Asp, Glu)
Amino acids having basic side chains (Lys, Arg, His)
Amino acids having amide side chains (Asn, Gin)
Amino acids having hydroxy side chains (Ser, Thr)
Amino acids having sulphur-containing side chains (Cys, Met),
Neutral, weakly hydrophobic amino acids (Pro, Ala, Gly, Ser, Thr)
Hydrophilic, acidic amino acids (Gin, Asn, Glu, Asp), and
Hydrophobic amino acids (Leu, Ile, Val)

Particular preferred conservative amino acids substitution groups are: Val-Leu-Ile, Phe-Tyr, Lys-Arg, Ala-Val, and Asn-Gln.

In some embodiments, the antibody of the conjugates described herein comprises a heavy chain having an amino acid sequence with 80% or more amino acid sequence identity (for example, about 85% or more, 86% or more, 87% or more, 88% or more, 89% or more, 90% or more, 91% or more, 92% or more, 93% or more, 94% or more, 95% or more, 96% or more, 97% or more, 98% or more, 99% or more sequence identity) to a heavy chain described herein. In some embodiments, the antibody of the conjugates described herein comprises a light chain having an amino acid sequence with 80% or more amino acid sequence identity (for example, about 85% or more, 86% or more, 87% or more, 88% or more, 89% or more, 90% or more, 91% or more, 92% or more, 93% or more, 94% or more, 95% or more, 96% or more, 97% or more, 98% or more, 99% or more sequence identity) to a light chain described herein.

In some embodiments, the antibody of the conjugates described herein comprises a heavy chain having an amino acid sequence identical to the amino acid sequence of a heavy chain described herein, except that it includes 1, 2, 3, 4, 5, 6, 7, 8, 9 or 10 amino acid modifications (e.g., substitutions, insertions and/or deletions) relative to the amino acid sequence of the heavy chain described herein. In some embodiments, the antibody of the conjugates described herein comprises a light chain having an amino acid sequence identical to the amino acid sequence of a light chain described herein, except that it includes 1, 2, 3, 4, 5, 6, 7, 8, 9 or 10 amino acid modifications (e.g., substitutions, insertions and/or deletions) relative to the amino acid sequence of the light chain described herein.

Reduction of Immunogenicity

The antibodies disclosed herein may be modified. For example, to make them less immunogenic to a human subject. This may be achieved using any of a number of techniques familiar to the person skilled in the art. Some of these techniques are described in more detail below.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class I-binding motifs by, for example, comparison with databases of MHC-binding motifs (such as the "motifs" database hosted at wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;

(c) defining for the non-human antibody to be humanized, a set of heavy and light chain surface exposed amino acid residues using the set of framework positions generated in step (b);

(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;

(e) substituting, in the amino acid sequence of the non-human antibody to be humanized, the set of heavy and light chain surface exposed amino acid residues defined in step (c) with the set of heavy and light chain surface exposed amino acid residues identified in step (d);

(f) constructing a three-dimensional model of the variable region of the non-human antibody resulting from the substituting specified in step (e);

(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and (h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in *Methods* 36, 43-60 (2005).

Epitope Binding Domain

As used herein, the term epitope binding domain refers to a domain which is able to specifically recognize and bind an antigenic epitope. The classic example of an epitope binding domain would be an antibody paratope comprising a $V_H$ domain and a $V_L$ domain forming an antigen binding site.

The sequences of the antibody heavy chain variable regions and/or the light chain variable regions disclosed herein may be modified by, for example, insertions, substitutions and/or deletions to the extent that the epitope binding domain maintains the ability to bind to the cognate antigen. The skilled person can ascertain the maintenance of this activity by performing the functional assays described herein, or known in the art. Accordingly, in some embodiments the heavy chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion. In some embodiments the light chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion. In some embodiments the antibodies of the disclosure include comprising $V_H$ and $V_L$ domains with amino acid sequences that are identical to the sequences described herein.

Therapeutic Index

As used herein, the term "therapeutic index is used as a comparison of the amount of a therapeutic agent that causes the therapeutic effect to the amount that causes death (in animal studies) or toxicity (in human studies).

$$\text{Therapeutic index} = LD_{50}/ED_{50}(\text{animal studies}), \text{ or} = TD_{50}/ED_{50}(\text{human studies}),$$

where LD=lethal dose for 50% of the population, TD=toxic dose for 50% of the population, and ED=minimum effective dose for 50% of the population. The levels of "effective" and "toxic" doses can be readily determined by a medical practitioner or person skilled in the art. When comparing the therapeutic indexes of the site-specific and non-site-specific conjugates, the levels of "effective" and "toxic" are determined in an identical manner Otherwise Identical The term "otherwise identical non site-specific conjugate" as used herein refers to a conjugate which is identical to the defined or claimed site-specific conjugate in all respects apart from the position(s) at which the Drug units ($D^L$) are conjugated to antibody heavy chain constant region, or a portion thereof. Specifically, in the defined or claimed site-specific conjugate Drug units ($D^L$) are uniformly and consistently conjugated to the specified residue(s), whereas in an otherwise identical non site-specific the degree and position of conjugation of Drug unit ($D^L$) to the antibody is variable from batch to batch.

For example, in one embodiment of a site specific antibody-drug conjugate of the disclosure there are two Drug units ($D^L$), one conjugated to each of the position 442 residues (kabat numbering) of the two antibody heavy chain constant regions, or a portions thereof. The 'otherwise identical non site-specific conjugate' for this example would be an antibody with identical amino acid sequence and polypeptide structure, also with two conjugated Drug unit ($D^L$); however, the Drug units ($D^L$) would not uniformly and consistently conjugated to each 442 position, but rather conjugated to a selection of different positions the precise combination of which varies from conjugate to conjugate within a population (for example, conjugation may be via lysine side chains or by reduced interchain disulfide bonds).

As described herein, properties such as affinity, therapeutic index and stability are bulk properties measured at a population level, as opposed to being measured at a molecular level. Thus, the comparisons made herein between the properties of a site-specific conjugate and an "otherwise identical non site-specific conjugate" are comparisons of properties exhibited by populations of those molecules.

Functional Moieties

The humanised antibody of the disclosure may be conjugated to a functional moiety. Examples of functional moieties include an amino acid, a peptide, a protein, a polysaccharide, a nucleoside, a nucleotide, an oligonucleotide, a nucleic acid, a drug, a hormone, a lipid, a lipid assembly, a synthetic polymer, a polymeric microparticle, a biological cell, a virus, a reporter (such as a fluorophore, a chromophore, or a dye), a toxin, a hapten, an enzyme, a binding member (such as an antibody, or an antibody fragment), a radioisotope, solid matrixes, semisolid matrixes and combinations thereof, or an organic moiety.

Examples of a drug include a cytotoxic agent, a chemotherapeutic agent, a peptide, a peptidomimetic, a protein scaffold, DNA, RNA, siRNA, microRNA, and a peptidonucleic acid. In preferred embodiments the functional moiety is a PBD drug moiety. In other embodiments the humanised antibody is conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J Immunol., 6: 1567), and VEGf (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-I"), interleukin-2 ("IL-2"), interleukin-4 ("IL-4"), interleukin-6 ("IL-6"), interleukin-7 ("IL-7"), interleukin-9 ("IL-9"), interleukin-15 ("IL-15"), interleukin-12 ("IL-12"), granulocyte macrophage colony stimulating factor ("GMCSF"), and granulocyte colony stimulating factor ("G-CSF")), or a growth factor (e.g., growth hormone ("GH")).

Examples of a reporter include a fluorophore, a chromophore, a radionuclide, and an enzyme. Such antibody-reporter conjugates can be useful for monitoring or prognosing the development or progression of a disorder (such as, but not limited to cancer) as part of a clinical testing procedure, such as determining the efficacy of a particular therapy. Such diagnosis and detection can accomplished by fusing or conjugating the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, bioluminescent materials, such as but not limited to, luciferase, luciferin, and aequorin; radioactive materials, such as but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{88}$Ga, $^{67}$Ga), germanium ($^{68}$Ge), holmium ($^{166}$Ho), indium ($^{151}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{85}$Zn); positron emitting metals using various positron emission tomographies, and nonradioactive paramagnetic metal ions.

Examples of a binding member include an antibody or antibody fragment, and biotin and/or streptavidin.

A toxin, cytotoxin or cytotoxic agent includes any agent that is detrimental to cells. Examples of toxins include radioisotopes such as $^{131}$I, a ribosome inactivating protein such as *Pseudomonas* exotoxin (PE38 fragment), plant or bacterial toxins such as ricin, the α-chain of ricin, saporin, pokeweed antiviral protein, diphtheria toxin, or *Pseudomonas* exotoxin A (Kreitman and Pastan (1998) Adv. Drug Delivery Rev. 31:53). Other toxins and cytotoxins include, e.g., a cytostatic or cytocidal agent, or a radioactive metal ion, e.g., alpha-emitters. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homo logs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Chemical toxins can also be taken from the group chosen from duocarmycin (U.S. Pat. Nos. 5,703,080; 4,923,990), methotrexate, doxorubicin, melphalan, chlorambucil, ARA-C, vindesine, mitomycin C, cisplatinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, In one embodiment, the cytotoxic agent is chosen from an enediyne, a lexitropsin, a duocarmycin, a taxane, a puromycin, a dolastatin, a maytansinoid, and a *Vinca* alkaloid. In other embodiments, the cytotoxic agent is paclitaxel, docetaxel, CC-I 065, SN-3 8, topotecan, morpholino-doxorubicin, rhizoxin, cyanomorpholino-doxorubicin, dolastatin-10, echinomycin, combretastatin, calicheamicin, maytansine, DM-I, an auristatin or other dolastatin derivatives, such as auristatin E or auristatin F, AEB, AEVB, AEFP, MMAE (monomethylauristatin E), MMAF (monomethylauristatin F), eleutherobin or netropsin. In certain embodiments, the cytoxic agent is Maytansine or Maytansinoids, and derivatives thereof, wherein an antibodies (full length or fragments) of the disclosure are conjugated to one or more maytansinoid molecules. Maytansinoids are mitototic inhibitors which act by inhibiting tubulin polymerization. In other embodiments the toxin is a small molecule or protein toxins, such as, but not limited to abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin BI, fumonisin B2, aflatoxin, maurotoxin, agitoxin, charybdotoxin, margatoxin, slotoxin, scyllatoxin, hefutoxin, calciseptine, taicatoxin, calcicludine, geldanamycin, gelonin, lotaustralin, ocratoxin A, patulin, ricin, strychnine, trichothecene, zearlenone, and tetradotoxin. Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, P APII, and PAP-S), *Momordica charantia* inhibitor, curcin, crotin, *Sapaonaria officinalis* inhibitor, gelonin, mitogellin, restrictocin, phenomycin, enomycin and the tricothecenes.

The humanized antibody may be modified by conjugation to an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms. In certain embodiments, the cytotoxic or cytostatic agent is a dolastatin. In more specific embodiments, the dolastatin is of the auristatin class. In a specific embodiment of the disclosure, the cytotoxic or cytostatic agent is MMAE. In another specific embodiment of the disclosure, the cytotoxic or cytostatic agent is AEFP. In another specific embodiment of the disclosure, the cytotoxic or cytostatic agent is MMAF.

The humanized antibody and antigen-binding fragments can comprise one or more organic moieties that are covalently bonded, directly or indirectly, to the antibody. Each organic moiety that is bonded to an antibody or antigen-binding fragment described herein can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the present disclosure. Hydrophilic polymers suitable for modifying antibodies described herein can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody described herein has a molecular weight of about 800 to about 150,000 Daltons as a separate molecular entity. For example PEG5000 and PEG20,000, wherein the numerical component of the name is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies described herein can be saturated or can contain one or more units of unsaturation. Fatty acids that are suitable for modifying antibodies described herein include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-δ 9-octadecanoate (C18, oleate), all cis-δ 5,8,11,14-eicosatetraenoate (C20, arachidonate), octanedioic acid, tetradecanedioic acid, octadecanedioic acid, docosanedioic acid, and similar fatty acids. Suitable fatty acid esters include mono-esters of dicarboxylic acids that comprise a linear or branched lower alkyl group. The lower alkyl group can comprise from one to about twelve, preferably one to about six, carbon atoms.

The above conjugates can be prepared using suitable methods, such as by reaction with one or more modifying agents: a "modifying agent" as the term is used herein, refers to a suitable organic group (e.g., hydrophilic polymer, a fatty acid, a fatty acid ester) that comprises an activating group; aAn "activating group" is a chemical moiety or functional group that can, under appropriate conditions, react with a second chemical group thereby forming a covalent bond between the modifying agent and the second chemical group.

For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetraethylene glycol, —(CH2)3-, —NH—(CH2)6-NH—, —(CH2)2-NH— and —CH2-O—CH2-CH2-O—CH2-CH2-O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid.

(See, for example, Thompson, et al., WO 92/16221 the entire teachings of which are incorporated herein by reference.)

The above conjugates can be produced by reacting a human antibody or antigen-binding fragment with a modifying agent. For example, the organic moieties can be bonded to the antibody in a non-site-specific manner by employing an amine-reactive modifying agent, for example, an NHS ester of PEG. Modified human antibodies or antigen-binding fragments can also be prepared by reducing disulfide bonds (e.g., inter-chain disulfide bonds) of an antibody or antigen-binding fragment. The reduced antibody or antigen-binding fragment can then be reacted with a thiol-reactive modifying agent to produce the modified antibody described herein. Modified human antibodies and antigen-binding fragments comprising an organic moiety that is bonded to specific sites of an antibody described herein can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, $-CH=CH_2$), 1-propenyl ($-CH=CH-CH_3$), 2-propenyl (allyl, $-CH-CH=CH_2$), isopropenyl (1-methylvinyl, $-C(CH_3)=CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl ($-C\equiv CH$) and 2-propynyl (propargyl, $-CH_2-C\equiv CH$).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_5$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and,

N4: tetrazole (C5).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic"

acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein $R^1$ and $R^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein $R^1$ and $R^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. $R^1$ and $R^2$ may together form a cyclic structure, as in, for example, succinimidyl, maleimidyl, and phthalimidyl:

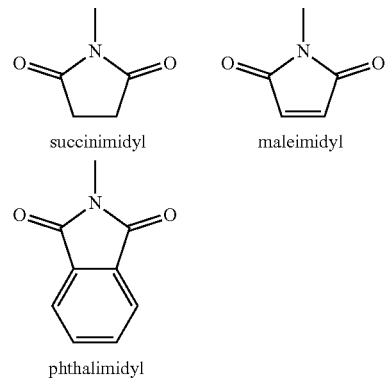

succinimidyl    maleimidyl phthalimidyl

Aminocarbonyloxy: —OC(=O)NR$^1$R$^2$, wherein $R^1$ and $R^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R¹)CONR²R³ wherein R² and R³ are independently amino substituents, as defined for amino groups, and R¹ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, and —NMeCONEt₂.

Guanidino: —NH—C(=NH)NH₂.

Tetrazolyl: a five membered aromatic ring having four nitrogen atoms and one carbon atom,

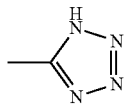

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine (amidino): —C(=NR)NR₂, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH₂, —C(=NH)NMe₂, and —C(=NMe)NMe₂.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH₃ and —SSCH₂CH₃.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH₃ and —S(=O)CH₂CH₃.

Sulfone (sulfonyl): —S(=O)₂R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)₂C₄F₉ (nonaflyl), —S(=O)₂CH₂CF₃ (tresyl), —S(=O)₂CH₂CH₂NH₂ (tauryl), —S(=O)₂Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO₂H.

Sulfonic acid (sulfo): —S(=O)₂OH, —SO₃H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH₃ (methoxysulfinyl; methyl sulfinate) and —S(=O)OCH₂CH₃ (ethoxysulfinyl; ethyl sulfinate).

Sulfonate (sulfonic acid ester): —S(=O)₂OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)₂OCH₃ (methoxysulfonyl; methyl sulfonate) and —S(=O)₂OCH₂CH₃ (ethoxysulfonyl; ethyl sulfonate). Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH₃ and —OS(=O)CH₂CH₃.

Sulfonyloxy: —OS(=O)₂R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)₂CH₃ (mesylate) and —OS(=O)₂CH₂CH₃ (esylate).

Sulfate: —OS(=O)₂OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)₂OCH₃ and —SO(=O)₂OCH₂CH₃.

Sulfamyl (sulfamoyl; sulfinic acid amide; sulfinamide): —S(=O)NR¹R², wherein R¹ and R² are independently amino substituents, as defined for amino groups. Examples of sulfamyl groups include, but are not limited to, —S(=O)NH₂, —S(=O)NH(CH₃), —S(=O)N(CH₃)₂, —S(=O)NH(CH₂CH₃), —S(=O)N(CH₂CH₃)₂, and —S(=O)NHPh.

Sulfonamido (sulfinamoyl; sulfonic acid amide; sulfonamide): —S(=O)₂NR¹R², wherein R¹ and R² are independently amino substituents, as defined for amino groups. Examples of sulfonamido groups include, but are not limited to, —S(=O)₂NH₂, —S(=O)₂NH(CH₃), —S(=O)₂N(CH₃)₂, —S(=O)₂NH(CH₂CH₃), —S(=O)₂N(CH₂CH₃)₂, and —S(=O)₂NHPh.

Sulfamino: —NR¹S(=O)₂OH, wherein R¹ is an amino substituent, as defined for amino groups. Examples of sulfamino groups include, but are not limited to, —NHS(=O)₂OH and —N(CH₃)S(=O)₂OH.

Sulfonamino: —NR¹S(=O)₂R, wherein R¹ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH3)2, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated C$_{3-12}$alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Carbamate nitrogen protecting group: the term "carbamate nitrogen protecting group" pertains to a moiety which masks the nitrogen in the imine bond, and these are well known in the art. These groups have the following structure:

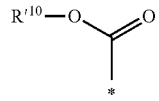

wherein R'$^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Hemi-aminal nitrogen protecting group: the term "hemi-aminal nitrogen protecting group" pertains to a group having the following structure:

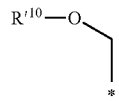

wherein R'$^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference.

The groups Carbamate nitrogen protecting group and Hemi-aminal nitrogen protecting group may be jointly termed a "nitrogen protecting group for synthesis".

Conjugates

The present disclosure provides a conjugate comprising a PBD compound connected to the antibody via a Linker Unit.

In one embodiment, the conjugate comprises the antibody connected to a spacer connecting group, the spacer connected to a trigger, the trigger connected to a self-immolative linker, and the self-immolative linker connected to the N10 position of the PBD compound. Such a conjugate is illustrated below:

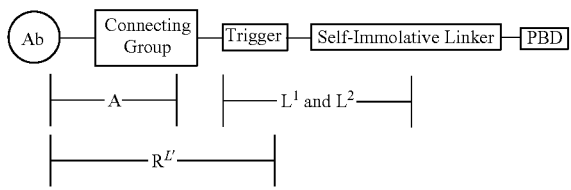

where Ab is the antibody as defined above and PBD is a pyrrolobenzodiazepine compound (D), as described herein. The illustration shows the portions that correspond to $R^{L'}$, A, $L^1$ and $L^2$ in certain embodiments of the disclosure. $R^{L'}$ may be either $R^{L1'}$ or $R^{L2'}$. D is $D^L$ with $R^{L1'}$ or $R^{L2'}$ removed.

The present disclosure is suitable for use in providing a PBD compound to a preferred site in a subject. In the preferred embodiments, the conjugate allows the release of an active PBD compound that does not retain any part of the linker. There is no stub present that could affect the reactivity of the PBD compound.

The linker attaches the antibody to the PBD drug moiety D through covalent bond(s). The linker is a bifunctional or multifunctional moiety which can be used to link one or more drug moiety (D) and an antibody unit (Ab) to form antibody-drug conjugates (ADC). The linker ($R^L$) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g. N-terminus or amino acid side chain such as lysine, of the antibody (Ab) can form a bond with a functional group of a linker or spacer reagent, PBD drug moiety (D) or drug-linker reagent ($D^L$, $D-R^L$), where $R^L$ can be $R^{L1}$ or $R^{L2}$.

The linkers of the ADC preferably prevent aggregation of ADC molecules and keep the ADC freely soluble in aqueous media and in a monomeric state.

The linkers of the ADC are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

In another embodiment, the linker may be substituted with groups which modulate aggregation, solubility or reactivity. For example, a sulfonate substituent may increase water solubility of the reagent and facilitate the coupling reaction of the linker reagent with the antibody or the drug moiety, or facilitate the coupling reaction of Ab-L with $D^L$, or $D^L$-L with Ab, depending on the synthetic route employed to prepare the ADC.

In one embodiment, L-$R^{L'}$ is a group:

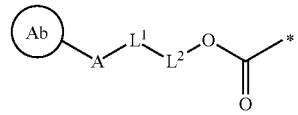

where the asterisk indicates the point of attachment to the Drug Unit (D), Ab is the antibody (L), $L^1$ is a linker, A is a connecting group connecting $L^1$ to the antibody, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present disclosure.

$L^1$ may comprise a contiguous sequence of amino acids. The amino acid sequence may be the target substrate for enzymatic cleavage, thereby allowing release of L-$R^{L'}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker.

In one embodiment, $L^2$ is a substrate for enzymatic activity, thereby allowing release of L-$R^{L'}$ from the N10 position.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:
—C(=O)NH—,
—C(=O)O—,
—NHC(=O)—,
—OC(=O)—,

—OC(=O)O—,

—NHC(=O)O—,

—OC(=O)NH—, and

—NHC(=O)NH—.

An amino group of L¹ that connects to L² may be the N-terminus of an amino acid or may be derived from an amino group of an amino acid side chain, for example a lysine amino acid side chain.

A carboxyl group of L¹ that connects to L² may be the C-terminus of an amino acid or may be derived from a carboxyl group of an amino acid side chain, for example a glutamic acid amino acid side chain.

A hydroxyl group of L¹ that connects to L² may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and L² together form the group:

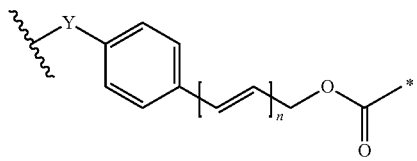

where the asterisk indicates the point of attachment to the N10 position, the wavy line indicates the point of attachment to the linker L¹, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

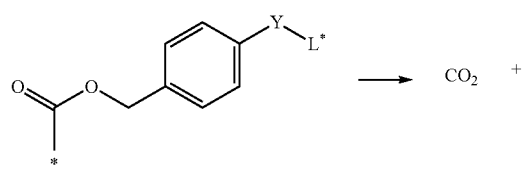

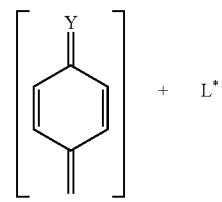

where L* is the activated form of the remaining portion of the linker. These groups have the advantage of separating the site of activation from the compound being protected. As described above, the phenylene group may be optionally substituted.

In one embodiment described herein, the group L* is a linker L¹ as described herein, which may include a dipeptide group.

In another embodiment, —C(=O)O— and L² together form a group selected from:

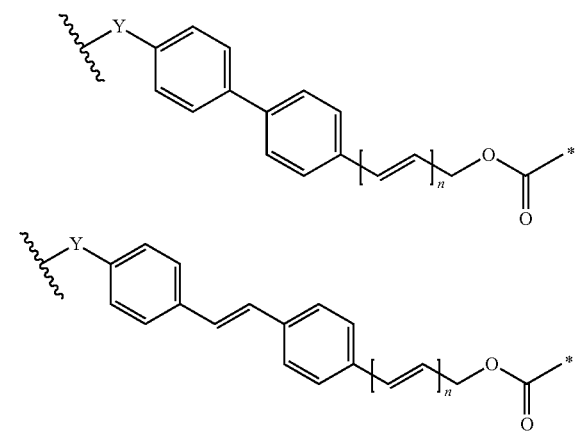

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and L² together form a group selected from:

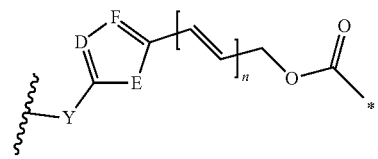

where the asterisk, the wavy line, Y, and n are as defined above, E is O, S or NR, D is N, CH, or CR, and F is N, CH, or CR.

In one embodiment, D is N.

In one embodiment, D is CH.

In one embodiment, E is O or S.

In one embodiment, F is CH.

In a preferred embodiment, the linker is a cathepsin labile linker.

In one embodiment, $L^1$ comprises a dipeptide The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
Phe-Lys-,
Val-Ala-,
Val-Lys-,
Ala-Lys-,
Val-Cit-,
Phe-Cit-,
Leu-Cit-,
Ile-Cit-,
Phe-Arg-,
Trp-Cit-
where Cit is citrulline.

Preferably, the group —$X_1$—$X_2$— in dipeptide, —NH—$X_1$—$X_2$—CO—, is selected from:
Phe-Lys-,
Val-Ala-,
Val-Lys-,
Ala-Lys-,
Val-Cit-.

Most preferably, the group —$X_1$—$X_2$— in dipeptide, —NH—$X_1$—$X_2$—CO—, is -Phe-Lys- or -Val-Ala-.

Other dipeptide combinations may be used, including those described by Dubowchik et al., *Bioconjugate Chemistry*, 2002, 13, 855-869, which is incorporated herein by reference.

In one embodiment, the amino acid side chain is derivatised, where appropriate. For example, an amino group or carboxy group of an amino acid side chain may be derivatised. In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the disclosure, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO—PABC—. The PABC group is connected directly to the N10 position.

Preferably, the self-immolative linker and the dipeptide together form the group —NH-Phe-Lys-CO—NH-PABC—, which is illustrated below:

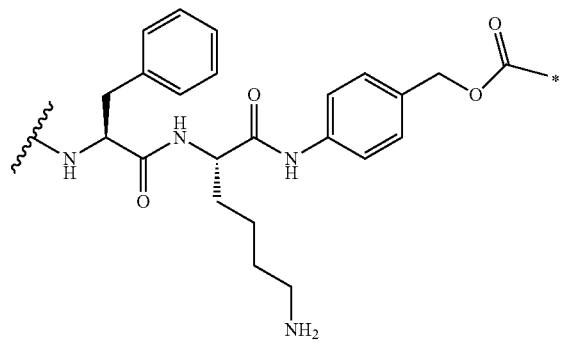 [SMILES: *N[C@@H](Cc1ccccc1)C(=O)N[C@@H](CCCCN)C(=O)Nc1ccc(COC(C)=O)cc1]

where the asterisk indicates the point of attachment to the N10 position, and the wavy line indicates the point of attachment to the remaining portion of the linker $L^1$ or the point of attachment to A. Preferably, the wavy line indicates the point of attachment to A.

The side chain of the Lys amino acid may be protected, for example, with Boc, Fmoc, or Alloc, as described above.

Alternatively, the self-immolative linker and the dipeptide together form the group —NH-Val-Ala-CO—NH—PABC—, which is illustrated below:

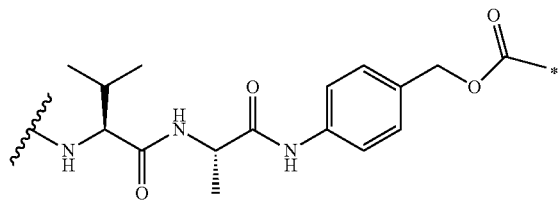 [SMILES: *N[C@H](C(=O)N[C@@H](C)C(=O)Nc1ccc(COC(C)=O)cc1)C(C)C]

where the asterisk and the wavy line are as defined above.

Alternatively, the self-immolative linker and the dipeptide together form the group —NH-Val-Cit-CO—NH—PABC—, which is illustrated below:

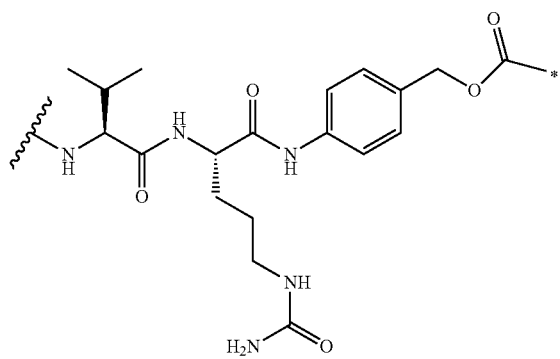 [SMILES: *N[C@H](C(=O)N[C@@H](CCCNC(N)=O)C(=O)Nc1ccc(COC(C)=O)cc1)C(C)C]

where the asterisk and the wavy line are as defined above.

In one embodiment, A is a covalent bond. Thus, $L^1$ and the antibody are directly connected. For example, where $L^1$ comprises a contiguous amino acid sequence, the N-terminus of the sequence may connect directly to the antibody.

Thus, where A is a covalent bond, the connection between the antibody and $L^1$ may be selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—C(=O)NHC(=O)—,
—S—,
—S—S—,
—CH₂C(=O)—, and
=N—NH—.

An amino group of $L^1$ that connects to the antibody may be the N-terminus of an amino acid or may be derived from an amino group of an amino acid side chain, for example a lysine amino acid side chain.

An carboxyl group of $L^1$ that connects to the antibody may be the C-terminus of an amino acid or may be derived from a carboxyl group of an amino acid side chain, for example a glutamic acid amino acid side chain.

A hydroxyl group of $L^1$ that connects to the antibody may be derived from a hydroxyl group of an amino acid side chain, for example a serine amino acid side chain.

A thiol group of $L^1$ that connects to the antibody may be derived from a thiol group of an amino acid side chain, for example a serine amino acid side chain.

The comments above in relation to the amino, carboxyl, hydroxyl and thiol groups of $L^1$ also apply to the antibody.

In one embodiment, $L^2$ together with —OC(=O)— represents:

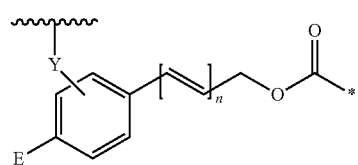

where the asterisk indicates the point of attachment to the N10 position, the wavy line indicates the point of attachment to $L^1$, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, $NO_2$, R or OR. Preferably n is 0 or 1, most preferably 0.

E is selected such that the group is susceptible to activation, e.g. by light or by the action of an enzyme. E may be —$NO_2$ or glucoronic acid. The former may be susceptible to the action of a nitroreductase, the latter to the action of a β-glucuronidase.

In this embodiment, the self-immolative linker will allow for release of the protected compound when E is activated, proceeding along the lines shown below (for n=0):

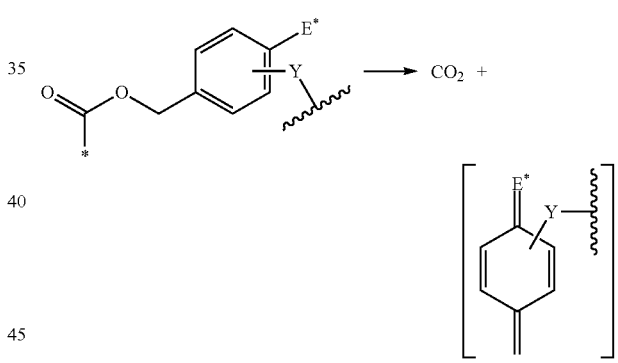

where the asterisk indicates the point of attachment to the N10 position, E* is the activated form of E, and Y is as described above. These groups have the advantage of separating the site of activation from the compound being protected. As described above, the phenylene group may be optionally further substituted.

The group Y may be a covalent bond to $L^1$.
The group Y may be a functional group selected from:
—C(=O)—
—NH—
—O—
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH, —C(=O)NHC(=O)—, and

—S—.

Where $L^1$ is a dipeptide, it is preferred that Y is —NH— or —C(=O)—, thereby to form an amide bond between $L^1$ and Y. In this embodiment, the dipeptide sequence need not be a substrate for an enzymatic activity.

In another embodiment, A is a spacer group. Thus, $L^1$ and the antibody are indirectly connected.

$L^1$ and A may be connected by a bond selected from:

—C(=O)NH—,

—C(=O)O—,

—NHC(=O)—,

—OC(=O)—,

—OC(=O)O—,

—NHC(=O)O—,

—OC(=O)NH—, and

—NHC(=O)NH—.

In one embodiment, the group A is:

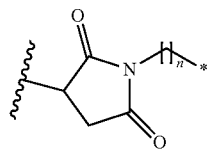

where the asterisk indicates the point of attachment to $L^1$, the wavy line indicates the point of attachment to the antibody, and n is 0 to 6. In one embodiment, n is 5.

In one embodiment, the group A is:

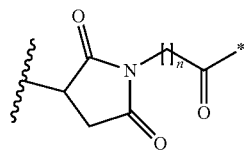

where the asterisk indicates the point of attachment to $L^1$, the wavy line indicates the point of attachment to the antibody, and n is 0 to 6. In one embodiment, n is 5.

In one embodiment, the group A is:

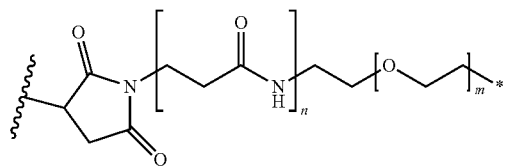

where the asterisk indicates the point of attachment to $L^1$, the wavy line indicates the point of attachment to the antibody, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the group A is:

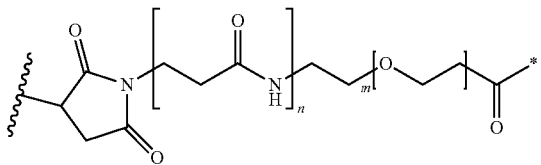

where the asterisk indicates the point of attachment to $L^1$, the wavy line indicates the point of attachment to the antibody, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the connection between the antibody and A is through a thiol residue of the antibody and a maleimide group of A.

In one embodiment, the connection between the antibody and A is:

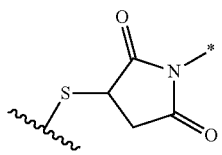 [SMILES: *SC1CC(=O)N(*)C1=O]

where the asterisk indicates the point of attachment to the remaining portion of A and the wavy line indicates the point of attachment to the remaining portion of the antibody. In this embodiment, the S atom is typically derived from the antibody.

In each of the embodiments above, an alternative functionality may be used in place of the maleimide-derived group shown below:

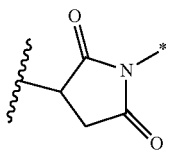

where the wavy line indicates the point of attachment to the antibody as before, and the asterisk indicates the bond to the remaining portion of the A group.

In one embodiment, the maleimide-derived group is replaced with the group:

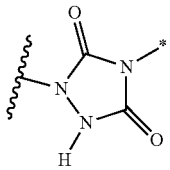

where the wavy line indicates point of attachment to the antibody, and the asterisk indicates the bond to the remaining portion of the A group.

In one embodiment, the maleimide-derived group is replaced with a group, which optionally together with the antibody, is selected from:

—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—S—,
—CH$_2$C(=O)—
—C(=O)CH$_2$—,
=N—NH—, and
—NH—N=.

In one embodiment, the maleimide-derived group is replaced with a group, which optionally together with the antibody, is selected from:

where the wavy line indicates either the point of attachment to the antibody or the bond to the remaining portion of the A group, and the asterisk indicates the other of the point of attachment to the antibody or the bond to the remaining portion of the A group.

Other groups suitable for connecting $L^1$ to the antibody are described in WO 2005/082023.

In one embodiment, the Connecting Group A is present, the Trigger $L^1$ is present and Self-Immolative Linker $L^2$ is absent. Thus, $L^1$ and the Drug unit are directly connected via a bond. Equivalently in this embodiment, $L^2$ is a bond. This may be particularly relevant when $D^L$ is of Formula II.

$L^1$ and D may be connected by a bond selected from:
—C(=O)N<,
—C(=O)O—,
—NHC(=O)—,
—OC(=O)—,
—OC(=O)O—,
—NHC(=O)O—,
—OC(=O)N<, and
—NHC(=O)N<,
where N< or O— are part of D.

In one embodiment, $L^1$ and D are preferably connected by a bond selected from:
—C(=O)N<, and
—NHC(=O)—.

In one embodiment, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —X$_1$—X$_2$— in dipeptide, —NH—X$_1$—X$_2$—CO—, is selected from:

Phe-Lys-,
Val-Ala-,
Val-Lys-,
Ala-Lys-,
Val-Cit-,
Phe-Cit-,
Leu-Cit-,
Ile-Cit-,
Phe-Arg-, and
Trp-Cit-;

where Cit is citrulline. In such a dipeptide, —NH— is the amino group of X$_1$, and CO is the carbonyl group of X$_2$.

Preferably, the group —X$_1$—X$_2$— in dipeptide, —NH—X$_1$—X$_2$—CO—, is selected from:

Phe-Lys-,
Val-Ala-,
Val-Lys-,
Ala-Lys-, and
Val-Cit-.

Most preferably, the group —X$_1$—X$_2$— in dipeptide, —NH—X$_1$—X$_2$—CO—, is -Phe-Lys- or -Val-Ala-.

Other dipeptide combinations of interest include:

Gly-Gly-,
Pro-Pro-, and
Val-Glu-.

Other dipeptide combinations may be used, including those described above.

In one embodiment, $L^1$-D is:

where —NH—X$_1$—X$_2$—CO is the dipeptide, —N< is part of the Drug unit, the asterisk indicates the points of attachment to the remainder of the Drug unit, and the wavy line indicates the point of attachment to the remaining portion of $L^1$ or the point of attachment to A. Preferably, the wavy line indicates the point of attachment to A.

In one embodiment, the dipeptide is valine-alanine and $L^1$-D is:

where the asterisks, —N< and the wavy line are as defined above.

In one embodiment, the dipeptide is phenylalanine-lysine and $L^1$-D is:

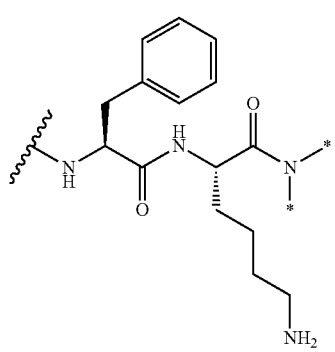 [SMILES: *N[C@@H](Cc1ccccc1)C(=O)N[C@@H](CCCCN)C(=O)N(*)*]

where the asterisks, —N< and the wavy line are as defined above.

In one embodiment, the dipeptide is valine-citrulline.

In one embodiment, the groups A-$L^1$ are:

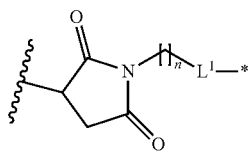

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

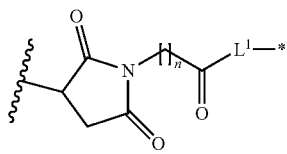

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

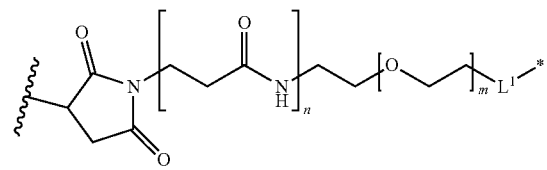

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-$L^1$ are:

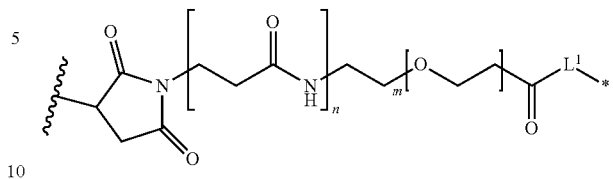

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 7, preferably 3 to 7, most preferably 3 or 7.

In one embodiment, the groups A-$L^1$ are:

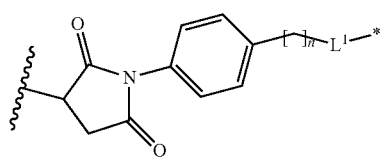

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

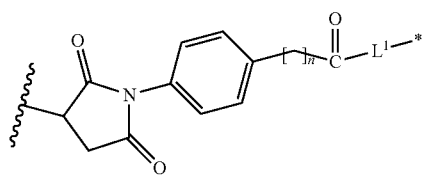

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

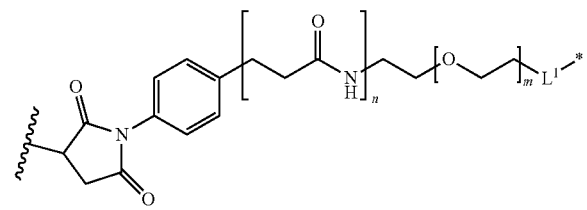

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L$^1$ is:

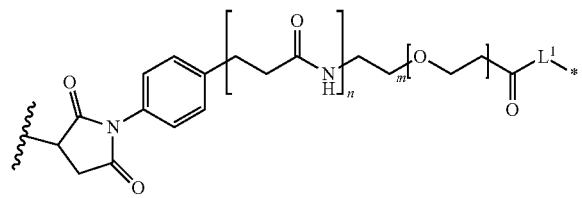

where the asterisk indicates the point of attachment to L$^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L$^1$ are:

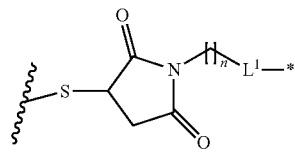

where the asterisk indicates the point of attachment to L$^2$ or D, S is a sulfur group of the Ligand unit, the wavy line indicates the point of attachment to the rest of the Ligand unit, and n is 0 to 6. In one embodiment, n is 5.

In one embodiment, the group A-L$^1$ are:

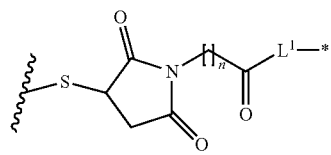

where the asterisk indicates the point of attachment to L$^2$ or D, S is a sulfur group of the Ligand unit, the wavy line indicates the point of attachment to the remainder of the Ligand unit, and n is 0 to 6. In one embodiment, n is 5.

In one embodiment, the groups A$^1$-L$^1$ are:

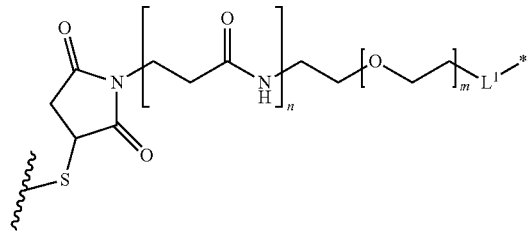

where the asterisk indicates the point of attachment to L$^2$ or D, S is a sulfur group of the Ligand unit, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A$^1$-L$^1$ are:

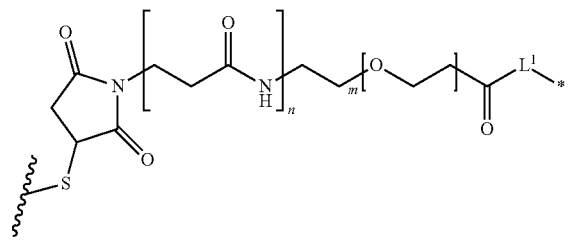

where the asterisk indicates the point of attachment to L$^2$ or D, the wavy line indicates the point of attachment to the Ligand unit, n is 0 or 1, and m is 0 to 30. In a preferred embodiment, n is 1 and m is 0 to 10, 1 to 7, preferably 4 to 8, most preferably 4 or 8.

In one embodiment, the groups A$^1$-L$^1$ are:

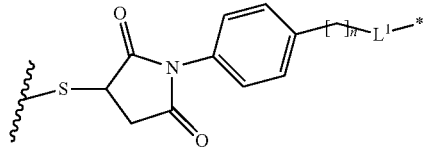

where the asterisk indicates the point of attachment to L$^2$ or D, the wavy line indicates the point of attachment to the remainder of the Ligand unit, and n is 0 to 6. In one embodiment, n is 5.

In one embodiment, the groups A$^1$-L$^1$ are:

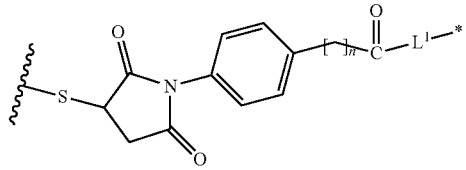

where the asterisk indicates the point of attachment to L$^2$ or D, the wavy line indicates the point of attachment to the remainder of the Ligand unit, and n is 0 to 6. In one embodiment, n is 5.

In one embodiment, the groups A$^1$-L$^1$ are:

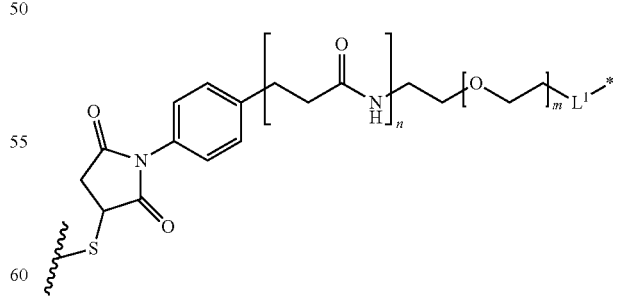

where the asterisk indicates the point of attachment to L$^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

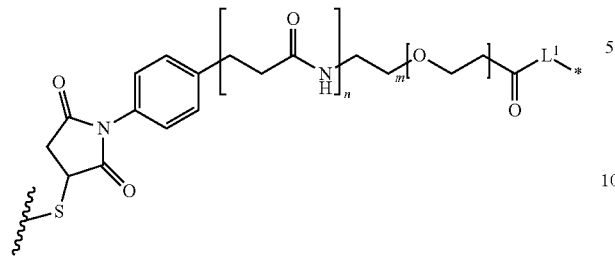

where the asterisk indicates the point of attachment to $L^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

The group $R^{L'}$ is derivable from the group $R^L$. The group $R^L$ may be converted to a group $R^{L'}$ by connection of an antibody to a functional group of $R^L$. Other steps may be taken to convert $R^L$ to $R^{L'}$. These steps may include the removal of protecting groups, where present, or the installation of an appropriate functional group.

$R^L$

Linkers can include protease-cleavable peptidic moieties comprising one or more amino acid units. Peptide linker reagents may be prepared by solid phase or liquid phase synthesis methods (E. Schröder and K. Lübke, *The Peptides*, volume 1, pp 76-136 (1965) Academic Press) that are well known in the field of peptide chemistry, including t-BOC chemistry (Geiser et al "Automation of solid-phase peptide synthesis" in *Macromolecular Sequencing and Synthesis*, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

Exemplary amino acid linkers include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Amino acid side chains include those occurring naturally, as well as minor amino acids and non-naturally occurring amino acid analogs, such as citrulline. Amino acid side chains include hydrogen, methyl, isopropyl, isobutyl, sec-butyl, benzyl, p-hydroxybenzyl, —$CH_2OH$, —$CH(OH)$$CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3$ NHCHO, —$(CH_2)_4NHC(=NH)NH_2$, —$(CH_2)_4$ $NH_2$, —$(CH_2)_4NHCOCH_3$, —$(CH_2)_4NHCHO$, —$(CH_2)_3$ $NHCONH_2$, —$(CH_2)_4NHCONH_2$, —$CH_2CH_2CH(OH)$ $CH_2NH_2$, 2-pyridylmethyl-, 3-pyridylmethyl-, 4-pyridylmethyl-, phenyl, cyclohexyl, as well as the following structures:

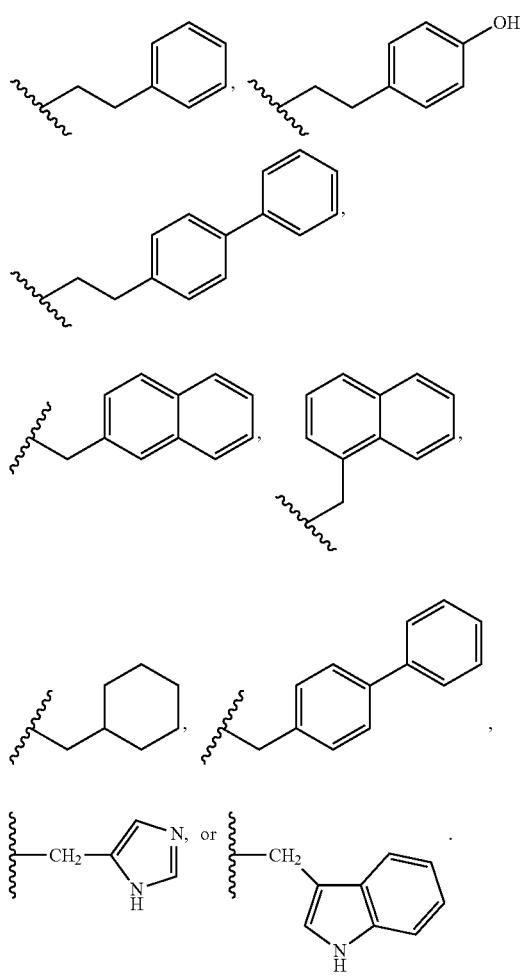

When the amino acid side chains include other than hydrogen (glycine), the carbon atom to which the amino acid side chain is attached is chiral. Each carbon atom to which the amino acid side chain is attached is independently in the (S) or (R) configuration, or a racemic mixture. Drug-linker reagents may thus be enantiomerically pure, racemic, or diastereomeric.

In exemplary embodiments, amino acid side chains are selected from those of natural and non-natural amino acids, including alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, norleucine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit).

An exemplary valine-citrulline (val-cit or vc) dipeptide linker reagent useful for constructing a linker-PBD drug moiety intermediate for conjugation to an antibody, having a para-aminobenzylcarbamoyl (PAB) self-immolative spacer has the structure:

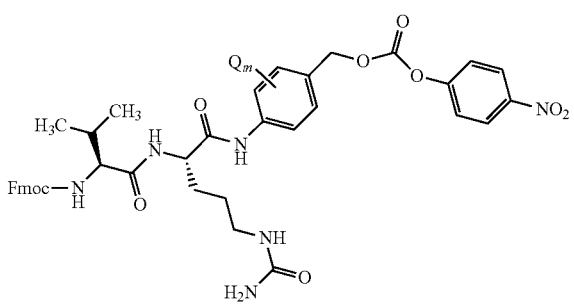

where $Q$ is $C_1$-$C_8$ alkyl, —O—($C_1$-$C_8$ alkyl), -halogen, —NO$_2$ or —CN; and m is an integer ranging from 0-4.

An exemplary phe-lys(Mtr) dipeptide linker reagent having a p-aminobenzyl group can be prepared according to Dubowchik, et al. (1997) Tetrahedron Letters, 38:5257-60, and has the structure:

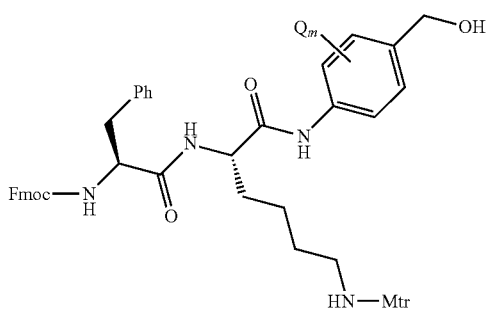

where Mtr is mono-4-methoxytrityl, Q is $C_1$-$C_8$ alkyl, —O—($C_1$-$C_8$ alkyl), -halogen, —NO$_2$ or —ON; and m is an integer ranging from 0-4.

The "self-immolative linker" PAB (para-aminobenzyloxycarbonyl), attaches the drug moiety to the antibody in the antibody drug conjugate (Carl et al (1981) J. Med. Chem. 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other examples of self-immolative spacers besides PAB include, but are not limited to: (i) aromatic compounds that are electronically similar to the PAB group such as 2-aminoimidazol-5-methanol derivatives (Hay et al. (1999) Bioorg. Med. Chem. Lett. 9:2237), thiazoles (U.S. Pat. No. 7,375,078), multiple, elongated PAB units (de Groot et al (2001) J. Org. Chem. 66:8815-8830); and ortho or para-aminobenzylacetals; and (ii) homologated styryl PAB analogs (U.S. Pat. No. 7,223, 837). Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo [2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacers useful in ADC.

In one embodiment, a valine-citrulline dipeptide PAB analog reagent has a 2,6 dimethyl phenyl group and has the structure:

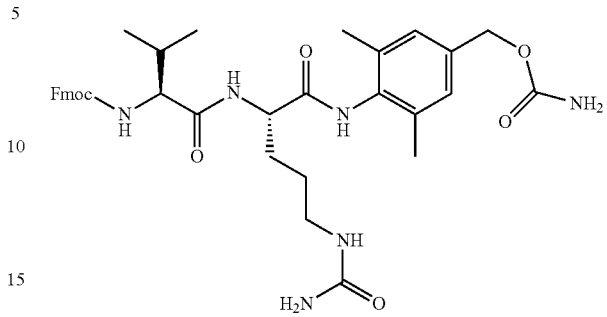

Linker reagents useful for the antibody drug conjugates of the disclosure include, but are not limited to: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and bis-maleimide reagents: DTME, BMB, BMDB, BMH, BMOE, 1,8-bis-maleimidodiethyleneglycol (BM(PEO)$_2$), and 1,11-bis-maleimidotriethyleneglycol (BM(PEO)$_3$), which are commercially available from Pierce Biotechnology, Inc., ThermoScientific, Rockford, Ill., and other reagent suppliers. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, PBD drug moiety, or linker intermediate include iodoacetamide, bromoacetamide, vinyl pyridine, disulfide, pyridyl disulfide, isocyanate, and isothiocyanate.

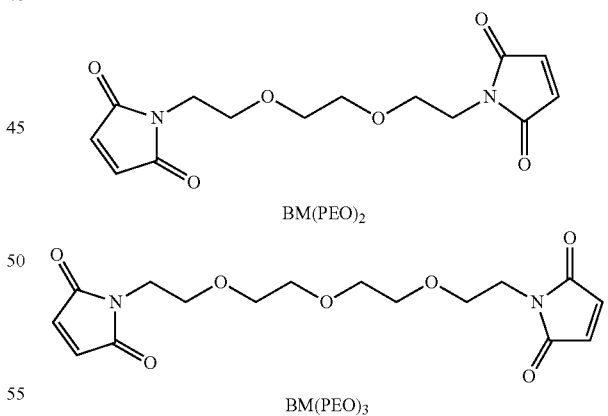

Other embodiments of linker reagents are: N-succinimidyl-4-(2-pyridylthio)pentanoate (SPP), N-succinimidyl-3-(2-pyridyldithio) propionate (SPDP, Carlsson et al (1978) Biochem. J. 173:723-737), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345; WO 02/088172; US 2003130189; US2003096743; WO 03/026577; WO 03/043583; and WO 04/032828.

The Linker may be a dendritic type linker for covalent attachment of more than one drug moiety through a branching, multifunctional linker moiety to an antibody (US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic or branched linker.

One exemplary embodiment of a dendritic type linker has the structure:

The group $R^c$ is intended to be removable under the same conditions as those required for the removal of the group $R^{10}$, for example to yield an N10-C11 imine bond, a carbinolamine and so on. The capping group acts as a protecting group for the intended functionality at the N10 position. The capping group is intended not to be reactive towards an antibody. For example, $R^C$ is not the same as $R^L$.

Compounds having a capping group may be used as intermediates in the synthesis of dimers having an imine monomer. Alternatively, compounds having a capping group may be used as conjugates, where the capping group is removed at the target location to yield an imine, a carbinolamine, a substituted carbinolamine and so on. Thus, in this embodiment, the capping group may be referred to as a therapeutically removable nitrogen protecting group, as defined in the inventors' earlier application WO 00/12507.

In one embodiment, the group $R^C$ is removable under the conditions that cleave the linker $R^L$ of the group $R^{10}$. Thus, in one embodiment, the capping group is cleavable by the action of an enzyme.

In an alternative embodiment, the capping group is removable prior to the connection of the linker $R^L$ to the antibody. In this embodiment, the capping group is removable under conditions that do not cleave the linker $R^L$.

Where a compound includes a functional group $G^1$ to form a connection to the antibody, the capping group is removable prior to the addition or unmasking of $G^1$.

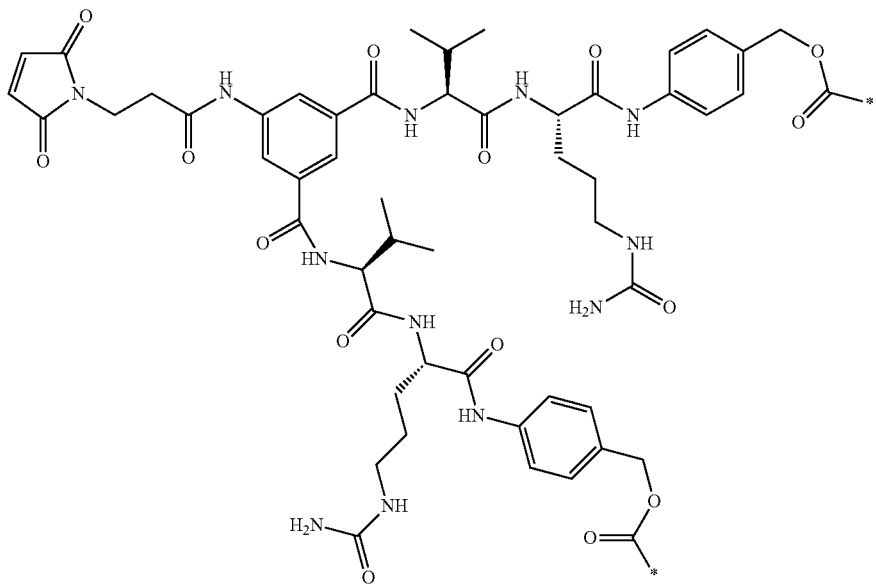 [SMILES: *C(=O)OCc1ccc(NC(=O)[C@H](CCCNC(N)=O)NC(=O)[C@@H](NC(=O)c2cc(NC(=O)CCN3C(=O)C=CC3=O)cc(C(=O)N[C@H](C(=O)N[C@@H](CCCNC(N)=O)C(=O)Nc3ccc(COC(*)=O)cc3)C(C)C)c2)C(C)C)cc1]

where the asterisk indicate the point of attachment to the N10 position of a PBD moiety.

$R^c$, Capping Group

The conjugate of the first aspect of the disclosure may have a capping group $R^C$ at the N10 position.

The group $R^C$ is removable from the N10 position of the PBD moiety to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinolamine.

In one embodiment, $R^C$, may be a protecting group that is removable to leave an N10-C11 imine bond, a carbinolamine, a substituted carbinolamine, or, where $QR^{11}$ is $OSO_3M$, a bisulfite adduct. In one embodiment, $R^C$ is a protecting group that is removable to leave an N10-C11 imine bond.

The capping group may be used as part of a protecting group strategy to ensure that only one of the monomer units in a dimer is connected to an antibody.

The capping group may be used as a mask for a N10-C11 imine bond. The capping group may be removed at such time as the imine functionality is required in the compound. The capping group is also a mask for a carbinolamine, a substituted carbinolamine, and a bisulfite adduct, as described above.

$R^C$ may be an N10 protecting group, such as those groups described in the inventors' earlier application, WO 00/12507. In one embodiment, $R^C$ is a therapeutically removable nitrogen protecting group, as defined in the inventors' earlier application, WO 00/12507.

In one embodiment, $R^C$ is a carbamate protecting group.

In one embodiment, the carbamate protecting group is selected from:

Alloc, Fmoc, Boc, Troc, Teoc, Psec, Cbz and PNZ.

Optionally, the carbamate protecting group is further selected from Moc.

In one embodiment, $R_C$ is a linker group $R^L$ lacking the functional group for connection to the antibody.

This application is particularly concerned with those $R_C$ groups which are carbamates.

In one embodiment, $R_C$ is a group:

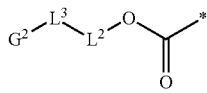

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

Where $L^3$ and $L^2$ are both covalent bonds, $G^2$ and OC(=O) together form a carbamate protecting group as defined above.

$L^1$ is as defined above in relation to $R^{10}$.

$L^2$ is as defined above in relation to $R^{10}$.

Various terminating groups are described below, including those based on well known protecting groups.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from:

Alloc, Fmoc, Boc, Troc, Teoc, Psec, Cbz and PNZ.

Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, NHR and NRR'. Preferably, $G^3$ is NRR'.

In one embodiment $G^2$ is the group:

where the asterisk indicates the point of attachment to $L^3$, n is 0 to 6 and $G^4$ is selected from OH, OR, SH, SR, COOR, $CONH_2$, CONHR, CONRR', $NH_2$, NHR, NRR', $NO_2$, and halo. The groups OH, SH, $NH_2$ and NHR are protected. In one embodiment, n is 1 to 6, preferably n is 5. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Most preferably $G^4$ is OMe.

In one embodiment, the group $G^2$ is:

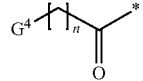

where the asterisk indicates the point of attachment to $L^3$, and n and $G^4$ are as defined above.

In one embodiment, the group $G^2$ is:

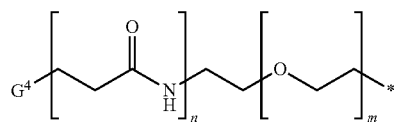

where the asterisk indicates the point of attachment to $L^3$, n is 0 or 1, m is 0 to 50, and $G^4$ is selected from OH, OR, SH, SR, COOR, $CONH_2$, CONHR, CONRR', $NH_2$, NHR, NRR', $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

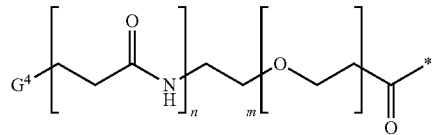

where the asterisk indicates the point of attachment to $L^3$, and n, m and $G^4$ are as defined above.

In one embodiment, the group $G^2$ is:

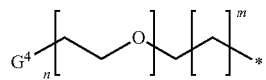

where n is 1-20, m is 0-6, and $G^4$ is selected from OH, OR, SH, SR, COOR, $CONH_2$, CONHR, CONRR', $NH_2$, NHR, NRR', $NO_2$, and halo. In one embodiment, n is 1-10. In another embodiment, n is 10 to 50, preferably 20 to 40. In one embodiment, n is 1. In one embodiment, m is 1. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

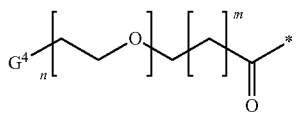

where the asterisk indicates the point of attachment to $L^3$, and n, m and $G^4$ are as defined above.

In each of the embodiments above $G^4$ may be OH, SH, $NH_2$ and NHR. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, $NH_2$ or NHR are protected with Boc, Moc, Z—Cl, Fmoc, Z, or Alloc.

In one embodiment, the group $G^2$ is present in combination with a group $L^3$, which group is a dipeptide.

The capping group is not intended for connection to the antibody. Thus, the other monomer present in the dimer serves as the point of connection to the antibody via a linker.

Accordingly, it is preferred that the functionality present in the capping group is not available for reaction with an antibody. Thus, reactive functional groups such as OH, SH, $NH_2$, COOH are preferably avoided. However, such functionality may be present in the capping group if protected, as described above.

Embodiments

Embodiments of the present disclosure include ConjA wherein the antibody is as defined above.

Embodiments of the present disclosure include ConjB wherein the antibody is as defined above.

Embodiments of the present disclosure include ConjC wherein the antibody is as defined above.

Embodiments of the present disclosure include ConjD wherein the antibody is as defined above.

Embodiments of the present disclosure include ConjE wherein the antibody is as defined above.

Embodiments of the present disclosure include ConjF wherein the antibody is as defined above.

Embodiments of the present disclosure include ConjG wherein the antibody is as defined above.

Embodiments of the present disclosure include ConjH wherein the antibody is as defined above.

Drug Loading

The drug loading is the average number of PBD drugs per antibody, e.g. antibody. Where the compounds of the disclosure are bound to native cysteines, drug loading may range from 1 to 8 drugs ($D^L$) per antibody, i.e. where 1, 2, 3, 4, 5, 6, 7, and 8 drug moieties are covalently attached to the antibody. Compositions of conjugates include collections of antibodies, conjugated with a range of drugs, from 1 to 8. Where the compounds of the disclosure are bound to lysines, drug loading may range from 1 to 80 drugs ($D^L$) per antibody, although an upper limit of 40, 20, 10 or 8 may be preferred. Compositions of conjugates include collections of antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present disclosure which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Alternatively, site-specific conjugation can be achieved by engineering antibodies to contain unnatural amino acids in their heavy and/or light chains as described by Axup et al. ((2012), Proc Natl Acad Sci USA. 109(40):16101-16116). The unnatural amino acids provide the additional advantage that orthogonal chemistry can be designed to attach the linker reagent and drug.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the disclosure include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per antibody is in the range 1 to 20. In some embodiments the range is selected from 1 to 8, 2 to 8, 2 to 6, 2 to 4, and 4 to 8.

In some embodiments, there is one dimer pyrrolobenzodiazepine group per antibody.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The disclosure includes compounds where a solvent adds across the imine bond of the PBD moiety, which is illustrated below where the solvent is water or an alcohol (R$^A$OH, where R$^A$ is C$_{1-4}$ alkyl):

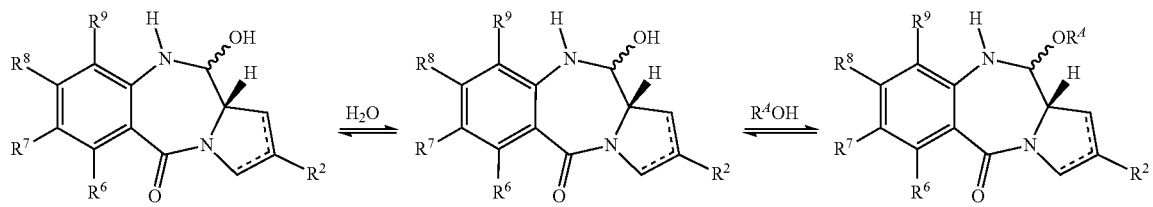

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the disclosure may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the disclosure may contain asymmetric or chiral centers, and therefore exist in different stereoisomeric forms. It is intended that all stereoisomeric forms of the compounds of the disclosure, including but not limited to, diastereomers, enantiomers and atropisomers, as well as mixtures thereof such as racemic mixtures, form part of the present disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or I meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

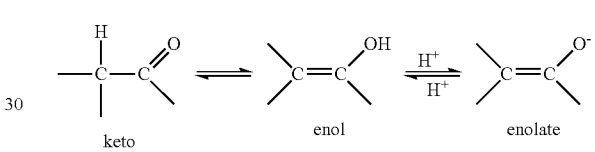

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the disclosure include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present disclosure, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this disclosure any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity

In Vitro Cell Proliferation Assays

Generally, the cytotoxic or cytostatic activity of an antibody-drug conjugate (ADC) is measured by: exposing mammalian cells having receptor proteins to the antibody of the ADC in a cell culture medium; culturing the cells for a period from about 6 hours to about 5 to 7 days; and measuring cell viability. Cell-based in vitro assays are used to measure viability (proliferation), cytotoxicity, and induction of apoptosis (caspase activation) of an ADC of the disclosure.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 µl per well) into black 96 well plates. Plates of adherent cell lines are incubated overnight to allow adherence. Suspension cell cultures can be used on the day of seeding.

A stock solution (1 ml) of ADC (20 µg/ml) is made in the appropriate cell culture medium. Serial 10-fold dilutions of stock ADC are made in 15 ml centrifuge tubes by serially transferring 100 µl to 900 µl of cell culture medium.

Four replicate wells of each ADC dilution (100 µl) are dispensed in 96-well black plates, previously plated with cell suspension (100 µl), resulting in a final volume of 200 µl. Control wells receive cell culture medium (100 µl).

If the doubling time of the cell line is greater than 30 hours, ADC incubation is for 5 days, otherwise a four day incubation is done.

At the end of the incubation period, cell viability is assessed with the Alamar blue assay.

AlamarBlue (Invitrogen) is dispensed over the whole plate (20 µl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

Use

The conjugates of the disclosure may be used to provide a PBD compound at a target location.

The target location is preferably a proliferative cell population, such as a population of proliferative cancer cells. Other targets locations include a quiescent cell population, such as a population of quiescent cancer cells, or a population of cancer stem cells The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound ReIA, ReIB, ReIC, ReID, ReIE or ReIG. Thus, the conjugate may be used to selectively provide a compound ReIA, ReIB, ReIC, ReID, ReIE or ReIG to the target location.

The linker may be cleaved by an enzyme present at the target location.

The target location may be in vitro, in vivo or ex vivo.

The antibody-drug conjugate (ADC) compounds of the disclosure include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the disclosure selectively deliver an effective dose of a cytotoxic agent to tumor tissue whereby greater selectivity, i.e. a lower efficacious dose, may be achieved.

Thus, in one aspect, the present disclosure provides a conjugate compound as described herein for use in therapy.

In a further aspect there is also provides a conjugate compound as described herein for use in the treatment of a proliferative disease. A second aspect of the present disclosure provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to prostate cancers, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to, non-Hodgkin Lymphoma including diffuse large B-cell lymphoma (DLBCL), follicular lymphoma, (FL), Mantle Cell lymphoma (MCL), chronic lymphatic lymphoma (CLL) nd leukemias such as Hairy cell leukemia (HCL), Hairy cell leukemia variant (HCL-v) and Acute Lymphoblastic Leukaemia (ALL).

It is contemplated that the antibody-drug conjugates (ADC) of the present disclosure may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteritis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present disclosure may be used in a method of therapy. Also provided is a method of treatment, comprising administering to a subject in need of treatment a therapeutically-effective amount of a conjugate compound of the disclosure. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the disclosure may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentaazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylmelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1l (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®); (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™ OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present disclosure, and for use in accordance with the present disclosure, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present disclosure pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the disclosure will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Drug Conjugates

Antibody drug conjugates may be prepared by several routes, employing organic chemistry reactions, conditions, and reagents known to those skilled in the art, including reaction of a nucleophilic group of an antibody with a drug-linker reagent. This method may be employed to prepare the antibody-drug conjugates of the disclosure.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present disclosure. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus. In one preferred embodiment, the subject/patient is a human.

Further Preferences

The following preferences may apply to all aspects of the disclosure as described above, or may relate to a single aspect. The preferences may be combined together in any combination.

In some embodiments, $R^{6'}$, $R^{7'}$, $R^{9'}$, and Y' are preferably the same as $R^6$, $R^7$, $R^9$, and Y respectively.

Dimer Link

Y and Y' are preferably O.

R" is preferably a $C_{3-7}$ alkylene group with no substituents. More preferably R" is a $C_3$, $C_5$ or $C_7$ alkylene. Most preferably, R" is a $C_3$ or $C_5$ alkylene.

$R^6$ to $R^9$ $R^9$ is preferably H.

$R^6$ is preferably selected from H, OH, OR, SH, $NH_2$, nitro and halo, and is more preferably H or halo, and most preferably is H.

$R^7$ is preferably selected from H, OH, OR, SH, SR, $NH_2$, NHR, NRR', and halo, and more preferably independently selected from H, OH and OR, where R is preferably selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. $-NMe_2$); $-(OC_2H_4)_qOMe$, where q is from 0 to 2; nitrogen-containing Cr heterocyclyls, including morpholino, piperidinyl and N-methyl-piperazinyl.

These preferences apply to $R^{9'}$, $R^{6'}$ and $R^{7'}$ respectively.

$R^{12}$

When there is a double bond present between C2' and C3', $R^{12}$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

(d)

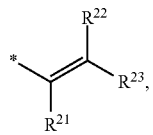

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(e)

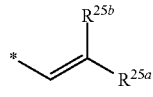

wherein one of $R^{25a}$ and $R^{25b}$ is H and the other is selected from: phenyl, which phenyl is optionally substituted by a group selected from halo methyl, methoxy; pyridyl; and thiophenyl; and (f)

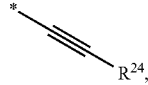

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{12}$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{12}$ is preferably phenyl. In other embodiments, $R^{12}$ is preferably thiophenyl, for example, thiophen-2-yl and thiophen-3-yl.

When $R^{12}$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6- yl, isoquinolin-7-yl and isoquinolin-8-yl. Of these isoquinolin-3-yl and isoquinolin-6-yl may be preferred.

When $R^{12}$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^{12}$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{12}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{12}$ Substituents, when $R^{12}$ is a $C_{5-10}$ Aryl Group

If a substituent on $R^{12}$ when $R^{12}$ is a $C_{5-10}$ aryl group is halo, it is preferably F or Cl, more preferably Cl.

If a substituent on $R^{12}$ when $R^{12}$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^{12}$ when $R^{12}$ is a $C_{5-10}$ aryl group is $C_{1-7}$ alkyl, it may preferably be a $C_{1-4}$ alkyl group (e.g. methyl, ethyl, propyl, butyl).

If a substituent on $R^{12}$ when $R^{12}$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^{12}$ when $R^{12}$ is a $C_{5-10}$ aryl group is bis-oxy-$C_{1-3}$ alkylene, this is preferably bis-oxy-methylene or bis-oxy-ethylene.

If a substituent on $R^{12}$ when $R^{12}$ is a $C_{5-10}$ aryl group is ester, this is preferably methyl ester or ethyl ester.

Particularly preferred substituents when $R^{12}$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituent for $R^{12}$ are dimethylaminopropyloxy and carboxy.

Particularly preferred substituted $R^{12}$ groups when $R^{12}$ is a $C_{5-10}$ aryl group include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^{12}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{12}$ is $C_{3-6}$ saturated cycloalkyl, it may be cyclopropyl, cyclobutyl, cyclopentyl or cyclohexyl. In some embodiments, it may be cyclopropyl.

When $R^{12}$ is

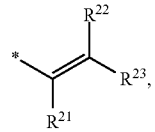

R each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5. In some embodiments, the total number of carbon atoms in the $R^{12}$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{21}$ is H.
In some embodiments, $R^{22}$ is H.
In some embodiments, $R^{23}$ is H.
In some embodiments, $R^{21}$ and $R^{22}$ are H.
In some embodiments, $R^{21}$ and $R^{23}$ are H.
In some embodiments, $R^{22}$ and $R^{23}$ are H.

An $R^{12}$ group of particular interest is:

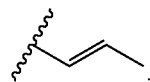 [SMILES: */C=C/C]

When $R^{12}$ is

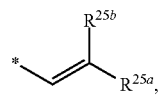

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{12}$ is

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

When there is a single bond present between C2' and C3', $R^{12}$ is

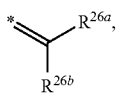

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester.

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H selected from methyl and ethyl.

$R^2$

The above preferences for $R^{12}$ apply equally to $R^2$.

$R^{22}$

In some embodiments, $R^{22}$ is of formula IIa.

A in $R^{22}$ when it is of formula IIa may be phenyl group or a $C_{5-7}$ heteroaryl group, for example furanyl, thiophenyl and pyridyl. In some embodiments, A is preferably phenyl.

$Q^2$-X may be on any of the available ring atoms of the $C_{5-7}$ aryl group, but is preferably on a ring atom that is not adjacent the bond to the remainder of the compound, i.e. it is preferably β or γ to the bond to the remainder of the compound. Therefore, where the $C_{5-7}$ aryl group (A) is phenyl, the substituent ($Q^2$-X) is preferably in the meta- or para-positions, and more preferably is in the para-position.

In some embodiments, $Q^1$ is a single bond. In these embodiments, $Q^2$ is selected from a single bond and —Z—$(CH_2)_n$—, where Z is selected from a single bond, O, S and NH and is from 1 to 3. In some of these embodiments, $Q^2$ is a single bond. In other embodiments, $Q^2$ is —Z—$(CH_2)_n$—. In these embodiments, Z may be O or S and n may be 1 or n may be 2. In other of these embodiments, Z may be a single bond and n may be 1.

In other embodiments, $Q^1$ is —CH=CH—.

In other embodiments, $R^{22}$ is of formula IIb. In these embodiments, $R^{C1}$, $R^{C2}$ and $R^{C3}$ are independently selected from H and unsubstituted $C_{1-2}$ alkyl. In some preferred embodiments, $R^{C1}$, $R^{C2}$ and $R^{C3}$ are all H. In other embodiments, $R^{C1}$, $R^{C2}$ and $R^{C3}$ are all methyl. In certain embodiments, $R^{C1}$, $R^{C2}$ and $R^{C3}$ are independently selected from H and methyl.

X is a group selected from the list comprising: O—$R^{L2'}$, S—$R^{L2'}$, $CO_2$—$R^{L2'}$, $COR^{L2'}$, NH—C(=O)—$R^{L2'}$, NHNH—$R^{L2'}$, CONHNH—$R^{L2'}$,

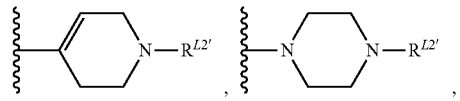

$NR^NR^{L2'}$, wherein $R^N$ is selected from the group comprising H and $C_{1-4}$ alkyl. X may preferably be: OH, SH, $CO_2$H, —N=C=O or $NHR^N$, and may more preferably be: O—$R^{L2'}$, S—$R^{L2'}$, $CO_2$—$R^{L2'}$, —NH—C(=O)—$R^{L2'}$ or NH—$R^{L2'}$. Particularly preferred groups include: O—$R^{L2'}$, S—$R^{L2'}$ and NH—$R^{L2'}$, with NH—$R^{L2'}$ being the most preferred group.

In some embodiments $R^{22}$ is of formula IIc. In these embodiments, it is preferred that Q is $NR^NR^{L2'}$. In other embodiments, Q is O—$R^{L2'}$. In further embodiments, Q is S—$R^{L2'}$. $R^N$ is preferably selected from H and methyl. In some embodiment, $R^N$ is H. In other embodiments, $R^N$ is methyl.

In some embodiments, $R^{22}$ may be -A-$CH_2$—X and -A-X. In these embodiments, X may be O—$R^{L2'}$, S—$R^{L2'}$, $CO_2$—$R^{L2'}$, CO—$R^{L2'}$ and NH—$R^{L2'}$. In particularly preferred embodiments, X may be NH—$R^{L2'}$.

$R^{10}$, $R^{11}$

In some embodiments, $R^{10}$ and $R^{11}$ together form a double bond between the nitrogen and carbon atoms to which they are bound.

In some embodiments, $R^{11}$ is OH.

In some embodiments, $R^{11}$ is OMe.

In some embodiments, $R^{11}$ is $SO_zM$, where z is 2 or 3 and M is a monovalent pharmaceutically acceptable cation.

$R^{11a}$

In some embodiments, $R^{11a}$ is OH.

In some embodiments, $R^{11a}$ is OMe.

In some embodiments, $R^{11a}$ is $SO_zM$, where z is 2 or 3 and M is a monovalent pharmaceutically acceptable cation.

$R^{20}$, $R^{21}$

In some embodiments, $R^{20}$ and $R^{21}$ together form a double bond between the nitrogen and carbon atoms to which they are bound.

In some embodiments $R^{20}$ is H.

In some embodiments, $R^{20}$ is $R^C$.

In some embodiments, $R^{21}$ is OH.

In some embodiments, $R^{21}$ is OMe.

In some embodiments, $R^{21}$ is $SO_zM$, where z is 2 or 3 and M is a monovalent pharmaceutically acceptable cation.

$R^{30}$, $R^{31}$

In some embodiments, $R^{30}$ and $R^{31}$ together form a double bond between the nitrogen and carbon atoms to which they are bound.

In some embodiments, $R^{31}$ is OH.

In some embodiments, $R^{31}$ is OMe.

In some embodiments, $R^{31}$ is $SO_zM$, where z is 2 or 3 and M is a monovalent pharmaceutically acceptable cation.

M and z

It is preferred that M is a monovalent pharmaceutically acceptable cation, and is more preferably $Na^+$.

z is preferably 3.

Preferred conjugates of the first aspect of the present disclosure may have a $D^L$ of formula
Ia
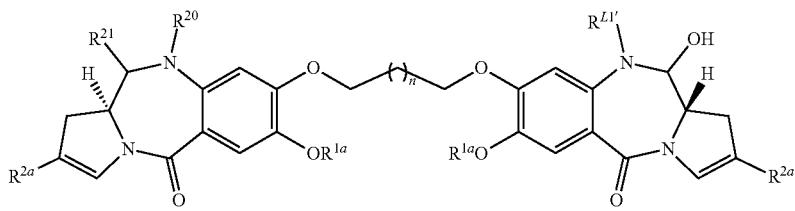
where
$R^{L1'}$, $R^{20}$ and $R^{21}$ are as defined above;
n is 1 or 3;
$R^{1a}$ is methyl or phenyl; and
$R^{2a}$ is selected from:
(a)
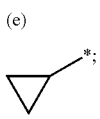
(b)
(c)
(d)
(e) 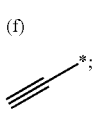
(f)
(g) 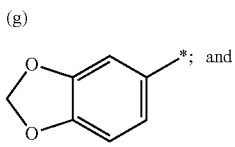; and
(h) 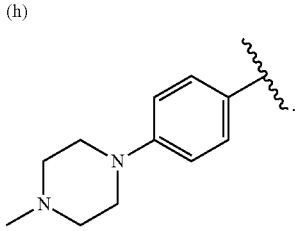
Preferred conjugates of the first aspect of the present disclosure may have a $D^L$ of formula
Ib
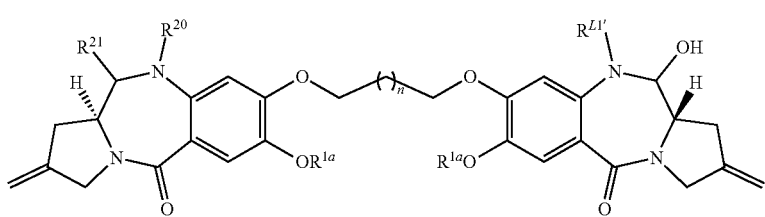

where
$R^{L1'}$, $R^{20}$ and $R^{21}$ are as defined above;
n is 1 or 3; and
$R^{1a}$ is methyl or phenyl.

Preferred conjugates of the first aspect of the present disclosure may have a $D^L$ of formula Ic

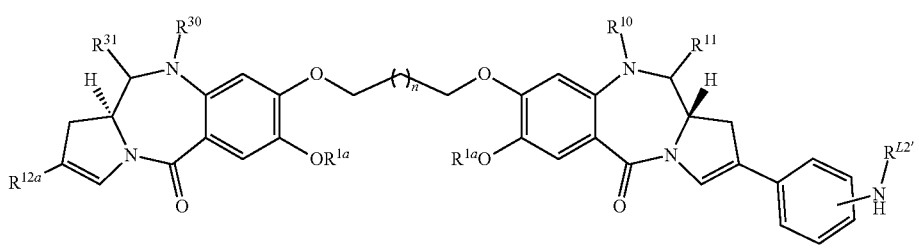

Ic where $R^{L2'}$, $R^{10}$, $R^{11}$, $R^{30}$ and $R^{31}$ are as defined above
n is 1 or 3;
$R^{12a}$ is selected from:

(a)

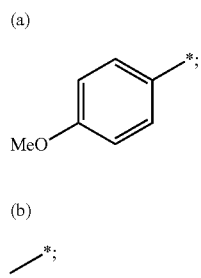

(b)

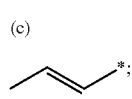

(c)

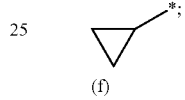

(d)

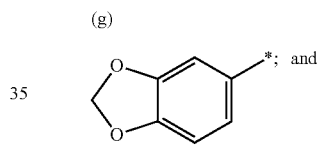

-continued (e)

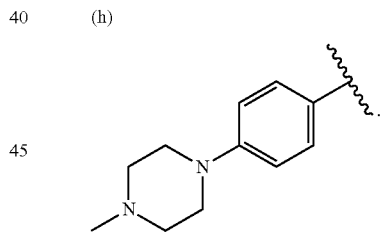

(f)

(g)

(h)

the amino group is at either the meta or para positions of the phenyl group.

Preferred conjugates of the first aspect of the present disclosure may have a $D^L$ of formula Id

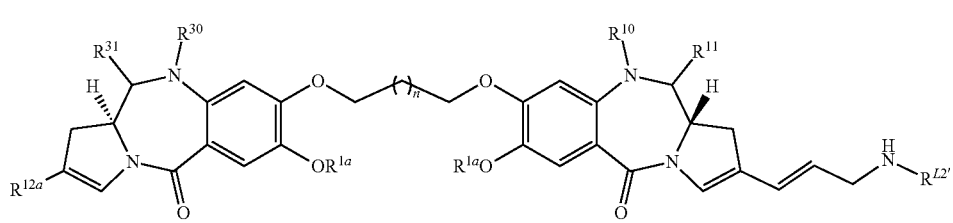

Id where $R^{L2'}$, $R^{10}$, $R^{11}$, $R^{30}$ and $R^{31}$ are as defined above
n is 1 or 3;
$R^{1a}$ is methyl or phenyl;
$R^{12a}$ is selected from:

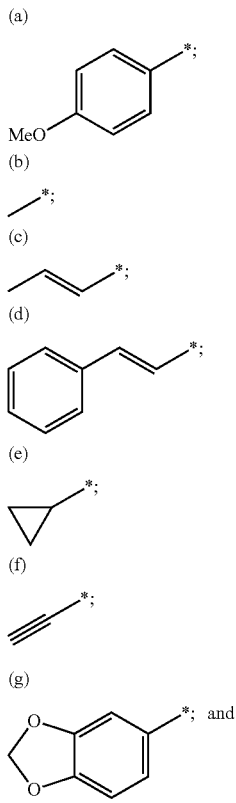

(a)

(b)

(c)

(d)

(e)

(f)

(g)

(h)

$R^{12a}$ is selected from:

(a)
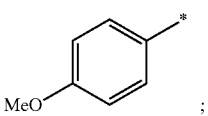

(b)

(c)

(d)
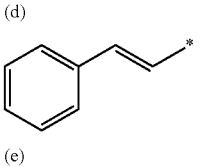

(e)

(f)

(g)
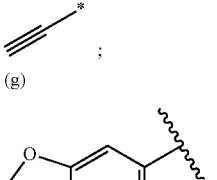
; and (h)
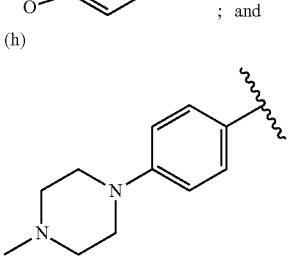

Examples

General Experimental Methods

Optical rotations were measured on an ADP 220 polarimeter (Bellingham Stanley Ltd.) and concentrations (c) are Preferred conjugates of the first aspect of the present disclosure may have a $D^L$ of formula Ie

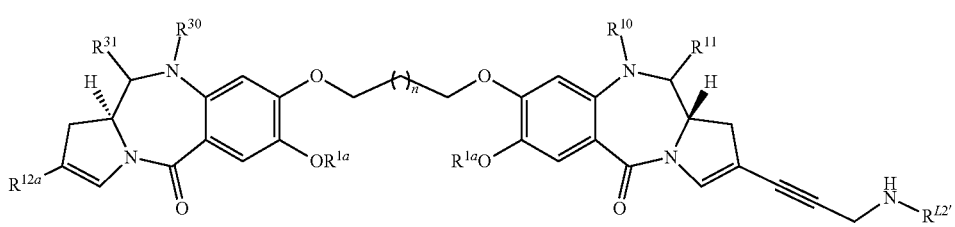

where $R^{L2'}$, $R^{10}$, $R^{11}$, $R^{30}$ and $R^{31}$ are as defined above
n is 1 or 3;
$R^{1a}$ is methyl or phenyl;

given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS Conditions:

The HPLC (Waters Alliance 2695) was run using a mobile phase of water (A) (formic acid 0.1%) and acetonitrile (B) (formic acid 0.1%). Gradient: initial composition 5% B held over 1.0 min, then increase from 5% B to 95% B over a 3 min period. The composition was held for 0.1 min at 95% B, then returned to 5% B in 0.03 minutes and hold there for 0.87 min. Total gradient run time equals 5 minutes.

Flow rate 3.0 mL/min, 400 µL was split via a zero dead volume tee piece which passes into the mass spectrometer. Wavelength detection range: 220 to 400 nm. Function type: diode array (535 scans). Column: Phenomenex Onyx Monolithic C18 50×4.60 mm.

The reverse phase flash purification conditions were as follows: The Flash purification system (Varian 971-Fp) was run using a mobile phase of water (A) and acetonitrile (B). Gradient: initial composition 5% B over 20 C.V. (Column Volume) then 5% B to 70% B within 60 C.V. The composition was held for 15 C.V. at 95% B, and then returned to 5% B in 5 C.V. and held at 5% B for 10 C.V. Total gradient run time equals 120 C.V. Flow rate 6.0 mL/min. Wavelength detection range: 254 nm. Column: Agilent AX1372-1 SF10-5.5gC8.

Preparative HPLC: Reverse-phase ultra-high-performance liquid chromatography (UPLC) was carried out on Phenomenex Gemini NX 5µ C-18 columns of the following dimensions: 150×4.6 mm for analysis, and 150×21.20 mm for preparative work. All UPLC experiments were performed with gradient conditions. Eluents used were solvent A ($H_2O$ with 0.1% Formic acid) and solvent B ($CH_3CN$ with 0.1% Formic acid). Flow rates used were 1.0 ml/min for analytical, and 20.0 ml/min for preparative HPLC. Detection was at 254 and 280 nm.

Example 1: Formation of Conjugates

Conjugation of AbHJ, AbDJ, AbBJ

Antibodies AbHJ, AbDJ, AbBJ were prepared for reduction in a buffer containing 1 mM EDTA in PBS pH 7.4 at an antibody concentration of 1-10 mg/mL. TCEP reductant was added to the batch as a 50-fold molar excess with respect to the antibody and the reduction mixture was heated at +37° C. for 3 hours in an incubator with slow orbital shaking. After confirming by RP-HPLC that reduction was complete, the antibody was cooled down to room temperature and buffer exchanged into PBS buffer containing 1 mM EDTA to remove excess TCEP. Reduced antibody was reoxidised by the addition of 50 mM dehydroascorbic acid (DHAA) as a 50 fold molar excess with respect to antibody, and the reoxidation mixture is allowed to proceed for a total of 2 hours with HPLC monitoring, then sterile filtered to remove DHAA. Conjugation was initiated by the addition of 10 mM drug linker stock diluted into DMSO (to a final 10% v/v concentration) and 10 fold excess relative to the antibody. The conjugation reaction was incubated for 16 hours at room temperature. Post conjugation the reaction was quenched with a 10 fold molar excess of N-acetyl cysteine and incubated for an additional 30 mins. The final product was exchanged into formulation buffer (30 mM Histidine, 200 mM sorbitol, 0.02% Tween-20) and analysed by SEC, HIC, RP-HPLC.

Conjugation of AbLJ

Initial attempts to conjugate AbLJ directly or following complete reduction/re-oxidation results in a complete lack of conjugation confirming that the unpaired heavy chain Cys were disulphide bridged together and would re-oxidise at the same rate as the heavy-heavy disulphide bonds. A site specific reduction process based on literature precedent (mAbs 1:6, 563-571; November/December, 2009) was attempted both in solution and on a resin. Both approaches were successful but the solid phase approach had certain practical advantages:

Avoided the need for process optimization to increase protein concentration during reduction—to maintain concentration during subsequent steps Results in concentration not dilution of the reduced antibody Ensures excellent toxin linker removal which can require multiple passes down G25 or TFF for a solution based process It is expected that many resins will be capable of supporting this process with the requirement for the resin being:

Ability to capture the educed antibody from the reduction process

Lack of affinity/binding of Cys

No blocking of the target free thiol

An example of a resin likely to work for this is Protein A. Solid Phase

AbLJ (25.5 mg, 5.1 mg/mL in PBS) was conjugated with Compound E in a multi-step process. In the first step the AbLJ antibody was buffer exchanged into 20 mM HEPES pH 8.0 via G25 column chromatography (NAP25, GE Healthcare) and diluted to 1 mg/mL. Cysteine was then added to 5 mM final concentration from a freshly prepared stock of 500 mM in deionised water. The site specific reduction process was allowed to proceed for 90 minutes at 37° C. The reduced AbLJ was then captured on a 2 mL column of protein L mimetic resin to achieve fast and complete removal of the reductant (FabSorbent F1P HF, Prometic biosciences Ltd). The column was immediately washed with 20 column volumes of phosphate buffered saline (PBS) and then with PBS containing 5% v/v of dimethylacetamide (DMA). The resin was suspended in 10 mL of PBS, 5% v/v DMA containing Compound E at 5 fold molar excess over antibody and allowed to conjugate for 60 minutes at room temperature. The column was then washed with 20 column volumes of PBS containing 5% v/v of dimethylacetamide (DMA) and then 20 column volumes of phosphate buffered saline (PBS). The purified conjugate was then eluted from the resin with 0.1M Glycine pH 3.0 and immediately buffer exchanged into 30 mM Histidine, 200 mM sorbitol pH 6 via G25 column chromatography (HiTrap G25, GE Healthcare). Polysorbate 20 was then added to 0.01% w/v from a freshly prepared stock of 1% w/v Polysorbate 20 in deionised water. The formulated conjugate was then subjected to a sterilizing grade filtration via a 0.22 µm, polyethersulfone membrane (Steriflip, EMD Millipore).

The AbLJ-ConjE ADC was analysed by hydrophobic interaction chromatography (HIC) to determine the amount of DAR<2 relative to unwanted DAR<2 and DAR>2 species. The percentage of on-target heavy-chain conjugation was determined by RP-HPLC and monomer content be size exclusion chromatography.

Solution Phase

AbLJ (25.5 mg, 5.1 mg/mL in PBS) was conjugated with Compound E in a multi-step process. In the first step the AbLJ antibody was buffer exchanged into 20 mM HEPES pH 8.0 via G25 column chromatography (NAP25, GE Healthcare) and diluted to 1 mg/mL. Cysteine was then added to 5 mM final concentration from a freshly prepared stock of 500 mM in deionised water. The site specific reduction process was allowed to proceed for 90 minutes at 37° C. The reduced AbLJ was then buffer exchanged into PBS, 5% v/v DMA via G25 column chromatography (NAP25, GE Healthcare) and Compound E added at a 5 fold molar excess over antibody and allowed to conjugate for 60 minutes at room temperature. The conjugate was then buffer exchanged into 30 mM Histidine, 200 mM sorbitol pH 6 via G25 column chromatography (HiTrap G25, GE Healthcare). Polysorbate 20 was then added to 0.01% w/v from a freshly prepared stock of 1% w/v Polysorbate 20 in deionised water. The formulated conjugate was then subjected to a sterilizing grade filtration via a 0.22 µm, polyethersulfone membrane (Steriflip, EMD Millipore).

The AbLJ-ConjE ADC was analysed by hydrophobic interaction chromatography (HIC) to determine the amount of DAR<2 relative to unwanted DAR<2 and DAR>2 species. The percentage of on-target heavy-chain conjugation was determined by RP-HPLC and monomer content be size exclusion chromatography.

Conjugation #2 of AbLJ

AbLJ-ConjE 4 mL (approx. 5 mg/mL) AbLJ in PBS is buffer exchanged into 20 mM Tris/Cl, 1M Lysine, 5 mM EDTA pH 8.0 using a G25 fine desalting column (GE Healthcare HiPrep 26/10).

The antibody was diluted to 1 mg/mL (approx. 20 mL volume) based on UV absorbance and reduction initiated by the addition of N-acetyl cysteine (500 mM NAC in water, Sigma A7250) to 5 mM final concentration. The reduction process was allowed to proceed for 75 minutes. The reduction process is stopped by removal of the NAC by binding the reduced protein in batch mode to a protein A mimetic resin.

2 mL Fabsorbent™ F1P HF (Prometics Biosciences) was pre-equilibrated with phosphate buffered saline, filtered to remove the PBS and then suspended in the reduced antibody solution and mixed gently on a roller for 15 minutes. The resin is washed 5 times with 10 mL of 20 mM Tris/Cl, 5 mM EDTA. The washed resin was then suspended in 10 mL volumes of 20 mM Tris/Cl, 5 mM EDTA, 5% v/v Dimethylacetamide (DMA). Compound E was added to 5 equivalents relative to total antibody from a 10 mM stock solution in DMA. This conjugation reaction was mixed gently on a roller for 60 minutes. The resin bound conjugate was then washed sequentially with 3×10 mL of PBS/5% v/v DMA followed by 3×10 mL of PBS.

The conjugate was released from the resin by suspending the resin in 10 mL of 0.1M Glycine pH 3.0 for 5 minutes and the conjugate containing supernatant collected by filtering off the resin The elution process was repeated and the two elution fractions combined and immediately formulated by buffer exchange into 30M Histidine/Cl, 200 mM sorbitol pH 6.0 using a G25 fine desalting column (GE Healthcare PD10 or HiPrep 26/10). Polysorbate 20 was then added to 0.02% w/v from a 10% w/v stock solution in water.

The final formulated conjugate was 0.2 um filtered (Steriflip-GP PES filtration unit, Merck Millipore).

Site-specific conjugation to the heavy chain and average DAR are determined by RP-HPLC (PLRP) and monomer content by size exclusion chromatography as described above. The final conjugate had an average DAR of 1.8 and a monomer/HMW content of 95.2 and 1.6% respectively.

Conjugation of AbLJ(LALA)

AbLJ(LALA)-ConjE

The AbLJ(LALA) antibody was conjugated to Compound E exactly as described above for Conjugation #2 of AbLJ.

The final conjugate had an average DAR of 1.8 and a monomer/HMW content of 95% and 1.8% respectively.

DAR Determination

Antibody or ADC (ca. 35 µg in 35 µL) was reduced by addition of 10 µL borate buffer (100 mM, pH 8.4) and 5 µL DTT (0.5 M in water), and heated at 37° C. for 15 minutes. The sample was diluted with 1 volume of acetonitrile: water: formic acid (49%: 49%: 2% v/v), and injected onto a Widepore 3.6ρ XB-C18 150×2.1 mm (P/N 00F-4482-AN) column (Phenomenex Aeris) at 80° C., in a UPLC system (Shimadzu Nexera) with a flow rate of 1 ml/min equilibrated in 75% Buffer A (Water, Trifluoroacetic acid (0.1% v/v) (TFA), 25% buffer B (Acetonitrile:water:TFA 90%:10%: 0.1% v/v). Bound material was eluted using a gradient from 25% to 55% buffer B in 10 min. Peaks of UV absorption at 214 nm were integrated. The following peaks were identified for each ADC or antibody: native antibody light chain (L0), native antibody heavy chain (H0), and each of these chains with added drug-linkers (labelled L1 for light chain with one drug and H1, H2, H3 for heavy chain with 1, 2 or 3 attached drug-linkers). The UV chromatogram at 330 nm was used for identification of fragments containing drug-linkers (i.e., L1, H1, H2, H3).

A PBD/protein molar ratio was calculated for both light chains and heavy chains:

$$\frac{Drug}{Protein}\text{ ratio on light chain} = \frac{\%\text{ Area at 214 nm for } L1}{\%\text{ Area at 214 nm for } L0 \text{ and } L1}$$

$$\frac{Drug}{Protein}\text{ ratio on heavy chain} = \frac{\sum_{n=0}^{3} n \times (\%\text{ area at 214 nm for } Hn)}{\sum_{n=0}^{3} \%\text{ area at 214 nm for } Hn}$$

Final DAR is calculated as:

$$DAR = 2 \times \left(\frac{Drug}{Protein}\text{ ratio on light chain} + \frac{Drug}{Protein}\text{ ratio on heavy chain}\right)$$

DAR measurement is carried out at 214 nm because it minimises interference from drug-linker absorbance.

| Test | AbHJ-ConjE | AbDJ-ConjE | AbBJ-ConjE | AbLJ-ConjE |
|---|---|---|---|---|
| Visual | Clear, colourless, particulate free | Clear, colourless, particulate free | Clear, colourless, particulate free | 0.63 |
| C (by A280/330 nm) in mg/ml* | 0.77* | 1.0* | Nd* | Nd |
| C (SEC 214 nm) in mg/mL* | 0.88* | Nd* | 1.18* | 1.8 |
| DAR by HIC | 1.5 | 1.9 | 1.7 | 1.8 |
| DAR by PLRP | 1.5 | 1.9 | 1.8 | 100% |
| SEC (% monomer) | 99.4% | 98.1% | 95.6% | Nd |
| Free drug-linker | <LOD | <LOD | <LOD | Nd |
| DMA | DMA not used | DMA not used | DMA not used | 0.63 |

*Two concentration methods were used: SEC (214 nm) vs known concentration reference sample or A280/A330 as described in patent. When data was available concentration was recalculated using this formula.

Example 2: In Vitro Cytotoxicity of Conjugates

Cytotoxicity Assay

The concentration and viability of cultures of suspended cells (at up to $1 \times 10^6$/ml) were determined by mixing 1:1 with Trypan blue and counting clear (live)/blue (dead) cells with a haemocytometer. The cell suspension was diluted to the required seeding density (generally $10^5$/ml) and dispensed into 96-well flat bottomed plates. For Alamar blue assay, 100 µl/well was dispensed in black-well plates. For MTS assay, 50 µl/well was dispensed in clear-well plates. A stock solution (1 ml) of ADC (20 µg/ml) was made by dilution of filter-sterile ADC into cell culture medium. A set of 8×10-fold dilutions of stock ADC were made in a 24 well plate by serial transfer of 100 µl onto 900 µl of cell culture medium. Each ADC dilution (100 µl/well for Alamar blue, 50 µl/well for MTS) was dispensed into 4 replicate wells of the 96-well plate, containing cell suspension. Control wells received the same volume of culture medium only. After incubation for 4 days, cell viability was measured by either Alamar blue or MTS assay.

AlamarBlue® (Invitrogen, catalogue number DAL1025) was dispensed (20 µl per well) into each well and incubated for 4 hours at 37° C. in the $CO_2$-gassed incubator. Well fluorescence was measured at excitation 570 nm, emission 585 nm. Cell survival (%) was calculated from the ratio of mean fluorescence in the 4 ADC-treated wells compared to the mean fluorescence in the 4 control wells (100%).

MTS (Promega, catalogue number G5421) was dispensed (20 µl per well) into each well and incubated for 4 hours at 37° C. in the $CO_2$-gassed incubator. Absorbance was measured at 490 nm. Cell survival (%) was calculated from the mean absorbance in the 4 ADC-treated wells compared to the mean absorbance in the 4 control wells (100%). Dose response curves were generated from the mean data of 3 replicate experiments and the $EC_{50}$ was determined by fitting data to a sigmoidal dose-response curve with variable slope using Prism (GraphPad, San Diego, Calif.).

Results

In order to produce site-specific versions of the ADCs, engineered versions of the AbJ antibody was conjugated the PBD warhead linker ConjE. The engineered AbJ antibodies were transiently produced in CHO cells. The in vitro cytotoxic efficacy of the site-specific ADCs were compared to wild-type AbJ-ADC conjugate (AbJ-ConjE).

AbJ→
An antibody comprising:
 a heavy chain comprising the amino acid sequence of SEQ ID NO.110;
 a light chain comprising the amino acid sequence of SEQ ID NO.150;
 a VH domain; and
 a VL domain.

AbJ-ConjE→AbJ stochastically conjugated to Compound E

AbHJ-ConjE→
An antibody comprising:
 a heavy chain comprising the amino acid sequence of SEQ ID NO.111;
 a light chain comprising the amino acid sequence of SEQ ID NO.150;
 a VH domain; and
 a VL domain;
 conjugated to Compound E at C105 of SEQ ID NO.150.

AbDJ-ConjE→
An antibody comprising:
 a heavy chain comprising the amino acid sequence of SEQ ID NO.115;
 a light chain comprising the amino acid sequence of SEQ ID NO.150;
 a VH domain; and
 a VL domain;
 conjugated to Compound E at C105 of SEQ ID NO.150.

AbBJ-ConjE→
An antibody comprising:
 a heavy chain comprising the amino acid sequence of SEQ ID NO.113;
 a light chain comprising the amino acid sequence of SEQ ID NO.151;
 a VH domain; and
 a VL domain;
 conjugated to Compound E at C103 of SEQ ID NO.113.

AbLJ-ConjE→
An antibody comprising:
 a heavy chain comprising the amino acid sequence of SEQ ID NO.110;
 a light chain comprising the amino acid sequence of SEQ ID NO.151;
 a VH domain; and
 a VL domain;
 conjugated to Compound E at C103 of SEQ ID NO.110.

| ADC candidate | Binding EC50 (ng/ml) | Cytotoxicity IC50 (ng/ml) |
|---|---|---|
| AbJ | 59 | — |
| AbJ-ConjE | 44 | 56 |
| AbHJ-ConjE | 55 | 18 |
| AbDJ-ConjE | 44 | 12 |
| AbBJ-ConjE | 49 | 23 |

No significant differences were reported in the EC50 values when the site-specific AbJ conjugates were compared to the corresponding wild-type conjugates.

Example 3

In Vivo Efficacy of Site-Specific and Non-Site Specific Conjugates 8 to 12 weeks old male CB.17 SCID mice were implanted with $1 \times 10^7$ tumor cells in 50% Matrigel s.c. in flank. On Day 1 of the study, mice bearing established xenografts (average size of 100-150 mm$^3$) were sorted into treatment groups (n=10), and dosing was initiated at either 0.33 mg/kg or 1.0 mg/kg. Tumors were measured twice per week until the study was ended.

Results

The various ADCs were tested in the xenograft model. At 0.3 mg/kg qd×1, AbHJ-ConjE and AbBJ-ConjE were equally efficacious providing tumor stasis for 30 days. AbDJ-ConjE was slightly more efficacious providing tumor stasis for up to 35 days. At 1.0 mg/kg qd×1, AbBJ-ConjE, AbHJ-ConjE and AbDJ-ConjE provided tumor stasis for 55, 70 and >95 days.

Example 4

Plasma/Serum Stability of Site-Specific and Non-Site Specific Conjugates: Stochastically conjugated ADCs (AbJ) and site-specifically conjugated ADCs ADCs were spiked in cyano or human plasma or PBS at a concentration of 60 ug/ml and incubated at 37° C. for 24 h, one and three weeks.

After one week samples were harvested and in vitro cytoxicity of the ADCs was determined. ADC instability would result in a loss of potently on the cells due to release of warhead from the ADC.

$GI_{50}$ data were generated by least squares fitting $OD_{490}$ data derived from the CellTiter 96® AQueous One Solution Cell Proliferation Assay (MTS) to a sigmoidal, 4PL X is log(concentration) algorithm using Graph Pad Prism v6.03. Cells were cultured for 6 days with the ADC-plasma mix, before MTS assay as described in the application.

| | | $GI_{50}$ (ng/ml) in cells | | | |
|---|---|---|---|---|---|
| | Unfrozen control | Days at 37° C. before storage at −80° C. until assay | | | |
| | | 0 | 1 | 7 | 21 |
| | Human plasma stability | | | | |
| AbJ-ConjE | 16.8 | 65.0 | 95.9 | 62.4 | 480.9 |
| AbBJ-ConjE | 12.8 | 22.5 | 18.1 | 48.0 | 287.1 |
| AbHJ-ConjE | 11.3 | 9.0 | 10.7 | 39.5 | 234.8 |
| AbDJ-ConjE | 7.1 | 7.2 | 7.6 | 20.2 | 258.2 |
| | Cynomolgus monkey plasma stability | | | | |
| AbJ-ConjE | 16.8 | 26.2 | 32.1 | 74.4 | 111.8 |
| AbBJ-ConjE | 12.8 | 14.0 | 19.6 | 56.7 | 74.4 |
| AbHJ-ConjE | 11.3 | 9.8 | 13.3 | 24.3 | 44.4 |
| AbDJ-ConjE | 7.1 | 7.6 | 8.7 | 13.0 | 48.2 |

AbBJ-ConjE, AbDJ-ConjE and AbHJ-ConjE showed improved stability when compared to the stochastic conjugate AbJ-ConjE in human and cynomolgus plasma upon 1, 7 or 21 days incubation at 37° C.

Example 5

Tolerability of Different Site-Specific Conjugates.

The effect of the mutation of the residues at Kabat EU positions 234 and 235 on the tolerability of the ADCs to rats was investigated.

Single dose studies were performed in male sprague-dawley rats, with necropsy on day 21 following dosing. Bodyweights and food consumption were monitored frequently with in-life sampling for clinical pathology (blood on days 8 and 21) and repeated sampling for pharmacokinetics. At necropsy, macroscopic observations were taken with selected organs weighed and retained for possible histopathology.

Results

AbLJ-ConjE→
An antibody comprising:
  a heavy chain comprising the amino acid sequence of SEQ ID NO.1103;
  a light chain comprising the amino acid sequence of SEQ ID NO.151;
  a VH domain; and
  a VL domain;
  conjugated to Compound E at C103 of SEQ ID NO.1103.

AbLJ(LALA)-ConjE→
An antibody comprising:
  a heavy chain comprising the amino acid sequence of SEQ ID NO.1103;
  a light chain comprising the amino acid sequence of SEQ ID NO.151;
  a VH domain; and
  a VL domain;
  conjugated to Compound E at C103 of SEQ ID NO.1103.

The VH and VL domains present in the AbLJ-ConjE conjugate were identical to those present in the AbLJ (LALA)-ConjE conjugate.

| Rat toxicology study observations[1] | AbLJ-ConjE (2 mg/kg) | AbLJ(LALA)-ConjE (2 mg/kg) |
|---|---|---|
| Clinical observations | Moderate raised hair/ hunched posture & pale extremities | Mild raised hair/ hunched posture |
| Bodyweight gain[2] | −78% | −45% |
| Haematology[3] | | |
| Reticulocytes | −93% | −56% |
| Platelets | −72% | −60% |
| Neutrophils | −98% | −97% |
| Anemia | Minimal | Minimal |
| Organ weights[4] | | |
| Liver | −23% | −12% |
| Lung | +16% | +16% |
| Thymus | −81% | −73% |
| Spleen | −41% | −33% |
| Kidney | −27% | −17% |
| Testis | −23% | −19% |

[1] 21 day study, single dose on day 1 (male SD rats)
[2] associated with reduced food intake
[3] nadir on day 8, trending towards recovery by day 21
[4] absolute organ weights The results indicate that mutation of the residues at Kabat EU positions 234 and 235 substantially improves ADC tolerability.

Example 6

Pharmacokinetics of Different Site-Specific Conjugates.

The effect of the mutation of the residues at Kabat EU positions 234 and 235 on the pharmacokinetics was investigated. AbLJ-ConjE and AbLJ(LALA)-ConjE as described above in Example 5 were used.

Rats were dosed with 2 mg/kg of ADC and serum samples were taken frequently until day 20. A fit-for-purpose ELISA was developed for measuring conjugated antibody. Calibration curve, QCs and study samples were diluted in a low adhesion plate and added to a plate coated with a mouse monoclonal antibody directed against anti-SG3249. After incubation and washing, the plate was incubated with a mouse monoclonal antibody to human Fc-HRP conjugated.

As substrate, 3,3',5,5'-Tetramethylbenzidine (TMB) was used, the reaction stopped with 1M HCl and the plate read at 450 nm absorbance at a Versamax plate reader. The Lower Limit Of Quantification (LLOQ) was 750 ng/ml in rat serum. All samples were measured using the PBD-ADC specific assay and the measured terminal half-lifes (mean of three animals) for AbLJ(LALA)-ConjE and AbLJ-ConjE were calculated using Phoenix 64 WinNonlin 6.4 (Pharsight) software.

Results

| ADC | Terminal Half life (h) |
|---|---|
| AbLJ(LALA)-ConjE | 306.3 |
| AbLJ-ConjE | 200.1 |

The results indicate that mutation of the residues at Kabat EU positions 234 and 235 substantially improves ADC terminal half-life.

Example 7

Reduced Systemic Toxicity

AbCJ specific for human antigen X, was engineered to contain a cysteine instead of a serine at position 442 (designated as AbCJX) and conjugated to drug-linkers ConjH and ConjE.

The toxicity of AbCJX-ConjH and AbCJX-ConjE in cynomolgus monkey was compared to that of AbBJX-ConjE (the AbBJ-ConjE antibody described above in Example 2, specific for human antigen X).

The study used three cynomolgus monkeys per group (males or females), the monkeys being approximately 3 years old (4 kg) at dosing. All animals were dosed once on day 1, with data presented up to day 22 for surviving animals.

Results

Due to adverse clinical signs, including bleeding associated with marked platelet depletion, animals were either found dead or euthanized early with AbCJX-ConjH (by day 13) and with AbCJX-ConjE (by day 16); see FIG. 1. AbBJX-ConjE did not induce significant platelet depletion and monkeys received a second dose at day 21.

Example 8

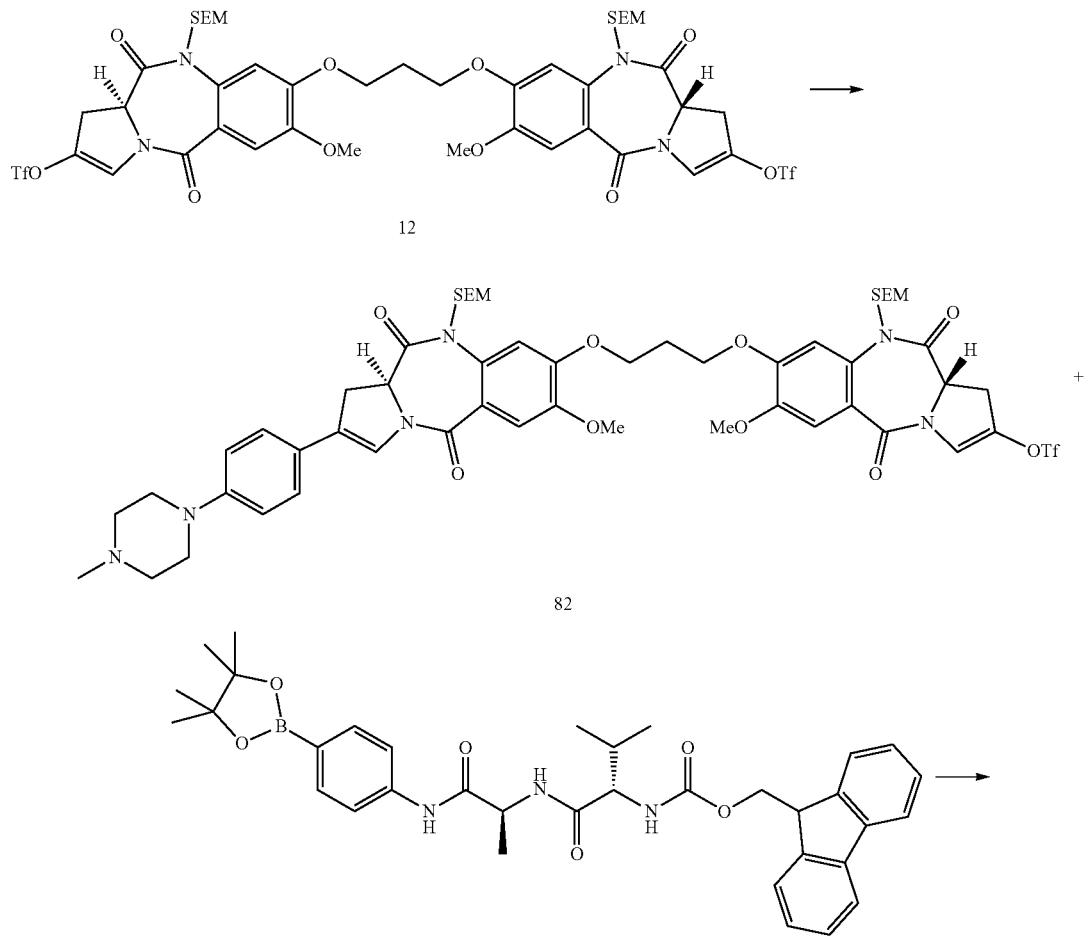

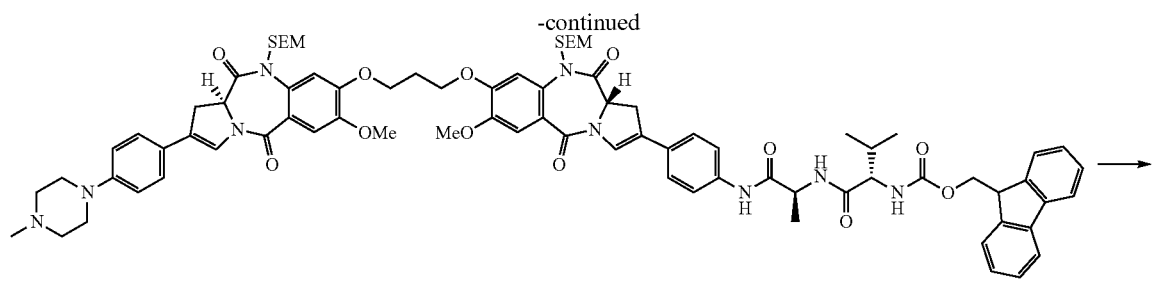

83

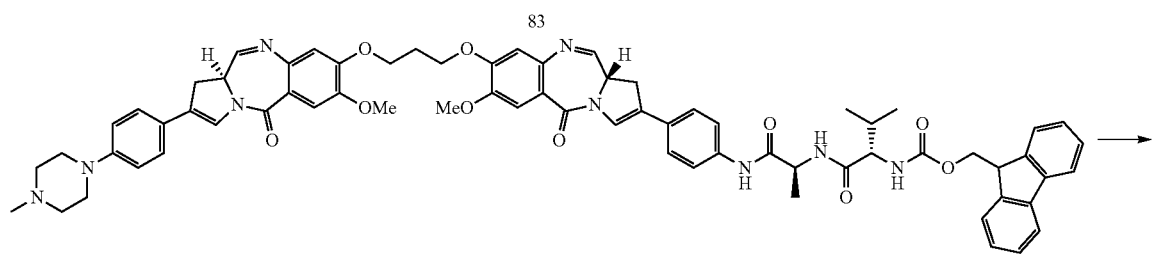

84

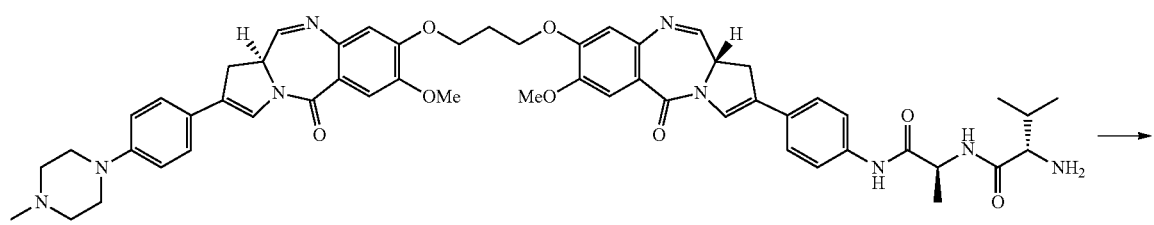

85

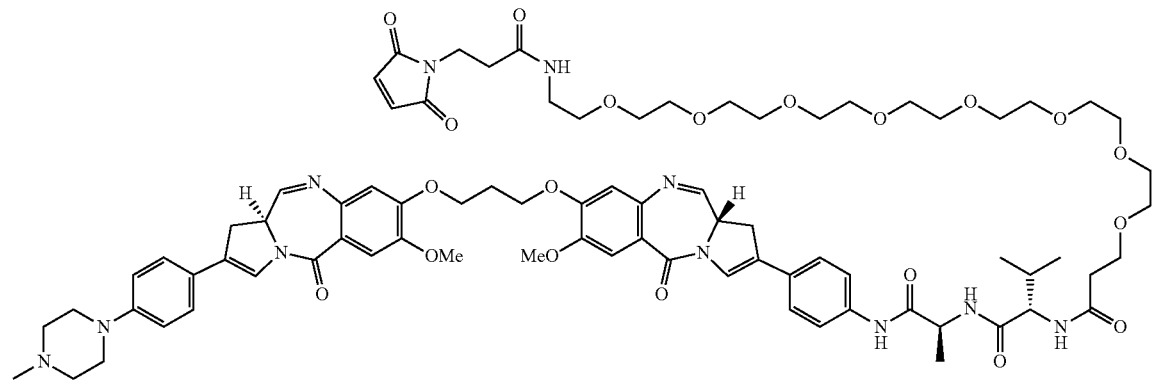

86

(a)(S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl trifluoromethanesulfonate (82)

Pd(PPh₃)₄ (20.6 mg, 0.018 mmol) was added to a stirred mixture of the bis-enol triflate 12 (500 mg, 0.44 mmol) (Compound 8a in WO 2010/043880), N-methyl piperazine boronic ester (100 mg, 0.4 mmol), Na₂CO₃ (218 mg, 2.05 mmol), MeOH (2.5 mL), toluene (5 mL) and water (2.5 mL). The reaction mixture was allowed to stir at 300° under a nitrogen atmosphere for 24 hours after which time all the boronic ester has consumed. The reaction mixture was then evaporated to dryness before the residue was taken up in EtOAc (100 mL) and washed with H₂O (2×50 mL), brine (50 mL), dried (MgSO₄), filtered and evaporated under reduced pressure to provide the crude product. Purification by flash chromatography (gradient elution: 80:20 v/v Hexane/EtOAc to 60:40 v/v Hexane/EtOAc) afforded product 82 as a yellowish foam (122.6 mg, 25%).

LC/MS 3.15 min (ES+) m/z (relative intensity) 1144 ([M+H]⁺, 20%).

(b) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl)carbamate (83)

PBD-triflate 82 (359 mg, 0.314 mmol), boronic pinacol ester 20 (250 mg, 0.408 mmol) (Compound 20 in WO 2014/057073) and triethylamine (0.35 mL, 2.51 mmol) were dissolved in a mixture of toluene/MeOH/H$_2$O, 2:1:1 (3 mL). The microwave vessel was purged and filled with argon three times before tetrakis(triphenylphosphine)palladium(0) (21.7 mg, 0.018 mmol) was added and the reaction mixture placed in the microwave at 80° C. for 10 minutes. Subsequently, CH$_2$Cl$_2$ (100 mL) was added and the organics were washed with water (2×50 mL) and brine (50 mL) before being dried with MgSO$_4$, filtered and the volatiles removed by rotary evaporation under reduced pressure. The crude product was purified by silica gel chromatography column (CHCl$_3$/MeOH, 100% to 9:1) to afford pure 83 (200 mg, 43% yield). LC/MS 3.27 min (ES+) m/z (relative intensity) 1478 ([M+H]$^+$, 100%).

(c) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (84)

A solution of Super-Hydride® (0.34 mL, 1M in THF) was added dropwise to a solution of SEM-dilactam 83 (200 mg, 0.135 mmol) in THF (5 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with MgSO$_4$, filtered and the solvent removed by rotary evaporation under reduced pressure. The crude product was dissolved in MeOH (6 mL), CH$_2$Cl$_2$ (3 mL), water (1 mL) and enough silica gel to form a thick stirring suspension. After 5 days, the suspension was filtered through a sintered funnel and washed with CH$_2$Cl$_2$/MeOH (9:1) (100 mL) until the elution of the product was complete. The organic layer was washed with brine (2×50 mL), dried with MgSO$_4$, filtered and the solvent removed by rotary evaporation under reduced pressure. Purification by silica gel column chromatography (100% CHCl$_3$ to 96% CHCl$_3$/4% MeOH) afforded the product 84 as a yellow solid (100 mg, 63%). LC/MS 2.67 min (ES+) m/z (relative intensity) 1186 ([M+H]$^+$, 5%).

(d) (S)-2-amino-N—((S)-1-((4-((R)-7-methoxy-8-(3-(((R)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)-3-methylbutanamide (85)

Excess piperidine was added (0.1 mL, 1 mmol) to a solution of PBD 84 (36.4 mg, 0.03 mmol) in DMF (0.9 mL). The mixture was allowed to stir at room temperature for 20 min, at which point the reaction had gone to completion (as monitored by LC/MS). The reaction mixture was diluted with CH$_2$Cl$_2$ (50 mL) and the organic phase was washed with H$_2$O (3×50 mL) until complete piperidine removal. The organic phase was dried over MgSO$_4$, filtered and excess solvent removed by rotary evaporation under reduced pressure to afford crude product 85 which was used as such in the next step. LC/MS 2.20 min (ES+) m/z (relative intensity) 964 ([M+H]*-, 5%).

(e) 1-(3-(2,5-dioxo-2,5-dihydro-1H-pyrrol-1-yl)propanamido)-N-((2S)-1-(((2S)-1-((4-(7-methoxy-8-(3-((7-methoxy-2-(4-(4-methylpiperazin-1-yl)phenyl)-5-oxo-5,11a-dihydro-1H-benzo[e]pyrrolo[1,2-a][1,4]diazepin-8-yl)oxy)propoxy)-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-3,6,9,12,15,18,21,24-octaoxaheptacosan-27-amide (86)

EDCl hydrochloride (8 mg, 0.042 mmol) was added to a suspension of Maleimide-PEG$_8$-acid (25 mg, 0.042 mmol) in dry CH$_2$Cl$_2$ (4 mL) under argon atmosphere. PBD 85 (42 mg, crude) was added straight away and stirring was maintained until the reaction was complete (3 hours). The reaction was diluted with CH$_2$Cl$_2$ and the organic phase was washed with H$_2$O and brine before being dried over MgSO$_4$, filtered and excess solvent removed by rotary evaporation under reduced pressure by rotary evaporation under reduced pressure. The product was purified by careful silica gel chromatography (slow elution starting with 100% CHCl$_3$ up to 9:1 CHCl$_3$/MeOH) followed by reverse phase HPLC to remove unreacted maleimide-PEG$_8$-acid. The product 86 was isolated in 10% over two steps (6.6 mg). LC/MS 1.16 min (ES+) m/z (relative intensity) 770.20 ([M+2H]$^+$, 40%).

Example 9—Alternative Synthesis of Compound 83

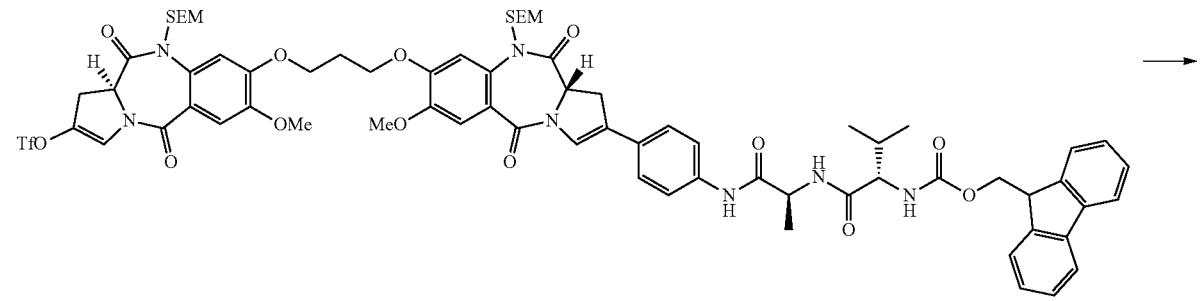

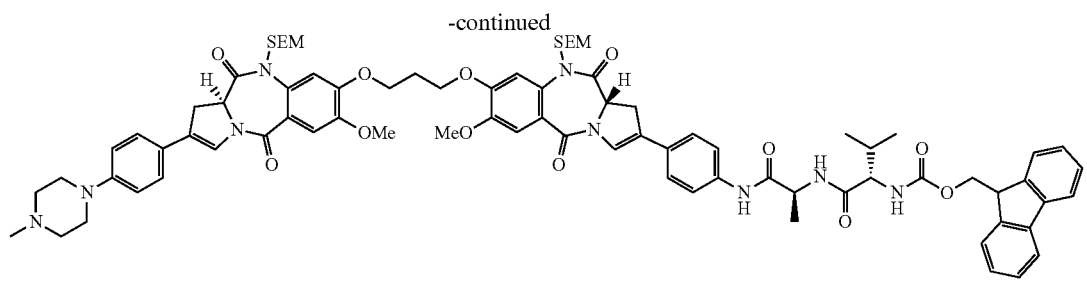

83

(9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl)carbamate (83)

PBD-triflate 21 (469 mg, 0.323 mmol)(Compound 21 in WO 2014/057073), boronic pinacol ester (146.5 mg, 0.484 mmol) and Na₂CO₃ (157 mg, 1.48 mmol) were dissolved in a mixture of toluene/MeOH/H₂O, 2:1:1 (10 mL). The reaction flask was purged with argon three times before tetrakis(triphenylphosphine)palladium(0) (7.41 mg, 0.0064 mmol) was added and the reaction mixture heated to 30° C. overnight. The solvents were removed under reduced pressure and the residue was taken up in H₂O (50 mL) and extracted with EtOAc (3×50 mL). The combined organics were washed with brine (100 mL), dried with MgSO₄, filtered and the volatiles removed by rotary evaporation under reduced pressure. The crude product was purified by silica gel column chromatography (CHCl₃ 100% to CHCl₃/MeOH 95%:5%) to afford pure 83 in 33% yield (885 mg). LC/MS 3.27 min (ES+) m/z (relative intensity) 1478 ([M+H]⁺, 100%).

Example 10

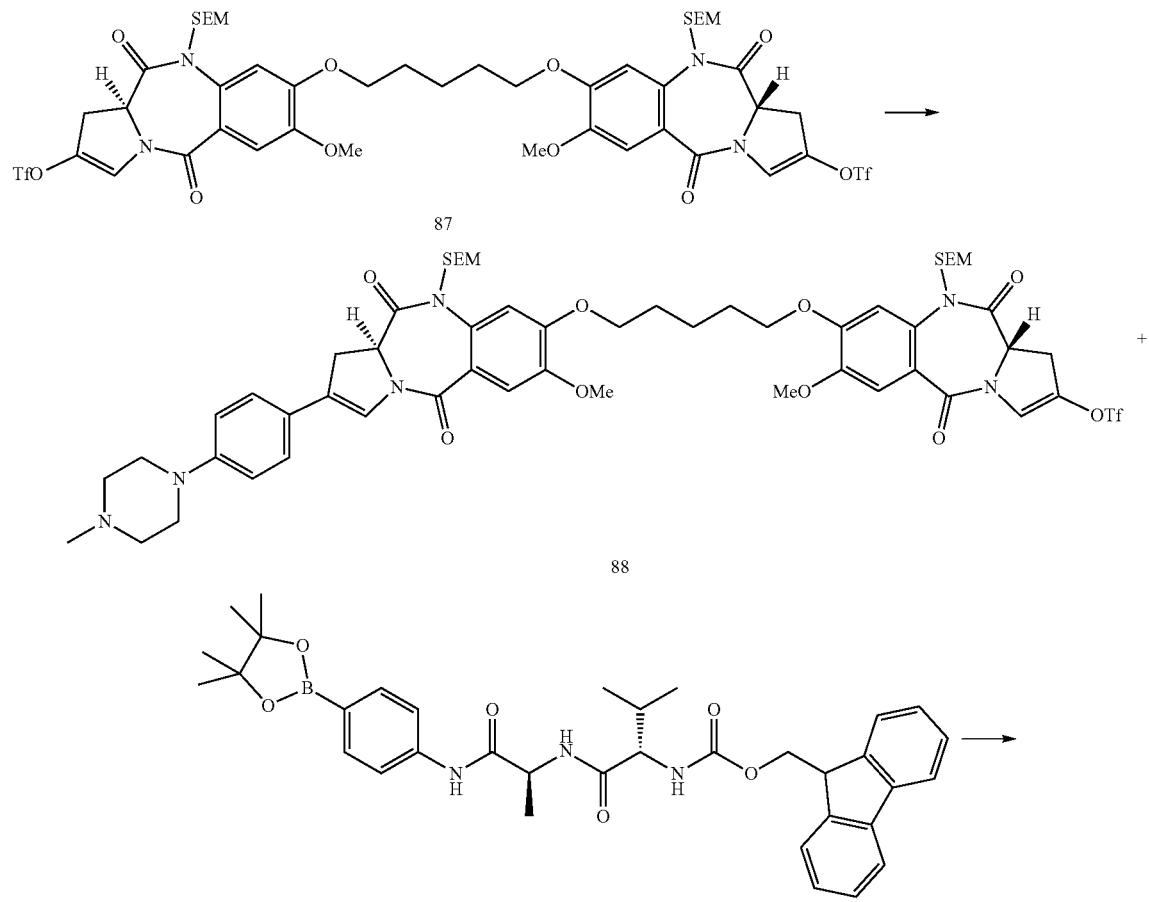

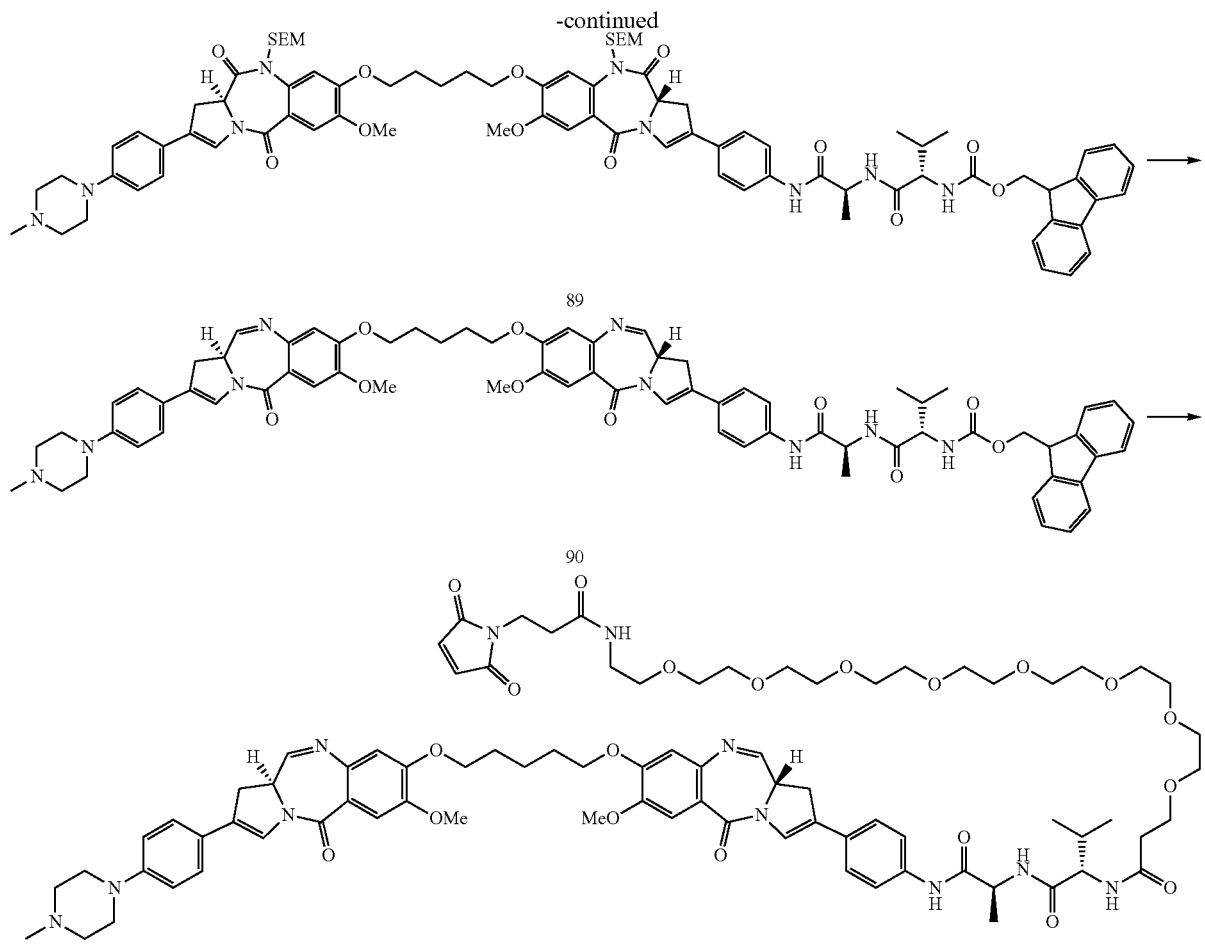

(a) (S)-7-methoxy-8-((5-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (88)

Pd(PPh$_3$)$_4$ (30 mg, 26 μmol) was added to a stirred mixture of the bis-enol triflate 87 (1 g, 0.87 mmol)(Compound 8b in WO 2010/043880), 4-(4-methylpiperazin-1-yl)phenylboronic acid, pinacol ester (264 mg, 0.87 mmol), Na$_2$CO$_3$ (138 mg, 1.30 mmol), EtOH (5 mL), toluene (10 mL) and water (5 mL). The reaction mixture was allowed to stir under a nitrogen atmosphere overnight at room temperature after which time the complete consumption of starting material was observed by TLC (EtOAc) and LC/MS (1.52 min (ES+) m/z (relative intensity) 1171.40 ([M+H]$^+$, 100)). The reaction mixture was diluted with EtOAc (400 mL) and washed with H$_2$O (2×300 mL), brine (200 mL), dried (MgSO$_4$), filtered and evaporated under reduced pressure to provide the crude product. Purification by flash chromatography (gradient elution: 100:0 v/v EtOAc/MeOH to 85:15 v/v EtOAc/MeOH) afforded the asymmetrical triflate 88 (285 mg, 28%). $^1$H NMR (400 MHz, CDCl3) δ 7.39 (s, 1H), 7.37-7.29 (m, 4H), 7.23 (d, J=2.8 Hz, 2H), 7.14 (t, J=2.0 Hz, 1H), 6.89 (d, J=9.0 Hz, 2H), 5.54 (d, J=10.0 Hz, 2H), 4.71 (dd, J=10.0, 2.6 Hz, 2H), 4.62 (td, J=10.7, 3.5 Hz, 2H), 4.13-4.01 (m, 4H), 3.97-3.87 (m, 8H), 3.85-3.75 (m, 2H), 3.74-3.63 (m, 2H), 3.31-3.22 (m, 4H), 3.14 (tdd, J=16.2, 10.8, 2.2 Hz, 2H), 2.73-2.56 (m, 4H), 2.38 (d, J=2.4 Hz, 3H), 2.02-1.92 (m, 4H), 1.73 (dd, J=9.4, 6.0 Hz, 2H), 1.04-0.90 (m, 4H), 0.05-0.00 (m, 18H). MS (ES$^+$) m/z (relative intensity) 1171.40 ([M+H]$^+$, 100).

(b) (9H-fluoren-9-yl)methyl ((S)-1-(((S)-1-((4-((S)-7-methoxy-8-((5-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)phenyl)amino)-1-oxopropan-2-yl)amino)-3-methyl-1-oxobutan-2-yl) carbamate (89)

Pd(PPh$_3$)$_4$ (8 mg, 7 μmol) was added to a stirred mixture of the asymmetrical triflate 88 (269 mg, 0.23 mmol), Fmoc-Val-Ala-4-aminophenylboronic acid, pinacol ester 20 (210 mg, 0.34 mmol), Na$_2$CO$_3$ (36.5 mg, 0.34 mmol), EtOH (5 mL), toluene (10 mL), THF (1 mL), and water (5 mL). The reaction mixture was allowed to stir under a nitrogen atmosphere at 35° C. for 2 hours after which time the complete consumption of starting material was observed by TLC (80:20 v/v EtOAc/MeOH) and LC/MS (1.68 min (ES+) m/z (relative intensity) 1508.10 ([M+H]$^+$, 100)). The reaction mixture was diluted with EtOAc (100 mL) and washed with H$_2$O (1×100 mL), brine (200 mL), dried (MgSO$_4$), filtered and evaporated under reduced pressure to provide the crude product. Purification by flash chromatography (gradient elution: 100:0 v/v EtOAc/MeOH to 80:20 v/v EtOAc/MeOH) afforded the SEM protected dimer 89 (240 mg, 69%). $^1$H NMR (400 MHz, CDCl$_3$) δ 8.42 (s, 1H), 7.76 (d, J=7.5 Hz, 2H), 7.63-7.49 (m, 4H), 7.45-7.28 (m, 9H), 7.25 (d, J=2.9 Hz, 1H), 6.87 (t, J=14.0 Hz, 2H), 6.41 (s, 1H), 5.63-5.49 (m, 2H), 5.25 (s, 1H), 4.71 (d, J=10.1 Hz, 2H), 4.68-4.57 (m, 2H), 4.49 (d, J=6.7 Hz, 2H), 4.20 (s, 1H), 4.16-4.02 (m, 4H), 4.00-3.87 (m, 7H), 3.86-3.61 (m, 7H), 3.30-3.21 (m, 4H), 3.19-3.05 (m, 2H), 2.69-2.54 (m, 4H), 2.37 (s, 3H), 2.04-1.92 (m, 4H), 1.91-1.79 (m, 4H), 1.72 (s, 2H), 1.46 (d, J=6.9 Hz, 3H), 1.04-0.82 (m, 8H), 0.04-0.02 (m, 18H). MS (ES$^+$) m/z (relative intensity) 1508.10 ([M+H]$^+$, 100).

(c) (9H-fluoren-9-yl)methyl ((S)-1-(((S)-1-((4-((S)-7-methoxy-8-((5-(((S)-7-methoxy-2-(4-(4-methylpiperazin-1-yl)phenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)carbamate (90)

Super hydride (0.358 mL, 0.358 mmol, 1.0 M in THF) was added dropwise to a stirred solution of the SEM-tetralactam 89 (216 mg, 0.143 mmol) in anhydrous THF (10 mL) at −78° C. The reaction mixture was allowed to stir for 3 hours after which time the complete conversion of starting material directly was observed by LC/MS (1.37 min (ES+) m/z (relative intensity) 608.15 (([M+2H]$^{2+}$)/2, 100)). The reaction mixture was carefully diluted with H$_2$O (100 mL) and extracted with DCM (100 mL). The organic layers was washed with brine (100 mL), dried over MgSO$_4$, filtered and evaporated under reduced pressure to provide the intermediate SEM-carbinolamine. The white solids were immediately dissolved in MeOH (100 mL), DCM (10 mL) and H$_2$O (20 mL) and treated with flash silica gel (50 g). The thick suspension was allowed to stir at room temperature for 4 days after which time the formation of a significant quantity of desired product was observed by TLC (90:10 v/v CHCl$_3$/MeOH). The reaction mixture was filtered through a porosity 3 sinter funnel and the pad rinsed slowly and thoroughly with 90:10 v/v CHCl$_3$/MeOH until no further product eluted (checked by TLC). The filtrate was washed with brine (100 mL), dried (MgSO$_4$), filtered and evaporated in vacuo, followed by high vacuum drying, to provide the crude product. Purification by flash chromatography (gradient elution:HPLC grade 98:2 v/v CHCl$_3$/MeOH to 88:12 v/v CHCl$_3$/MeOH) gave 90 as a mixture of carbinolamine ethers and imine (80 mg, 46%). $^1$H NMR (400 MHz, CDCl$_3$) δ 8.52 (s, 1H), 7.87 (d, J=3.9 Hz, 2H), 7.75 (d, J=7.5 Hz, 2H), 7.66-7.26 (m, 12H), 6.90 (d, J=8.8 Hz, 2H), 6.81 (s, 1H), 6.64 (d, J=6.0 Hz, 1H), 5.37 (d, J=5.7 Hz, 1H), 4.74-4.58 (m, 2H), 4.54-4.31 (m, 4H), 4.26-3.98 (m, 6H), 3.94 (s, 2H), 3.86 (dd, J=13.6, 6.6 Hz, 1H), 3.63-3.48 (m, 2H), 3.37 (dd, J=16.5, 5.6 Hz, 2H), 3.31-3.17 (m, 4H), 2.66-2.51 (m, 4H), 2.36 (s, 3H), 2.16 (d, J=5.1 Hz, 1H), 2.06-1.88 (m, 4H), 1.78-1.55 (m, 6H), 1.46 (d, J=6.8 Hz, 3H), 0.94 (d, J=6.8 Hz, 6H). MS (ES$^+$) m/z (relative intensity) 608.15 (([M+2H]$^{2+}$)/2, 100).

(d) 1-(3-(2,5-dioxo-2,5-dihydro-1H-pyrrol-1-yl)propanamido)-N—((S)-1-(((S)-1-((4-((S)-7-methoxy-8-((5-(((S)-7-methoxy-2-(4-(4-methylpiperazin-1-yl)phenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-3,6,9,12,15,18,21,24-octaoxaheptacosan-27-amide (91)

Piperidine (0.2 mL) was added to a solution of 90 (77 mg, 63.4 μmol) in DMF (1 mL). The reaction mixture was allowed to stir for 20 minutes. The reaction mixture was carefully diluted with DCM (50 mL) and washed with water (50 mL). The organic layers was washed with brine (100 mL), dried over MgSO$_4$, filtered and evaporated under reduced pressure to provide the unprotected valine intermediate. The crude residue was immediately redissolved in chloroform (5 mL). Mal(Peg)$_8$-acid (56 mg, 95 μmol) and EDCI (18 mg, 95 μmol) were added, followed by methanol (0.1 mL). The reaction was allowed to stir for 3 hours at room temperature at which point completion was observed by TLC and LC/MS (1.19 min (ES+) m/z (relative intensity) 784.25 (([M+2H]$^{2+}$)/2, 100)). The reaction mixture was diluted with chloroform (50 mL), washed with water (100 mL), dried (MgSO$_4$), filtered and evaporated in vacuo, followed by high vacuum drying, to provide the crude product. Purification by flash chromatography (gradient elution:HPLC grade 96:4 v/v CHCl$_3$/MeOH to 90:10 v/v CHCl$_3$/MeOH) gave 91 as a yellow solid (43 mg, 43%). $^1$H NMR (400 MHz, CDCl$_3$) δ 8.73 (s, 1H), 7.88 (dd, J=7.6, 3.9 Hz, 2H), 7.75 (d, J=8.6 Hz, 2H), 7.52 (d, J=2.0 Hz, 2H), 7.44 (s, 1H), 7.40-7.28 (m, 4H), 6.91 (d, J=8.8 Hz, 2H), 6.81 (s, 2H), 6.69 (s, 2H), 6.48 (s, 1H), 4.72-4.63 (m, 1H), 4.46-4.34 (m, 2H), 4.25-4.03 (m, 6H), 3.95 (s, 4H), 3.84 (dd, J=17.2, 10.1 Hz, 4H), 3.72-3.46 (m, 30H), 3.44-3.32 (m, 4H), 3.30-3.20 (m, 4H), 2.75-2.63 (m, 1H), 2.59 (s, 4H), 2.55-2.43 (m, 3H), 2.37 (s, 3H), 2.29 (dd, J=12.7, 6.7 Hz, 1H), 2.03-1.89 (m, 4H), 1.72 (d, J=22.7 Hz, 8H), 1.46 (d, J=7.2 Hz, 3H), 1.01 (dd, J=11.5, 6.9 Hz, 6H). MS (ES$^+$) m/z (relative intensity) 784.25 (([M+2H]$^{2+}$)/2, 100).

Example 11

(i) (S)-((pentane-1,5-diylbis(oxy))bis(2-amino-5-methoxy-4,1-phenylene))bis(((S)-2-(((tert-butyldimethylsilyl)oxy)methyl)-4-methyl-2,3-dihydro-1H-pyrrol-1-yl)methanone) (98)

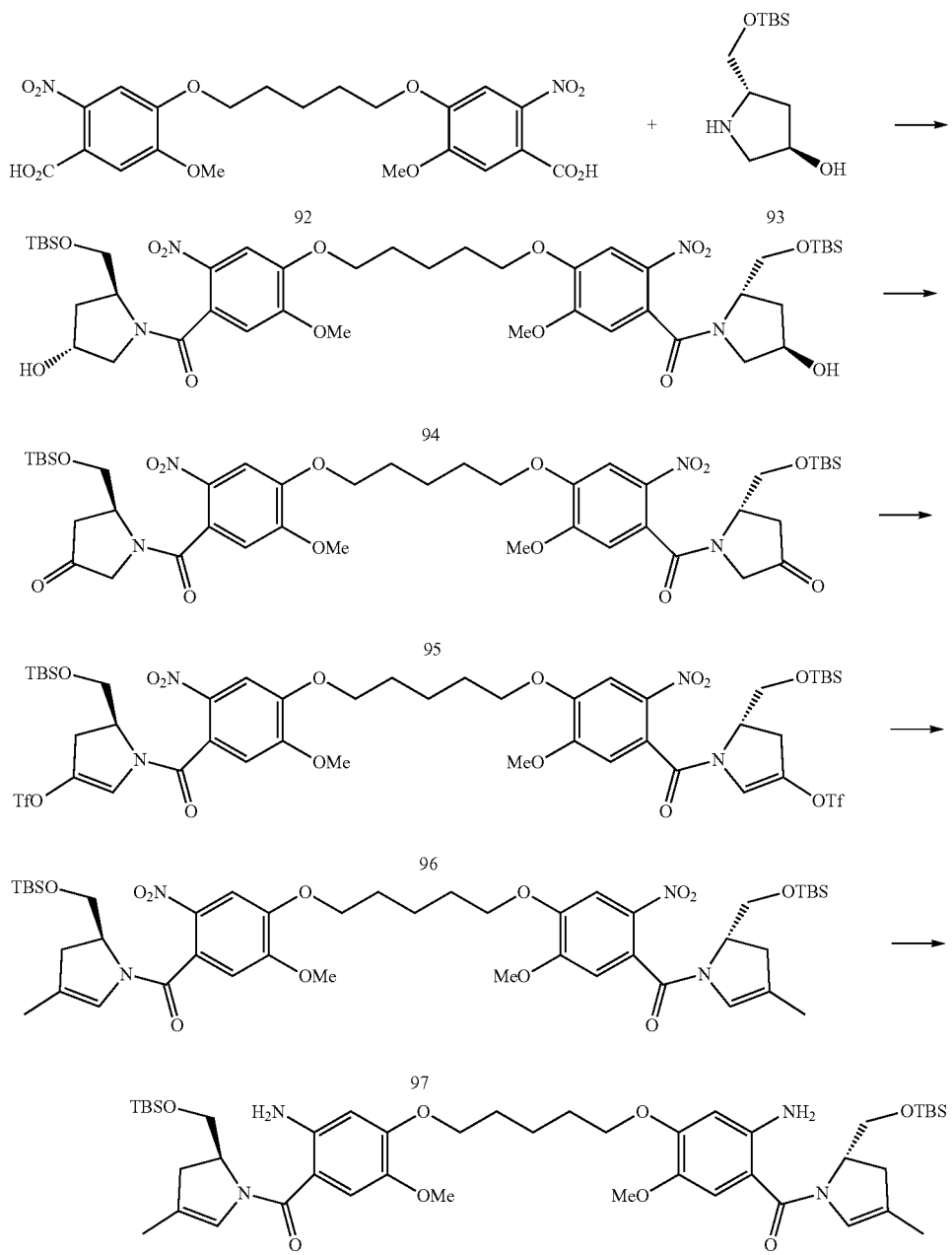

(a) (S,R)-((pentane-1,5-diylbis(oxy))bis(5-methoxy-2-nitro-4,1-phenylene))bis(((2S,4R)-2-(((tert-butyldimethylsilyl)oxy)methyl)-4-hydroxypyrrolidin-1-yl)methanone) (94)

Anhydrous DMF (approx. 0.5 mL) was added dropwise to a stirred suspension of 4,4'-(pentane-1,5-diylbis(oxy))bis(5-methoxy-2-nitrobenzoic acid) (92) (36.64 g, 74.0 mmol) and oxalyl chloride (18.79 mL, 0.222 mol, 3.0 eq.) in anhydrous DCM (450 mL) until vigorous effervescence occurred and the reaction mixture was left to stir overnight. The reaction mixture was evaporated to dryness, and triturated with diethyl ether. The resulting yellow precipitate was filtered from solution, washed with diethyl ether (100 mL) and immediately added to a solution of (3R,5S)-5-((tert-butyldimethylsilyloxy) methyl) pyrrolidin-3-ol (93) (39.40 g, 0.170 mol, 2.3 eq.) and anhydrous triethylamine (82.63 mL, 0.592 mol, 8 eq.) in anhydrous DCM (400 mL) at −40° C. The reaction mixture was allowed to slowly warm to room temperature (over 2.5 hours) after which, LCMS analysis indicated complete reaction. DCM (250 mL) was added and the mixture was transferred into a separating funnel. The organic layer was washed successively with 0.1M HCl (2×800 mL), saturated NaHCO$_3$ (500 mL) and brine (300 mL). After drying over MgSO$_4$ and filtration, evaporation of the solvent left the product as a yellow foam (62.8 g, 92%). LC/MS: RT 1.96 min; MS (ES+) m/z (relative intensity) 921.45 ([M+H]$^+$, 100).

(b) (5S,5'S)-1,1'-(4,4'-(pentane-1,5-diylbis(oxy))bis (5-methoxy-2-nitrobenzoyl))bis(5-(((tert-butyldimethylsilyl)oxy)methyl)pyrrolidin-3-one) (95)

Trichloroisocyanuric acid (21.86 g, 94.07 mmol, 1.4 eq) was added in one portion to a solution of diol 94 (61.90 g, 67.20 mmol) and TEMPO (2.10 g, 13.44 mmol, 0.2 eq) in anhydrous DCM (500 mL) under an atmosphere of argon at 0° C. The reaction mixture was stirred at 0° C. for 20 minutes after which, LCMS analysis of the reaction mixture showed complete reaction. The reaction mixture was diluted with DCM (400 mL) and washed with saturated sodium bicarbonate (500 mL), 0.2 M sodium thiosulfate solution (600 mL), brine (400 mL) and dried (MgSO$_4$). Evaporation of the solvent gave the crude product. Flash chromatography [gradient elution 80% n-hexane/20% ethyl acetate to 100% ethyl acetate] gave pure 95 as yellow solid (49.30 g, 80%). LC/MS: RT 2.03 min; MS (ES+) m/z (relative intensity) 917.55 ([M+H]$^+$, 100).

(c) (5S,5'S)-1,1'-(4,4'-(pentane-1,5-diylbis(oxy))bis (5-methoxy-2-nitrobenzoyl))bis(5-(((tert-butyldimethylsilyl)oxy)methyl)-4,5-dihydro-1H-pyrrole-3,1-diyl) bis(trifluoromethanesulfonate), (96)

Triflic anhydride (24.19 mL, 0.144 mol, 6.0 eq) was added dropwise to a vigorously stirred solution of bis-ketone 95 (21.98 g, 23.96 mmol) in anhydrous DCM (400 mL) containing 2,6-lutidine (22.33 mL, 0.192 mol, 8.0 eq) at −40° C. The reaction mixture was stirred at −40° C. for 30 min after which, LCMS analysis indicated complete reaction. Reaction mixture was rapidly diluted with DCM (500 mL) and washed with ice-cold water (600 mL), ice-cold saturated sodium bicarbonate (400 mL) and brine (500 mL), dried over MgSO$_4$, filtered and evaporated to leave a crude brown oil. Flash chromatography [gradient elution 80% n-hexane/20% ethyl acetate to 66% n-hexane/33% ethyl acetate] gave pure 96 as a brown foam (16.40 g, 58%). LC/MS: RT 2.28 min; MS (ES+) m/z (relative intensity) no data.

(d) (S)-((pentane-1,5-diylbis(oxy))bis(5-methoxy-2-nitro-4,1-phenylene))bis(((S)-2-(((tert-butyldimethylsilyl)oxy)methyl)-4-methyl-2,3-dihydro-1H-pyrrol-1-yl)methanone) (97)

Triflate 96 (5.06 g, 4.29 mmol), methyl boronic acid (1.80 g, 30.00 mmol, 7 eq) and triphenylarsine (1.05 g, 3.43 mmol, 0.8 eq) were dissolved in anhydrous dioxane and stirred under argon. Pd (II) bisbenzonitrile chloride was then added and the reaction mixture heated rapidly to 80° C. for 20 min. Reaction mixture cooled, filtered through Celite (washed through with ethyl acetate), filtrate washed with water (500 mL), brine (500 mL), dried over MgSO$_4$, filtered and evaporated. Flash chromatography [gradient elution 50% n-hexane/50% ethyl acetate] gave pure 97 as a brown foam (4.31 g, 59%). LC/MS: RT 2.23 min; MS (ES+) m/z (relative intensity) 913.50 ([M+H]$^+$, 100).

(e) (S)-((pentane-1,5-diylbis(oxy))bis(2-amino-5-methoxy-4,1-phenylene))bis(((S)-2-(((tert-butyldimethylsilyl)oxy)methyl)-4-methyl-2,3-dihydro-1H-pyrrol-1-yl)methanone) (98)

Zinc dust (26.48 g, 0.405 mol, 36.0 eq) was added in one portion to a solution of bis-nitro compound 97 (10.26 g, 11.24 mmol) in 5% formic acid/methanol (200 mL) keeping the temperature between 25-30° C. with the aid of a cold water bath. The reaction was stirred at 30° C. for 20 minutes after which, LCMS showed complete reaction. The reaction mixture was filtered through Celite to remove the excess zinc, which was washed with ethyl acetate (600 mL). The organic fractions were washed with water (500 mL), saturated sodium bicarbonate (500 mL) and brine (400 mL), dried over MgSO$_4$ and evaporated. Flash chromatography [gradient elution 100% chloroform to 99% chloroform/1% methanol] gave pure 98 as an orange foam (6.22 g, 65%). LC/MS: RT 2.20 min; MS (ES+) m/z (relative intensity) 853.50 ([M+H]$^+$, 100).

(ii) 4-((R)-2-((R)-2-(((allyloxy)carbonyl)amino)-3-methylbutanamido)propanamido)benzyl 4-((10R, 13R)-10-isopropyl-13-methyl-8,11-dioxo-2,5-dioxa-9,12-diazatetradecanamido)benzyl ((S)-(pentane-1, 5-diylbis(oxy))bis(2-((S)-2-(hydroxymethyl)-4-methyl-2,3-dihydro-1H-pyrrole-1-carbonyl)-4-methoxy-5,1-phenylene))dicarbamate (103)

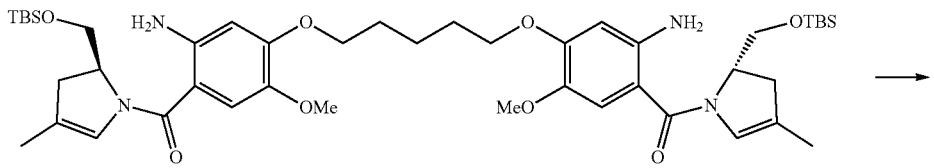

-continued
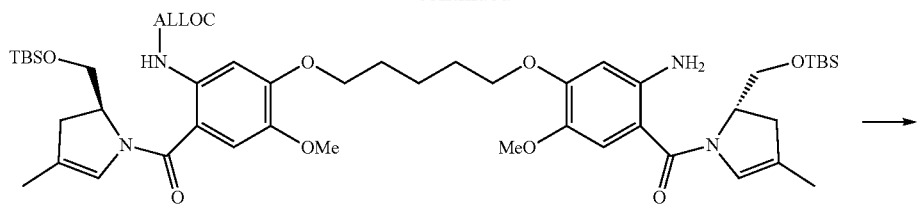
99
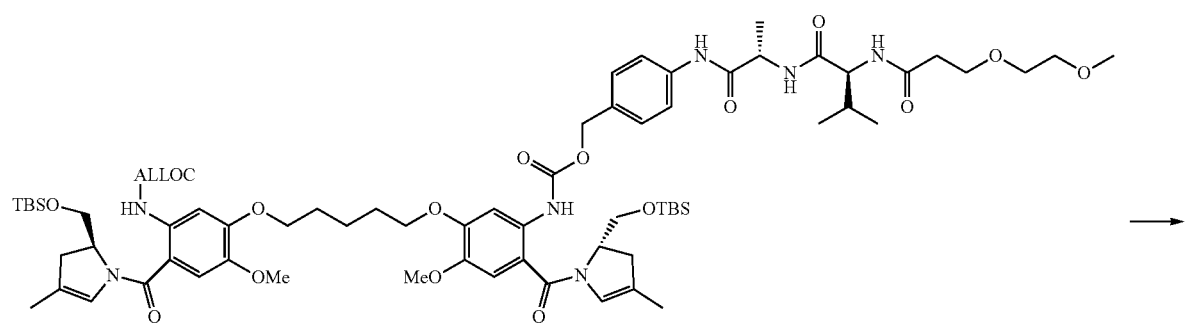
100
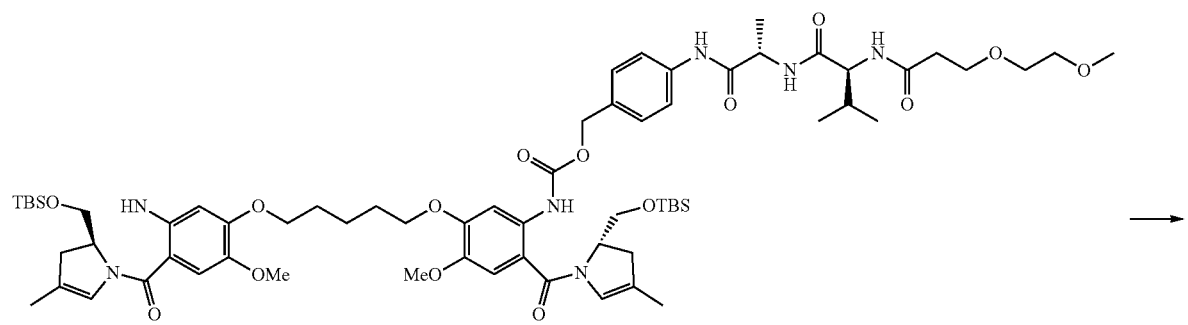
101
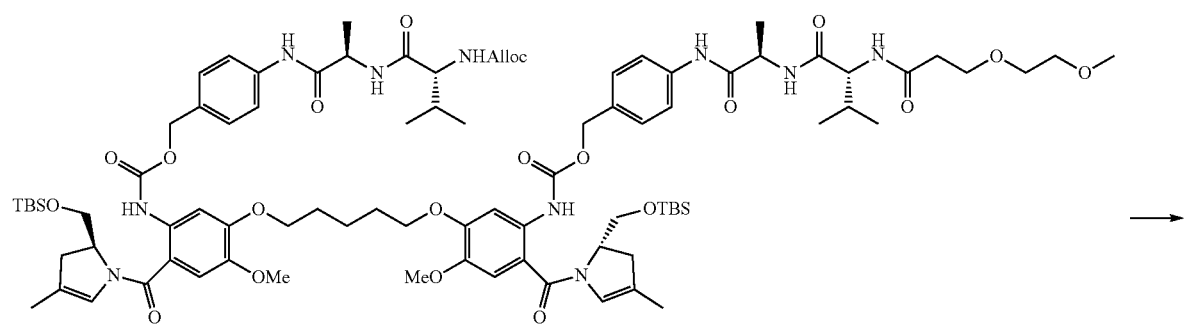
102

-continued

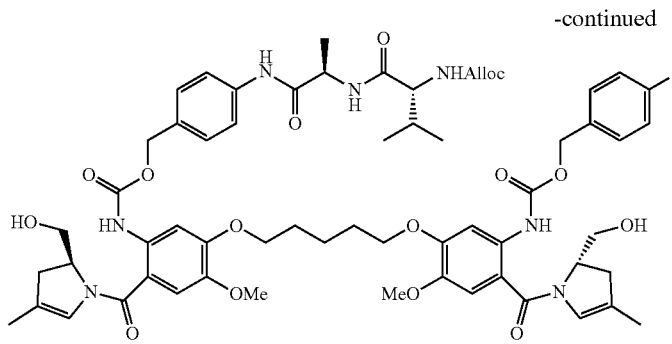 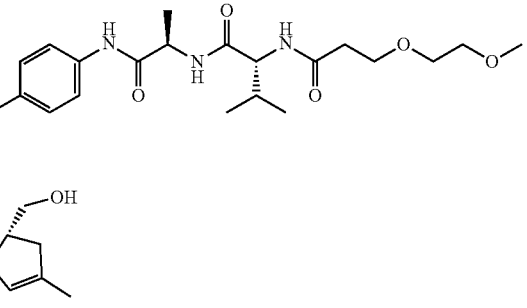

103

(a) Allyl (5-((5-(5-amino-4-((S)-2-(((tert-butyldimethylsilyl)oxy)methyl)-4-methyl-2,3-dihydro-1H-pyrrole-1-carbonyl)-2-methoxyphenoxy)pentyl)oxy)-2-((S)-2-(((tert-butyldimethylsilyl)oxy)methyl)-4-methyl-2,3-dihydro-1H-pyrrole-1-carbonyl)-4-methoxyphenyl)carbamate (99)

Pyridine (1.156 mL, 14.30 mmol, 1.5 eq) was added to a solution of the bis-aniline 98 (8.14 g, 9.54 mmol) in anhydrous DCM (350 mL) at −78° C. under an atmosphere of argon. After 5 minutes, allyl chloroformate (0.911 mL, 8.58 mmol, 0.9 eq) was added and the reaction mixture allowed to warm to room temperature. The reaction mixture was diluted with DCM (250 mL), washed with saturated $CuSO_4$ solution (400 mL), saturated sodium bicarbonate (400 mL) and brine (400 mL), dried over $MgSO_4$. Flash chromatography [gradient elution 66% n-hexane/33% ethyl acetate to 33% n-hexane/66% ethyl acetate] gave pure 99 as an orange foam (3.88 g, 43%). LC/MS: RT 2.27 min; MS (ES+) m/z (relative intensity) 937.55 ([M+H]+, 100).

(b) Allyl 4-((10S,13S)-10-isopropyl-13-methyl-8,11-dioxo-2,5-dioxa-9,12-diazatetradecanamido)benzyl ((S)-(pentane-1,5-diylbis(oxy))bis(2-((S)-2-(((tert-butyldimethylsilyl)oxy)methyl)-4-methyl-2,3-dihydro-1H-pyrrole-1-carbonyl)-4-methoxy-5,1-phenylene))dicarbamate (100)

Triethylamine (0.854 mL, 6.14 mmol, 2.2 eq) was added to a stirred solution of the aniline 99 (2.62 g, 2.79 mmol) and triphosgene (0.30 g, 1.00 mmol, 0.36 eq) in anhydrous THF (50 mL) under argon 0° C. The reaction mixture was stirred at room temperature for 5 minutes. LCMS analysis of an aliquot quenched with methanol, showed formation of the isocyanate. A solution of $mPEG_2$-Val-Ala-PAB-OH (1.54 g, 3.63 mmol, 1.3 eq) and triethylamine (0.583 mL, 4.19 mmol, 1.5 eq) in dry THF (50 mL) was added in one portion and the resulting mixture was stirred overnight at 40° C. The solvent of the reaction mixture was evaporated leaving a crude product. Flash chromatography [gradient elution 100% chloroform to 98% chloroform/2% methanol] gave pure 100 as a light orange solid (2.38 g, 62%). LC/MS: RT 2.29 min; MS (ES+) m/z (relative intensity) no data.

(c) 4-((10S,13S)-10-isopropyl-13-methyl-8,11-dioxo-2,5-dioxa-9,12-diazatetradecanamido)benzyl (5-((5-(5-amino-4-((S)-2-(((tert-butyldimethylsilyl)oxy)methyl)-4-methyl-2,3-dihydro-1H-pyrrole-1-carbonyl)-2-methoxyphenoxy)pentyl)oxy)-2-((S)-2-(((tert-butyldimethylsilyl)oxy)methyl)-4-methyl-2,3-dihydro-1H-pyrrole-1-carbonyl)-4-methoxyphenyl)carbamate (101)

Tetrakis(triphenylphosphine)palladium (39 mg, 0.034 mmol, 0.02 eq) was added to a stirred solution of 100 (2.35 g, 1.69 mmol) and pyrrolidine (0.35 mL, 4.24 mmol, 2.5 eq) in anhydrous DCM (25 mL) under argon at room temperature. Reaction mixture allowed to stir for 45 min then diluted with DCM (100 mL), washed with saturated ammonium chloride solution (100 mL), brine (100 mL), dried over $MgSO_4$, filtered and evaporated. Flash chromatography [gradient elution 100% chloroform to 95% chloroform/5% methanol] gave pure 101 as a yellow solid (1.81 g, 82%). LC/MS: RT 2.21 min; MS (ES+) m/z (relative intensity) 1303.65 ([M+H]+, 100).

(d) 4-((R)-2-((R)-2-(((allyloxy)carbonyl)amino)-3-methylbutanamido)propanamido)benzyl 4-((10R,13R)-10-isopropyl-13-methyl-8,11-dioxo-2,5-dioxa-9,12-diazatetradecanamido)benzyl ((S)-(pentane-1,5-diylbis(oxy))bis(2-((S)-2-(((tert-butyldimethylsilyl)oxy)methyl)-4-methyl-2,3-dihydro-1H-pyrrole-1-carbonyl)-4-methoxy-5,1-phenylene))dicarbamate (102)

Triethylamine (0.419 mL, 3.01 mmol, 2.2 eq) was added to a stirred solution of the aniline 101 (1.78 g, 1.37 mmol) and triphosgene (0.15 g, 0.49 mmol, 0.36 eq) in anhydrous THF (50 mL) under argon 0° C. The reaction mixture was stirred at room temperature for 5 min. LCMS analysis of an aliquot quenched with methanol, showed formation of the isocyanate. A solution of Alloc-Val-Ala-PAB-OH (0.67 g, 1.78 mmol, 1.3 eq) and triethylamine (0.29 mL, 2.05 mmol, 1.5 eq) in dry THF (45 mL) was added in one portion and the resulting mixture was stirred overnight at 40° C. The solvent of the reaction mixture was evaporated leaving a crude product. Flash chromatography [gradient elution 100% ethyl acetate to 97% ethyl acetate/3% methanol] gave pure 102 as a pale yellow solid (1.33 g, 57%). LC/MS: RT 2.21 min; MS (ES+) m/z (relative intensity) no data.

(e) 4-((R)-2-((R)-2-(((allyloxy)carbonyl)amino)-3-methylbutanamido)propanamido)benzyl 4-((10R,13R)-10-isopropyl-13-methyl-8,11-dioxo-2,5-dioxa-9,12-diazatetradecanamido)benzyl ((S)-(pentane-1,5-diylbis(oxy))bis(2-((S)-2-(hydroxymethyl)-4-methyl-2,3-dihydro-1H-pyrrole-1-carbonyl)-4-methoxy-5,1-phenylene))dicarbamate (103)

Tetra-n-butylammonium fluoride (1 M, 1.52 mL, 1.52 mmol, 2.0 eq) was added to a solution of the TBS protected compound 102 (1.30 g, 0.76 mmol) in anhydrous THF (15 mL). The reaction mixture was stirred at room temperature for 4 hours. The reaction mixture was diluted with chloroform (100 mL) and washed sequentially with water (40 mL) and brine (40 mL). The organic phase was dried over MgSO₄ and evaporated to leave a yellow solid. Flash chromatography [gradient elution 95% ethyl acetate/5% methanol to 90% ethyl acetate/10% methanol] gave pure 103 as a pale yellow solid (1.00 g, 89%). LC/MS: RT 1.60 min; MS (ES+) m/z (relative intensity) 1478.45 (100).

(iii) (11S,11aS)-4-((2R,5R)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzil 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (106)

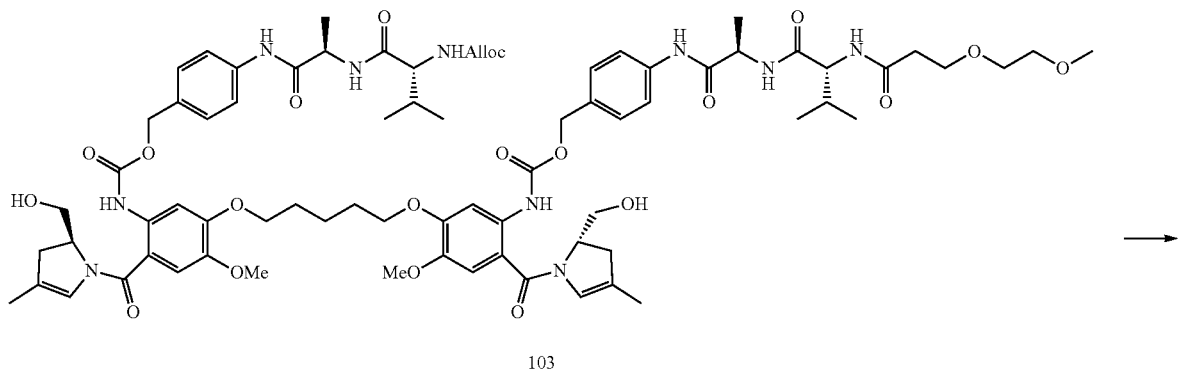

103

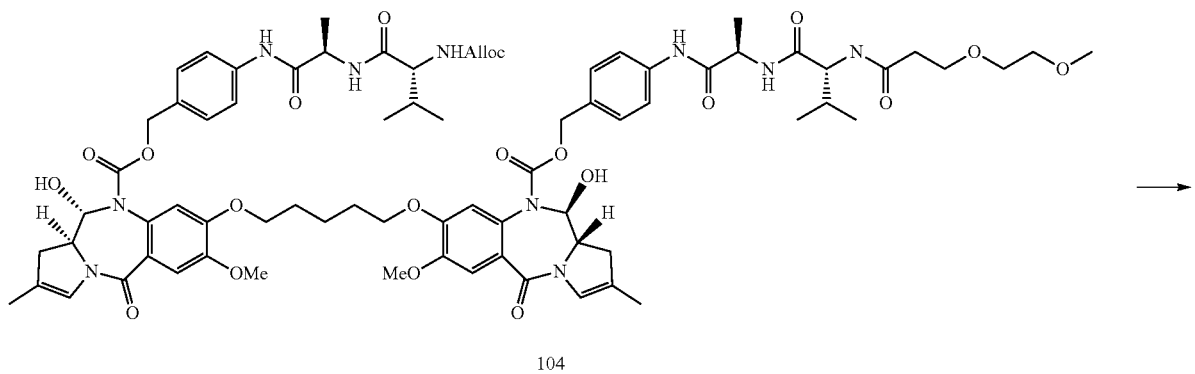

104

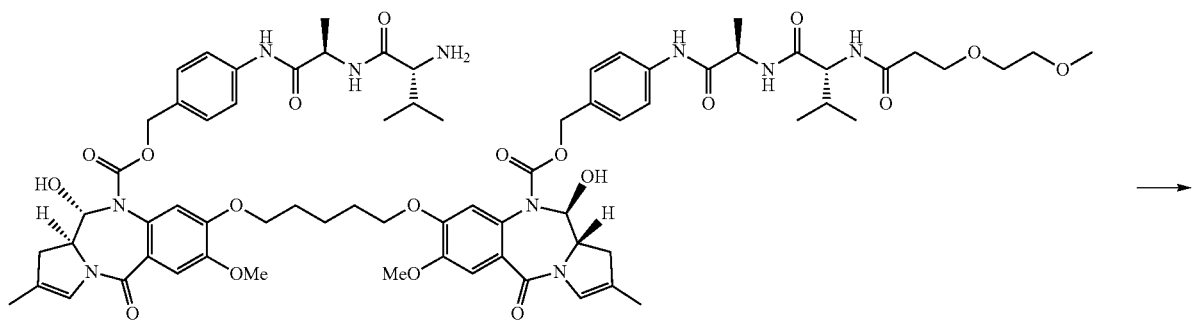

105

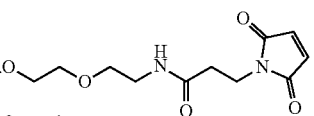
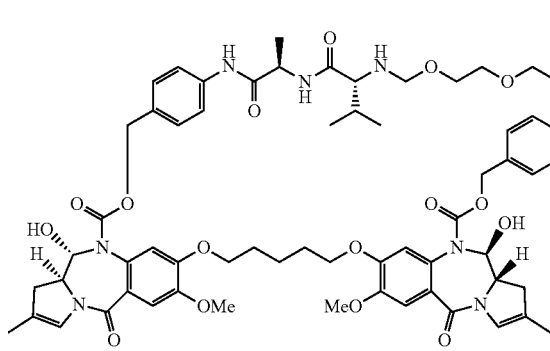

106

(a) (11S,11aS)-4-((R)-2-((R)-2-(((allyloxy)carbonyl) amino)-3-methylbutanamido)propanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (104)

Dess-Martin periodinane (0.59 g, 1.38 mmol, 2.1 eq) was added to a stirred solution of 103 (0.97 g, 0.66 mmol) in anhydrous DCM under argon at room temperature. The reaction mixture was allowed to stir for 4 hours. Reaction mixture diluted with DCM (100 mL), washed with saturated sodium bicarbonate solution (3×100 mL), water (100 mL), brine (100 mL), dried over MgSO$_4$, filtered and evaporated. Flash chromatography [gradient elution 100% chloroform to 95% chloroform/5% methanol] gave pure 104 as a pale yellow solid (0.88 g, 90%). LC/MS: RT 1.57 min; MS (ES+) m/z (relative intensity) 1473.35 (100).

(b) (11S,11aS)-4-((R)-2-((R)-2-amino-3-methylbutanamido)propanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (105)

Tetrakis(triphenylphosphine)palladium (5 mg, 0.004 mmol, 0.06 eq) was added to a solution of 104 (105 mg, 0.071 mmol) and pyrrolidine (7 µL, 0.086 mmol, 1.2 eq) in anhydrous DCM (5 mL). The reaction mixture was stirred 15 minutes then diluted with chloroform (50 mL) and washed sequentially with saturated aqueous ammonium chloride (30 mL) and brine (30 mL). The organic phase was dried over magnesium sulphate, filtered and evaporated. Flash chromatography [gradient elution 100% chloroform to 90% chloroform/10% methanol] gave pure 105 as a pale yellow solid (54 mg, 55%). LC/MS: RT 1.21 min; MS (ES+) m/z (relative intensity) 1389.50 (100).

(c) (11S,11 aS)-4-((2R,5R)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (106)

N-(3-Dimethylaminopropyl)-N'-ethylcarbodiimide (28 mg, 0.146 mmol, 1 eq) was added to a solution of 105 (203 mg, 0.146 mmol) and maleimide-PEG$_8$ acid (87 mg, 0.146 mmol) in chloroform (5 mL). The reaction was stirred for 1.5 h then diluted with chloroform (50 mL), washed with water (50 mL), brine (30 mL), dried over magnesium sulphate, filtered and evaporated. Flash chromatography [gradient elution 100% DCM to 90% DCM/10% methanol] gave 106 as a pale yellow solid (205 mg, 72%). LC/MS: RT 5.75 min; MS (ES+) m/z (relative intensity) 982.90 (100), 1963.70 (5).

Example 12: Activity of Released Compounds

K562 Assay

K562 human chronic myeloid leukaemia cells were maintained in RPM1 1640 medium supplemented with 10% fetal calf serum and 2 mM glutamine at 37° C. in a humidified atmosphere containing 5% CO$_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates (10$^4$ cells per well, 8 wells per sample). Plates were then kept in the dark at 37° C. in a humidified atmosphere containing 5% CO$_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 µL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Abbreviations

Ac acetyl
Acm acetamidomethyl
Alloc allyloxycarbonyl
Boc di-tert-butyl dicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N-10 imine protecting group: 3-(2-methoxyethoxy)propanoate-Val-Ala-PAB
MC-OSu maleimidocaproyl-O—N-succinimide
Moc methoxycarbonyl
MP maleimidopropanamide
Mtr 4-methoxy-2,3,6-trimethylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
TBDMS tert-butyldimethylsilyl
TBDPS tert-butyldiphenylsilyl
Teoc 2-(trimethylsilyl)ethoxycarbonyl
Tos tosyl
Troc 2,2,2-trichloroethoxycarbonyl chloride
Trt trityl
Xan xanthyl

STATEMENTS OF INVENTION

1. A conjugate of formula L-(DL)p, where DL is of formula I or II:

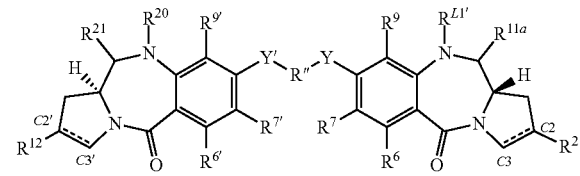

I

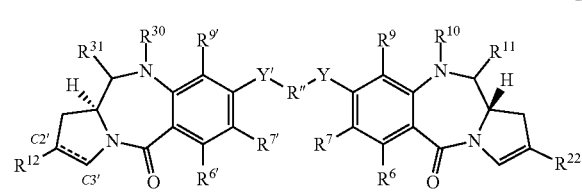

II wherein:
L is an antibody (Ab) which binds CD22;
when there is a double bond present between C2' and C3', $R^{12}$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

(id)

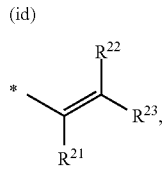

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

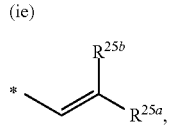

wherein one of $R^{25a}$ and $R^{25b}$ is H and the other is selected from: phenyl, which phenyl is optionally substituted by a group selected from halo, methyl, methoxy; pyridyl; and thiophenyl; and (if)

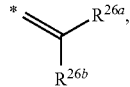

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{12}$ is

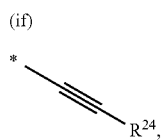

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound; or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

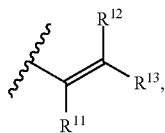

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

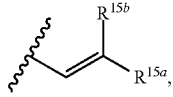

wherein one of $R^{15a}$ and $R^{15b}$ is H and the other is selected from: phenyl, which phenyl is optionally substituted by a group selected from halo, methyl, methoxy; pyridyl; and thiophenyl; and (ie)

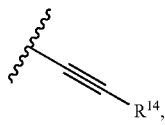

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

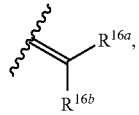

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula-IIIa, formula-IIIb or formula IIIc:

(a)

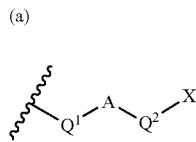

IIIa where A is a $C_{5-7}$ aryl group, and either (i) $Q^1$ is a single bond, and $Q^2$ is selected from a single bond and —Z—$(CH_2)_n$—, where Z is selected from a single bond, O, S and NH and n is from 1 to 3; or (ii) $Q^1$ is —CH=CH—, and $Q^2$ is a single bond;

(b)

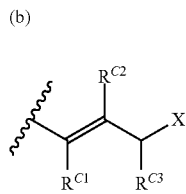

IIIb where;

$R^{C1}$, $R^{C2}$ and $R^{C3}$ are independently selected from H and unsubstituted $C_{1-2}$ alkyl;

(c)

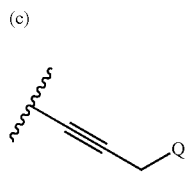

IIIc where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

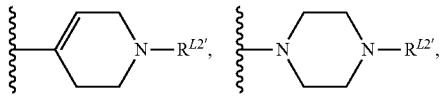

NR$^N$R$^{L2'}$, wherein R$^N$ is selected from the group comprising H and C$_{1-4}$ alkyl;
R$^{L2'}$ is a linker for connection to the antibody (Ab);
R$^{10}$ and R$^{11}$ either together form a double bond between the nitrogen and carbon atoms to which they are bound or;
R$^{10}$ is H and R$^{11}$ is selected from OH, OR$^A$ and SO$_z$M;

R$^{30}$ and R$^{31}$ either together form a double bond between the nitrogen and carbon atoms to which they are bound or;
R$^{30}$ is H and R$^{31}$ is selected from OH, OR$^A$ and SO$_z$M.

2. The conjugate according to statement 1, wherein the conjugate is not:

ConjA

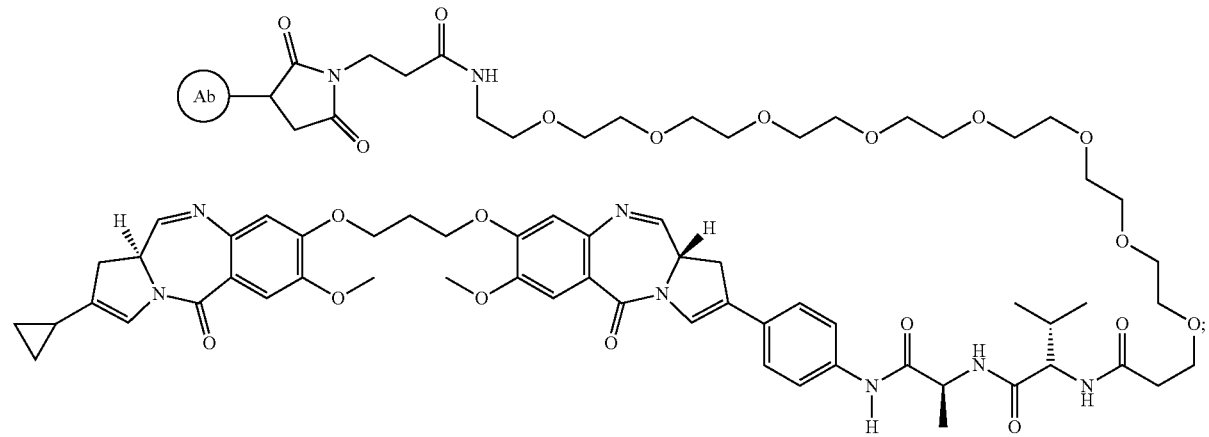

ConjB

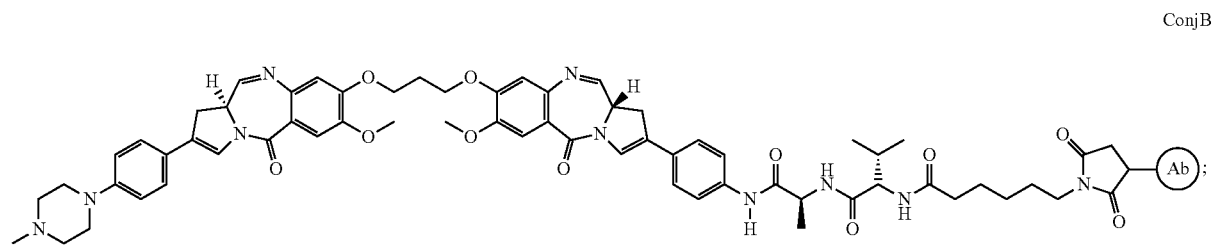

ConjC

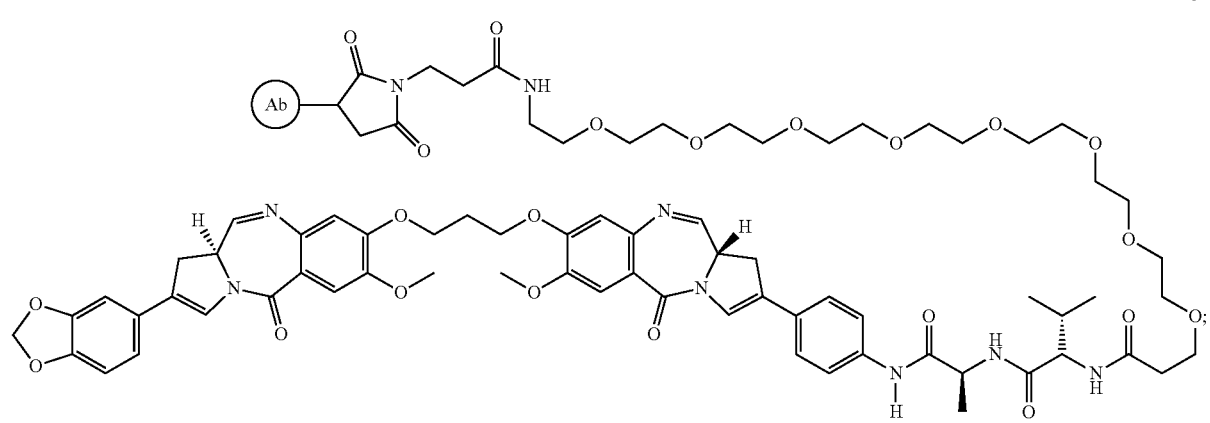

ConjD

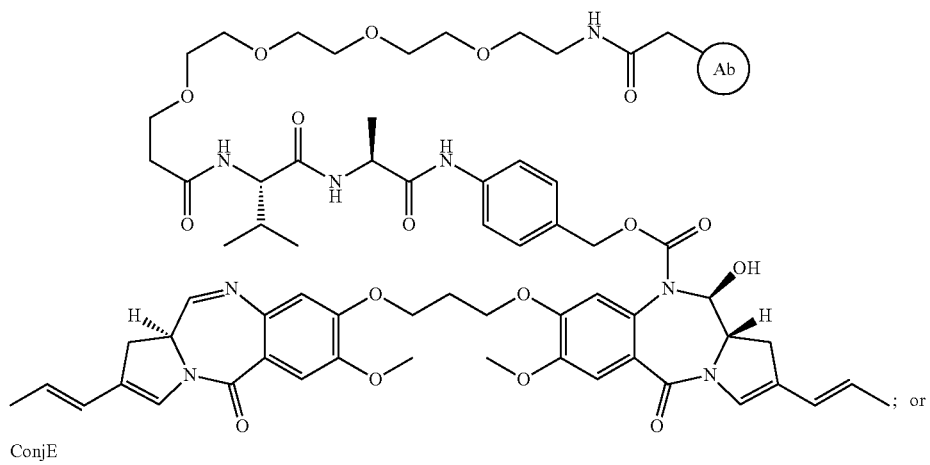

ConjE

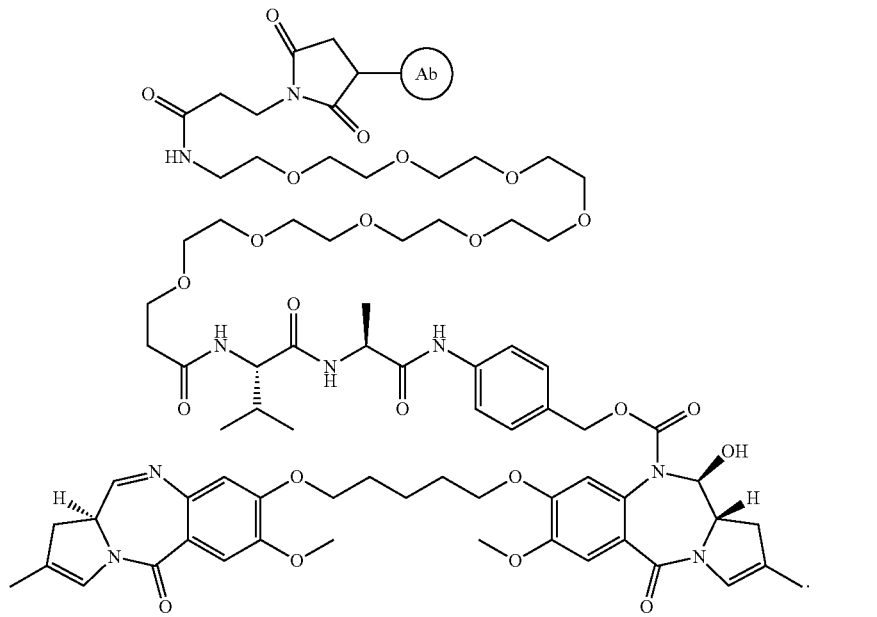

3. The conjugate according to either statement 1 or statement 2, wherein $R^7$ is selected from H, OH and OR.

4. The conjugate according to statement 3, wherein $R^7$ is a $C_{1-4}$ alkyloxy group.

5. The conjugate according to any one of statements 1 to 4, wherein Y is O.

6. The conjugate according to any one of the preceding statements, wherein $R^{11}$ is $C_{3-7}$ alkylene.

7. The conjugate according to any one of statements 1 to 6, wherein $R^9$ is H.

8. The conjugate according to any one of statements 1 to 7, wherein $R^6$ is selected from H and halo.

9. The conjugate according to any one of statements 1 to 8, wherein there is a double bond between C2' and C3', and $R^{12}$ is a $C_{5-7}$ aryl group.

10. The conjugate according to statement 9, wherein $R^{12}$ is phenyl.

11. The conjugate according to any one of statements 1 to 8, wherein there is a double bond between C2' and C3', and $R^{12}$ is a $C_{8-10}$ aryl group.

12. The conjugate according to any one of statements 9 to 11, wherein $R^{12}$ bears one to three substituent groups.

13. The conjugate according to any one of statements 9 to 12, wherein the substituents are selected from methoxy, ethoxy, fluoro, chloro, cyano, bis-oxy-methylene, methyl-piperazinyl, morpholino and methyl-thiophenyl.

14. The conjugate according to any one of statements 1 to 8, wherein there is a double bond between C2' and C3', and $R^{12}$ is a $C_{1-5}$ saturated aliphatic alkyl group.

15. A compound according to statement 14, wherein $R^{12}$ is methyl, ethyl or propyl.

16. The conjugate according to any one of statements 1 to 8, wherein there is a double bond between C2' and C3', and $R^{12}$ is a $C_{3-6}$ saturated cycloalkyl group.

17. The conjugate according to statement 16, wherein $R^{12}$ is cyclopropyl.

18. The conjugate according to any one of statements 1 to 8, wherein there is a double bond between C2' and C3', and $R^{12}$ is a group of formula:

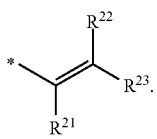

19. The conjugate according to statement 18, wherein the total number of carbon atoms in the $R^{12}$ group is no more than 4.

20. The conjugate according to statement 19, wherein the total number of carbon atoms in the $R^{12}$ group is no more than 3.

21. The conjugate according to any one of statements 18 to 20, wherein one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

22. The conjugate according to any one of statements 18 to 20, wherein two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

23. The conjugate according to any one of statements 1 to 8, wherein there is a double bond between C2' and C3', and $R^{12}$ is a group of formula:

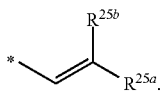

24. The conjugate according to statement 23, wherein $R^{12}$ is the group:

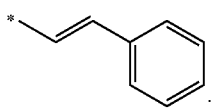

25. The conjugate according to any one of statements 1 to 8, wherein there is a double bond between C2' and C3', and $R^{12}$ is a group of formula:

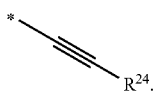

26. The conjugate according to statement 25, wherein $R^{24}$ is selected from H, methyl, ethyl, ethenyl and ethynyl.

27. The conjugate according to statement 26, wherein $R^{24}$ is selected from H and methyl.

28. The conjugate according to any one of statements 1 to 8, wherein there is a single bond between C2' and C3', $R^{12}$ is

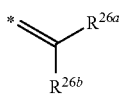

R and $R^{26a}$ and $R^{26b}$ are both H.

29. The conjugate according to any one of statements 1 to 8, wherein there is a single bond between C2' and C3', $R^{12}$ is

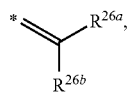

and $R^{26a}$ and $R^{26b}$ are both methyl.

30. The conjugate according to any one of statements 1 to 8, wherein there is a single bond between C2' and C3', $R^{12}$ is

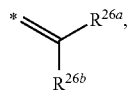

one of $R^{26a}$ and $R^{26b}$ is H, and the other is selected from $C_{1-4}$ saturated alkyl, $C_{2-3}$ alkenyl, which alkyl and alkenyl groups are optionally substituted.

[Formula I]

31. The conjugate according to any one of statements 1 to 30, wherein there is a double bond between C2 and C3, and $R^2$ is a $C_{5-7}$ aryl group.

32. The conjugate according to statement 31, wherein $R^2$ is phenyl.

33. The conjugate according to any one of statements 1 to 30, wherein there is a double bond between C2 and C3, and $R^1$ is a $C_{8-10}$ aryl group.

34. A compound according to any one of statements 31 to 33, wherein $R^2$ bears one to three substituent groups.

35. The conjugate according to any one of statements 31 to 34, wherein the substituents are selected from methoxy, ethoxy, fluoro, chloro, cyano, bis-oxy-methylene, methyl-piperazinyl, morpholino and methyl-thiophenyl.

36. The conjugate according to any one of statements 1 to 30, wherein there is a double bond between C2 and C3, and $R^2$ is a $C_{1-5}$ saturated aliphatic alkyl group.

37. The conjugate according to statement 36, wherein $R^2$ is methyl, ethyl or propyl.

38. The conjugate according to any one of statements 1 to 30, wherein there is a double bond between C2 and C3, and $R^2$ is a $C_{3-6}$ saturated cycloalkyl group.

39. The conjugate according to statement 38, wherein $R^2$ is cyclopropyl.

40. The conjugate according to any one of statements 1 to 30, wherein there is a double bond between C2 and C3, and $R^2$ is a group of formula:

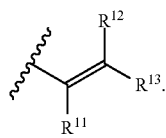

41. The conjugate according to statement 40, wherein the total number of carbon atoms in the $R^2$ group is no more than 4.

42. The conjugate according to statement 41, wherein the total number of carbon atoms in the $R^2$ group is no more than 3.

43. The conjugate according to any one of statements 40 to 42, wherein one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl.

44. The conjugate according to any one of statements 40 to 42, wherein two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

45. The conjugate according to any one of statements 1 to 30, wherein there is a double bond between C2 and C3, and $R^2$ is a group of formula:

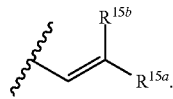

46. The conjugate according to statement 45, wherein $R^2$ is the group:

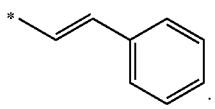

47. The conjugate according to any one of statements 1 to 30, wherein there is a double bond between C2 and C3, and $R^2$ is a group of formula:

48. The conjugate according to statement 47, wherein $R^{14}$ is selected from H, methyl, ethyl, ethenyl and ethynyl.

49. The conjugate according to statement 47, wherein $R^{14}$ is selected from H and methyl.

50. The conjugate according to any one of statements 1 to 30, wherein there is a single bond between C2 and C3, $R^2$ is

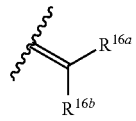

and $R^{16a}$ and $R^{16b}$ are both H.

51. The conjugate according to any one of statements 1 to 30, wherein there is a single bond between C2 and C3, $R^2$ is

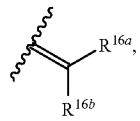

and $R^{16a}$ and $R^{16b}$ are both methyl.

52. The conjugate according to any one of statements 1 to 30, wherein there is a single bond between 02 and 03, $R^2$ is

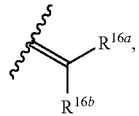

one of $R^{16a}$ and $R^{16b}$ is H, and the other is selected from $C_{1-4}$ saturated alkyl, $C_{2-3}$ alkenyl, which alkyl and alkenyl groups are optionally substituted.

53. The conjugate according to any one of statements 1 to 52, wherein $R^{11a}$ is OH.

54. The conjugate according to any one of statements 1 to 53, wherein $R^{21}$ is OH.

55. The conjugate according to any one of statements 1 to 53, wherein $R^{21}$ is OMe.

56. The conjugate according to any one of statements 1 to 55, wherein $R^{20}$ is H.

57. The conjugate according to any one of statements 1 to 55, wherein $R^{20}$ is $R^C$.

58. The conjugate according to statement 57, wherein $R^C$ is selected from the group consisting of: Alloc, Fmoc, Boc, and Troc.

59. The conjugate according to statement 57, wherein $R_C$ is selected from the group consisting of: Teoc, Psec, Cbz and PNZ.

60. The conjugate according to statement 57, wherein $R^C$ is a group:

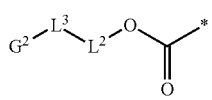

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

61. The conjugate according to statement 60, wherein $G^2$ is Ac or Moc or is selected from the group consisting of: Alloc, Fmoc, Boc, Troc, Teoc, Psec, Cbz and PNZ.

62. The conjugate according to any one of statements 1 to 53, wherein $R^{20}$ and $R^{21}$ together form a double bond between the nitrogen and carbon atoms to which they are bound.

[Formula II]

63. The conjugate according to any one of statements 1 to 30, wherein $R^{22}$ is of formula IIIa, and A is phenyl.

64. The conjugate according to any one of statements 1 to 30 and statement 63, wherein $R^{22}$ is of formula IIa, and $Q^1$ is a single bond.

65. The conjugate according to statement 63, wherein $Q^2$ is a single bond.

66. The conjugate according to statement 63, wherein $Q^2$ is —Z—$(CH_2)_n$—, Z is O or S and n is 1 or 2.

67. The conjugate according any one of statements 1 to 30 and statement 63, wherein $R^{22}$ is of formula IIIa, and $Q^1$ is —CH=CH—. 68. The conjugate according to any one of statements 1 to 30, wherein $R^{22}$ is of formula IIIb, and $R^{C1}$, $R^{C2}$ and $R^{C3}$ are independently selected from H and methyl.

69. The conjugate according to statement 68, wherein $R^{C1}$, $R^{C2}$ and $R^{C3}$ are all H.

70. The conjugate according to statement 68, wherein $R^{C1}$, $R^{C2}$ and $R^{C3}$ are all methyl.

71. The conjugate according to any one of statements 1 to 30 and statements 63 to 70, wherein $R^{22}$ is of formula IIIa or formula IIIb and X is selected from $O-R^{L2'}$, $S-R^{L2'}$, $CO_2-R^{L2'}$, $-N-C(=O)-R^{L2'}$ and $NH-R^{L2'}$.

72. The conjugate according to statement 71, wherein X is $NH-R^{L2'}$.

73. The conjugate according to any one of statements 1 to 30, wherein $R^{22}$ is of formula IIIc, and Q is $NR^N-R^{L2'}$.

74. The conjugate according to statement 73, wherein $R^N$ is H or methyl.

75. The conjugate according to any one of statements 1 to 30, wherein $R^{22}$ is of formula IIIc, and Q is $O-R^{L2'}$ or $S-R^{L2'}$.

76. The conjugate according to any one of statements 1 to 30 and statements 63 to 75, wherein $R^{11}$ is OH.

77. The conjugate according to any one of statements 1 to 30 and statements 63 to 75, wherein $R^{11}$ is OMe.

78. The conjugate according to any one of statements 1 to 30 and statements 63 to 77, wherein $R^{10}$ is H.

79. The conjugate according to any one of statements 1 to 30 and statements 63 to 75, wherein $R^{10}$ and $R^{11}$ together form a double bond between the nitrogen and carbon atoms to which they are bound.

80. The conjugate according to any one of statements 1 to 30 and statements 63 to 79, wherein $R^{31}$ is OH.

81. The conjugate according to any one of statements 1 to 30 and statements 63 to 79, wherein $R^{31}$ is OMe.

82. The conjugate according to any one of statements 1 to 30 and statements 63 to 81, wherein $R^{30}$ is H.

83. The conjugate according to any one of statements 1 to 30 and statements 63 to 79, wherein $R^{30}$ and $R^{31}$ together form a double bond between the nitrogen and carbon atoms to which they are bound.

84. The conjugate according to any one of statements 1 to 83, wherein $R^{6'}$, $R^{7'}$, $R^{9'}$, and Y' are the same as $R^6$, $R^7$, $R^9$, and Y. 85. The conjugate according to any one of statements 1 to 84 wherein, wherein $L-R^{L1'}$ or $L-R^{L2'}$ is a group:

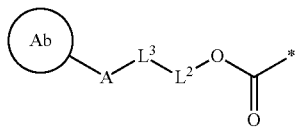

where the asterisk indicates the point of attachment to the PBD, Ab is the antibody, $L^1$ is a cleavable linker, A is a connecting group connecting $L^1$ to the antibody, $L^2$ is a covalent bond or together with $-OC(=O)-$ forms a self-immolative linker.

86. The conjugate of statement 85, wherein $L^1$ is enzyme cleavable.

87. The conjugate of statement 85 or statement 86, wherein $L^1$ comprises a contiguous sequence of amino acids.

88. The conjugate of statement 87, wherein $L^1$ comprises a dipeptide and the group $-X_1-X_2-$ in dipeptide, $-NH-X_1-X_2-CO-$, is selected from:
Phe-Lys-,
Val-Ala-,
Val-Lys-,
Ala-Lys-,
Val-Cit-,
Phe-Cit-,
Leu-Cit-,
Ile-Cit-,
Phe-Arg-,
Trp-Cit-.

89. The conjugate according to statement 88, wherein the group $-X_1-X_2-$ in dipeptide, $-NH-X_1-X_2-CO-$, is selected from:
Phe-Lys-,
Val-Ala-,
Val-Lys-,
Ala-Lys-,
Val-Cit-.

90. The conjugate according to statement 89, wherein the group $-X_1-X_2-$ in dipeptide, $-NH-X_1-X_2-CO-$, is -Phe-Lys-, -Val-Ala- or -Val-Cit-.

91. The conjugate according to any one of statements 88 to 90, wherein the group $X_2-CO-$ is connected to $L^2$.

92. The conjugate according to any one of statements 88 to 91, wherein the group $NH-X_1-$ is connected to A.

93. The conjugate according to any one of statements 88 to 92, wherein $L^2$ together with $OC(=O)$ forms a self-immolative linker.

94. The conjugate according to statement 93, wherein $C(=O)O$ and $L^2$ together form the group:

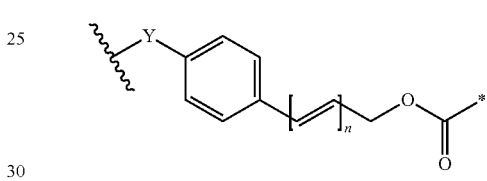

where the asterisk indicates the point of attachment to the PBD, the wavy line indicates the point of attachment to the linker $L^1$, Y is NH, O, $C(=O)NH$ or $C(=O)O$, and n is 0 to 3.

95. The conjugate according to statement 94, wherein Y is NH.

96. The conjugate according to statement 94 or statement 95, wherein n is 0.

97. The conjugate according to statement 95, wherein $L^1$ and $L^2$ together with $-OC(=O)-$ comprise a group selected from:

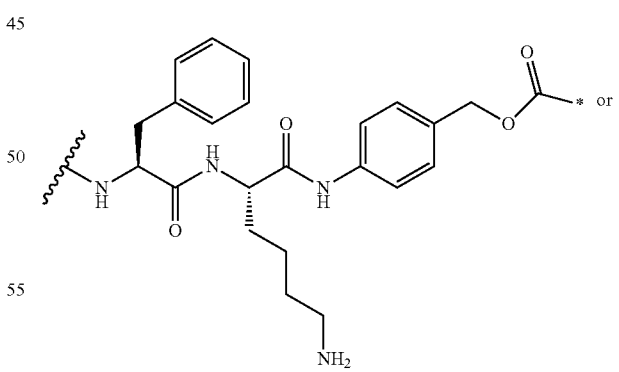

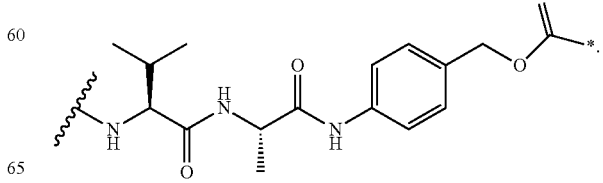

where the asterisk indicates the point of attachment to the PBD, and the wavy line indicates the point of attachment to the remaining portion of the linker $L^1$ or the point of attachment to A.

98. The conjugate according to statement 97, wherein the wavy line indicates the point of attachment to A.

99. The conjugate according to any one of statements 85 to 98, wherein A is:

(i)

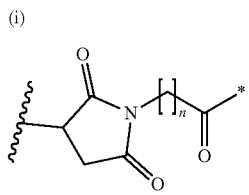

ConjA where the asterisk indicates the point of attachment to $L^1$, the wavy line indicates the point of attachment to the antibody, and n is 0 to 6; or (ii)

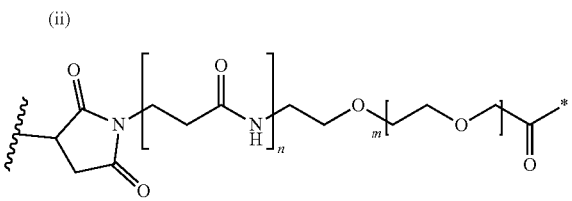

where the asterisk indicates the point of attachment to $L^1$, the wavy line indicates the point of attachment to the antibody, n is 0 or 1, and m is 0 to 30.

100. A conjugate according to statement 1 of formula

ConjA

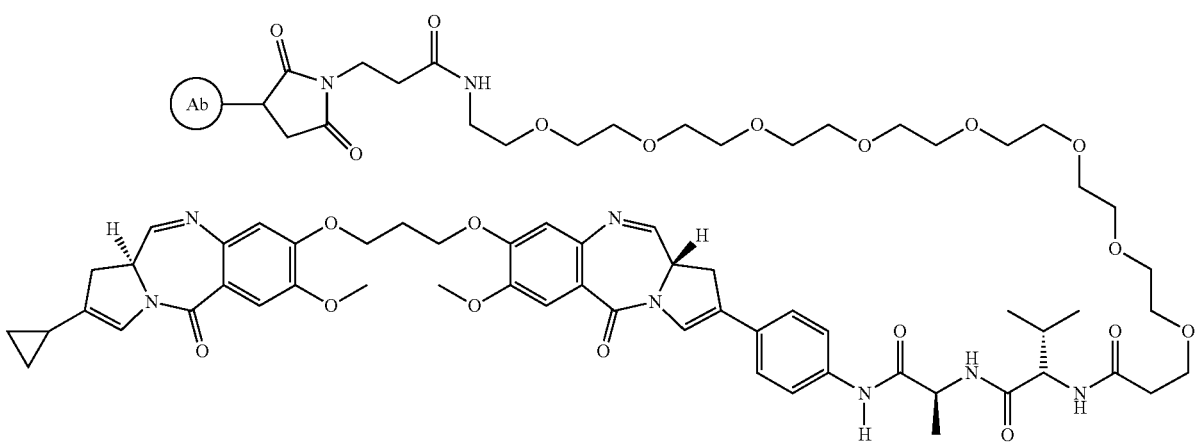

ConjB

ConjB

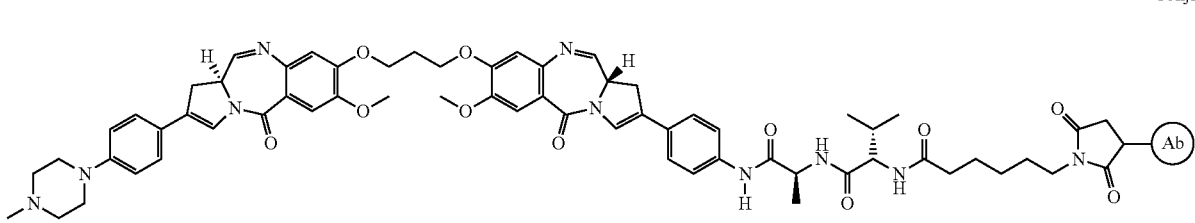

-continued
ConjC
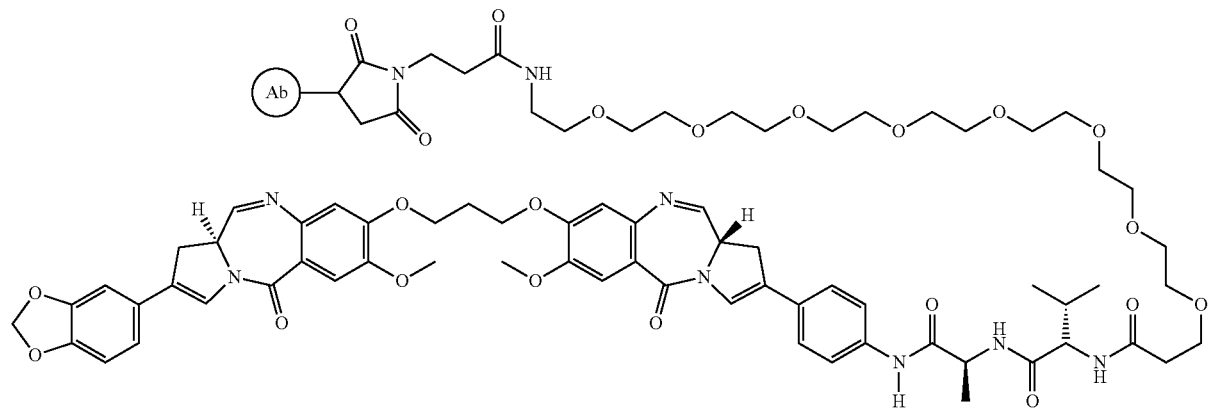
ConjD
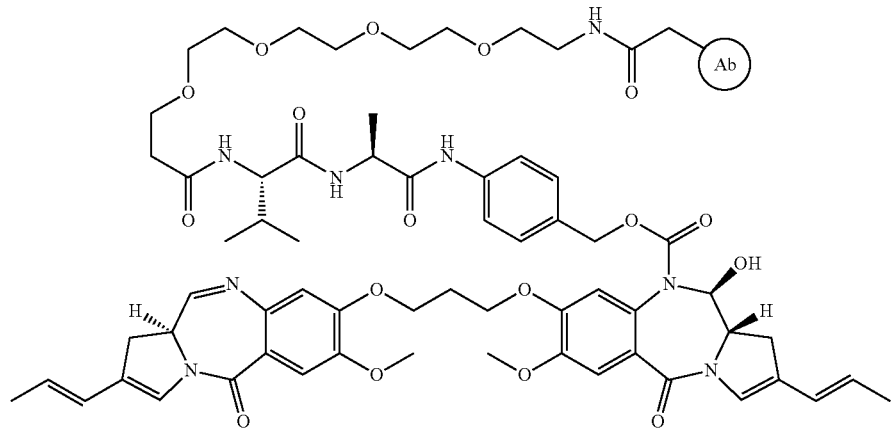
ConjE
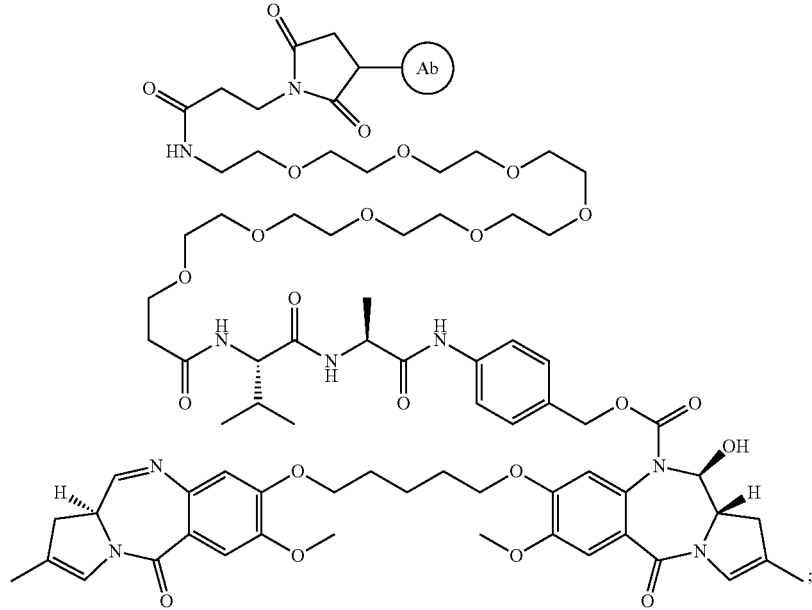

-continued

ConjF

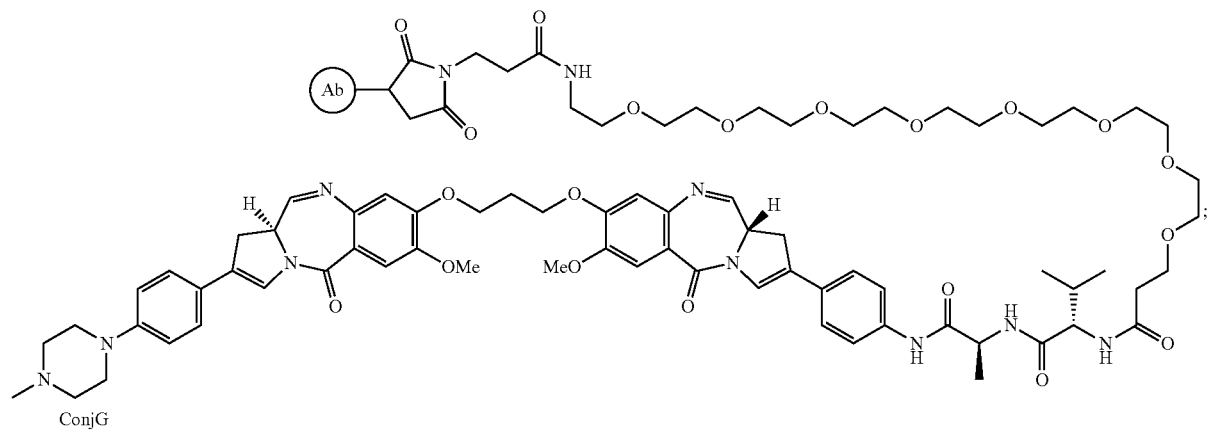

ConjF

ConjG

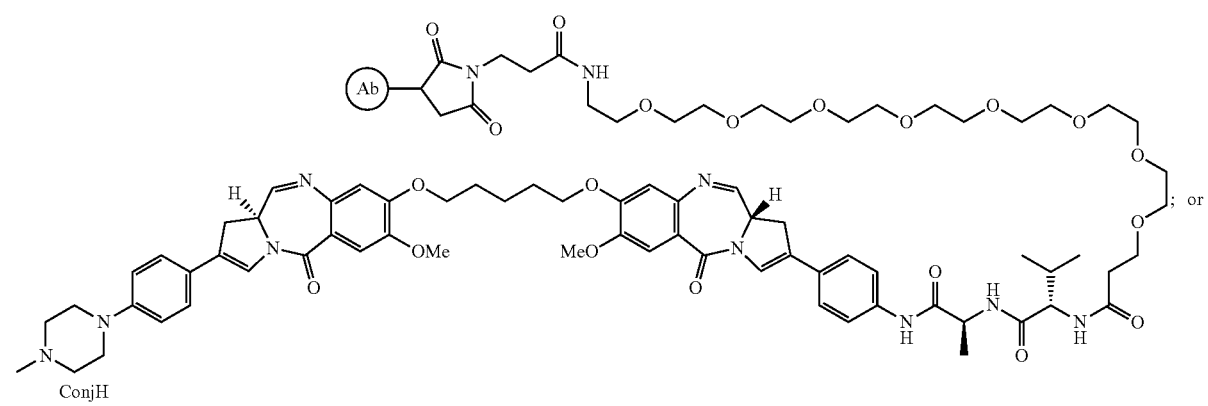

ConjG; or

ConjH

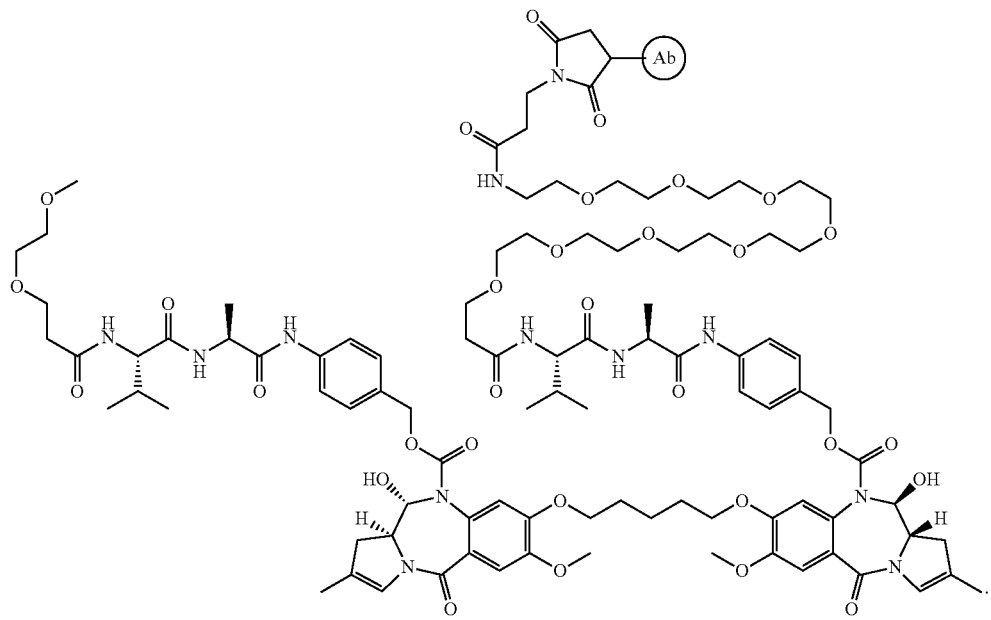

ConjH.

101. The conjugate according to any one of statements 1 to 100 wherein the antibody comprises an amino acid substitution of an interchain cysteine residue by an amino acid that is not cysteine and the conjugation of the drug moiety to the antibody is at an interchain cysteine residue.

102. The conjugate according to statement 101 wherein the antibody comprises a heavy chain comprising the amino acid sequence of SEQ ID NO.110 or fragment thereof, SEQ ID NO.120 or fragment thereof, SEQ ID NO.130 or fragment thereof, or SEQ ID NO.140 or fragment thereof.

103. The conjugate according to statement 102 wherein the drug moiety is conjugated to the cysteine at position 103 of SEQ ID NO.110, the cysteine at position 14 of SEQ ID NO.120, the cysteine at position 103 of SEQ ID NO.120, the cysteine at position 14 of SEQ ID NO.130, or the cysteine at position 14 of SEQ ID NO.140.

104. The conjugate according to either one of statements 102 or 103 wherein the antibody comprises:
a light chain comprising the amino acid sequence of SEQ ID NO. 150, or fragment thereof, wherein the cysteine at position 105, if present, is substituted by an amino acid that is not cysteine; or
a light chain comprising the amino acid sequence of SEQ ID NO. 160, or fragment thereof, wherein the cysteine at position 102, if present, is substituted by an amino acid that is not cysteine.

105. The conjugate according to statement 101 wherein the antibody comprises:
a heavy chain comprising the amino acid sequence of SEQ ID NO.110 and light chain comprising the amino acid sequence of SEQ ID NO.151, SEQ ID NO.152, SEQ ID NO.153, SEQ ID NO.161, SEQ ID NO.162, or SEQ ID NO.163;
optionally wherein the drug moiety is conjugated to the cysteine at position 103 of SEQ ID NO.110.

106. The conjugate according to statement 101 wherein the antibody comprises:
a heavy chain comprising the amino acid sequence of SEQ ID NO.110, or fragment thereof, wherein the cysteine at position 103 of SEQ ID NO.110, if present, is substituted by an amino acid that is not cysteine;
a heavy chain comprising the amino acid sequence of SEQ ID NO.120, or fragment thereof, wherein each of the cysteines at positions 14 and 103 of SEQ ID NO.120, if present, is substituted by an amino acid that is not cysteine;
a heavy chain comprising the amino acid sequence of SEQ ID NO.130, or fragment thereof, wherein the cysteine at position 14 in SEQ ID NO: 130, if present, is substituted by an amino acid that is not cysteine; or
a heavy chain comprising the amino acid sequence of SEQ ID NO.140, or fragment thereof, wherein the cysteine at position 14 in SEQ ID NO: 140, if present, is substituted by an amino acid that is not cysteine.

107. The conjugate according to statement 106 wherein the antibody comprises a light chain comprising the amino acid sequence of SEQ ID NO. 150 or SEQ ID NO. 160.

108. The conjugate according to statement 101 wherein the antibody comprises:
a heavy chain comprising the amino acid sequence of SEQ ID NO.111 and a light chain comprising the amino acid sequence of SEQ ID NO.150 or SEQ ID NO.160.

109. The conjugate according to statement 101 wherein the antibody comprises:
a heavy chain comprising the amino acid sequence of SEQ ID NO.112 and a light chain comprising the amino acid sequence of SEQ ID NO.150 or SEQ ID NO.160.

110. The conjugate according to any one of statements 107 to 109 wherein the drug moiety is conjugated to the cysteine at position 105 of SEQ ID NO.150, or the cysteine at position 102 of SEQ ID NO.160.

111. The conjugate according to statement 101 wherein the antibody comprises:
a heavy chain comprising the amino acid sequence of SEQ ID NO.110, or fragment thereof, wherein each of the cysteines at positions 109 and 112 in SEQ ID NO: 110, if present, is substituted by an amino acid that is not cysteine;
a heavy chain comprising the amino acid sequence of SEQ ID NO.120, or fragment thereof, wherein each of the cysteines at positions 103, 106, and 109 in SEQ ID NO: 120, if present, is substituted by an amino acid that is not cysteine;
a heavy chain comprising the amino acid sequence of SEQ ID NO.120, or fragment thereof, wherein each of the cysteines at positions 14, 106, and 112 in SEQ ID NO: 120, if present, is substituted by an amino acid that is not cysteine;
a heavy chain comprising the amino acid sequence of SEQ ID NO.130, or fragment thereof, wherein each of the cysteines at positions 111, 114, 120, 126, 129, 135, 141, 144, 150, 156, and 159 in SEQ ID NO: 130, if present, is substituted by an amino acid that is not cysteine; or
a heavy chain comprising the amino acid sequence of SEQ ID NO.140, or fragment thereof, wherein each of the cysteines at positions 106 and 109 in SEQ ID NO: 140, if present, is substituted by an amino acid that is not cysteine.

112. The conjugate according to statement 111 the cysteine at position 102 in SEQ ID NO: 120, if present, is also substituted by an amino acid that is not cysteine.

113. The conjugate according to either one of statements 111 or 112 wherein the drug moiety is conjugated to the cysteine at position 103 of SEQ ID NO.110, the cysteine at position 14 of SEQ ID NO.120, the cysteine at position 103 of SEQ ID NO.120, the cysteine at position 14 of SEQ ID NO.130, or the cysteine at position 14 of SEQ ID NO.140.

114. The conjugate according to any one of statements 111 to 113 wherein the antibody comprises:
a light chain comprising the amino acid sequence of SEQ ID NO. 150, or fragment thereof, wherein the cysteine at position 105, if present, is substituted by an amino acid that is not cysteine; or
a light chain comprising the amino acid sequence of SEQ ID NO. 160, or fragment thereof, wherein the cysteine at position 102, if present, is substituted by an amino acid that is not cysteine.

115. The conjugate according to statement 101 wherein the antibody comprises:
a heavy chain comprising the amino acid sequence of SEQ ID NO.113 and a light chain comprising the amino acid sequence of SEQ ID NO.151, SEQ ID NO.152, SEQ ID NO.153, SEQ ID NO.161, SEQ ID NO.162, or SEQ ID NO.163;
optionally wherein the drug moiety is conjugated to the cysteine at position 103 of SEQ ID NO.113.

116. The conjugate according to statement 101 wherein the antibody comprises:
a heavy chain comprising the amino acid sequence of SEQ ID NO.114 and a light chain comprising the amino acid sequence of SEQ ID NO.151, SEQ ID NO.152, SEQ ID NO.153, SEQ ID NO.161, SEQ ID NO.162, or SEQ ID NO.163;
optionally wherein the drug moiety is conjugated to the cysteine at position 103 of SEQ ID NO.114.

117. The conjugate according to statement 101 wherein the antibody comprises:
a heavy chain comprising the amino acid sequence of SEQ ID NO.110, or fragment thereof, wherein each of the cysteines at positions 103, 109 and 112 in SEQ ID NO: 110, if present, is substituted by an amino acid that is not cysteine;

a heavy chain comprising the amino acid sequence of SEQ ID NO.120, or fragment thereof, wherein each of the cysteines at positions 14, 103, 106 and 109 in SEQ ID NO: 120, if present, is substituted by an amino acid that is not cysteine;

a heavy chain comprising the amino acid sequence of SEQ ID NO.130, or fragment thereof, wherein each of the cysteines at positions 14, 111, 114, 120, 126, 129, 135, 141, 144, 150, 156, and 159 in SEQ ID NO: 130, if present, is substituted by an amino acid that is not cysteine; or a heavy chain comprising the amino acid sequence of SEQ ID NO.140, or fragment thereof, wherein each of the cysteines at positions 14, 106, and 109 in SEQ ID NO: 140, if present, is substituted by an amino acid that is not cysteine.

118. The conjugate according to statement 117 wherein the antibody comprises a light chain comprising the amino acid sequence of SEQ ID NO. 150 or SEQ ID NO. 160.

119. The conjugate according to statement 101 wherein the antibody comprises a heavy chain comprising the amino acid sequence of SEQ ID NO.115 and a light chain comprising the amino acid sequence of SEQ ID NO. 150 or SEQ ID NO. 160.

120. The conjugate according to statement 101 wherein the antibody comprises a heavy chain comprising the amino acid sequence of SEQ ID NO.116 and a light chain comprising the amino acid sequence of SEQ ID NO. 150 or SEQ ID NO. 160.

121. The conjugate according to statement 118 wherein the drug moiety is conjugated to the cysteine at position 105 of SEQ ID NO.150, the cysteine at position 102 of SEQ ID NO.160

122. The conjugate according to any one of statements 1 to 100 wherein the antibody comprises a heavy chain having a substitution of the amino acid at position 234 in the EU index set forth in Kabat and/or a substitution of the residue at position 235 in the EU index set forth in Kabat.

123. The conjugate according to statement 122 wherein the antibody comprises a heavy chain having a substitution of the amino acid at position 234 in the EU index set forth in Kabat and a substitution of the residue at position 235 in the EU index set forth in Kabat.

124. The conjugate according to statement 122 wherein the antibody comprises a heavy chain comprising the amino acid sequence of SEQ ID NO.110, and wherein the leucine at position 117 and/or the leucine at position 118 is substituted by an amino acid that is not leucine.

125. The conjugate according to statement 124 wherein the antibody comprises a heavy chain comprising the amino acid sequence of SEQ ID NO.110, and wherein the leucine at position 117 and the leucine at position 118 are substituted by an amino acid that is not leucine.

126. The conjugate according to statement 122 wherein the antibody comprises a heavy chain comprising the amino acid sequence of SEQ ID NO.130, and wherein the leucine at position 164 and/or the leucine at position 165 is substituted by an amino acid that is not leucine.

127. The conjugate according to statement 126 wherein the antibody comprises a heavy chain comprising the amino acid sequence of SEQ ID NO.130, and wherein the leucine at position 164 and the leucine at position 165 are substituted by an amino acid that is not leucine.

128. The conjugate according to statement 122 wherein the antibody comprises a heavy chain comprising the amino acid sequence of SEQ ID NO.140, and wherein the leucine at position 115 is substituted by an amino acid that is not leucine.

129. The conjugate according to any one of statements 102 to 121 wherein:
the leucine at position 117 in SEQ ID NO: 110 and/or the leucine at position 118 in SEQ ID NO: 110 is substituted by an amino acid that is not leucine;
the leucine at position 164 in SEQ ID NO: 130 and/or the leucine at position 165 in SEQ ID NO: 130 is substituted by an amino acid that is not leucine; or
the leucine at position 115 in SEQ ID NO: 140 is substituted by an amino acid that is not leucine.

130. The conjugate according to statement 129 wherein:
the leucine at position 117 in SEQ ID NO: 110 and the leucine at position 118 in SEQ ID NO: 110 are substituted by an amino acid that is not leucine; or
the leucine at position 164 in SEQ ID NO: 130 and the leucine at position 165 in SEQ ID NO: 130 are substituted by an amino acid that is not leucine.

131. The conjugate according to any one of statements 122 to 130 wherein the substituted amino acids are replaced by alanine, glycine, valine, or isoleucine.

132. The conjugate according to any one of statements 122 to 131 wherein the substituted amino acids are replaced by alanine.

133. The conjugate according to any one of statements 1 to 132 wherein the antibody comprises a VH domain having the amino acid sequence of SEQ ID NO. 1.

134. The conjugate according to statement 133 wherein the antibody further comprises a VL domain having the amino acid sequence of SEQ ID NO. 2.

135. The conjugate according to any one of the preceding statements wherein the antibody in an intact antibody.

136. The conjugate according to any one of the preceding statements wherein the antibody is humanised, deimmunised or resurfaced.

137. The conjugate according to any one of the preceding statements wherein the conjugate has a maximum tolerated dose in rat at least 2.0 mg/kg delivered as a single-dose.

138. The conjugate according to any one of the preceding statements wherein the drug loading (p) of drugs (D) to antibody (Ab) is 2 or 4.

139. The conjugate according to any one of statements 1 to 138, for use in therapy.

140. The conjugate according to any one of statements 1 to 138, for use in the treatment of a proliferative disease in a subject.

141. The conjugate according to statement 140, wherein the disease is cancer.

142. A pharmaceutical composition comprising the conjugate of any one of statements 1 to 138 and a pharmaceutically acceptable diluent, carrier or excipient.

143. The pharmaceutical composition of statement 142 further comprising a therapeutically effective amount of a chemotherapeutic agent.

144. Use of a conjugate according to any one of statements 1 to 138 in the preparation of a medicament for use in the treatment of a proliferative disease in a subject.

145. A method of treating cancer comprising administering to a patient the pharmaceutical composition of statement 142.

146. The method of statement 145 wherein the patient is administered a chemotherapeutic agent, in combination with the conjugate.

SEQUENCES
SEQ ID NO. 1 (Epratuzumab VH):
QVQLVQSGAEVKKPGSSVKVSCKASGYTFTSYWLHWVRQAPGQGLEWIGYINPRNDYTE

YNQNFKDKATITADESTNTAYMELSSLRSEDTAFYFCARRDITTFYWGQG

SEQ ID NO. 2 (Epratuzumab VL):
DIQLTQSPSSLSASVGDRVTMSCKSSQSVLYSANHKNYLAWYQQKPGKAPKLLIYWASTRE

SGVPSRFSGSGSGTDFTFTISSLQPEDIATYYCHQYLSSWTFGQG

CD22

SEQ ID NO. 110 (IgG1 HC constant region)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPELLGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1101 (IgG1 HC constant region, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPEALGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1102 (IgG1 HC constant region, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1103 (IgG1 HC constant region, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1104 (IgG1 HC constant region, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1105 (IgG1 HC constant region, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1106 (IgG1 HC constant region, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 111 (IgG1 HC constant region, HJ C→S)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPELLGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1111 (IgG1 HC constant region, HJ C→S, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPEALGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1112 (IgG1 HC constant region, HJ C→S, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1113 (IgG1 HC constant region, HJ C→S, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1114 (IgG1 HC constant region, HJ C→S, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1115 (IgG1 HC constant region, HJ C→S, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1116 (IgG1 HC constant region, HJ C→S, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 112 (IgG1 HC constant region, HJ C→V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPELLGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1121 (IgG1 HC constant region, HJ C→V, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPEALGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1122 (IgG1 HC constant region, HJ C→V, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1123 (IgG1 HC constant region, HJ C→V, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1124 (IgG1 HC constant region, HJ C→V, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1125 (IgG1 HC constant region, HJ C→V, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1126 (IgG1 HC constant region, HJ C→V, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTCPPCPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 113 (IgG1 HC constant region, BJ C→S)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPELLGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1131 (IgG1 HC constant region, BJ C→S, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPEALGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1132 (IgG1 HC constant region, BJ C→S, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1133 (IgG1 HC constant region, BJ C→S, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1134 (IgG1 HC constant region, BJ C→S, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1135 (IgG1 HC constant region, BJ C→S, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1136 (IgG1 HC constant region, BJ C→S, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTSPPSPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 114 (IgG1 HC constant region, BJ C→V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPELLGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1141 (IgG1 HC constant region, BJ C→V, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPEALGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1142 (IgG1 HC constant region, BJ C→V, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1143 (IgG1 HC constant region, BJ C→V, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1144 (IgG1 HC constant region, BJ C→V, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1145 (IgG1 HC constant region, BJ C→V, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1146 (IgG1 HC constant region, BJ C→V, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTVPPVPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 115 (IgG1 HC constant region, DJ C→S)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPELLGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 1151 (IgG1 HC constant region, DJ C→S, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPEALGGPS

VFLFPPKPKDTLMISRTPEVTCVVVDVSHEDPEVKFNWYVDGVEVHNAKTKPREEQYNSTY

RWSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1152 (IgG1 HC constant region, DJ C→S, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1153 (IgG1 HC constant region, DJ C→S, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1154 (IgG1 HC constant region, DJ C→S, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1155 (IgG1 HC constant region, DJ C→S, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1156 (IgG1 HC constant region, DJ C→S, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTSPPSPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 116 (IgG1 HC constant region, DJ C→V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPELLGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 1161 (IgG1 HC constant region, DJ C→V, L117A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPEALGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1162 (IgG1 HC constant region, DJ C→V, L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPELAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1163 (IgG1 HC constant region, DJ C→V, L117A & L118A)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPEAAGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1164 (IgG1 HC constant region, DJ C→V, L117G & L118G)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPEGGGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1165 (IgG1 HC constant region, DJ C→V, L117V & L118V)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPEVVGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQREPQVYTLPPSREEMTKN

QVSLTCLVKGFYPSDIAVEWESNGQPENNYKTTPPVLDSDGSFFLYSKLTVDKSRWQQGN

VFSCSVMHEALHNHYTQKSLSLSPGK

SEQ ID NO. 1166 (IgG1 HC constant region, DJ C→V, L117I & L118I)
ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSVDKTHTVPPVPAPEIIGGPSV

FLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQREPQVYTLPPSREEMTKNQ

VSLTCLVKGFYPSDIAVEWESNGQPENNYKTTPPVLDSDGSFFLYSKLTVDKSRWQQGNV

FSCSVMHEALHNHYTQKSLSLSPGK

SEQ ID NO. 120 (IgG2 HC constant region)
ASTKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVV

SVLTVVHQDWLNGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDKSRWQQGNVFS

CSVMHEALHNHYTQKSLSLSPGK

SEQ ID NO. 130 (IgG3 HC constant region)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPELLGGPSVFLFPPKPKDTL

MISRTPEVTCVVVDVSHEDPEVQFNWYVDGVEVHNAKTKPREEQYNSTYRVVSVLTVLHQ

DWLNGKEYKCKVSNKALPAPIEKTISKTKGQPREPQVYTLPPSREEMTKNQVSLTCLVKGF

YPSDIAVEWESSGQPENNYKTTPPVLDSDGSFFLYSKLTVDKSRWQQGNIFSCSVMHEAL

HNHFTQKSLSLSPGK

SEQ ID NO. 131 (IgG3 HC constant region, L164A)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPEALGGPSVFLFPPKPKDTL

MISRTPEVTCVVVDVSHEDPEVQFNWYVDGVEVHNAKTKPREEQYNSTYRVVSVLTVLHQ

DWLNGKEYKCKVSNKALPAPIEKTISKTKGQPREPQVYTLPPSREEMTKNQVSLTCLVKGF

YPSDIAVEWESSGQPENNYKTTPPVLDSDGSFFLYSKLTVDKSRWQQGNIFSCSVMHEAL

HNHFTQKSLSLSPGK

SEQ ID NO. 132 (IgG3 HC constant region, L165A)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPELAGGPSVFLFPPKPKDTL

MISRTPEVTCVVVDVSHEDPEVQFNWYVDGVEVHNAKTKPREEQYNSTYRVVSVLTVLHQ

DWLNGKEYKCKVSNKALPAPIEKTISKTKGQPREPQVYTLPPSREEMTKNQVSLTCLVKGF

YPSDIAVEWESSGQPENNYKTTPPVLDSDGSFFLYSKLTVDKSRWQQGNIFSCSVMHEAL

HNHFTQKSLSLSPGK

SEQ ID NO. 133 (IgG3 HC constant region, L164A & L165A)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPEAAGGPSVFLFPPKPKDTL

MISRTPEVTCVVVDVSHEDPEVQFNWYVDGVEVHNAKTKPREEQYNSTYRVVSVLTVLHQ

DWLNGKEYKCKVSNKALPAPIEKTISKTKGQPREPQVYTLPPSREEMTKNQVSLTCLVKGF

YPSDIAVEWESSGQPENNYKTTPPVLDSDGSFFLYSKLTVDKSRWQQGNIFSCSVMHEAL

HNHFTQKSLSLSPGK

SEQ ID NO. 134 (IgG3 HC constant region, L164G & L165G)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPEGGGGPSVFLFPPKPKDTL

MISRTPEVTCVVVDVSHEDPEVQFNWYVDGVEVHNAKTKPREEQYNSTYRVVSVLTVLHQ

DWLNGKEYKCKVSNKALPAPIEKTISKTKGQPREPQVYTLPPSREEMTKNQVSLTCLVKGF

YPSDIAVEWESSGQPENNYKTTPPVLDSDGSFFLYSKLTVDKSRWQQGNIFSCSVMHEAL

HNHFTQKSLSLSPGK

SEQ ID NO. 135 (IgG3 HC constant region, L164V & L165V)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPEVVGGPSVFLFPPKPKDTL

MISRTPEVTCVVVDVSHEDPEVQFNWYVDGVEVHNAKTKPREEQYNSTYRVVSVLTVLHQ

DWLNGKEYKCKVSNKALPAPIEKTISKTKGQPREPQVYTLPPSREEMTKNQVSLTCLVKGF

YPSDIAVEWESSGQPENNYKTTPPVLDSDGSFFLYSKLTVDKSRWQQGNIFSCSVMHEAL

HNHFTQKSLSLSPGK

SEQ ID NO. 136 (IgG3 HC constant region, L164I & L165I)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSCD

TPPPCPRCPEPKSCDTPPPCPRCPEPKSCDTPPPCPRCPAPEIIGGPSVFLFPPKPKDTLMI

SRTPEVTCVVVDVSHEDPEVQFNWYVDGVEVHNAKTKPREEQYNSTYRWSVLTVLHQD

WLNGKEYKCKVSNKALPAPIEKTISKTKGQPREPQVYTLPPSREEMTKNQVSLTCLVKGFY

PSDIAVEWESSGQPENNYKTTPPVLDSDGSFFLYSKLTVDKSRWQQGNIFSCSVMHEALH

NHFTQKSLSLSPGK

SEQ ID NO. 140 (IgG4 HC constant region)
ASTKGPSVFPLAPCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPSCPAPEFLGGPSVFL

FPPKPKDTLMISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSRWQEGNVF

SCSVMHEALHNHYTQKSLSLSLGK

SEQ ID NO. 141 (IgG4 HC constant region, L115A)
ASTKGPSVFPLAPCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPSCPAPEFAGGPSVFL

```
-continued
FPPKPKDTLMISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSRWQEGNVF

SCSVMHEALHNHYTQKSLSLSLGK

SEQ ID NO. 142 (IgG4 HC constant region, L115G)
ASTKGPSVFPLAPCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPSCPAPEFGGGPSVFL

FPPKPKDTLMISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSRWQEGNVF

SCSVMHEALHNHYTQKSLSLSLGK

SEQ ID NO. 143 (IgG4 HC constant region, L115V)
ASTKGPSVFPLAPCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPSCPAPEFVGGPSVFL

FPPKPKDTLMISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSRWQEGNVF

SCSVMHEALHNHYTQKSLSLSLGK

SEQ ID NO. 144 (IgG4 HC constant region, L115I)
ASTKGPSVFPLAPCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPSCPAPEFIGGPSVFLF

PPKPKDTLMISRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPPSQEEMTKNQVS

LTCLVKGFYPSDIAVEWESNGQPENNYKTTPPVLDSDGSFFLYSRLTVDKSRWQEGNVFS

CSVMHEALHNHYTQKSLSLSLGK

SEQ ID NO. 150 (κLC constant region)
VAAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

SEQ ID NO. 151 (κLC constant region, C105S)
VAAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGES

SEQ ID NO. 152 (κLC constant region, C105V))
VAAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEV

SEQ ID NO. 153 (κLC constant region, C105del))
VAAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGE

SEQ ID NO. 160 (λLC constant region)
KAAPSVTLFPPSSEELQANKATLVCLISDFYPGAVTVAWKADSSPVKAGVETTTPSKQSN

NKYAASSYLSLTPEQWKSHRSYSCQVTHEGSTVEKTVAPTECS

SEQ ID NO. 161 (λLC constant region, C102S)
KAAPSVTLFPPSSEELQANKATLVCLISDFYPGAVTVAWKADSSPVKAGVETTTPSKQSN

NKYAASSYLSLTPEQWKSHRSYSCQVTHEGSTVEKTVAPTESS
```

-continued

SEQ ID NO. 162 (λLC constant region, C102V)
KAAPSVTLFPPSSEELQANKATLVCLISDFYPGAVTVAWKADSSPVKAGVETTTPSKQSN

NKYAASSYLSLTPEQWKSHRSYSCQVTHEGSTVEKTVAPTEVS

SEQ ID NO. 163 (λLC constant region, C102 & S103del)
KAAPSVTLFPPSSEELQANKATLVCLISDFYPGAVTVAWKADSSPVKAGVETTTPSKQSN

NKYAASSYLSLTPEQWKSHRSYSCQVTHEGSTVEKTVAPTE

---

The invention claimed is:

1. A conjugate of formula ConjE:

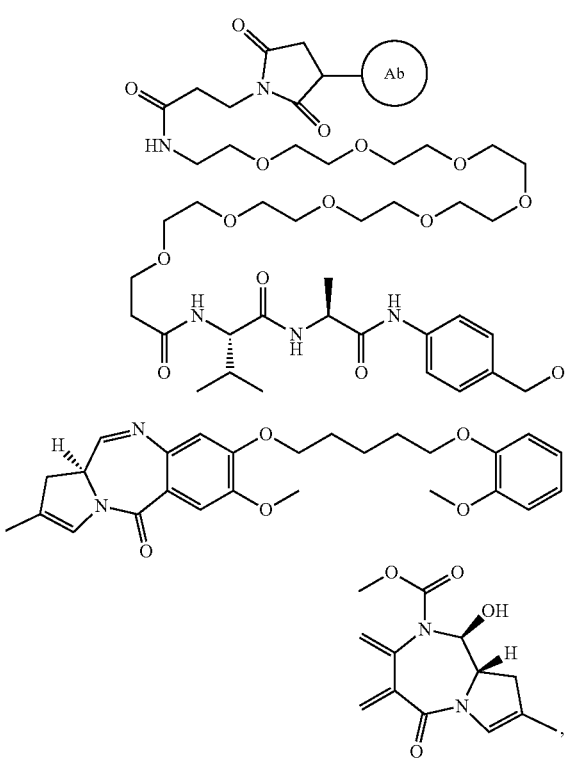

ConjE wherein Ab is an antibody which binds CD22 and comprises:
a VH domain having the amino acid sequence of SEQ ID NO. 1;
a VL domain having the amino acid sequence of SEQ ID NO. 2; and
heavy chains comprising an amino acid substitution of each of HC226 and HC229 according to the EU index as set forth in Kabat,
light chains each having an amino acid substitution of the interchain cysteine residue κLC214 or λLC213 according to the EU index as set forth in Kabat, and
heavy chains each retaining the unsubstituted interchain cysteine HC220 according to the EU index as set forth in Kabat, wherein the conjugation of the drug moiety to the antibody is at HC220 according to the EU index as set forth in Kabat.

2. The conjugate of claim 1, wherein the antibody comprises:
a heavy chain constant region comprising the amino acid sequence of SEQ ID NO.110, wherein each of the cysteines at positions 109 and 112 in SEQ ID NO: 110 is substituted by an amino acid that is not cysteine;
a light chain constant region comprising:
the amino acid sequence of SEQ ID NO. 150, wherein the cysteine at position 105 is substituted by an amino acid that is not cysteine; or
the amino acid sequence of SEQ ID NO. 160, wherein the cysteine at position 102 is substituted by an amino acid that is not cysteine;
wherein the drug moiety is conjugated to the cysteine at position 103 of SEQ ID NO.110.

3. The conjugate of claim 1, wherein the antibody comprises:
a heavy chain constant region comprising the amino acid sequence of SEQ ID NO.113 or SEQ ID NO.114, and
a light chain constant region comprising the amino acid sequence of SEQ ID NO.151, SEQ ID NO.152, SEQ ID NO.153, SEQ ID NO.161, SEQ ID NO.162, or SEQ ID NO.163;
wherein the drug moiety is conjugated to the cysteine at position 103 of SEQ ID NO.113 or 114.

4. The conjugate of claim 1, wherein the antibody comprises:
a heavy chain constant region comprising an amino acid sequence with 99% or more sequence identity to the amino acid sequence of SEQ ID NO.114, and
a light chain constant region comprising the amino acid sequence of SEQ ID NO.151;
wherein the drug moiety is conjugated to the cysteine at position 103 of SEQ ID NO.114.

5. The conjugate of claim 1, wherein the antibody comprises a heavy chain having a substitution of the amino acid at position 234 in the EU index set forth in Kabat and/or a substitution of the amino acid at position 235 in the EU index set forth in Kabat.

6. The conjugate of claim 5, wherein the amino acids are substituted by alanine, glycine, valine, or isoleucine.

7. The conjugate of claim 1, wherein the antibody is an intact antibody.

8. The conjugate of claim 1, wherein the antibody is humanised, deimmunized, or resurfaced.

9. A pharmaceutical composition comprising the conjugate of claim 1 and a pharmaceutically acceptable diluent, carrier, or excipient.

10. The pharmaceutical composition of claim 9, further comprising a therapeutically effective amount of a chemotherapeutic agent.

* * * * *